US008399450B2

(12) United States Patent
Michellys et al.

(10) Patent No.: US 8,399,450 B2
(45) Date of Patent: Mar. 19, 2013

(54) COMPOUNDS AND COMPOSITIONS AS PROTEIN KINASE INHIBITORS

(75) Inventors: Pierre-Yves Michellys, San Marcos, CA (US); Wei Pei, San Diego, CA (US); Thomas H. Marsilje, San Diego, CA (US); Wenshuo Lu, San Diego, CA (US); Bei Chen, San Diego, CA (US); Tetsuo Uno, San Diego, CA (US); Yunho Jin, San Diego, CA (US); Tao Jiang, San Diego, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 13/172,357

(22) Filed: Jun. 29, 2011

(65) Prior Publication Data

US 2011/0257154 A1 Oct. 20, 2011

Related U.S. Application Data

(63) Continuation of application No. 11/943,436, filed on Nov. 20, 2007, now Pat. No. 8,039,479.

(60) Provisional application No. 60/869,299, filed on Dec. 8, 2006.

(51) Int. Cl.
A61K 31/4164 (2006.01)
A61K 31/535 (2006.01)
A61K 31/497 (2006.01)
A61K 31/505 (2006.01)
C07D 413/12 (2006.01)
C07D 403/12 (2006.01)
C07D 239/02 (2006.01)

(52) U.S. Cl. ............ 514/210.18; 514/235; 514/252; 514/275; 544/112; 544/295; 544/323; 544/324

(58) Field of Classification Search ........... 514/210.18, 514/235, 252, 275; 544/112, 295, 323, 324
See application file for complete search history.

(56) References Cited

U.S. PATENT DOCUMENTS

| | | | |
|---|---|---|---|
| 3,361,749 A | 1/1968 | Matter et al. | |
| 3,432,493 A | 3/1969 | Short | |
| 5,958,935 A | 9/1999 | Davis et al. | |
| 6,048,866 A | 4/2000 | Hutchings et al. | |
| 6,093,716 A | 7/2000 | Davis et al. | |
| 6,114,333 A | 9/2000 | Davis et al. | |
| 6,235,746 B1 | 5/2001 | Davis et al. | |
| 6,593,326 B1 | 7/2003 | Bradbury et al. | |
| 7,241,769 B2 | 7/2007 | Stadtmueller et al. | |
| 7,514,446 B2 | 4/2009 | Davis-Ward et al. | |
| 7,671,063 B2 | 3/2010 | Baenteli et al. | |
| 2005/0261295 A1 | 11/2005 | Stadtmueller et al. | |
| 2006/0100227 A1* | 5/2006 | Baenteli et al. ........ | 514/275 |
| 2006/0247241 A1 | 11/2006 | Garcia-Echeverria et al. | |
| 2008/0132504 A1 | 6/2008 | Garcia-Echeverria et al. | |
| 2008/0293708 A1 | 11/2008 | Kawahara et al. | |
| 2009/0131436 A1 | 5/2009 | Imbach et al. | |

FOREIGN PATENT DOCUMENTS

| | | |
|---|---|---|
| EP | 1054004 A1 | 11/2000 |
| EP | 1184376 B1 | 2/2005 |
| WO | 9719065 A1 | 5/1997 |
| WO | 9841512 A1 | 9/1998 |
| WO | 9950250 A1 | 10/1999 |
| WO | 0012485 A1 | 3/2000 |
| WO | 0039101 A1 | 7/2000 |
| WO | 0078731 A1 | 12/2000 |
| WO | 0125220 A1 | 4/2001 |
| WO | 0160816 A1 | 8/2001 |
| WO | 0164654 A1 | 9/2001 |
| WO | 0164655 A1 | 9/2001 |
| WO | 0164656 A1 | 9/2001 |
| WO | 0185699 A2 | 11/2001 |
| WO | 0185700 A2 | 11/2001 |
| WO | 02056888 A2 | 7/2002 |
| WO | 03016306 A1 | 2/2003 |
| WO | 03018021 A1 | 3/2003 |
| WO | 03030909 A1 | 4/2003 |
| WO | 03063794 A2 | 8/2003 |
| WO | 03066601 A1 | 8/2003 |
| WO | 03078404 A1 | 9/2003 |
| WO | 03094920 A1 | 11/2003 |
| WO | 03095448 A1 | 11/2003 |
| WO | 2004002964 A1 | 1/2004 |
| WO | 2004046118 A2 | 6/2004 |
| WO | 2004056786 A1 | 7/2004 |
| WO | 2004074244 A2 | 9/2004 |
| WO | 2004080980 A1 | 9/2004 |
| WO | 2004089286 A2 | 10/2004 |
| WO | 2005013996 A2 | 2/2005 |
| WO | 2005016894 A1 | 2/2005 |
| WO | 2005026130 A1 | 3/2005 |
| WO | 2005026158 A1 | 3/2005 |
| WO | 2006021454 A2 | 3/2006 |
| WO | 2006021457 A2 | 3/2006 |
| WO | 2006068770 A1 | 6/2006 |
| WO | 2006074057 A2 | 7/2006 |
| WO | 2006133426 A2 | 12/2006 |

(Continued)

OTHER PUBLICATIONS

Traxler, Peter M. , "Protein Tyrosine Kinase Inhibitors in Cancer Treatment," Expert Opinion on Therapeutic Patents, vol. 7, No. 6, pp. 571-588, 1997.

(Continued)

*Primary Examiner* — James O Wilson
*Assistant Examiner* — Ebenezer O Sackey
(74) *Attorney, Agent, or Firm* — Emily Tongco Wu; Genomics Institute of the Novartis Research Foundation

(57) ABSTRACT

The invention provides novel pyrimidine and pyridine derivatives and pharmaceutical compositions thereof, and methods for using such compounds. For example, the pyrimidine and pyridine derivatives of the invention may be used to treat, ameliorate or prevent a condition which responds to inhibition of anaplastic lymphoma kinase (ALK) activity, focal adhesion kinase (FAK), zeta-chain-associated protein kinase 70 (ZAP-70), insulin-like growth factor (IGF-1R), or a combination thereof.

15 Claims, No Drawings

FOREIGN PATENT DOCUMENTS

| WO | 2008051547 A1 | 5/2008 |
| WO | 2009032694 A1 | 3/2009 |
| WO | 2009032703 A1 | 3/2009 |

OTHER PUBLICATIONS

Simone et al., Oncology: Introduction, Cecil Textbook of Medicine, 20th Edition, vol. 1, pp. 1004-1010, 1997.

Basford et al., CAPLUS Abstract 41:763, pp. 7810-7812,1947.

Coopman et al., "The Syk Tyrosine Kinase Suppresses Malignant Growth of Human Breast Cancer Cells," Nature, vol. 406, pp. 742-747, Aug. 17, 2000.

USPTO Notice of Allowance, dated Oct. 4, 2010, of U.S. Appl. No. 10/568,367 (U.S. Patent Publication No. 2008/0132504).

USPTO Notice of Allowance, dated Feb. 7, 2011, of U.S. Appl. No. 10/549,250 (U.S. Patent Publication No. 2006/0247241).

USPTO Notice of Allowance, dated Dec. 27, 2010, of U.S. Appl. No. 10/507,060 (U.S. Patent Publication No. 2006/0100227).

USPTO Notice of Allowance, dated Nov. 12, 2010, of U.S. Appl. No. 11/660,714 (U.S. Patent Publication No. 2008/0293708).

Ghosh et al., "2,4-Bis(arylamino)-5-methylpyrimidines as Antimicrobial Agents," Journal of Medicinal Chemistry, vol. 10, No. 5, pp. 974-975, Sep. 1967.

Ghosh Dolly, "2,4-Bis(Arylamino)-6-Methyl Pyrimidines as Antimicrobial Agents," Journal of the Indian Chemical Society, vol. 58, No. 5, pp. 512-513, May 1981.

Ghoneim et al., "Synthesis and Evaluation of some 2-, 4- and 2,4-Di-substituted-6-methylpyrimidine Derivatives for Antimicrobial Activity," Journal of the Indian Chemical Society, vol. 63, No. 10, pp. 914-917, Oct. 1986.

Van Seventer et al., "Focal adhesion kinase regulates β1 integrin-dependent T cell migration through an HEF1 effector pathway," European Journal of Immunology, 31: 1417-1427, 2001.

Dirks et al., "Expression and Functional Analysis of the Anaplastic Lymphoma Kinase (ALK) Gene in Tumor Cell Lines," Int. J. Cancer: 100, 49-56, 2002.

Osajima-Hakomori et al., "Biological Role of Anaplastic Lymphoma Kinase in Neuroblastoma," American Journal of Pathology, vol. 167, No. 1, pp. 213-222, Jul. 2005.

Galkin, et al., "Identification of NVP-TAE684, a potent, selective, and efficacious inhibitors of NPM-ALK, PNAS, Jan. 2, 2007, pp. 270-275, vol. 104, No. 1.

\* cited by examiner

COMPOUNDS AND COMPOSITIONS AS PROTEIN KINASE INHIBITORS

CROSS-REFERENCE TO RELATED APPLICATIONS

This application is a continuation of U.S. application Ser. No. 11/943,436, which claims the benefit of U.S. provisional application Ser. No. 60/869,299, filed Dec. 8, 2006, and is incorporated by reference herein in its entirety.

TECHNICAL FIELD

The invention relates to protein kinase inhibitors, more particularly novel pyrimidine and pyridine derivatives and pharmaceutical compositions thereof, and their use as pharmaceuticals.

BACKGROUND ART

Anaplastic lymphoma kinase (ALK), a member of the insulin receptor superfamily of receptor tyrosine kinases, has been implicated in oncogenesis in hematopoietic and non-hematopoietic tumors. The aberrant expression of full-length ALK receptor proteins has been reported in neuroblastomas and glioblastomas; and ALK fusion proteins have occurred in anaplastic large cell lymphoma. The study of ALK fusion proteins has also raised the possibility of new therapeutic treatments for patients with ALK-positive malignancies. (Pulford et al., Cell. Mol. Life. Sci. 61:2939-2953 (2004)).

Focal Adhesion Kinase (FAK) is a key enzyme in the integrin-mediated outside-in signal cascade (D. Schlaepfer et al., Prog Biophys Mol Biol 1999, 71, 43578). The trigger in the signal transduction cascade is the autophosphorylation of Y397. Phosphorylated Y397 is a SH2 docking site for Src family tyrosine kinases; the bound c-Src kinase phosphorylates other tyrosine residues in FAK. Among them, phosphorylated Y925 becomes a binding site for the SH2 site of Grb2 small adaptor protein. This direct binding of Grb2 to FAK is one of the key steps for the activation of down stream targets such as the Ras-ERK2/MAP kinase cascade.

Zeta-chain-associated protein kinase 70 (ZAP-70), a member of the protein tyrosine kinase family, is of potential prognostic importance in chronic lymphocytic leukemia (CLL). ZAP-70, known to be of importance in T and NK cell signaling but absent in normal peripheral B cells, is expressed in the majority of the poorer prognosis unmutated CLL and absent in most cases with mutated IgVH genes. ZAP-70 is also expressed in a minority of other B cell tumors. (Orchard et al., Leuk. Lymphoma 46:1689-98 (2005)).

Insulin-like growth factor (IGF-1) signaling is highly implicated in cancer, with the IGF-1 receptor (IGF-1R) as the predominating factor. IGR-1R is important for tumor transformation and survival of malignant cells, but is only partially involved in normal cell growth. Targeting of IGF-1R has been suggested to be a promising option for cancer therapy. (Larsson et al., Br. J. Cancer 92:2097-2101 (2005)).

Because of the emerging disease-related roles of ALK, FAK, ZAP-70 and IGF-1R, there is a continuing need for compounds which may be useful for treating and preventing a disease which responds to inhibition of ALK, FAK, ZAP-70 and/or IGF-1R.

DISCLOSURE OF THE INVENTION

The invention relates to novel pyrimidine and pyridine derivatives and pharmaceutical compositions thereof, and their use as pharmaceuticals.

In one aspect, the invention provides a having Formula (1):

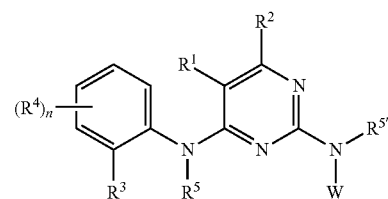

or pharmaceutically acceptable salts thereof; wherein W is

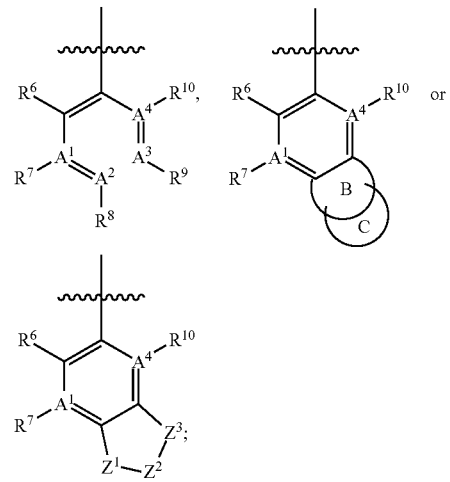

$A^1$ and $A^4$ are independently C or N;
each $A^2$ and $A^3$ is C, or one of $A^2$ and $A^3$ is N when $R^6$ and $R^7$ form a ring;
B and C are independently an optionally substituted 5-7 membered carbocyclic ring, aryl, heteroaryl or heterocyclic ring containing N, O or S;
$Z^1$, $Z^2$ and $Z^3$ are independently $NR^{11}$, C=O, CR—OR, $(CR_2)_{1-2}$ or =C—$R^{12}$;
$R^1$ and $R^2$ are independently halo, $OR^{12}$, $NR(R^{12})$, $SR^{12}$, or an optionally substituted $C_{1-6}$ alkyl, $C_{2-6}$ alkenyl or $C_{2-6}$ alkynyl; or one of $R^1$ and $R^2$ is H;
$R^3$ is $(CR_2)_{0-2}SO_2R^{12}$, $(CR_2)_{0-2}SO_2NRR^{12}$, $(CR_2)_{0-2}CO_{1-2}R^{12}$, $(CR_2)_{0-2}CONRR^{12}$ or cyano;
$R^4$, $R^6$, $R^7$ and $R^{10}$ are independently an optionally substituted $C_{1-6}$ alkyl, $C_{2-6}$ alkenyl or $C_{2-6}$ alkynyl; $OR^{12}$, $NR(R^{12})$, halo, nitro, $SO_2R^{12}$, $(CR_2)_pR^{13}$ or X; or $R^4$, $R^7$ and $R^{10}$ are independently H;
R, $R^5$ and $R^{5'}$ are independently H or $C_{1-6}$ alkyl;
$R^8$ and $R^9$ are independently $C_{1-6}$ alkyl, $C_{2-6}$ alkenyl, $C_{2-6}$ alkynyl, halo or X, or one of $R^8$ and $R^9$ is H when $R^1$ and $R^2$ form a ring; and provided one of $R^8$ and $R^9$ is X;
alternatively, $R^1$ and $R^2$, or $R^6$ and $R^7$, $R^7$ and $R^8$, or $R^9$ and $R^{10}$, when attached to a carbon atom may form an optionally substituted 5-7 membered monocyclic or fused carbocyclic ring, aryl, or heteroaryl or heterocyclic ring comprising N, O and/or S; or $R^7$, $R^8$, $R^9$ and $R^{10}$ are absent when attached to N;
$R^{11}$ is H, $C_{1-6}$ alkyl, $C_{2-6}$ alkenyl, $(CR_2)_pCO_{1-2}R$, $(CR_2)_pOR$, $(CR_2)_pR^{13}$, $(CR_2)_pNRR^{12}$, $(CR_2)_pCONRR^{12}$ or $(CR_2)_pSO_{1-2}R^{12}$;
$R^{12}$ and $R^{13}$ are independently an optionally substituted 3-7 membered saturated or partially unsaturated carbocyclic ring, or a 5-7 membered heterocyclic ring comprising N, O and/or S; aryl or heteroaryl; or $R^{12}$ is H, $C_{1-6}$ alkyl;

X is $(CR_2)_qY$, cyano, $CO_{1-2}R^{12}$, $CONR(R^{12})$, $CONR(CR_2)_pNR(R^{12})$, $CONR(CR_2)_pOR^{12}$, $CONR(CR_2)_pSR^{12}$, $CONR(CR_2)_pS(O)_{1-2}R^{12}$ or $(CR_2)_{1-6}NR(CR_2)_pOR^{12}$;

Y is an optionally substituted 3-12 membered carbocyclic ring, a 5-12 membered aryl, or a 5-12 membered heteroaryl or heterocyclic ring comprising N, O and/or S and attached to $A^2$ or $A^3$ or both via a carbon atom of said heteroaryl or heterocyclic ring when q in $(CR_2)_qY$ is 0; and n, p and q are independently 0-4.

In the above Formula (1), $R^1$ may be halo or $C_{1-6}$ alkyl; $R^2$ is H or $NH_2$; or $R^1$ and $R^2$ together form an optionally substituted 5-6 membered aryl, or heteroaryl or heterocyclic ring comprising 1-3 nitrogen atoms. In other examples, $R^3$ in Formula (1) may be $SO_2R^{12}$, $SO_2NH_2$, $SO_2NRR^{12}$, $CO_2NH_2$, $CONRR^{12}$, $CO_{1-2}R^{12}$, or cyano; and $R^{12}$ is $C_{1-6}$ alkyl, an optionally substituted $C_{3-7}$ cycloalkyl, $C_{3-7}$ cycloalkenyl, pyrrolidinyl, piperazinyl, piperidinyl, morpholinyl or azetidinyl. In yet other examples, $R^5$, $R^{5'}$, $R^7$ and $R^{10}$ in Formula (1) are independently H, and n is 0. In other examples, $R^6$ in Formula (1) may be halo or $OR^{12}$, and $R^{12}$ is $C_{1-6}$ alkyl.

In one embodiment, the invention provides compounds having Formula (2):

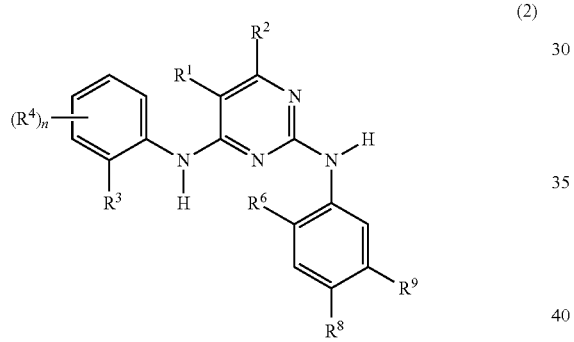

(2)

wherein $R^1$ is halo or $C_{1-6}$ alkyl;

$R^2$ is H; or $R^1$ and $R^2$ together form an optionally substituted 5-6 membered heteroaryl or heterocyclic ring comprising one or two nitrogen atoms;

$R^6$ is isopropoxy or methoxy;

one of $R^8$ and $R^9$ is $(CR_2)_qY$ and the other is $C_{1-6}$ alkyl, cyano, $CO_{1-2}R^{12}$, $CONR(R^{12})$ or $CONR(CR_2)_pNR(R^{12})$;

Y is an optionally substituted $C_{3-7}$ cycloalkyl, $C_{3-7}$ cycloalkenyl, or phenyl; or Y is pyridyl, pyrazolyl, isoxazolyl, imidazolyl, thiazolyl, benzimidazolyl, pyrrolidinyl, piperazinyl, piperidinyl, morpholinyl, azetidinyl, heptamethyleneimine or octamethyleneimine, each of which is attached to the phenyl ring via a carbon atom when q in $(CR_2)_qY$ is 0;

n is 0-1; and q is 0-4.

In the above Formula (2), one of $R^8$ and $R^9$ may be $(CR_2)_qY$ and the other is $C_{1-6}$ alkyl; and n and q are independently 0. In some examples, Y is pyrrolidinyl, piperidinyl, azetidinyl. In other examples, $R^1$ is halo or $C_{1-6}$ alkyl; and $R^2$ is H.

In another embodiment, the invention provides compounds having Formula (3A) or (3B):

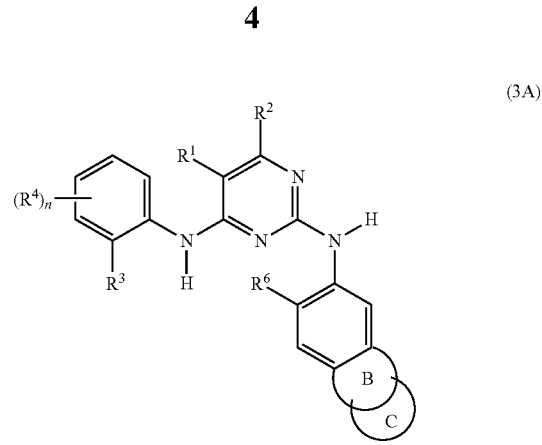

(3A)

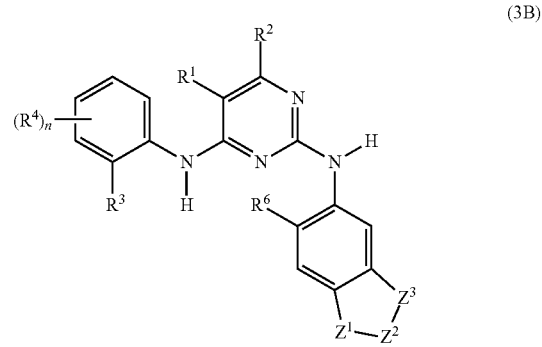

(3B)

wherein B and C together form

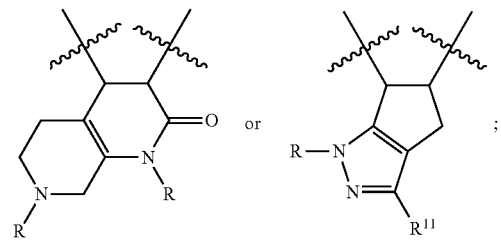

$Z^1$, $Z^2$ and $Z^3$ together form

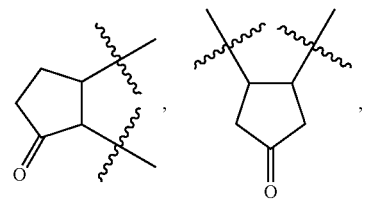

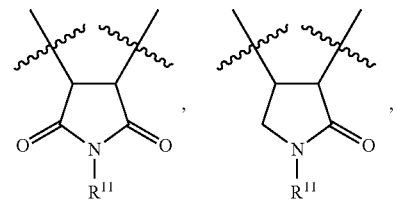

-continued

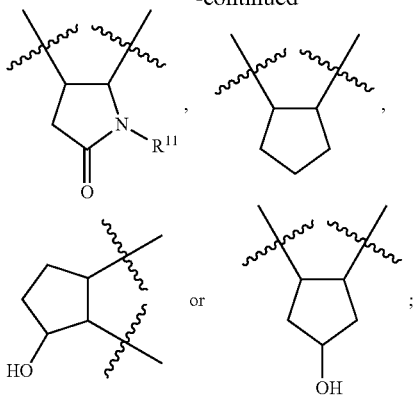

or tautomers thereof;

$R^1$ is halo or $C_{1-6}$ alkyl;

$R^2$ is H; or $R^1$ and $R^2$ together form an optionally substituted 5-7 membered carbocyclic ring, aryl, or heteroaryl or heterocyclic ring comprising N, O and/or S; and $R^6$ is isopropoxy or methoxy.

In the above Formula (3A) or (3B), each $R^{11}$ may be $(CR_2)_pCO_{1-2}R$, $(CR_2)_pOR$, $(CR_2)_pR^{13}$, $(CR_2)_pNRR^{12}$ or $(CR_2)_pCONRR^{12}$;

R and $R^{12}$ are independently H or $C_{1-6}$ alkyl; and $R^{13}$ is an optionally substituted piperidinyl, azetidiyl, tetrahydropyranyl, cyclohexyl, morpholinyl, pyrrolidinyl, heptamethyleneimine, octamethyleneimine, a bicyclic amine or diamine derivative, quinuclidin-3-yl, 8-methyl-8-aza-bicyclo[3.2.1]oct-6-yl], or 9-methyl-9-aza-bicyclo[4.2.1]nonan-7-yl.

In yet another embodiment, the invention provides compounds having Formula (4A) or Formula (4B):

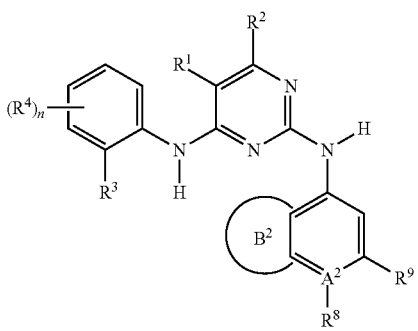 (4A)

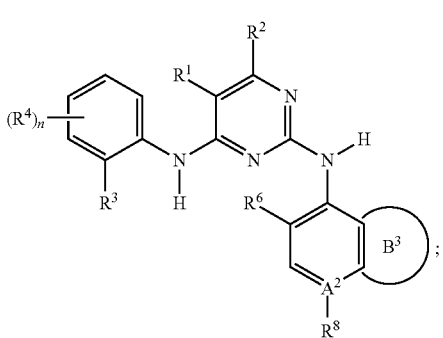 (4B)

wherein $R^1$ is halo or $C_{1-6}$ alkyl;

$R^2$ is H; or $R^1$ and $R^2$ together form an optionally substituted 5-7 membered carbocyclic ring, aryl, or heteroaryl or heterocyclic ring comprising N, O and/or S;

$R^6$ is isopropoxy or methoxy; and $B^2$ and $B^3$ are independently an optionally substituted 5-6 membered aryl or heteroaryl containing N, O or S.

In another aspect, the invention provides compounds having Formula (5):

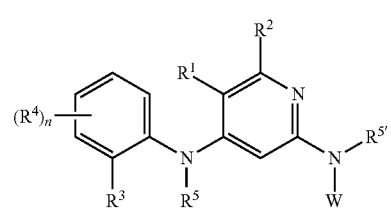 (5)

or pharmaceutically acceptable salts thereof; wherein W is

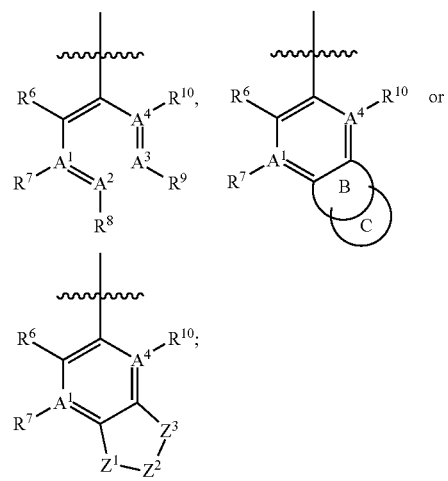

$A^1$ and $A^4$ are independently C or N;

each $A^2$ and $A^3$ is C, or one of $A^2$ and $A^3$ is N when $R^6$ and $R^7$ form a ring;

B and C are independently an optionally substituted 5-7 membered carbocyclic ring, aryl, heteroaryl or heterocyclic ring containing N, O or S;

$Z^1$, $Z^2$ and $Z^3$ are independently $NR^{11}$, C=O, CR—OR, $(CR_2)_{1-2}$ or =C—$R^{12}$;

$R^1$ and $R^2$ are independently halo, $OR^{12}$, $NR(R^{12})$, $SR^{12}$, or an optionally substituted $C_{1-6}$ alkyl, $C_{2-6}$ alkenyl or $C_{2-6}$ alkynyl; or one of $R^1$ and $R^2$ is H;

$R^3$ is $(CR_2)_{0-2}SO_2R^{12}$, $(CR_2)_{0-2}SO_2NRR^{12}$, $(CR_2)_{0-2}CO_{1-2}R^{12}$, $(CR_2)_{0-2}CONRR^{12}$ or cyano;

$R^4$, $R^6$, and $R^7$ and $R^{10}$ when attached to a carbon atom, are independently H, an optionally substituted $C_{1-6}$ alkyl, $C_{2-6}$ alkenyl or $C_{2-6}$ alkynyl; $OR^{12}$, $NR(R^{12})$, halo, nitro, $SO_2R^{12}$, $(CR_2)_pR^{13}$ or X; provided $R^6$ and $R^7$ are not both H;

R, $R^5$ and $R^{5'}$ are independently H or $C_{1-6}$ alkyl;

$R^8$ and $R^9$ are independently $C_{1-6}$ alkyl, $C_{2-6}$ alkenyl, $C_{2-6}$ alkynyl, halo or X, or one of $R^8$ and $R^9$ is H; and provided one of $R^8$ and $R^9$ is X;

alternatively, $R^1$ and $R^2$, or $R^6$ and $R^7$, $R^7$ and $R^8$, or $R^9$ and $R^{10}$, when attached to a carbon atom may form an optionally substituted 5-7 membered monocyclic or fused carbocyclic ring, aryl, or heteroaryl or heterocyclic ring comprising N, O and/or S; or $R^7$, $R^8$, $R^9$ and $R^{10}$ are absent when attached to N;

$R^{11}$ is H, $C_{1-6}$ alkyl, $C_{2-6}$ alkenyl, $(CR_2)_pCO_{1-2}R$, $(CR_2)_pOR$, $(CR_2)_pR^{13}$, $(CR_2)_pNRR^{12}$, $(CR_2)_pCONRR^{12}$ or $(CR_2)_pSO_{1-2}R^{12}$;

$R^{12}$ and $R^{13}$ are independently an optionally substituted 3-7 membered saturated or partially unsaturated carbocyclic ring, or a 5-7 membered heterocyclic ring comprising N, O and/or S; aryl or heteroaryl; or $R^{12}$ is H, $C_{1-6}$ alkyl;

X is $(CR_2)_qY$, cyano, $CO_{1-2}R^{12}$, $CONR(R^{12})$, $CONR(CR_2)_pNR(R^{12})$, $CONR(CR_2)_pOR^{12}$, $CONR(CR_2)_pSR^{12}$, $CONR(CR_2)_pS(O)_{1-2}R^{12}$ or $(CR_2)_{1-6}NR(CR_2)_pOR^{12}$;

Y is an optionally substituted 3-12 membered carbocyclic ring, a 5-12 membered aryl, or a 5-12 membered heteroaryl or heterocyclic ring comprising N, O and/or S and attached to $A^2$ or $A^3$ or both via a carbon atom of said heteroaryl or heterocyclic ring when q in $(CR_2)_qY$ is 0; and n, p and q are independently 0-4.

In yet another aspect, the present invention provides pharmaceutical compositions comprising a compound having Formula (1), (2), (3A), (3B), (4A), (4B) or (5), and a pharmaceutically acceptable excipient.

In yet another aspect, the invention provides methods for modulating ALK, FAK, ZAP-70 and/or IGF-1R, comprising administering to a system or a subject in need thereof, a therapeutically effective amount of a compound having Formula (1), (2), (3A), (3B), (4A), (4B) or (5), or pharmaceutically acceptable salts or pharmaceutical compositions thereof, thereby modulating said ALK, FAK, ZAP-70 and/or IGF-1R. The invention also provides methods to treat, ameliorate or prevent a condition which responds to inhibition of ALK, FAK, ZAP-70 and/or IGF-1R, comprising administering to a system or subject in need of such treatment an effective amount of a compound having Formula (1), (2), (3A), (3B), (4A), (4B) or (5), or pharmaceutically acceptable salts or pharmaceutical compositions thereof, and optionally in combination with a second therapeutic agent, thereby treating said condition. Alternatively, the present invention provides the use of a compound having Formula (1), (2), (3A), (3B), (4A), (4B) or (5) in the manufacture of a medicament for treating a condition mediated by ALK, FAK, ZAP-70 and/or IGF-1R. In particular embodiments, the compounds of the invention may be used alone or in combination with a second therapeutic agent to treat a condition mediated by ALK, wherein said condition is an autoimmune disease, a transplantation disease, an infectious disease or a cell proliferative disorder.

Furthermore, the invention provides methods for treating a cell proliferative disorder, comprising administering to a system or subject in need of such treatment an effective amount of a compound having Formula (1), (2), (3A), (3B), (4A), (4B) or (5), or pharmaceutically acceptable salts or pharmaceutical compositions thereof, and optionally in combination with a second therapeutic agent, thereby treating said condition. Alternatively, the present invention provides the use of a compound having Formula (1), (2), (3A), (3B), (4A), (4B) or (5) in the manufacture of a medicament for treating a cell-proliferative disorder. In particular examples, the compounds of the invention may be used alone or in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor.

In the above methods for using the compounds of the invention, a compound having Formula (1), (2), (3A), (3B), (4A), (4B) or (5) may be administered to a system comprising cells or tissues, or to a mammalian subject such as a human or animal subject.

Definitions

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., $CF_3$), or may have one or more carbons that is substituted or replaced with a heteroatom, such as NR, O or S (e.g., —$OCH_2CH_2O$—, alkylthiols, thioalkoxy, alkylamines, etc).

"Aryl" refers to a monocyclic or fused bicyclic aromatic ring containing carbon atoms. "Arylene" means a divalent radical derived from an aryl group. For example, an aryl group may be phenyl, indenyl, indanyl, naphthyl, or 1,2,3,4-tetrahydronaphthalenyl, which may be optionally substituted in the ortho, meta or para position.

"Heteroaryl" as used herein is as defined for aryl above, where one or more of the ring members is a heteroatom. Examples of heteroaryls include but are not limited to pyridyl, pyrazinyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, benzotriazolyl, tetrazolyl, pyrazolyl, thienyl, pyrrolyl, isoquinolinyl, purinyl, thiazolyl, tetrazinyl, benzothiazolyl, oxadiazolyl, benzoxadiazolyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring may contain N, O, S, —N=, —S—, —S(O), —S(O)$_2$—, or —NR— wherein R may be hydrogen, $C_{1-4}$alkyl or a protecting group. Examples of heterocyclic rings include but are not limited to morpholino, pyrrolidinyl, pyrrolidinyl-2-one, piperazinyl, piperidinyl, piperidinylone, 1,4-dioxa-8-aza-spiro[4.5]dec-8-yl, 1,2,3,4-tetrahydroquinolinyl, etc. Heterocyclic rings as used herein may encompass bicyclic amines and bicyclic diamines.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" or "administering" of the subject compound means providing a compound of the invention and prodrugs thereof to a subject in need of treatment.

MODES OF CARRYING OUT THE INVENTION

The invention provides novel pyrimidine and pyridine derivatives and pharmaceutical compositions thereof, and methods for using such compounds.

In one aspect, the invention provides a having Formula (1):

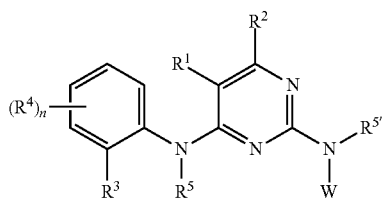

(1)

or pharmaceutically acceptable salts thereof; wherein W is

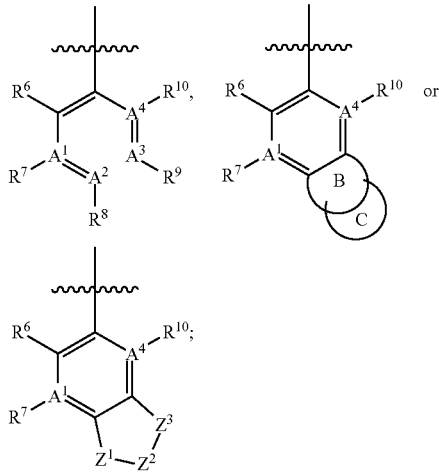

$A^1$ and $A^4$ are independently C or N;

each $A^2$ and $A^3$ is C, or one of $A^2$ and $A^3$ is N when $R^6$ and $R^7$ form a ring;

B and C are independently an optionally substituted 5-7 membered carbocyclic ring, aryl, heteroaryl or heterocyclic ring containing N, O or S;

$Z^1$, $Z^2$ and $Z^3$ are independently $NR^{11}$, C=O, CR—OR, $(CR_2)_{1-2}$ or =C—$R^{12}$;

$R^1$ and $R^2$ are independently halo, $OR^{12}$, $NR(R^{12})$, $SR^{12}$, or an optionally substituted $C_{1-6}$ alkyl, $C_{2-6}$ alkenyl or $C_{2-6}$ alkynyl; or one of $R^1$ and $R^2$ is H;

$R^3$ is $(CR_2)_{0-2}SO_2R^{12}$, $(CR_2)_{0-2}SO_2NRR^{12}$, $(CR_2)_{0-2}CO_{1-2}R^{12}$, $(CR_2)_{0-2}CONRR^{12}$ or cyano;

$R^4$, $R^6$, $R^7$ and $R^{10}$ are independently an optionally substituted $C_{1-6}$ alkyl, $C_{2-6}$ alkenyl or $C_{2-6}$ alkynyl; $OR^{12}$, $NR(R^{12})$, halo, nitro, $SO_2R^{12}$, $(CR_2)_pR^{13}$ or X; or $R^4$, $R^7$ and $R^{10}$ are independently H;

R, $R^5$ and $R^{5'}$ are independently H or $C_{1-6}$ alkyl;

$R^8$ and $R^9$ are independently $C_{1-6}$ alkyl, $C_{2-6}$ alkenyl, $C_{2-6}$ alkynyl, halo or X, or one of $R^8$ and $R^9$ is H when $R^1$ and $R^2$ form a ring; and provided one of $R^8$ and $R^9$ is X;

alternatively, $R^1$ and $R^2$, or $R^6$ and $R^7$, $R^7$ and $R^8$, or $R^9$ and $R^{10}$, when attached to a carbon atom may form an optionally substituted 5-7 membered monocyclic or fused carbocyclic ring, aryl, or heteroaryl or heterocyclic ring comprising N, O and/or S; or $R^7$, $R^8$, $R^9$ and $R^{10}$ are absent when attached to N;

$R^{11}$ is H, $C_{1-6}$ alkyl, $C_{2-6}$ alkenyl, $(CR_2)_pCO_{1-2}R$, $(CR_2)_pOR$, $(CR_2)_pR^{13}$, $(CR_2)_pNRR^{12}$, $(CR_2)_pCONRR^{12}$ or $(CR_2)_pSO_{1-2}R^{12}$;

$R^{12}$ and $R^{13}$ are independently an optionally substituted 3-7 membered saturated or partially unsaturated carbocyclic ring, or a 5-7 membered heterocyclic ring comprising N, O and/or S; aryl or heteroaryl; or $R^{12}$ is H, $C_{1-6}$ alkyl;

X is $(CR_2)_qY$, cyano, $CO_{1-2}R^{12}$, $CONR(R^{12})$, $CONR(CR_2)_pNR(R^{12})$, $CONR(CR_2)_pOR^{12}$, $CONR(CR_2)_pSR^{12}$, $CONR(CR_2)_pS(O)_{1-2}R^{12}$ or $(CR_2)_{1-6}NR(CR_2)_pOR^{12}$;

Y is an optionally substituted 3-12 membered carbocyclic ring, a 5-12 membered aryl, or a 5-12 membered heteroaryl or heterocyclic ring comprising N, O and/or S and attached to $A^2$ or $A^3$ or both via a carbon atom of said heteroaryl or heterocyclic ring when q in $(CR_2)_qY$ is 0; and n, p and q are independently 0-4.

In one embodiment, the invention provides compounds having Formula (2):

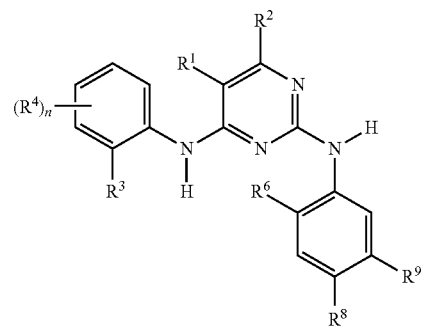

(2)

wherein $R^1$ is halo or $C_{1-6}$ alkyl;

$R^2$ is H; or $R^1$ and $R^2$ together form an optionally substituted 5-6 membered heteroaryl or heterocyclic ring comprising one or two nitrogen atoms;

$R^6$ is isopropoxy or methoxy;

one of $R^8$ and $R^9$ is $(CR_2)_qY$ and the other is $C_{1-6}$ alkyl, cyano, $CO_{1-2}R^{12}$, $CONR(R^{12})$ or $CONR(CR_2)_pNR(R^{12})$;

Y is an optionally substituted $C_{3-7}$ cycloalkyl, $C_{3-7}$ cycloalkenyl, or phenyl; or Y is pyridyl, pyrazolyl, isoxazolyl, imidazolyl, thiazolyl, benzimidazolyl, pyrrolidinyl, piperazinyl, piperidinyl, morpholinyl, azetidinyl, heptamethyleneimine or octamethyleneimine, each of which is attached to the phenyl ring via a carbon atom when q in $(CR_2)_qY$ is 0;

n is 0-1; and q is 0-4.

In another embodiment, the invention provides compounds having Formula (3A) or (3B):

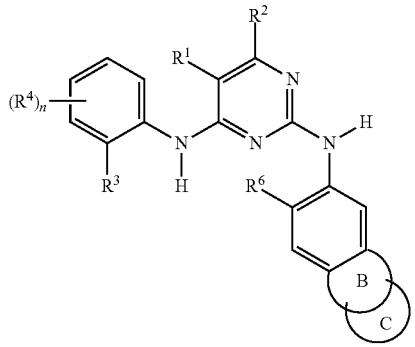
(3A)

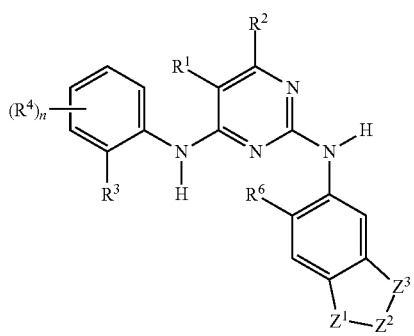
(3B)

wherein B and C together form

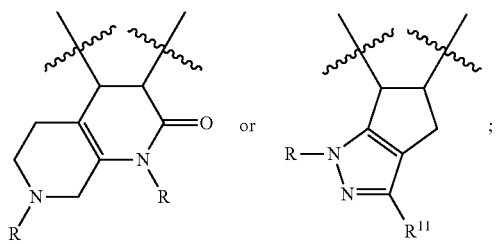

$Z^1$, $Z^2$ and $Z^3$ together form

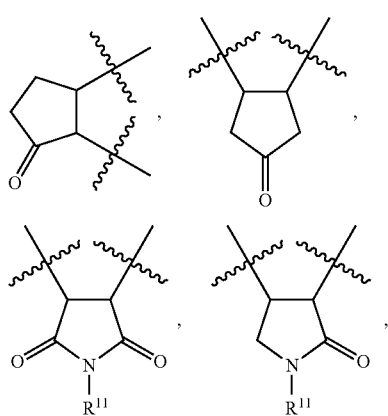

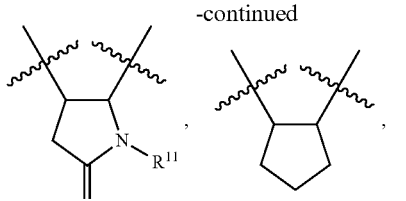

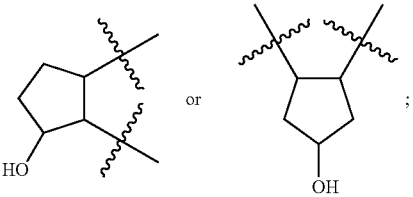

or tautomers thereof;

$R^1$ is halo or $C_{1-6}$ alkyl;

$R^2$ is H; or $R^1$ and $R^2$ together form an optionally substituted 5-7 membered carbocyclic ring, aryl, or heteroaryl or heterocyclic ring comprising N, O and/or S; and $R^6$ is isopropoxy or methoxy.

In yet another embodiment, the invention provides compounds having Formula (4A) or Formula (4B):

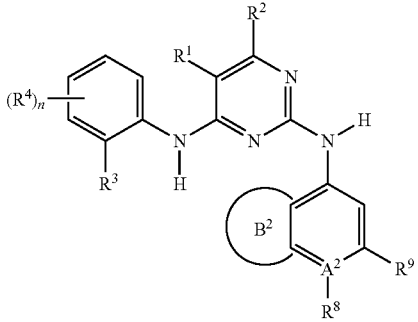
(4A)

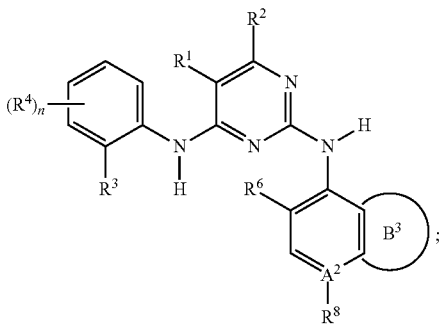
(4B)

wherein $R^1$ is halo or $C_{1-6}$ alkyl;

$R^2$ is H; or $R^1$ and $R^2$ together form an optionally substituted 5-7 membered carbocyclic ring, aryl, or heteroaryl or heterocyclic ring comprising N, O and/or S;

$R^6$ is isopropoxy or methoxy; and $B^2$ and $B^3$ are independently an optionally substituted 5-6 membered aryl or heteroaryl containing N, O or S.

In another aspect, the invention provides compounds having Formula (5):

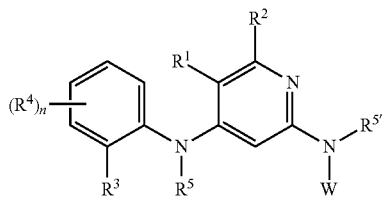

(5)

or pharmaceutically acceptable salts thereof; wherein W is

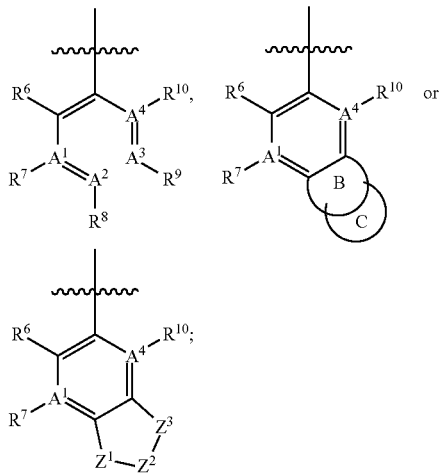

$A^1$ and $A^4$ are independently C or N;

each $A^2$ and $A^3$ is C, or one of $A^2$ and $A^3$ is N when $R^6$ and $R^7$ form a ring;

B and C are independently an optionally substituted 5-7 membered carbocyclic ring, aryl, heteroaryl or heterocyclic ring containing N, O or S;

$Z^1$, $Z^2$ and $Z^3$ are independently $NR^{11}$, C=O, CR—OR, $(CR_2)_{1-2}$ or =C—$R^{12}$;

$R^1$ and $R^2$ are independently halo, $OR^{12}$, $NR(R^{12})$, $SR^{12}$, or an optionally substituted $C_{1-6}$ alkyl, $C_{2-6}$ alkenyl or $C_{2-6}$ alkynyl; or one of $R^1$ and $R^2$ is H;

$R^3$ is $(CR_2)_{0-2}SO_2R^{12}$, $(CR_2)_{0-2}SO_2NRR^{12}$, $(CR_2)_{0-2}CO_{1-2}R^{12}$, $(CR_2)_{0-2}CONRR^{12}$ or cyano;

$R^4$, $R^6$, and $R^7$ and $R^{10}$ when attached to a carbon atom, are independently H, an optionally substituted $C_{1-6}$ alkyl, $C_{2-6}$ alkenyl or $C_{2-6}$ alkynyl; $OR^{12}$, $NR(R^{12})$, halo, nitro, $SO_2R^{12}$, $(CR_2)_pR^{13}$ or X; provided $R^6$ and $R^7$ are not both H;

R, $R^5$ and $R^{5'}$ are independently H or $C_{1-6}$ alkyl;

$R^8$ and $R^9$ are independently $C_{1-6}$ alkyl, $C_{2-6}$ alkenyl, $C_{2-6}$ alkynyl, halo or X, or one of $R^8$ and $R^9$ is H; and provided one of $R^8$ and $R^9$ is X;

alternatively, $R^1$ and $R^2$, or $R^6$ and $R^7$, $R^7$ and $R^8$, or $R^9$ and $R^{10}$, when attached to a carbon atom may form an optionally substituted 5-7 membered monocyclic or fused carbocyclic ring, aryl, or heteroaryl or heterocyclic ring comprising N, O and/or S; or $R^7$, $R^8$, $R^9$ and $R^{10}$ are absent when attached to N;

$R^{11}$ is H, $C_{1-6}$ alkyl, $C_{2-6}$ alkenyl, $(CR_2)_pCO_{1-2}R$, $(CR_2)_pOR$, $(CR_2)_pR^{13}$, $(CR_2)_pNRR^{12}$, $(CR_2)_pCONRR^{12}$ or $(CR_2)_pSO_{1-2}R^{12}$;

$R^{12}$ and $R^{13}$ are independently an optionally substituted 3-7 membered saturated or partially unsaturated carbocyclic ring, or a 5-7 membered heterocyclic ring comprising N, O and/or S; aryl or heteroaryl; or $R^{12}$ is H, $C_{1-6}$ alkyl;

X is $(CR_2)_qY$, cyano, $CO_{1-2}R^{12}$, $CONR(R^{12})$, $CONR(CR_2)_pNR(R^{12})$, $CONR(CR_2)_pOR^{12}$, $CONR(CR_2)_pSR^{12}$, $CONR(CR_2)_pS(O)_{1-2}R^{12}$ or $(CR_2)_{1-6}NR(CR_2)_pOR^{12}$;

Y is an optionally substituted 3-12 membered carbocyclic ring, a 5-12 membered aryl, or a 5-12 membered heteroaryl or heterocyclic ring comprising N, O and/or S and attached to $A^2$ or $A^3$ or both via a carbon atom of said heteroaryl or heterocyclic ring when q in $(CR_2)_qY$ is 0; and n, p and q are independently 0-4.

In each of the above formula, Y or $R^{13}$ may independently be heterocyclic rings, which may be a bicyclic amine or bicyclic diamine. Examples of bicyclic amine and bicyclic diamines include but are not limited to an optionally substituted hexanemethyleneimine; heptamethyleneimine; quinuclidine; 3-azabicyclo(3,3,0)octane; 3,8-diazabicyclo[3,2,1] octane; octahydro-1H-pyrido[3,4-C]azepine; octahydropyrrolizine; 6-azabicyclo[3,2,1]octane; 3-azabicyclo[3,2,1]octane; 2,5-diazabicyclo[2,2,1]heptane; 1-azabicyclo[2,2,1]heptane; 2-azabicyclo[2,2,1]heptane; 1,4-diazabicyclo[4,4,0]decane; 1,4-diazabicyclo[4,3,0]nonane; 1-azabicyclo[3,2,1]octane; 3-azabicyclo[3,3,0]octane; 8-azabicyclo[3,2,1]octane; 3,9-diazabicyclo[4,2,1]nonane; octahydropyrrolo[3,4-C]pyrrole; octahydropyrrolo[3,4-B]pyrrole; hexahydropyrrolo[3,2-B]pyrrole; hexahydropyrrolo[3,2-C]pyrrole; 1,4-diazacyclooctane; 1,5-diazacyclooctane; 3,7-diazabicyclo[4,2,0]octane; 3,7-diazabicyclo[3,3,1] nonane; octahydropyrrolo[3,4-C]pyridine; octahydropyrrolo[3,4-B]pyridine; octahydrocyclopenta[C]pyrrolidine; hexahydrocyclopenta[C]pyrrolidine; 8-azabicyclo[3,2,1]octane; decahydroquinoline; decahydroisoquinoline; decahydropyrido[3,4-B]azepine; decahydropyrido[4,3-B]azepine; 9-azabicyclo[3,3,1]nonane; bispidine; 3-azabicyclo[3,1,0] hexane; 8-azabicyclo[3,2,1]octane; 2-azabicyclo[3.3.1] nonane; tetrahydroquinoline; tetrahydroisoquinoline; 2,5-diazabicyclo[2,2,2]octane; decahydro-2,7-naphthyridine; 1,4-diazepane; azonane; octahydro-1H-indole; octahydro-1H-isoindole; 2-azabicyclo[3,3,0]octane; 6-azabicyclo[3,2,1] octane; 7-aza-bicyclo[2.2.1]heptane; decahydropyrazino[1,2-a]azepine; 3,8-diaza-bicyclo[3,2,1]octane; 3-azabicyclo[3,2,1]octane; 3-aza-tricyclo[4,2,1,0(2,5)]nonane; 2,6-diazaspiro[3,5]nonane; 6-azabicyclo[2,1,0]hexane, etc.

In each of the above formula, any asymmetric carbon atoms may be present in the (R)-, (S)- or (R,S)-configuration. The compounds may thus be present as mixtures of isomers or as pure isomers, for example, as pure enantiomers or diastereomers. The invention further encompasses possible tautomers of the inventive compounds.

In each of the above formula, each optionally substituted moiety may be substituted with $C_{1-6}$ alkyl, $C_{2-6}$ alkenyl or $C_{3-6}$ alkynyl, each of which may be optionally halogenated or optionally having a carbon that may be replaced or substituted with N, S, O, or a combination thereof (for example, hydroxyl$C_1$-$C_8$alkyl, $C_1$-$C_8$alkoxy$C_1$-$C_8$alkyl); halo, amino, amidino, $C_{1-6}$ alkoxy; hydroxyl, methylenedioxy, carboxy; $C_{1-8}$alkylcarbonyl, $C_{1-8}$alkoxycarbonyl, carbamoyl, $C_{1-8}$ alkylcarbamoyl, sulfamoyl, cyano, oxo, nitro, or an optionally substituted carbocyclic ring, heterocyclic ring, aryl or heteroaryl as previously described.

Pharmacology and Utility

The compounds of the invention and their pharmaceutically acceptable salts exhibit valuable pharmacological properties when tested in vitro in cell-free kinase assays and in cellular assays, and are therefore useful as pharmaceuticals.

In one aspect, compounds of Formula (1), (2), (3A), (3B), (4A), (4B) or (5) may inhibit the tyrosine kinase activity of anaplastic lymphoma kinase (ALK) and the fusion protein of NPM-ALK. This protein tyrosine kinase results from a gene fusion of nucleophosmin (NPM) and ALK, rendering the protein tyrosine kinase activity of ALK ligand independent. NPM-ALK plays a key role in signal transmission in a number of hematopoetic and other human cells leading to hematological and neoplastic diseases, for example in anaplastic large-cell lymphoma (ALCL) and non-Hodgkin's lymphomas (NHL), specifically in ALK+NHL or ALKomas, in inflammatory myofibroblastic tumors (IMT) and neuroblastomas. (Duyster et al. 2001 Oncogene 20, 5623-5637). In addition to NPM-ALK, other gene fusions have been identified in human hematological and neoplastic diseases; for example, TPM3-ALK (a fusion of nonmuscle tropomyosin with ALK).

The inhibition of ALK tyrosine kinase activity may be demonstrated using known methods, for example using the recombinant kinase domain of the ALK in analogy to the VEGF-R kinase assay described in J. Wood et al. Cancer Res. 60, 2178-2189 (2000). In general, in vitro enzyme assays using GST-ALK protein tyrosine kinase are performed in 96-well plates as a filter binding assay in 20 mM Tris HCl, pH=7.5, 3 mM $MgCl_2$, 10 mM $MnCl_2$, 1 mM DTT, 0.1 µCi/assay (=30 µl) [γ-$^{33}$P]-ATP, 2 µM ATP, 3 µg/mL poly (Glu, Tyr 4:1) Poly-EY (Sigma P-0275), 1% DMSO, 25 ng ALK enzyme. Assays are incubated for 10 min at ambient temperature. Reactions are terminated by adding 50 µl of 125 mM EDTA, and the reaction mixture is transferred onto a MAIP Multiscreen plate (Millipore, Bedford, Mass., USA), previously wet with methanol, and rehydrated for 5 min with $H_2O$. Following washing (0.5% $H_3PO_4$), plates are counted in a liquid scintillation counter. $IC_{50}$ values are calculated by linear regression analysis of the percentage inhibition.

Compounds of Formula (1), (2), (3A), (3B), (4A), (4B) or (5) may potently inhibit the growth of human NPM-ALK overexpressing murine BaF3 cells (DSMZ Deutsche Sammiung von Mikroorganismen and Zellkulturen GmbH, Germany). The expression of NPM-ALK may be achieved by transfecting the BaF3 cell line with an expression vector pClneo™ (Promega Corp., Madison Wis., USA) coding for NPM-ALK and subsequent selection of G418 resistant cells. Non-transfected BaF3 cells depend on IL-3 for cell survival. In contrast, NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and may result in antiproliferative activity. The antiproliferative activity of putative inhibitors of the NPM-ALK kinase can however be overcome by addition of IL-3, which provides growth signals through an NPM-ALK independent mechanism. An analogous cell system using FLT3 kinase has also been described (see, E Weisberg et al. Cancer Cell; 1, 433-443 (2002)).

The inhibitory activity of the compounds of the invention may be determined as follows. In general, BaF3-NPM-ALK cells (15,000/microtitre plate well) are transferred to 96-well microtitre plates. Test compounds dissolved in dimethyl sulfoxide (DMSO) are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of YOPRO™ staining [T Idziorek et al. J. Immunol. Methods; 185: 249-258 (1995)]: 25 µl of lysis buffer comprising 20 mM sodium citrate, pH 4.0, 26.8 mM sodium chloride, 0.4% NP40, 20 mM EDTA and 20 mM is added to each well. Cell lysis is completed within 60 min at room temperature and total amount of YOPRO™ bound to DNA is determined by measurement using the Cytofluor II 96-well reader (PerSeptive Biosystems) with the following settings: Excitation (nm) 485/20 and Emission (nm) 530/25.

$IC_{50}$ values may be determined by a computer-aided system using the formula:

$$IC_{50}=[(ABS_{test}-ABS_{start})/(ABS_{control}-ABS_{start})]\times 100. \text{ (ABS=absorption)}$$

The $IC_{50}$ value in those experiments is given as that concentration of the test compound in question that results in a cell count that is 50% lower than that obtained using the control without inhibitor. The compounds of the invention in free form or in pharmaceutically acceptable salt form, may exhibit valuable pharmacological properties, for example, as indicated by the in vitro tests described in this application. In general, compounds of the invention have $IC_{50}$ values from 1 nM to 10 µM. In some examples, compounds of the invention have $IC_{50}$ values from 0.01 µM to 5 µM. In other examples, compounds of the invention have $IC_{50}$ values from 0.01 µM to 1 µM, or more particularly from 1 nM to 10 µM. In yet other examples, compounds of the invention have $IC_{50}$ values of less than 1 nM or more than 10 µM. The compounds of the invention may exhibit a percentage inhibition of greater than 50%, or in other embodiments, may exhibit a percentage inhibition greater than about 70%, against ALK at 10 µM.

The antiproliferative action of the inventive compounds may also be determined in the human KARPAS-299 lymphoma cell line (DSMZ Deutsche Sammiung von Mikroorganismen and Zellkulturen GmbH, Braunschweig, Germany, described in WG Dirks et al. Int. J. Cancer 100, 49-56 (2002)) using the same methodology described above for the BaF3-NPM-ALK cell line. In some embodiments, compounds of the invention may exhibit inhibitory activity with an $IC_{50}$ in the range from approximately 0.01 to 1 µM. The action of the inventive compounds on autophosphorylation of the ALK may be determined in the human KARPAS-299 lymphoma cell line by means of an immunoblot as described in WG Dirks et al. Int. J. Cancer 100, 49-56 (2002).

In another aspect, the compounds of the invention may inhibit Focal Adhesion Kinase (FAK), and may be useful as pharmaceuticals to treat conditions caused by a malfunction of signal cascades connected with FAK, such as in the treatment of particular tumors. The inhibition of endogenous FAK signaling results in reduced motility, and in some cases induces cell death. On the other hand, enhancing FAK signaling by exogenous expression increases cell motility. In addition, FAK is overexpressed in invasive and metastatic epithelial, mesenchymal, thyroid and prostate cancers. Consequently, an inhibitor of FAK is likely to be a drug for anti-tumor growth and metastasis. The compounds of the invention may thus be useful to prevent and/or treat a vertebrate and more particularly a mammal, affected by a neoplastic disease, in particular breast tumor, cancer of the bowel (colon and rectum), stomach cancer and cancer of the ovary and prostate, non-small cell lung cancer, small cell lung cancer, cancer of liver, melanoma, bladder tumor and cancer of head and neck.

The relation between FAK inhibition and immuno-system is described e.g. in G. A. van Seventer et al., Eur. J. Immunol. 2001, 31, 1417-1427. Therefore, the compounds of the invention are, for example, useful to prevent and/or treat a vertebrate and more particularly a mammal, affected by immune system disorders, diseases or disorders mediated by T lymphocytes, B lymphocytes, mast cells and/or eosinophils e.g. acute or chronic rejection of organ or tissue allo- or xenografts, atherosclerosis, vascular occlusion due to vascular injury such as angioplasty, restenosis, hypertension, heart failure, chronic obstructive pulmonary disease, CNS disease such as Alzheimer disease or amyotrophic lateral sclerosis; cancer; infectious disease such as AIDS; septic shock or adult respiratory distress syndrome, ischemia/reperfusion injury e.g. myocardial infarction, stroke, gut ischemia, renal failure or hemorrhage shock, or traumatic shock.

In yet another aspect, the compounds of the invention may inhibit zeta chain-associate protein 70 (ZAP-70). ZAP-70 protein tyrosine kinase interaction of the agents of the invention may be demonstrated, for example, by their ability to prevent phosphorylation of LAT-11 (linker for activation of T cell) by human ZAP-70 protein tyrosine kinase in aqueous solution. Therefore, the compounds of the invention may be useful for the prevention or treatment of disorders or diseases where ZAP-70 inhibition plays a role.

The compounds of the invention may also inhibit insulin like growth-factor receptor 1 (IGF-1R), and may be useful in the treatment of IGF-1R mediated diseases. Examples of IGF-1R mediated diseases include but are not limited to proliferative diseases, such as tumors, for example breast, renal, prostate, colorectal, thyroid, ovarian, pancreas, neuronal, lung, uterine and gastro intestinal tumors, as well as osteosarcomas and melanomas. The efficacy of the compounds of the invention as inhibitors of IGF-1R tyrosine kinase activity may be demonstrated using a cellular capture ELISA. In this assay, the activity of the compounds of the invention against (IGF-1)-induced autophosphorylation of the IGF-1R is determined.

The compounds of the invention may also be useful in the treatment and/or prevention of acute or chronic inflammatory diseases or disorders or autoimmune diseases e.g. rheumatoid arthritis, osteoarthritis, systemic lupus erythematosus, Hashimoto's thyroiditis, multiple sclerosis, myasthenia gravis, diabetes (type I and II) and the disorders associated therewith, respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitis, seborrhoeic dermatitis), s inflammatory eye diseases, e.g. Sjoegren's syndrome, keratoconjunctivitis or uveitis, inflammatory bowel disease, Crohn's disease or ulcerative colitis.

In accordance with the foregoing, the present invention provides:

(1) a compound of the invention for use as a pharmaceutical;

(2) a compound of the invention for use as an ALK inhibitor, FAK inhibitor, ZAP-70 inhibitor and/or IGF-1R inhibitor, for example for use in any of the particular indications hereinbefore set forth;

(3) a pharmaceutical composition, e.g. for use in any of the indications herein before set forth, comprising a compound of the invention as active ingredient together with one or more pharmaceutically acceptable diluents or carriers;

(4) a method for the treatment of any particular indication set forth hereinbefore in a subject in need thereof which comprises administering an effective amount of a compound of the invention or a pharmaceutical composition comprising same;

(5) the use of a compound of the invention for the manufacture of a medicament for the treatment or prevention of a disease or condition in which ALK, FAK, ZAP-70 and/or IGF-1R activation plays a role or is implicated;

(6) the method as defined above under (4) comprising co-administration, e.g. concomitantly or in sequence, of a therapeutically effective amount of a compound of the invention and one or more further drug substances, said further drug substance being useful in any of the particular indications set forth hereinbefore;

(7) a combination comprising a therapeutically effective amount of a compound of the invention and one or more further drug substances, said further drug substance being useful in any of the particular indications set forth hereinbefore;

(8) use of a compound of the invention for the manufacture of a medicament for the treatment or prevention of a disease which responds to inhibition of the anaplastic lymphoma kinase;

(9) the use according to (8), wherein the disease to be treated is selected from anaplastic large cell lymphoma, non-Hodgkin's lymphomas, inflammatory myofibroblastic tumors, neuroblastomas and neoplastic diseases;

(10) the use according to (8) or (9), wherein the compound is or a pharmaceutically acceptable; salt of any one of the examples;

(11) a method for the treatment of a disease which responds to inhibition of the anaplastic lymphoma kinase, especially a disease selected from anaplastic large-cell lymphoma, non Hodgkin's lymphomas, inflammatory myofibroblastic tumors, neuroblastomas and neoplastic diseases, comprising administering an effective amount of a compound of the invention or a pharmaceutically acceptable salt thereof.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.01 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 100 mg, conveniently administered, for example, in divided doses up to four times a day or in retard form. Suitable unit dosage forms for oral administration comprise from ca. 1 to 50 mg active ingredient.

Compounds of the invention may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present invention in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the invention in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length $C_8$ to $C_{12}$ from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The compounds of the invention may be administered as the sole active ingredient, or together with other drugs useful against neoplastic diseases or useful in immunomodulating regimens. For example, the compounds of the invention may be used in accordance with the invention in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, I CD40, CD45, CD58, CD80, CD86, CD152, CD137, CD154, ICOS, LFA-1, VLA-4 or their ligands, or other immunomodulatory compounds, e.g. CTLA41 g.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

Processes for Making Compounds of the Invention

Compounds of Formula (1) may be prepared following Reaction Scheme I, in which each substituent is as defined in the Summary of the Invention:

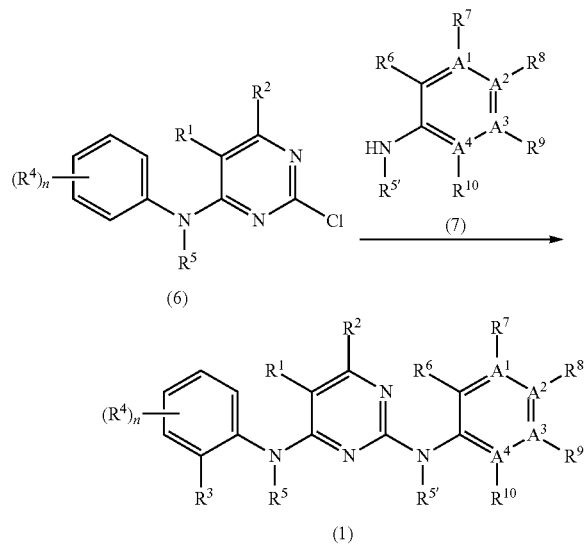

Reaction Scheme I

A compound of Formula (1) may be synthesized by reacting a compound of formula (6) with a compound of formula (7) in the presence of palladium catalyst (for example palladium acetate and the like), ligand (for example xantphos and the like) and base (for example cesium carbonate and the like) in a suitable solvent (for example, THF, and the like). The reaction proceeds in a temperature range of about 70° C. to about 180° C. and can take 10 min. to 8 hours to complete.

Alternatively, a compound of Formula (1) may be synthesized by reacting a compound of formula (6) with a compound of formula (7) in the presence of acid (for example HCl, TsOH and the like), in a suitable solvent (for example, 2-propanol, and the like). The reaction proceeds in a temperature range of about 70° C. to about 150° C. and can take up to 12 hours to complete.

Additional Processes for Making Compounds of the Invention

The compounds of the invention, including their salts, are also obtainable in the form of hydrates, or their crystals may include for example the solvent used for crystallization (present as solvates). Salts can usually be converted to compounds in free form, e.g., by treating with suitable basic agents, for example with alkali metal carbonates, alkali metal hydrogen carbonates, or alkali metal hydroxides, such as potassium carbonate or sodium hydroxide. In view of the close relationship between the novel compounds in free form and those in the form of their salts, including those salts that may be used as intermediates, for example in the purification or identification of the novel compounds, any reference to the free compounds hereinbefore and hereinafter is to be understood as referring also to the corresponding salts, as appropriate.

Salts of the inventive compounds with a salt-forming group may be prepared in a manner known per se. Acid addition salts of compounds of Formula (1), (2), (3A), (3B), (4A), (4B) or (5) may thus be obtained by treatment with an acid or with a suitable anion exchange reagent. Pharmaceutically acceptable salts of the compounds of the invention may be formed, for example, as acid addition salts, with organic or inorganic acids, from compounds of Formula (1), (2), (3A), (3B), (4A), (4B) or (5) with a basic nitrogen atom.

Suitable inorganic acids include, but are not limited to, halogen acids, such as hydrochloric acid, sulfuric acid, or phosphoric acid. Suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4 methylbenzenesulfonic acid, methylsulfuric acid, ethylsulfuric acid, dodecylsulfuric acid, N cyclohexylsulfamic acid, N-methyl-, N-ethyl- or N-propyl-sulfamic acid, or other organic protonic acids, such as ascorbic acid.

For isolation or purification purposes, it is also possible to use pharmaceutically unacceptable salts, for example picrates or perchlorates. For therapeutic use, only pharmaceutically acceptable salts or free compounds are employed (where applicable in the form of pharmaceutical preparations).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal may be found in T. W. Greene, "Protecting Groups in Organic Chemistry", 3$^{rd}$ edition, John Wiley and Sons, Inc., 1999.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubilities, reactivity, etc.) and may be readily separated by taking advantage of these dissimilarities. The diastereomers may be separated by fractionated crystallization, chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In summary, the compounds of the invention may be made by a process, which involves:
- (a) that of Reaction Scheme I; and
- (b) optionally converting a compound of the invention into a pharmaceutically acceptable salt;
- (c) optionally converting a salt form of a compound of the invention to a non-salt form;
- (d) optionally converting an unoxidized form of a compound of the invention into a pharmaceutically acceptable N-oxide;
- (e) optionally converting an N-oxide form of a compound of the invention to its unoxidized form;
- (f) optionally resolving an individual isomer of a compound of the invention from a mixture of isomers;
- (g) optionally converting a non-derivatized compound of the invention into a pharmaceutically acceptable prodrug derivative; and
- (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter. One of skill in the art will appreciate that the above transformations are only representative of methods for preparation of the compounds of the present invention, and that other well known methods can similarly be used. The present invention is further exemplified, but not limited, by the following and Examples that illustrate the preparation of the compounds of the invention.

Preparation of Intermediates

Intermediate 1

2-chloro-N-(2-(iso-propylsulfonyl)phenyl)-5-methylpyrimidin-4-amine

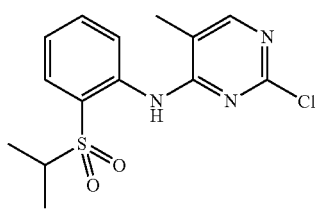 [SMILES: Cc1cnc(Cl)nc1Nc1ccccc1S(=O)(=O)C(C)C]

To a suspension of 730 mg of NaH in a mixture of DMF/DMSO (25/2.5 ml) is added drop-wise at 0° C., 2.53 g (12.69 mmol) of 2-(iso-propylsulfonyl)benzenamine in DMF/DMSO (10 ml, ratio 9/1). The solution is stirred 30 minutes at 0° C. and 4.11 g (25.3 mmol, 2 eq.) of 2,4-dichloro-5-methylpyrimidine diluted in 10 ml of DMF/DMSO (ratio: 9/1) is added dropwise. The solution is warmed-up to room temperature and stirred overnight. After work-up, the crude product is directly crystallized from cold $CH_3CN$ in several batches to afford 2-chloro-N-(2-(iso-propylsulfonyl)phenyl)-5-methylpyrimidin-4-amine as pale creamy colored crystals: ESMS m/z 326.1 (M+H$^+$).

Intermediate 2

Synthesis of 2,5-dichloro-N-(2-(iso-propylsulfonyl)phenyl)pyrimidin-4-amine

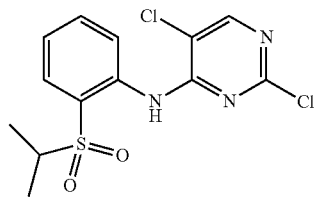 [SMILES: CC(C)S(=O)(=O)c1ccccc1Nc1nc(Cl)ncc1Cl]

Using the same procedure described for the synthesis of 2-chloro-N-(2-(iso-propylsulfonyl)phenyl)-5-methylpyrimidin-4-amine, 2,5-dichloro-N-(2-(iso-propylsulfonyl)phenyl)pyrimidin-4-amine is isolated as a creamy colored solid: ESMS m/z 346.0 (M+H$^+$).

Intermediate 3

2-chloro-4-fluoro-5-nitrotoluene

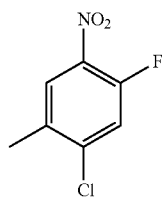

To a solution of 100 g (0.7 mol) of 2-chloro-4-fluorotoluene in 250 ml of concentrated $H_2SO_4$ is added portion-wise 85 g (0.875 mol) of $KNO_3$ at 0° C. (addition of the whole amount of $KNO_3$ is finished in about 1 hour). The reddish mixture is slowly warmed-up at room temperature overnight and quenched over crushed ice and extracted with EtOAc. The organic layers are combined, dried over $MgSO_4$ and concentrated. The crude oil is then purified over a large silica plug (eluent: 97/3 hexanes/EtOAc) to afford 2-chloro-4-fluoro-5-nitrotoluene as a pale yellow oil that solidifies upon standing. ¹H NMR (CDCl₃, 400 Mz): 7.97 (d, J=8.0 Hz, 1H), 7.32 (d, J=10.4 Hz, 1H), 2.43 (s, 3H).

Intermediate 4

2-chloro-4-isopropoxy-5-nitrotoluene

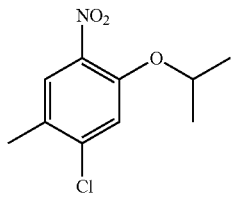

To a solution of 25 g (0.131 mol) of 2-chloro-4-fluoro-5-nitrotoluene in 250 ml of 2-propanol is added 208 g (0.659 mol, 5 eq.) of Cs₂CO₃. The mixture is stirred at 60° C. overnight and most of the 2-propanol is evaporated under reduced pressure. Water is added and the solution is extracted with EtOAc. The organic layers are combined, dried over MgSO₄, concentrated and the crude product filtrated over a silica plug (eluent: 95/5 hexanes/EtOAc) to afford 2-chloro-4-isopropoxy-5-nitrotoluene as a pale yellow fluffy solid.

Intermediate 5

2-methyl-4-nitro-5-isopropoxy-phenylboronic acid pinacol ester

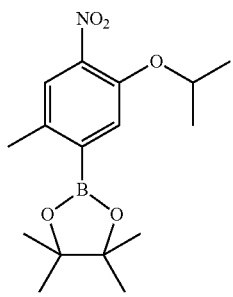 [SMILES: Cc1cc([N+](=O)[O-])c(OC(C)C)cc1B1OC(C)(C)C(C)(C)O1]

A mixture of 5.09 g 2-chloro-4-isopropoxy-5-nitrotoluene (0.02216 mol), 6.20 g (0.02437 mol) of pinacol diborane, 595 mg (0.00212 mol) of PCy₃, 1.014 g (0.00108 mol) of Pd₂dba₃ and 3.16 g (0.0322 mol) of KOAc in 100 ml of dry dioxane is heated to 100° C. overnight. After cooling to RT, the dark solution is filtered over Celite and the solvent evaporated under reduced pressure. The crude oil is purified with silica gel column chromatography (eluent: 95/5 hexanes/EtOAc) to afford 2-methyl-4-nitro-5-isopropoxy-phenylboronic acid pinacol ester as an oil that solidifies upon standing. ¹H NMR (CDCl₃, 400 Mz): 7.51 (s, 1H), 7.44 (s, 1H), 4.70 (m, 1H), 2.48 (s, 3H), 1.36 (d, J=7.6 Hz, 6H), 1.35 (s, 12H).

Intermediate 6

4-Trifluoromethanesulfonyloxy-3,6-dihydro-2H-pyridine-1-carboxylic acid tert-butyl ester

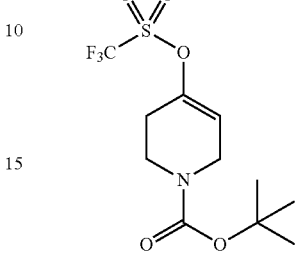

A solution of N-tert-Butoxycarbonyl-4-piperidone (10.17 g, 0.05 mol) in THF (100 mL) is added dropwise into a cooled (−78° C.), vigorously stirring solution of LDA (40 mL of 1.5 M solution in cyclohexanes, 0.06 mol) in THF (100 mL), under N₂. The reaction mixture is left at −78° C. for 30 min before adding a solution of phenyl trifluorosulfonimide (19.85 g, 0.055 mol) in THF (50 mL). Then the reaction mixture is warmed to room temperature and stirred for 3 h. The reaction is quenched at 0° C. with 100 mL of saturated aqueous NH₄Cl and filtered through Celite. The filtrate is added to 100 mL of EtOAc and the layers are separated. The organic layer is washed with H₂O, dried over MgSO₄ and concentrated. The crude product is purified by silica flash column chromatography (0-30% EtOAc in Hexanes as eluent and checked by TLC stained with 2% of KMnO₄ in EtOH) to afford 4-Trifluoromethanesulfonyloxy-3,6-dihydro-2H-pyridine-1-carboxylic acid tert-butyl ester as a yellow oil.

Intermediate 7

4-(5-Isopropoxy-2-methyl-4-nitro-phenyl)-3,6-dihydro-2H-pyridine-1-carboxylic acid tert-butyl ester

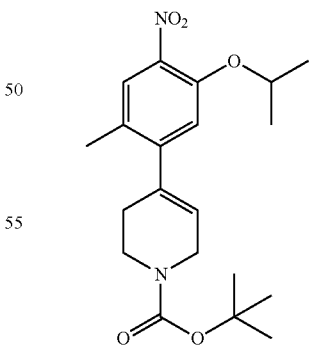

To a solution of 2-methyl-4-nitro-5-isopropoxy-phenylboronic acid pinacol ester (2.04 g, 6.4 mmol) and 4-Trifluoromethanesulfonyloxy-3,6-dihydro-2H-pyridine-1-carboxylic acid tert-butyl ester (3.2 g, 9.6 mmol) in 110 mL of DME/H₂O (10:1 V/V) is added Pd(PPh₃)₄ (365 mg, 0.32 mmol) and Cs₂CO₃ (4.2 g, 12.8 mmol). The reaction mixture is heated under N₂ at 80° C. overnight. After cooling to room temperature, the reaction is filtered through Celite and the filtrate is diluted with 100 mL of EtOAc, sequentially washed with H₂O, brine, and finally concentrated in vacuo. The crude product is purified by silica gel flash chromatography (5%-15% EtOAc in Hexanes as eluent) to afford 4-(5-Isopropoxy-2-methyl-4-nitro-phenyl)-3,6-dihydro-2H-pyridine-1-carboxylic acid tert-butyl ester as a yellow oil. ¹H NMR (CD₃OD, 400 Mz): 7.59 (s, 1H), 6.96 (s, 1H), 5.67 (broad s, 1H), 4.73 (m, 1H), 4.06 (m, 2H), 3.65 (m, 2H), 2.37 (m, 2H), 2.25 (s, 3H), 1.50 (s, 9H), 1.33 (d, J=6.0 Hz, 6H).

Intermediate 8

2-Chloro-4-isopropoxy-5-nitro-benzoic acid

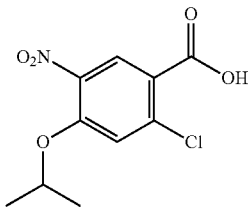 [SMILES: CC(C)Oc1cc(Cl)c(C(=O)O)cc1[N+](=O)[O-]]

A mixture of 2-chloro-4-fluoro-5-nitro-benzoic acid (5.0 g, 22.8 mmol) and cesium carbonate (29.7 g, 91.1 mmol) in 2-propanol (100 mL) is heated at 50° C. overnight. The solvent is removed in vacuo and 100 mL of water is added. Concentrated aqueous HCl is added dropwise to this solution at 0° C. until pH=2. The product precipitate which forms is isolated by filtration, washed by water and dried under vacuum to give 2-chloro-4-isopropoxy-5-nitro-benzoic acid.

Example 1

6-{5-Chloro-4-[2-(propane-2-sulfonyl)-phenylamino]-pyrimidin-2-ylamino}-5-isopropoxy-2-piperidin-4-yl-2,3-dihydro-isoindol-1-one (178)

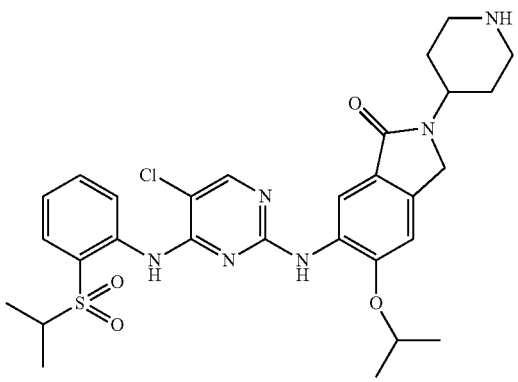 [SMILES: CC(C)Oc1cc2c(cc1Nc1ncc(Cl)c(Nc3ccccc3S(=O)(=O)C(C)C)n1)C(=O)N(C1CCNCC1)C2]

Steps 1 and 2: 4-(2-Chloro-4-isopropoxy-5-nitrobenzoylamino)-piperidine-1-carboxylic acid tert butyl ester

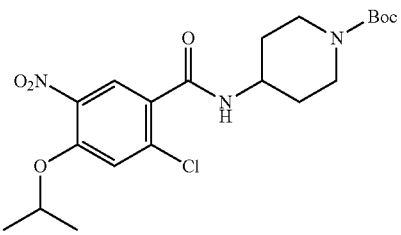 [SMILES: CC(C)Oc1cc(Cl)c(C(=O)NC2CCN(C(=O)OC(C)(C)C)CC2)cc1[N+](=O)[O-]]

To a solution of 2-chloro-4-isopropoxy-5-nitro-benzoic acid (Intermediate 8, 10 g, 38.5 mmol) in DCM (200 mL) and DMF (1 mL), is slowly added thionyl chloride (9.17 g, 77 mmol) via a syringe. The mixture is stirred for 3 hours, and is then concentrated to dryness. The obtained white solid, 2-chloro-4-isopropoxy-5-nitro-benzoyl chloride, is dried under vacuum. To a mixture of 4-amino-piperidine-1-carboxylic acid tert-butyl ester (1.44 g, 7.2 mmol) and triethylamine (3 mL, 21.6 mmol) in DCM (100 mL), is slowly added 2-chloro-4-isopropoxy-5-nitro-benzoyl chloride (2 g, 7.2 mmol) dissolved in DCM (10 mL) via syringe. The mixture is stirred at room temperature for 3 hours, and then is concentrated. The obtained solid is dissolved in ethyl acetate and is washed with water and brine respectively. After evaporation of the solvent, the title compound is obtained as light yellow solid, and is directly used for the next step without further purification.

Step 3: 4-(4-Isopropoxy-5-nitro-2-vinyl-benzoylamino)-piperidine-1-carboxylic acid tert-butyl ester

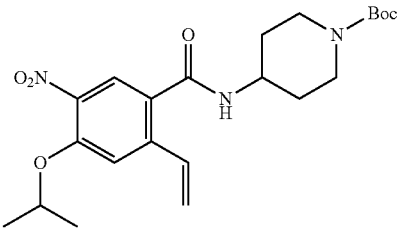 [SMILES: C=Cc1cc(OC(C)C)c([N+](=O)[O-])cc1C(=O)NC1CCN(C(=O)OC(C)(C)C)CC1]

To a mixture of 4-(2-chloro-4-isopropoxy-5-nitro-benzoylamino)-piperidine-1-carboxylic acid tert-butyl ester (7.2 mmol) obtained in the previous step, vinylboronic acid dibutyl ester (1.72 g, 9.4 mmol) and sodium carbonate (5.34 g, 50.4 mmol) in THF/H₂O (100/25 mL) is added dichlorobis(triphenylphosphine) palladium (II) (442 mg, 5% mmol). The mixture is purged with N₂ for 3 min and heated at 90° C. under N₂ for overnight in a round bottom flask equipped with a condenser. The mixture is cooled to room temperature and poured into saturated aqueous ammonia chloride solution. The mixture is extracted with ethyl acetate (3×100 mL). The organic extracts are combined, washed with brine and concentrated. The crude product is purified with silica gel column chromatography (40% ethyl acetate in hexanes) to afford 4-(4-isopropoxy-5-nitro-2-vinyl-benzoylamino)-piperidine-1-carboxylic acid tert-butyl ester as white solid.

Steps 4, 5 and 6: 4-(5-Isopropoxy-6-nitro-1-oxo-1,3-dihydro-isoindol-2-yl)-piperidine-1-carboxylic acid tert-butyl ester

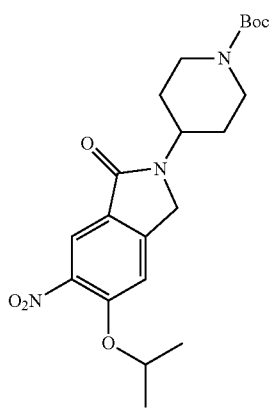 [SMILES: CC(C)Oc1cc2c(cc1[N+](=O)[O-])C(=O)N(C1CCN(C(=O)OC(C)(C)C)CC1)C2]

4-(4-Isopropoxy-5-nitro-2-vinyl-benzoylamino)-piperidine-1-carboxylic acid tert-butyl ester obtained from previous step (1.9 g, 4.38 mmol) is dissolved in DCM (100 mL) and is cooled to −78° C. $O_3$ (g) is bubbled into the solution until the solution's color turns blue/gray. The solution is then purged with $N_2$ (g) until the blue color disappears. The solution is warmed to room temperature and treated with triphenyl phosphine resin (5 g) pre-swelled in DCM (100 mL). After 30 min, the mixture is filtered, the filtrate is concentrated, and the resulting residue dissolved in DCM/TFA (100 mL/25 mL). To this mixture is added triethyl silane (4.6 mL, 17.5 mmol). The resulting mixture is stirred at room temperature overnight. The reaction mixture is concentrated and re-dissolved in DCM. The DCM solution is washed with 1N aqueous HCl (3×20 mL). The combined aqueous layer is treated with conc. aqueous NaOH until pH=12. The aqueous layer is extracted with ethyl acetate (3×30 mL). The combined organic layers are washed with brine, and dried over sodium sulfate. A light yellow solid is obtained after evaporation of the organic solvent.

The solid is dissolved in a mixture of methanol and triethylamine (100 mL, 9:1 v/v). To this mixture is added di-tert-butyl dicarbonate (680 mg, 3.1 mmol). After stirring at 50° C. for 30 minutes, the mixture is concentrated and purified by silica gel flash column chromatography (eluent: 40-50% ethyl acetate in hexanes) to afford 4-(5-Isopropoxy-6-nitro-1-oxo-1,3-dihydro-isoindol-2-yl)-piperidine-1-carboxylic acid tert-butyl ester as a white solid. $^1$H NMR (400 MHz, CDCl$_3$) δ 8.19 (s, 1H), 7.11 (s, 1H), 4.74 (q, 1H), 4.45-4.38 (m, 1H), 4.35 (s, 2H), 2.90-2.80 (m, 2H), 1.85-1.81 (m, 2H), 1.66-1.63 (m, 2H), 1.48 (s, 9H), 1.42 (d, 6H).

Steps 7, 8 and 9

To a solution of 4-(5-isopropoxy-6-nitro-1-oxo-1,3-dihydro-isoindol-2-yl)-piperidine-1-carboxylic acid tert-butyl ester from the previous step (850 mg, 2 mmol) in methanol, is added Pd/C (10% on carbon, 100 mg). The mixture is hydrogenated under 1 atm of hydrogen gas. After 4 hours, the mixture is filtered and concentrated. The obtained aniline, as yellow solid, is used for next step without additional purification. To a mixture of the crude product (2 mmol) from previous step, (2,5-dichloro-pyrimidin-4-yl)-[2-(propane-2-sulfonyl)-phenyl]-amine (Intermediate 2, 770 mg, 2.2 mmol), cesium carbonate (1.3 g, 4 mmol), and xantphos (115 mg, 0.2 mmol) in THF (20 mL), is added palladium acetate (22 mg, 5% mmol) in a microwave tube. The mixture is purged with $N_2$ for 3 min. The sealed tube is heated at 150° C. for 20 min under microwave irradiation. The mixture is cooled, filtered and concentrated. The residue is purified by silica gel flash column chromatography (eluent: 65% ethyl acetate in hexanes) to afford a yellow solid. The solid is treated with DCM/TFA (1/1, 10 mL) for 1 hour followed by concentration under vacuum. Final purification using preparative RP LC-MS affords 6-{5-Chloro-4-[2-(propane-2-sulfonyl)-phenylamino]-pyrimidin-2-ylamino}-5-isopropoxy-2-piperidin-4-yl-2,3-dihydro-isoindol-1-one (178) as a white solid. $^1$H NMR (400 MHz, CDCl$_3$) δ 10.38 (s, 1H), 10.13 (s, 1H), 9.60-9.50 (br, 1H), 9.34-9.21 (br, 1H), 8.46 (d, 1H), 8.26 (s, 1H), 8.08 (s, 1H), 7.91 (dd, 1H), 7.71 (m, 1H), 7.34 (t, 1H), 7.03 (s, 1H), 4.30 (m, 1H), 4.53 (m, 1H), 4.33 (s, 2H), 3.62 (m, 2H), 3.21-3.09 (m, 3H), 2.31-2.21 (m, 2H), 2.09-2.05 (m, 2H), 1.41 (d, 6H), 2.30 (d, 6H); ESMS m/z 599.2 (M+H$^+$).

Example 2

6-{5-Chloro-4-[2-(propane-2-sulfonyl)-phenylamino]-pyrimidin-2-ylamino}-5-isopropoxy-2-(1-methyl-piperidin-4-yl)-2,3-dihydro-isoindol-1-one (181)

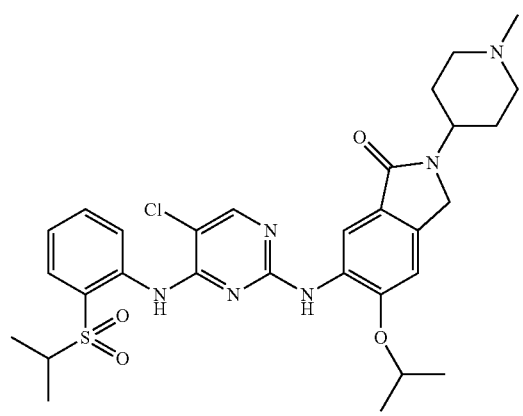 [SMILES: CC(C)Oc1cc2c(cc1Nc1ncc(Cl)c(Nc3ccccc3S(=O)(=O)C(C)C)n1)C(=O)N(C1CCN(C)CC1)C2]

Step 1: 5-Isopropoxy-2-(1-methyl-piperidin-4-yl)-6-nitro-indan-1-one

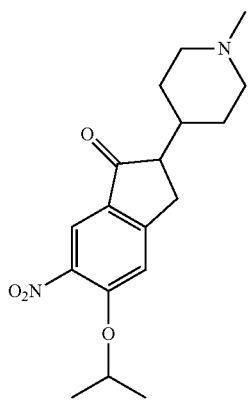 [SMILES: CC(C)Oc1cc2c(cc1[N+](=O)[O-])C(=O)C(C1CCN(C)CC1)C2]

To a solution of 5-isopropoxy-6-nitro-2-piperidin-4-yl-indan-1-one (Example 1, Step 5) in THF (5 mL) and methanol (5 mL) is added formaldehyde (104.2 uL, 1.39 mmol) and 10 drops of AcOH sequentially. The reaction mixture is stirred at room temperature for 1 h, then sodium cyanoborohydride (175.1 mg, 2.78 mmol) is added in one portion, and the reaction is stirred for an additional 30 min. The reaction is quenched by saturated aqueous $NH_4Cl$ and concentrated in vacuo to give an oily residue. This oil is partitioned between EtOAc and brine, the organic extract is dried over $Na_2SO_4$, filtered and concentrated under vacuum. Silica gel chromatography (5% MeOH in DCM) affords 5-isopropoxy-2-(1-methyl-piperidin-4-yl)-6-nitro-indan-1-one; MS m/z 333.2 (M+1).

Steps 2 and 3

Following the procedures previously described (Example 1, Steps 7 and 8) using the product from Step 1 generates the title compound 6-{5-Chloro-4-[2-(propane-2-sulfonyl)-phenylamino]-pyrimidin-2-ylamino}-5-isopropoxy-2-(1-methyl-piperidin-4-yl)-2,3-dihydro-isoindol-1-one (181) as a white solid. $^1H$ NMR 400 MHz (DMSO-$d_6$ with trace $D_2O$) δ 8.46 (d, 1H), 8.35 (s, 1H), 8.09 (s, 1H), 7.82 (d, 1H), 7.74 (t, 1H), 7.36 (t, 1H), 7.33 (s, 1H), 4.75 (m, 1H), 4.41 (s, 2H), 4.29 (m, 1H), 3.65 (m, 2H), 3.44 (m, 1H), 3.17 (t, 2H), 2.79 (s, 3H), 2.07 (m, 2H), 1.98 (d, 2H), 1.28 (d, 6H), 1.14 (d, 6H); MS m/z 613 (M+1).

Example 3

5-Methyl-$N^2$-[4-methyl-5-(1-methyl-1H-pyrazol-4-yl)-2-(piperidin-4-yloxy)-phenyl]-$N^4$-[2-(propane-2-sulfonyl)-phenyl]-pyrimidine-2,4-diamine (35)

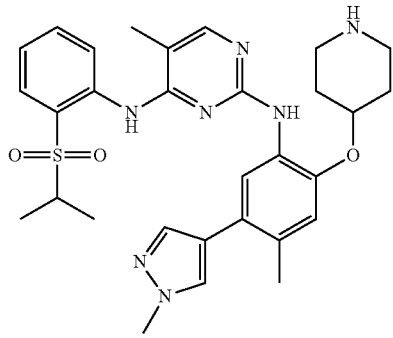 [SMILES: Cc1cc(OC2CCNCC2)c(Nc2ncc(C)c(Nc3ccccc3S(=O)(=O)C(C)C)n2)cc1-c1cnn(C)c1]

Step 1: 4-(4-Chloro-5-methyl-2-nitro-phenoxy)-piperidine-1-carboxylic acid tert-butyl ester

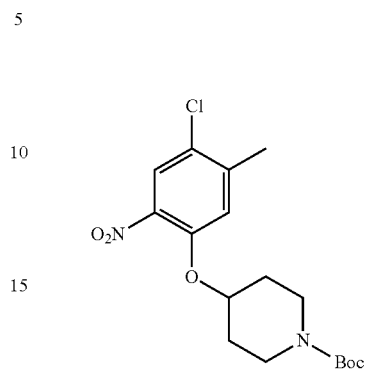

To a mixture of 4-Chloro-5-methyl-2-nitro-phenol (3.752 g, 20.0 mmol), 4-Hydroxy-piperidine-1-carboxylic acid tert-butyl ester (4.83 g, 24 mmol), and triphenylphosphine (6.23 g, 24 mmol) in 75 mL THF is added diisopropyl asodicarboxylate (4.73 mL, 245 mmol) in several portions at 22° C. for 1 h. The reaction is stirred at the same temperature for an additional 2 hrs. The reaction mixture is concentrated in vacuo. The residue is taken up in 50 mL ether, and let stand at 22° C. for 14 hrs. The resulting crystals are removed by filtration. The filtrate is concentrated in vacuo, and the residue is purified over a 330 g $SiO_2$ column (ISCO) using a gradient of 20 to 40% ethyl acetate in hexanes as eluent, affording 4-(4-Chloro-5-methyl-2-nitro-phenoxy)-piperidine-1-carboxylic acid tert-butyl ester as dark yellow viscous oil. MS (ES+); 315.1 (MH+−$C_4H_8$), 393.1 (MNa+).

Step 2: 4-[5-Methyl-4-(1-methyl-1H-pyrazol-4-yl)-2-nitro-phenoxy]-piperidine-1-carboxylic acid tert-butyl ester

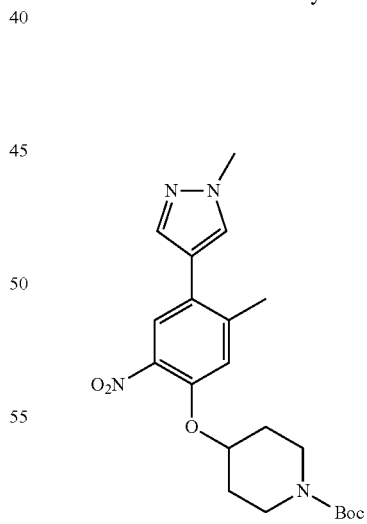

A mixture of 4-(4-Chloro-5-methyl-2-nitro-phenoxy)-piperidine-1-carboxylic acid tert-butyl ester from the previous step (375.8 mg, 1.01 mmol), 1-Methyl-4-(4,4,5,5-tetramethyl-[1,3,2]dioxaborolan-2-yl)-1H-pyrazole (Boron Molecular, 224.4 mg 1.08 mmol), potassium phosphate tribasic monohydrate (392 mg), $Pd_2(dba)_3$ (45 mg), and dicyclophosphinobiphenyl (43 mg) in 4 mL of 1,4-dioxane/$H_2O$ (3/1) is heated in a sealed tube at 150° C. for 20 min under microwave radiation. The reaction mixture is filtered through a small plug of Celite, dried over Na$_2$SO$_4$ and concentrated. The residue is purified using a SiO$_2$ column (ISCO), affording 4-[5-Methyl-4-(1-methyl-1H-pyrazol-4-yl)-2-nitro-phenoxy]-piperidine-1-carboxylic acid tert-butyl ester. MS (ES+); 417.3 (MH+), 439.2 (MNa+).

Steps 3, 4 and 5

Utilizing the same procedures described in the synthesis of Example 1 (Steps 7, 8 and 9) and final purification using preparative RP LC-MS affords 5-Methyl-N$^2$-[4-methyl-5-(1-methyl-1-pyrazol-4-yl)-2-(piperidin-4-yloxy)-phenyl]-N$^4$-[2-(propane-2-sulfonyl)-phenyl]-pyrimidine-2,4-diamine (35). MS (ES+): 576.3 (MH+).

Example 4

1-(5-{5-Chloro-4-[2-(propane-2-sulfonyl)-phenylamino]-pyrimidin-2-ylamino}-4-isopropoxy-2-methyl-phenyl)-ethanone (36)

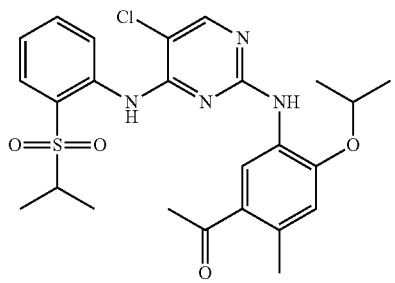 [SMILES: CC(=O)c1cc(Nc2ncc(Cl)c(Nc3ccccc3S(=O)(=O)C(C)C)n2)c(OC(C)C)cc1C]

Step 1: 2-(4-Isopropoxy-2-methyl-5-nitro-phenyl)-2-methyl-[1,3]dioxolane

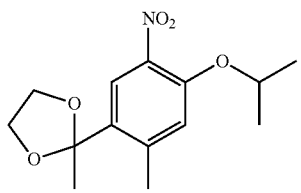 [SMILES: Cc1cc(OC(C)C)c([N+](=O)[O-])cc1C1(C)OCCO1]

A mixture of 1-(4-Isopropoxy-2-methyl-5-nitro-phenyl)-ethanone (0.788 g, 3.32 mmol), ethyleneglycol (1.8 mL), and p-toluenesulfonic acid monohydrate (6.3 mg) in 60 mL of benzene is heated at reflux with a Dean-Stark trap for 18 hrs. The reaction mixture is diluted with 100 mL of ethyl acetate and successively washed with 100 mL each of aqueous saturated NaHCO$_3$, H$_2$O, and saturated brine. The organic phase is dried over anhydrous Na$_2$SO$_4$, filtered and concentrated in vacuo, affording 2-(4-Isopropoxy-2-methyl-5-nitro-phenyl)-2-methyl-[1,3]dioxolane as yellow crystals. MS (ES+): 282.2 (MH+).

Steps 2 and 3: 5-Chloro-N2-[2-isopropoxy-4-methyl-5-(2-methyl-[1,3]dioxolan-2-yl)-phenyl]-N4-[2-(propane-2-sulfonyl)-phenyl]-pyrimidine-2,4-diamine

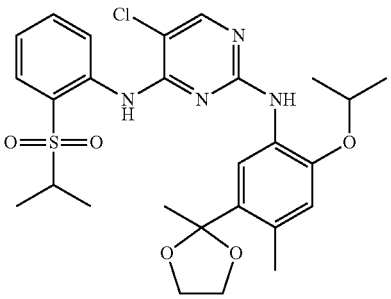 [SMILES: Cc1cc(OC(C)C)c(Nc2ncc(Cl)c(Nc3ccccc3S(=O)(=O)C(C)C)n2)cc1C1(C)OCCO1]

Utilizing the same procedures described in the synthesis of Example 1 (Steps 7 and 8), using 2-(4-Isopropoxy-2-methyl-5-nitro-phenyl)-2-methyl-[1,3]dioxolane from the previous step as starting material and purification using silica gel chromatography (gradient 2% to 20% EtOAc in hexanes) affords 5-Chloro-N2-[2-isopropoxy-4-methyl-5-(2-methyl-[1,3]dioxolan-2-yl)-phenyl]-N4-[2-(propane-2-sulfonyl)-phenyl]-pyrimidine-2,4-diamine as a white solid. MS (ES+): 561.2 (MH+).

Step 4

A solution of 5-Chloro-N2-[2-isopropoxy-4-methyl-5-(2-methyl-[1,3]dioxolan-2-yl)-phenyl]-N4-[2-(propane-2-sulfonyl)-phenyl]-pyrimidine-2,4-diamine from the previous step (84 mg, 0.15 mmol) in 5 mL 1,4-dioxane is treated with 1 mL of aqueous 1N HCl at 22° C. for 2 hrs. The reaction is worked up and affords 1-(5-{5-Chloro-4-[2-(propane-2-sulfonyl)-phenylamino]-pyrimidin-2-ylamino}-4-isopropoxy-2-methyl-phenyl)-ethanone (36). MS (ES+): 517.2 (MH+).

Example 5

N$^2$-{2-Isopropoxy-4-methyl-5-[1-(2-morpholin-4-yl-ethyl)-1H-pyrazol-4-yl]-phenyl}-5-methyl-N$^4$-[2-(propane-2-sulfonyl)-phenyl]-pyrimidine-2,4-diamine (37)

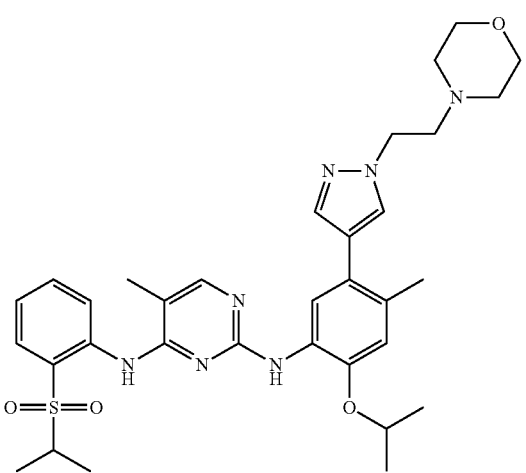 [SMILES: Cc1cc(OC(C)C)c(Nc2ncc(C)c(Nc3ccccc3S(=O)(=O)C(C)C)n2)cc1-c1cnn(CCN2CCOCC2)c1]

Step 1: 4-Bromo-5-methyl-2-nitro-phenol

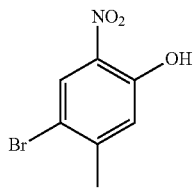

4-Bromo-3-methyl-phenol (1.122 g, 6.00 mmol) and Yb(CF₃SO₃)₃ (372 mg) in 30 mL dichloromethane is treated with 0.38 mL of conc. HNO₃ at 22° C. After stirring at the same temperature for 1 hr, an additional 0.1 mL of conc. HNO₃ is added, and the reaction is stirred for an additional hour. The reaction mixture is washed with H₂O, dried over anhydrous magnesium sulfate, filtered and concentrated. The residue is purified using a SiO₂ column (ISCO), affording a mixture of 4-Bromo-5-methyl-2-nitro-phenol as yellow crystals and its regioisomer by-product as orange crystals.

Step 2: 1-Bromo-4-isopropoxy-2-methyl-5-nitro-benzene

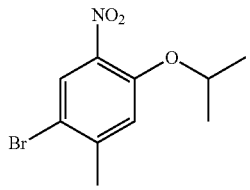

To a mixture of 4-Bromo-5-methyl-2-nitro-phenol from the previous step (0.66 g, 2.84 mmol), 2-propanol (0.262 mL), and triphenylphosphine (894 mg) in 10 mL THF is added diisopropyl asodicarboxylate (0.671 mL) at 22° C. The reaction mixture is concentrated in vacuo. The residue is purified using a SiO₂ column (ISCO), affording 1-Bromo-4-isopropoxy-2-methyl-5-nitro-benzene as a bright yellow solid.

Step 3: 5-Bromo-2-isopropoxy-4-methyl-phenylamine

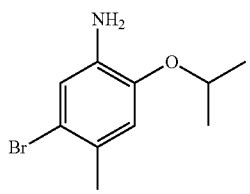

To 1-Bromo-4-isopropoxy-2-methyl-5-nitro-benzene from the previous step (0.734 g, 2.68 mmol) and iron (powder, 325 mesh, 1.05 g) in 20 mL ethanol is added 1 mL of 1N aqueous HCl with cooling in an ice bath. Following this addition, the reaction is heated at reflux for 2 hrs. Then an additional 0.5 g of iron is added and the reaction is heated at reflux for an additional 2 hrs. The reaction mixture is cooled down and filtered though a pad of Celite. The filtrate is concentrated in vacuo, affording 5-Bromo-2-isopropoxy-4-methyl-phenylamine as an orange oil. The product is used for the next step without further purification.

Step 4: N2-(5-Bromo-2-isopropoxy-4-methyl-phenyl)-5-methyl-N4-[2-(propane-2-sulfonyl)-phenyl]-pyrimidine-2,4-diamine

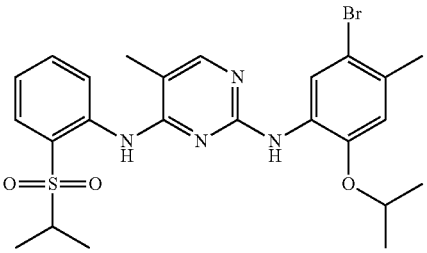 [SMILES: Cc1cc(OC(C)C)c(Nc2ncc(C)c(Nc3ccccc3S(=O)(=O)C(C)C)n2)cc1Br]

5-Bromo-2-isopropoxy-4-methyl-phenylamine from the previous step (537 mg, 2.20 mmol) and 2-chloro-N-(2-(isopropylsulfonyl)phenyl)-5-methylpyrimidin-4-amine (Intermediate 1, 652 mg, 2.00 mmol) in the presence of methanesulfonic acid (0.143 mL) in 4 mL 2-propanol are condensed at 140° C. for 30 min in a sealed tube under microwave irradiation. Following workup, N2-(5-Bromo-2-isopropoxy-4-methyl-phenyl)-5-methyl-N4-[2-(propane-2-sulfonyl)-phenyl]-pyrimidine-2,4-diamine is obtained. MS (ES+): 535.1 (MH+).

Step 5

A mixture of N2-(5-Bromo-2-isopropoxy-4-methyl-phenyl)-5-methyl-N4-[2-(propane-2-sulfonyl)-phenyl]pyrimidine-2,4-diamine from the previous step (53 mg, 0.099 mmol), 4-{2-[4-(4,4,5,5-Tetramethyl-[1,3,2]dioxaborolan-2-yl)-pyrazol-1-yl]-ethyl}-morpholine (Boron Molecular, 61 mg 0.20 mmol), K₃PO₄ (58 mg), Pd₂(dba)₃ (10 mg), and tricyclohexylphosphine (8 mg) in 1 mL of 1,4-dioxane/H2O (3/1 v/v) is heated in a sealed tube at 150° C. for 20 min under microwave radiation. The reaction mixture is filtered through a small plug of Celite and concentrated. Final purification using preparative RP LC-MS affords N2-{2-Isopropoxy-4-methyl-5-[1-(2-morpholin-4-yl-ethyl)-1H-pyrazol-4-yl]-phenyl}-5-methyl-N4-[2-(propane-2-sulfonyl)-phenyl]-pyrimidine-2,4-diamine (37). MS (ES+): 634.3 (MH+).

Example 6

5-Chloro-N2-(2-isopropoxy-5-methyl-4-morpholin-4-ylmethyl-phenyl)-N4-[2-(propane-2-sulfonyl)-phenyl]-pyrimidine-2,4-diamine (60)

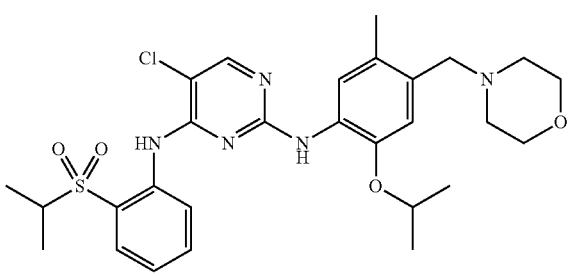 [SMILES: Cc1cc(Nc2ncc(Cl)c(Nc3ccccc3S(=O)(=O)C(C)C)n2)c(OC(C)C)cc1CN1CCOCC1]

Steps 1 and 2:
1-Chloro-5-isopropoxy-2-methyl-4-nitro-benzene

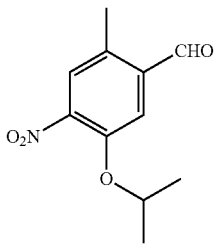 [SMILES: Cc1cc([N+](=O)[O-])c(OC(C)C)cc1C=O]

To a mixture of 1-chloro-2-methyl-4-nitro-5-isopropoxy-benzene (Intermediate 4, 870 mg, 3.77 mmol), vinylboronic acid dibutyl ester (1.24 mL, 5.6 mmol), and sodium carbonate (2.8 g, 26.4 mmol) in THF/H$_2$O (20/5 mL) is added dichlorobis(triphenylphospine) palladium (II) (132 mg, 5% mmol). The reaction tube is sealed, the mixture is purged with N$_2$ for 3 min and then heated at 90° C. under N$_2$ for overnight. The reaction is cooled to room temperature and poured into saturated aqueous ammonia chloride solution. The crude reaction mixture is extracted with ethyl acetate (3×100 mL). The organic extracts are combined, washed with brine and concentrated. The crude product is purified with silica gel column chromatography (10% ethyl acetate in hexanes) to afford 1-methyl-5-nitro-4-propoxy-2-vinyl-benzene as a yellow solid. 1-Methyl-5-nitro-4-propoxy-2-vinyl-benzene obtained from the previous step (360 mg, 1.63 mmol) is dissolved in DCM (20 mL) and is cooled to −78° C. O$_3$ (g) is bubbled into the solution until the solution's color turns blue/gray. The solution is then purged with N$_2$ (g) until the blue color disappears. The solution is warmed to room temperature and treated with triphenylphospine resin (2 g) pre-swelled in DCM (30 mL). After 30 min, the mixture is filtered, and the filtrate is concentrated to afford 2-methyl-4-nitro-5-propoxy-benzaldehyde as yellow solid.

Steps 3 and 4: 2-Isopropoxy-5-methyl-4-morpholin-4-ylmethyl-phenylamine

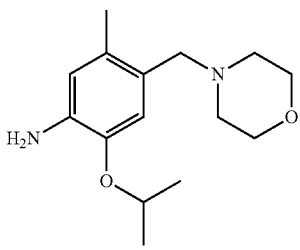 [SMILES: Cc1cc(N)c(OC(C)C)cc1CN1CCOCC1]

To a solution of 2-methyl-4-nitro-5-propoxy-benzaldehyde obtained in the previous step (34 mg, 0.152 mmol) in MeOH/THF (0.5/0.5 mL), is added acetic acid (5 drops). The mixture is stirred at room temperature for 1 hour. Sodium cyanoborohydride (20 mg, 0.30 mmol) is then added. After stirring for 30 min, the reaction is quenched by adding saturated aqueous ammonium chloride solution. The reaction mixture is extracted with ethyl acetate (3×5 mL). The organic phases are combined and concentrated to afford the amine product as an yellow oil which is directly used for the next step without further purification. To a solution of the product obtained in the previous step in methanol (5 mL), is added Pd/C (10% on carbon, 2 mg). The mixture is hydrogenated under 1 atm hydrogen. After 4 hours, the mixture is filtered and concentrated. The aniline product obtained (yellow solid), is used in the next step without further purification.

Step 5

To a mixture of the aniline product obtained in the previous step (0.152 mmol), (2,5-dichloro-pyrimidin-4-yl)-[2-(propane-2-sulfonyl)-phenyl]-amine (Intermediate 2, 52 mg, 0.152 mmol), cesium carbonate (99 mg, 0.30 mmol) and xantphos (8 mg, 0.02 mmol) in THF (2 mL), is added palladium acetate (2 mg, 5% mmol) in a microwave tube. The mixture is purged with N$_2$ for 3 min and then the sealed tube is heated at 150° C. for 20 min. under microwave irradiation. The reaction is filtered, concentrated, and purified by mass-trigger preparative RP LC-MS to afford the title compound 5-Chloro-N$^2$-(2-isopropoxy-5-methyl-4-morpholin-4-ylmethyl-phenyl)-N$^4$-[2-(propane-2-sulfonyl)-phenyl]-pyrimidine-2,4-diamine (60) as a yellow solid: $^1$H NMR (400 MHz, CDCl$_3$) δ 10.35 (s, 1H), 8.38 (d, 1H0, 7.93 (d, 1H), 7.59 (m, 2H), 7.41-7.36 (m, 2H), 4.70-4.63 (br, 1H), 4.30-4.18 (br, 2H), 4.15-4.10 (br, 2H), 4.00-3.97 (br, 2H), 3.52-3.46 (br, 2H), 3.20 (m, 1H), 2.95-2.84 (br, 2H), 2.24 (s, 3H), 1.31 (d, 12H); ESMS m/z 574.2 (M+H$^+$).

Example 7

5-Chloro-N$^2$-(2-isopropoxy-5-methyl-4-piperidin-4-yl-phenyl)-N$^4$-[2-(propane-2-sulfonyl)-phenyl]-pyrimidine-2,4-diamine (66)

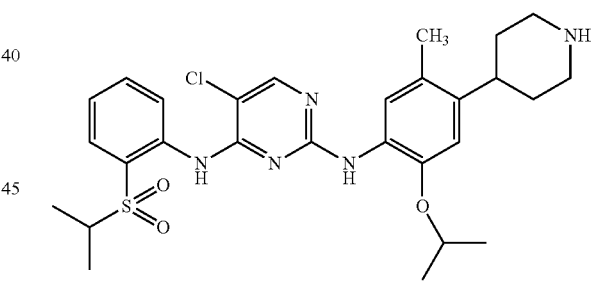

Step 1:
4-(5-Isopropoxy-2-methyl-4-nitro-phenyl)-pyridine

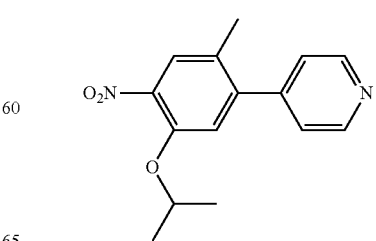

4-Pyridineboronic acid (147 mg, 1.20 mmol, 1.1 equiv.) is dissolved in a 2:1 v/v mixture of dioxane and $H_2O$ (15 mL) and $N_2$ is bubbled through for 5 minutes. Tris(dibenzylidene acetone)dipalladium (0) (100 mg, 0.109 mmol, 0.1 equiv.), 2-dicyclohexylphosphine-2'-6'-dimethoxy biphenyl (112 mg, 0.272 mmol, 0.25 equiv.), 1-chloro-5-isopropoxy-2-methyl-4-nitro-benzene (Intermediate 4, 250 mg, 1.09 mmol, 1.0 equiv.) and $K_3PO_4$ (462 mg, 2.18 mmol, 2.0 equiv.) are added under a $N_2$ blanket. The reaction vessel is sealed and heated with microwave irradiation to 150° C. for 20 min. After cooling to room temperature, the reaction is diluted with ethyl acetate and washed with 1 N aqueous NaOH (2×), the organic layer is then dried over $Na_2SO_4$ and filtered. After concentration, the crude product is purified by silica gel chromatography (gradient from hexanes to 30% ethyl acetate in hexanes) to give 4-(5-Isopropoxy-2-methyl-4-nitro-phenyl)-pyridine as a brown solid: ESMS m/z 273.1 (M+H$^+$).

Steps 2 and 3: 4-(4-Amino-5-isopropoxy-2-methyl-phenyl)-piperidine-1-carboxylic acid tert-butyl ester

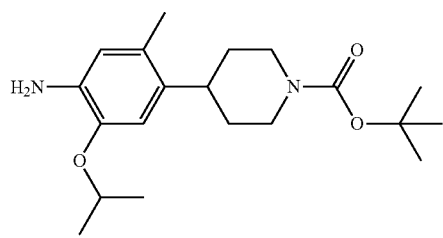

4-(5-Isopropoxy-2-methyl-4-nitro-phenyl)-pyridine from the previous step (438 mg, 1.61 mmol) dissolved in acetic acid (30 mL) is treated with TFA (0.24 mL, 3.22 mmol) and $PtO_2$ (176 mg, 40% w/w). The reaction mixture is vigorously stirred under 1 atm. $H_2$ for 36 hours. The reaction mixture is filtered and the filtrate is concentrated under vacuum. The resulting residue is diluted with ethyl acetate and washed with 1 N aqueous NaOH (2×), the organic layer is then dried over $Na_2SO_4$ and filtered. After concentration, the crude product (391 mg) is dissolved in anhydrous $CH_2Cl_2$ (30 mL). TEA is added (0.44 mL, 3.15, 2 equiv.) followed by $Boc_2O$ (344 mg, 1.57 equiv, 1 equiv.). The reaction is stirred at room temperature for 30 min. The reaction is concentrated under vacuum. The resulting residue is purified by silica gel chromatography (gradient from hexanes to 30% ethyl acetate in hexanes) to give 4-(4-amino-5-isopropoxy-2-methyl-phenyl)-piperidine-1-carboxylic acid tert-butyl ester as a sticky foam: ESMS m/z 293.1 (M−tBu+H)$^+$.

Steps 4 and 5

4-(4-Amino-5-isopropoxy-2-methyl-phenyl)-piperidine-1-carboxylic acid tert-butyl ester (170 mg, 0.488 mmol) from the previous step, (2,5-Dichloro-pyrimidin-4-yl)-[2-(propane-2-sulfonyl)-phenyl]-amine (Intermediate 2, 169 mg, 0.488 mmol, 1 equiv.), xantphos (28 mg, 0.049 mmol, 0.1 equiv.), palladium acetate (5.5 mg, 0.024 mmol, 0.05 equiv.), and $Cs_2CO_3$ (477 mg, 1.46 mmol, 3 equiv.) are dissolved in anhydrous THF (6 mL). $N_2$ is bubbled through the reaction mixture for 5 minutes and then the reaction vessel is sealed and heated with microwave irradiation to 150° C. for 20 min. The reaction is filtered and the filtrate concentrated under vacuum. After concentration, the crude product is purified by silica gel chromatography (gradient from hexanes to 30% ethyl acetate in hexanes) to give 4-(4-{5-chloro-4-[2-(propane-2-sulfonyl)-phenylamino]-pyrimidin-2-ylamino}-5-isopropoxy-2-methyl-phenyl)-piperidine-1-carboxylic acid tert-butyl ester as a yellow film: ESMS m/z 658.3 (M+H$^+$). This product (105 mg, 0.160 mmol) is dissolved in $CH_2Cl_2$ (3 mL) and treated with TFA (3 mL). After 45 min., the reaction is concentrated under vacuum. 1 N HCl in $Et_2O$ (5 mL×2) is added causing the product HCl salt to precipitate. The solvent is removed by decantation. The resulting 5-Chloro-N$^2$-(2-isopropoxy-5-methyl-4-piperidin-4-yl-phenyl)-N$^4$-[2-(propane-2-sulfonyl)-phenyl]-pyrimidine-2,4-diamine (66) is dried under high vacuum, generating an off-white powder: $^1$H NMR (400 MHz, DMSO-d$_6$+trace D$_2$O) δ 8.32 (s, 1H), 8.27 (d, 1H), 7.88 (d, 1H), 7.67 (dd, 1H), 7.45 (dd, 1H), 7.42 (s, 1H), 6.79 (s, 1H), 4.56-4.48 (m, 1H), 3.49-3.32 (m, 3H), 3.10-2.91 (m, 3H), 2.09 (s, 3H), 1.89-1.77 (m, 4H), 1.22 (d, 6H), 1.13 (d, 6H); ESMS m/z 558.1 (M+H$^+$).

Example 8

5-Chloro-N$^2$-[2-isopropoxy-5-methyl-4-(1-methyl-piperidin-4-yl)-phenyl]-N$^4$-[2-(propane-2-sulfonyl)-phenyl]-pyrimidine-2,4-diamine (67)

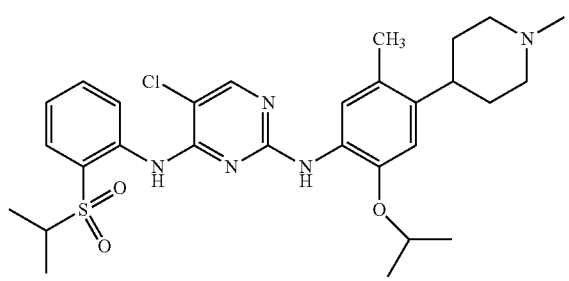 [SMILES: Cc1cc(Nc2ncc(Cl)c(Nc3ccccc3S(=O)(=O)C(C)C)n2)c(OC(C)C)cc1C1CCN(C)CC1]

Step 1: 4-(5-Isopropoxy-2-methyl-4-nitro-phenyl)-1-methyl-pyridinium iodide

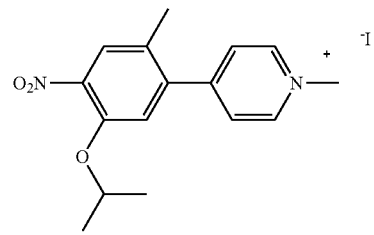

4-(5-Isopropoxy-2-methyl-4-nitro-phenyl)-pyridine (Example 7, Step 1, 217 mg, 0.797 mmol) is dissolved in anhydrous THF (9 mL). Iodomethane (0.10 mL, 1.61 mmol, 2 equiv.) is added and the reaction is stirred at 40° C. in a sealed tube for 2 days. The volatiles are removed under vacuum generating 4-(5-Isopropoxy-2-methyl-4-nitro-phenyl)-1-methyl-pyridinium iodide as a brown solid: ESMS m/z 287.1 (M$^+$).

Steps 2 and 3: 2-Isopropoxy-5-methyl-4-(1-methyl-piperidin-4-yl)-phenylamine

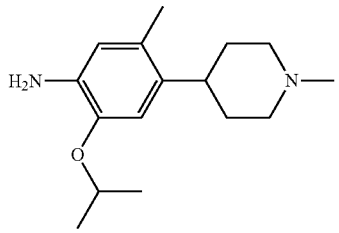

4-(5-Isopropoxy-2-methyl-4-nitro-phenyl)-1-methyl-pyridinium iodide from the previous step (0.697 mmol) is dissolved in CH$_3$OH (20 mL) and cooled to 0° C. NaBH$_4$ (264 mg, 6.97 mmol, 10 equiv.) is slowly added. After this addition is complete, the cooling bath is removed and the reaction is stirred at room temperature for 1 h. The reaction is quenched by the slow addition of 1N aqueous HCl (14 mL). The CH$_3$OH is partially removed by vacuum. The resulting residue is partitioned between EtOAc and 1 N aqueous NaOH. Additional 50% aqueous NaOH is added until the aqueous layer pH>12. The EtOAc layer is washed with 1 N aqueous NaOH (2×), the organic layer is then dried over Na$_2$SO$_4$, filtered, and concentrated under vacuum. After concentration, the crude product (175 mg) is dissolved in acetic acid (10 mL). TFA (0.15 mL, 3 equiv.) and PtO$_2$ (53 mg, 30% w/w) are added and the reaction is placed under 50 psi H$_2$ gas in a Parr Shaker for 14 h. The reaction mixture is filtered and the filtrate is concentrated under vacuum. The resulting residue is partitioned between EtOAc and 1 N aqueous NaOH. Additional 50% aqueous NaOH is added until the aqueous layer pH>12. The EtOAc layer is washed with 1 N aqueous NaOH (2×), the organic layer is then dried over Na$_2$SO$_4$, filtered, and concentrated under vacuum to give 2-Isopropoxy-5-methyl-4-(1-methyl-piperidin-4-yl)-phenylamine which is used in Step 4 without further purification: ESMS m/z 263.2 (M+H$^+$).

Step 4

Utilizing the same procedures described in the synthesis of Example 7 (Step 4) and final purification using preparative RP LC-MS affords 5-Chloro-N$^2$-[2-isopropoxy-5-methyl-4-(1-methyl-piperidin-4-yl)-phenyl]-N$^4$-[2-(propane-2-sulfonyl)-phenyl]-pyrimidine-2,4-diamine (67) as a pale yellow powder: (HCl salt, DMSO-d$_6$+trace D$_2$O) δ 8.28 (s, 1H), 8.19 (d, 1H), 7.86 (d, 1H), 7.66 (dd, 1H), 7.45 (dd, 1H), 7.37 (s, 1H), 6.77 (s, 1H), 4.56-4.49 (m, 1H), 3.51-3.37 (m, 3H), 3.16-3.08 (m, 2H), 2.98-2.88 (m, 1H), 2.77 (s, 3H), 2.05 (s, 3H), 1.90-1.81 (m, 4H), 1.19 (d, 6H), 1.11 (d, 6H); ESMS m/z 572.2 (M+H$^+$).

Example 9

2-[4-(4-{5-Chloro-4-[2-(propane-2-sulfonyl)-phenylamino]-pyrimidin-2-ylamino}-5-isopropoxy-2-methyl-phenyl)-piperidin-1-yl]-ethanol (72)

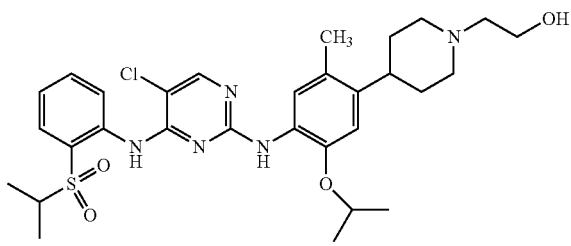 [SMILES: Cc1cc(Nc2ncc(Cl)c(Nc3ccccc3S(=O)(=O)C(C)C)n2)c(OC(C)C)cc1C1CCN(CCO)CC1]

5-Chloro-N$^2$-(2-isopropoxy-5-methyl-4-piperidin-4-yl-phenyl)-N$^4$-[2-(propane-2-sulfonyl)-phenyl]-pyrimidine-2,4-diamine (Example 7, 0.087 mmol) is dissolved in anhydrous DMF (1 mL). TEA (0.04 mL, 0.262 mmol, 3 equiv.) is added followed by 2-bromo-ethanol (0.019 mL, 0.262 mmol, 3 equiv.) dissolved in anhydrous DMF (0.7 mL). The reaction vessel is sealed and heated at 70° C. for 12 h. After cooling to room temperature, the reaction is diluted with ethyl acetate and washed with 1 N aqueous NaOH (5×), the organic layer is then dried over Na$_2$SO$_4$ and filtered. After concentration, the crude product is purified using preparative RP LC-MS to give 2-[4-(4-{5-Chloro-4-[2-(propane-2-sulfonyl)-phenylamino]-pyrimidin-2-ylamino}-5-isopropoxy-2-methyl-phenyl)-piperidin-1-yl]ethanol (72) as a yellow powder: ESMS m/z 602.2 (M+H$^+$).

Example 10

2-[4-(6-{5-Chloro-4-[2-(propane-2-sulfonyl)-phenylamino]-pyrimidin-2-ylamino}-5-isopropoxy-1-oxo-1,3-dihydro-isoindol-2-yl)-piperidin-1-yl]-acetamide (149)

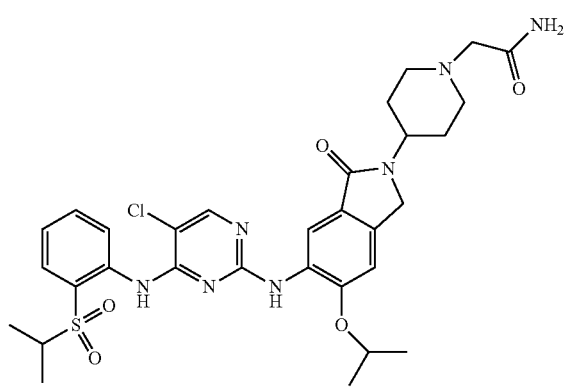 [SMILES: CC(C)Oc1cc2c(cc1Nc1ncc(Cl)c(Nc3ccccc3S(=O)(=O)C(C)C)n1)C(=O)N(C1CCN(CC(N)=O)CC1)C2]

To a mixture of 6-{5-Chloro-4-[2-(propane-2-sulfonyl)-phenylamino]-pyrimidin-2-ylamino}-5-isopropoxy-2-piperidin-4-yl-2,3-dihydro-isoindol-1-one (Example 1, 20 mg, 0.033 mmol) and triethylamine (23 uL, 0.165 mmol) in DMF (1.5 mL), is added 2-bromo-acetamide (10 mg, 0.066 mmol). The mixture is stirred at 60° C. for 4 hours. The reaction is filtered and the filtrate is purified by mass-trigger preparative RP LC-MS to afford the title compound 2-[4-(6-{5-Chloro-4-[2-(propane-2-sulfonyl)-phenylamino]-pyrimidin-2-ylamino}-5-isopropoxy-1-oxo-1,3-dihydro-isoindol-2-yl)-piperidin-1-yl]-acetamide (136) as a white solid: $^1$H NMR (400 MHz, MeOD-d$_4$) δ 8.41 (d, 1H), 8.27 (s, 1H), 8.21 (br, 1H), 7.93 (dd, 1H), 7.73 (m, 1H), 7.40 (dd, 1H), 7.30 (s, 1H), 4.52 (s, 2H), 4.45-4.37 (m, 1H), 4.19-4.15 (br, 2H), 3.87-3.78 (br, 2H), 2.37-2.19 (m, 2H), 2.20-2.15 (m, 1H), 1.40 (d, 6H), 1.25 (d, 6H); ESMS m/z 656.2 (M+H$^+$).

Example 11

4-(6-{5-Chloro-4-[2-(propane-2-sulfonyl)-phenylamino]-pyrimidin-2-ylamino}-5-isopropoxy-1-oxo-1,3-dihydro-isoindol-2-yl)-piperidine-1-carboxylic acid dimethylamide (155)

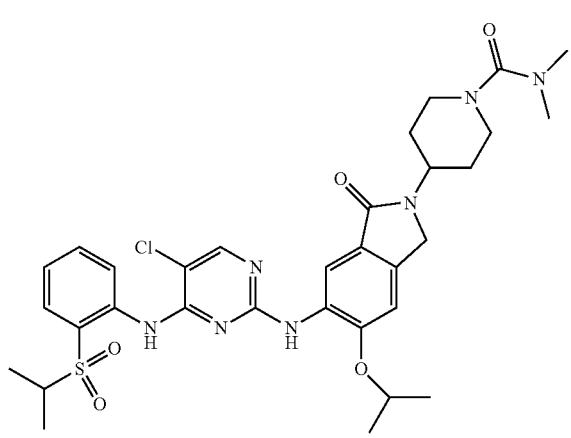

To a mixture of 6-{5-Chloro-4-[2-(propane-2-sulfonyl)-phenylamino]-pyrimidin-2-ylamino}-5-isopropoxy-2-piperidin-4-yl-2,3-dihydro-isoindol-1-one (Example 1, 20 mg, 0.033 mmol) and triethylamine (23 uL, 0.165 mmol) in DMF (1.5 mL) is added dimethylcarbamyl chloride (11 mg, 0.1 mmol). The mixture is stirred at room temperature for 1 hour. The reaction is filtered and the filtrate is purified by mass-trigger preparative RP LC-MS to afford the title compound 4-(6-{5-Chloro-4-[2-(propane-2-sulfonyl)-phenylamino]-pyrimidin-2-ylamino}-5-isopropoxy-1-oxo-1,3-dihydro-isoindol-2-yl)-piperidine-1-carboxylic acid dimethylamide (155) as a white solid: $^1$H NMR (400 MHz, MeOD-d$_4$) δ 8.29 (s, 1H), 8.26 (br, 1H), 7.96 (dd, 1H), 7.93 (s, 1H), 7.72 (dd, 1H), 7.48 (dd, 1H), 7.35 (s, 1H), 4.50 (s, 2H), 4.35-4.29 (m, 1H), 3.83 (d, 2H), 3.38-3.30 (m, 2H), 3.02-2.95 (m, 3H), 2.88 (s, 6H), 1.88-1.84 (m, 3H), 1.36 (d, 6H), 1.25 (d, 6H); ESMS m/z 670.2 (M+H$^+$).

Example 12

N2-(5-Ethynyl-2-isopropoxy-4-methyl-phenyl)-5-methyl-N4-[2-(propane-2-sulfonyl)-phenyl]-pyrimidine-2,4-diamine (257)

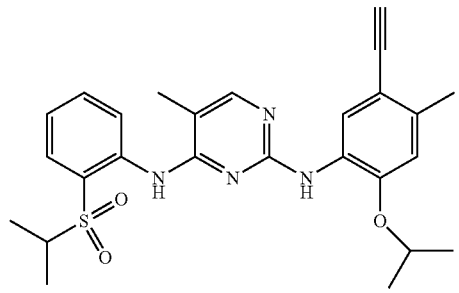 [SMILES: C#Cc1cc(Nc2ncc(C)c(Nc3ccccc3S(=O)(=O)C(C)C)n2)c(OC(C)C)cc1C]

Step 1: N2-(2-Isopropoxy-4-methyl-5-trimethylsilanylethynyl-phenyl)-5-methyl-N4-[2-(propane-2-sulfonyl)-phenyl]-pyrimidine-2,4-diamine

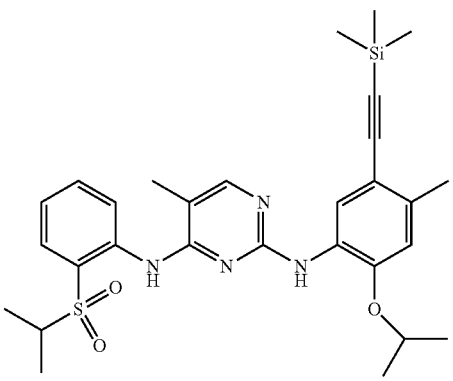 [SMILES: Cc1cc(OC(C)C)c(Nc2ncc(C)c(Nc3ccccc3S(=O)(=O)C(C)C)n2)cc1C#C[Si](C)(C)C]

A mixture of N2-(5-Bromo-2-isopropoxy-4-methyl-phenyl)-5-methyl-N4-[2-(propane-2-sulfonyl)-phenyl]-pyrimidine-2,4-diamine (Example 5, Step 4, 110 mg, 0.21 mmol), ethynyl-trimethyl-silane (0.14 mL), N,N-diisopropyl ethylamine (0.10 mL), PdCl$_2$(PhCN)$_2$ (12 mg), $^t$Bu$_3$PHBF$_4$ (17 mg), and CuI (4 mg) in 1 mL 1,4-dioxane is stirred at 22° C. for 20 hrs followed by heating at 60° C. for an additional 2 hrs. The reaction mixture is filtered through a small Celite plug and concentrated. The residue is purified over a 4 g SiO$_2$ column (ISCO) using a gradient of 0 to 20% ethyl acetate in hexanes as eluent, affording N2-(2-Isopropoxy-4-methyl-5-trimethylsilanylethynyl-phenyl)-5-methyl-N4-[2-(propane-2-sulfonyl)-phenyl]-pyrimidine-2,4-diamine as a yellow viscous oil.

Step 2

A solution of N2-(2-Isopropoxy-4-methyl-5-trimethylsilanylethynyl-phenyl)-5-methyl-N4-[2-(propane-2-sulfonyl)-phenyl]-pyrimidine-2,4-diamine from the previous step (0.102 g, 0.18 mmol) in 2.5 mL THF is treated with TBAF (0.5 mL, 1M in THF) and 30 µL AcOH at 22° C. for 2 hrs. The reaction mixture is concentrated and the residue is purified using a 4 g SiO$_2$ column (ISCO), affording N2-(5-Ethynyl-2-isopropoxy-4-methyl-phenyl)-5-methyl-N4-[2-(propane-2-sulfonyl)-phenyl]-pyrimidine-2,4-diamine (257). MS (ES+): 479.2 (MH+).

Example 13

4-(6-{5-Chloro-4-[2-(propane-2-sulfonyl)-phenylamino]-pyrimidin-2-ylamino}-5-isopropoxy-1-oxo-1,3-dihydro-isoindol-2-yl)-piperidine-1-carboxylic acid ethyl ester (175)

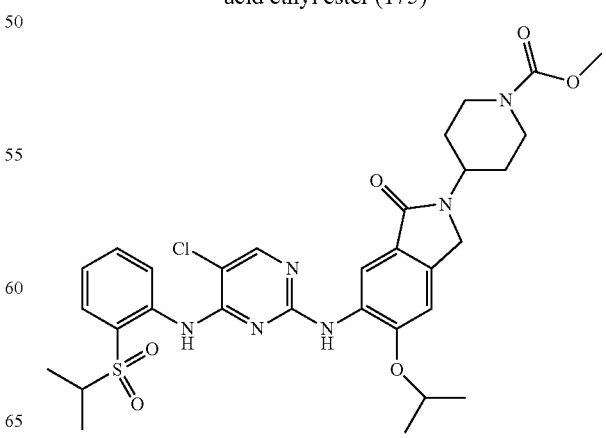

To a mixture of 6-{5-Chloro-4-[2-(propane-2-sulfonyl)-phenylamino]-pyrimidin-2-ylamino}-5-isopropoxy-2-piperidin-4-yl-2,3-dihydro-isoindol-1-one (Example 1, 15 mg, 0.025 mmol) and triethylamine (37.5 uL, 0.25 mmol) in DMF (0.5 mL), is added ethyl chloroformate (5.4 mg, 0.05 mmol). The mixture is stirred at room temperature for 1 hour. The crude reaction mixture is purified by mass-trigger preparative RP LC-MS to afford the title compound 4-(6-{5-chloro-4-[2-(propane-2-sulfonyl)-phenylamino]-pyrimidin-2-ylamino}-5-isopropoxy-1-oxo-1,3-dihydro-isoindol-2-yl)-piperidine-1-carboxylic acid ethyl ester (175) as a white solid. $^1$H NMR 400 MHz (DMSO-d$_6$ with trace D$_2$O) δ 8.55 (d, 1H), 8.32 (s, 1H), 8.14 (s, 1H), 7.82 (dd, 1H), 7.74 (t, 1H), 7.34 (t, 1H), 7.28 (s, 1H), 4.73 (m, 2H), 4.39 (s, 2H), 4.12 (m, 2H), 4.06 (q, 2H), 3.46 (m, 1H), 2.92 (m, 2H), 1.76 (m, 2H), 1.68 (m, 2H), 1.29 (d, 6H), 1.20 (t, 3H), 1.17 (d, 6H); MS m/z 671 (M+1).

Example 14

5-{5-Chloro-4-[2-(propane-2-sulfonyl)-phenylamino]-pyrimidin-2-ylamino}-6-isopropoxy-2-(1-methyl-piperidin-4-yl)-isoindole-1,3-dione (176)

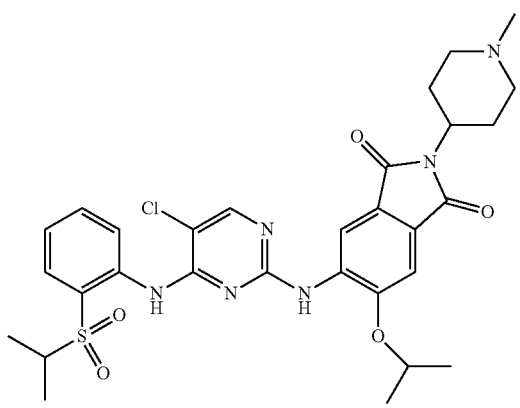 [SMILES: CC(C)Oc1cc2c(cc1Nc1ncc(Cl)c(Nc3ccccc3S(=O)(=O)C(C)C)n1)C(=O)N(C1CCN(C)CC1)C2=O]

Step 1: 4-(1-Hydroxy-6-isopropoxy-5-nitro-3-oxo-1,3-dihydro-isoindol-2-yl)-piperidine-1-carboxylic acid tert-butyl ester

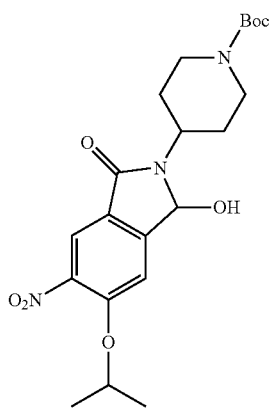 [SMILES: CC(C)Oc1cc2c(cc1[N+](=O)[O-])C(=O)N(C1CCN(C(=O)OC(C)(C)C)CC1)C2O]

4-(4-Isopropoxy-5-nitro-2-vinyl-benzoylamino)-piperidine-1-carboxylic acid tert-butyl ester (Example 1, Step 3, 1.2 g, 2.77 mmol) dissolved in 50 mL of DCM is cooled to −78° C. Ozone gas is bubbled through this solution until the starting material is consumed and then nitrogen gas is bubbled through the solution for 5 min. The reaction mixture is warmed to room temperature. Triphenylphosphine-resin (2.77 g) in 10 mL of DCM is added and the resulting mixture is stirred for 1.5 h. The resin is removed by filtration and the filtrate is concentrated. Silica gel chromatography (5% MeOH in DCM) affords 4-(1-hydroxy-6-isopropoxy-5-nitro-3-oxo-1,3-dihydro-isoindol-2-yl)-piperidine-1-carboxylic acid tert-butyl ester; MS m/z 336.2 (M−Boc+H$^+$).

Steps 2, 3 and 4: 5-Isopropoxy-2-(1-methyl-piperidin-4-yl)-6-nitro-indan-1,3-dione

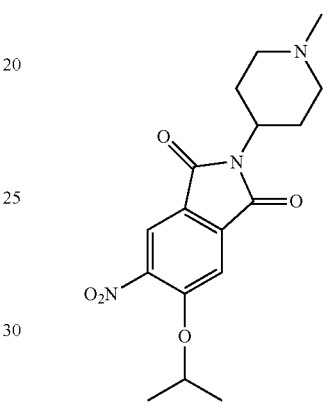

To the solution of 4-(1-hydroxy-6-isopropoxy-5-nitro-3-oxo-1,3-dihydro-isoindol-2-yl)-piperidine-1-carboxylic acid tert-butyl ester from the previous step (173.9 mg, 0.4 mmol) in DMF (4 mL) is added pyridinum dichromate (286.5 mg, 0.8 mmol) in one portion. After stirring at room temperature for 2 h, the reaction mixture is poured into 25 mL of water and the product is extracted with EtOAc. The organic extracts are dried over Na$_2$SO$_4$, filtered and concentrated in vacuo to give crude 4-(5-isopropoxy-6-nitro-1,3-dioxo-1,3-dihydro-isoindol-2-yl)-piperidine-1-carboxylic acid tert-butyl ester, which is directly used in the next step without further purification.

To a solution of 4-(5-isopropoxy-6-nitro-1,3-dioxo-1,3-dihydro-isoindol-2-yl)-piperidine-1-carboxylic acid tert-butyl ester generated in the previous step in 3 mL of DCM is added TFA (3 mL). The reaction mixture is stirred at room temperature for 1 h. After concentration, water (5 mL) is added to the crude reaction mixture, the resulting mixture is neutralized to pH=8 by adding NaHCO$_3$, and the product is extracted with DCM. The organic extracts are dried over Na$_2$SO$_4$, filtered and concentrated in vacuo to give crude 5-isopropoxy-6-nitro-2-piperidin-4-yl-isoindole-1,3-dione, which is directly used in the next step without further purification.

To a solution of the 5-isopropoxy-6-nitro-2-piperidin-4-yl-isoindole-1,3-dione generated in the previous step in THF (5 mL) and methanol (5 mL) are added formaldehyde (30 uL, 0.4 mmol) and 2 drops of AcOH sequentially. The reaction mixture is stirred at room temperature for 1 h, then sodium cyanoborohydride (50.4 mg, 0.8 mmol) is added in one portion and the resulting mixture is stirred for an additional 30 min. The reaction is quenched by the addition of saturated aqueous NH$_4$Cl followed by concentration in vacuo to give an oily residue. This oil is partitioned between EtOAc and brine. The organic extract is dried over Na$_2$SO$_4$, filtered and concentrated. Silica gel chromatography (5% MeOH in DCM) affords 5-isopropoxy-2-(1-methyl-piperidin-4-yl)-6-nitro-indan-1,3-dione; MS m/z 347.2 (M+1).

Steps 5 and 6

Following the procedures previously described (Example 1, Steps 7 and 8) using the product from Step 4 generates the title compound 5-{5-Chloro-4-[2-(propane-2-sulfonyl)-phenylamino]-pyrimidin-2-ylamino}-6-isopropoxy-2-(1-methyl-piperidin-4-yl)-isoindole-1,3-dione (176) as a yellow solid. $^1$H NMR 400 MHz (DMSO-d$_6$ with trace D$_2$O) δ 8.44 (s, 2H), 8.39 (s, 1H), 7.87 (dd, 1H), 7.78 (dt, 1H), 7.45 (s, 1H), 7.41 (m, 1H), 4.91 (m, 2H), 4.25 (m, 2H), 3.51 (m, 3H), 3.10 (m, 2H), 2.77 (s, 3H), 1.80 (m, 2H), 1.35 (d, 6H), 1.13 (d, 6H); MS m/z 627 (M+1).

Example 15

(2S,4S)-4-(6-{5-Chloro-4-[2-(propane-2-sulfonyl)-phenylamino]-pyrimidin-2-ylamino}-5-isopropoxy-1-oxo-1,3-dihydro-isoindol-2-yl)-pyrrolidine-2-carboxylic acid amide (177)

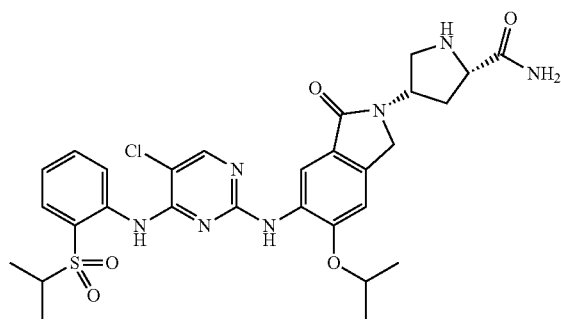

Step 1: (2S,4S)-4-(6-{5-Chloro-4-[2-(propane-2-sulfonyl)-phenylamino]-pyrimidin-2-ylamino}-5-isopropoxy-1-oxo-1,3-dihydro-isoindol-2-yl)-pyrrolidine-2-carboxylic acid methyl ester

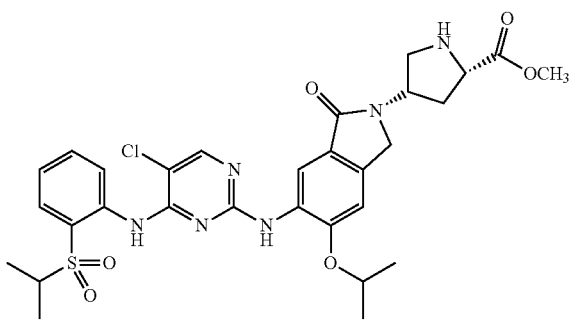

Following the procedures previously described (Example 1) using N-Boc-cis-4-amino-L-proline methyl ester in place of 4-amino-piperidine-1-carboxylic acid tert-butyl ester, generates (2S,4S)-4-(6-{5-Chloro-4-[2-(propane-2-sulfonyl)-phenylamino]-pyrimidin-2-ylamino}-5-isopropoxy-1-oxo-1,3-dihydro-isoindol-2-yl)-pyrrolidine-2-carboxylic acid methyl ester; MS m/z 643.2 (M+1).

Step 2

(2S,4S)-4-(6-{5-Chloro-4-[2-(propane-2-sulfonyl)-phenylamino]-pyrimidin-2-ylamino}-5-isopropoxy-1-oxo-1,3-dihydro-isoindol-2-yl)-pyrrolidine-2-carboxylic acid methyl ester generated in Step 1 (20 mg, 0.03 mmol) is dissolved in 7 N ammonia solution in MeOH (3 mL, 21 mmol). The resulting solution is heated using microwave irradiation to 120° C. for 1 h. After cooling to room temperature, the reaction mixture is concentrated in vacuo, neutralized to pH=8 with saturated aqueous NaHCO$_3$, and extracted with DCM. The organic extracts are dried over Na$_2$SO$_4$, filtered, and concentrated in vacuo to give (2S,4S)-4-(6-{5-Chloro-4-[2-(propane-2-sulfonyl)-phenylamino]-pyrimidin-2-ylamino}-5-isopropoxy-1-oxo-1,3-dihydro-isoindol-2-yl)-pyrrolidine-2-carboxylic acid amide (177) as a yellow solid. $^1$H NMR 400 MHz (DMSO-d$_6$ with trace D$_2$O) δ 8.47 (d, 1H), 8.25 (s, 1H), 8.07 (s, 1H), 7.78 (dd, 1H), 7.68 (m, 1H), 7.31 (t, 1H), 7.24 (s, 1H), 4.71 (m, 2H), 4.43 (dd, 2H), 3.60 (m, 1H), 3.44 (m, 1H), 3.35 (m, 1H), 2.63 (m, 1H), 2.28 (m, 1H), 1.22 (d, 6H), 1.10 (d, 6H); MS m/z 628 (M+1).

Example 16

5-Chloro-N2-[4-(4-dimethylamino-cyclohexyl)-2-isopropoxy-5-methyl-phenyl]-N4-[2-(propane-2-sulfonyl)-phenyl]-pyrimidine-2,4-diamine (21)

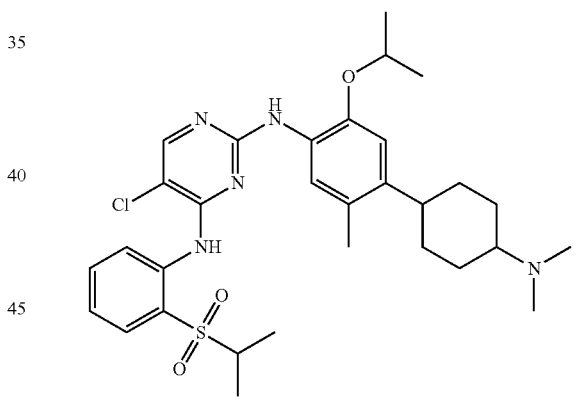

Step 1: 1,4-dioxaspiro[4.5]dec-7-en-8-yl trifluoromethanesulfonate

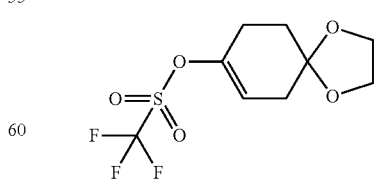

A solution of 0.5 M KHMDS in toluene (4.7 mL, 2.34 mmol) is added to a solution of 1,4-dioxaspiro[4.5]decan-8-one (1.80 mmol) and N-phenyltrifluoromethanesulfonimide (2.34 mmol) in dry THF (18 mL) at −78° C. under argon.

After stirring at −78° C. for 4 hours, the mixture is quenched with H₂O, extracted with diethyl ether and dried with MgSO₄. After workup and silica flash chromatography (hexane/EtOAc 90:10), 1,4-dioxaspiro[4.5]dec-7-en-8-yl trifluoromethanesulfonate is isolated: ¹H NMR (CDCl₃, 400 MHz) δ 5.66 (m, 1H), 3.98 (m. 4H), 2.53 (m, 2H), 2.40 (m, 2H), 1.90 (t, 2H). MS (ES+): 289.0 (M+1)⁺.

Step 2: 8-(5-isopropoxy-2-methyl-4-nitrophenyl)-1,4-dioxaspiro[4.5]dec-7-ene

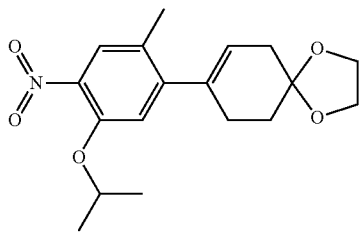 [SMILES: Cc1cc([N+](=O)[O-])c(OC(C)C)cc1C1=CCC2(CC1)OCCO2]

A stirred solution of the 1,4-dioxaspiro[4.5]dec-7-en-8-yl trifluoromethanesulfonate (0.03 mmol) and 2-(5-isopropoxy-2-methyl-4-nitrophenyl)-4,4,5,5-tetramethyl-1,3,2-dioxaborolane (Intermediate 5, 0.04 mmol) in THF (3 mL), containing [Pd(PPh₃)₄] (0.013 mmol) and K₃PO₄.H₂O (0.045 mmol), is heated to 80° C. under argon for 16 hours. After workup and silica flash chromatography (hexane/EtOAc 4:1), 8-(5-isopropoxy-2-methyl-4-nitrophenyl)-1,4-dioxaspiro[4.5]dec-7-ene is obtained. ¹H NMR (CDCl₃, 400 MHz) δ 7.62 (s, 1H), 6.82 (s, 1H), 5.74 (m, 1H), 4.65 (m, 1H), 4.04 (m, 4H), 2.47 (m, 4H), 2.27 (s, 3H), 1.89 (t, 2H), 1.29 (d, 6H). MS (ES+): 334.16 (M+1)⁺.

Step 3: 4-(5-isopropoxy-2-methyl-4-nitrophenyl)cyclohex-3-enone

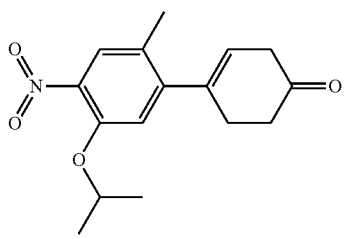 [SMILES: Cc1cc([N+](=O)[O-])c(OC(C)C)cc1C1=CCC(=O)CC1]

A solution of 8-(5-isopropoxy-2-methyl-4-nitrophenyl)-1,4-dioxaspiro[4.5]dec-7-ene (0.1 mmol) in 2.5 mL of TFA and CH₂Cl₂ (1:4 v/v), is stirred at room temperature for 6 hours. After workup and silica flash chromatography (hexane/EtOAc 4:1), 4-(5-isopropoxy-2-methyl-4-nitrophenyl)cyclohex-3-enone is obtained. ¹H NMR (CDCl₃, 400 MHz) δ 7.63 (s, 1H), 6.81 (s, 1H), 5.73 (m, 1H), 4.62 (m, 1H), 3.07 (m, 2H), 2.68 (m, 4H), 2.27 (s, 3H), 1.37 (d, 6H). MS (ES+): 290.13 (M+1)⁺.

Step 4: 4-(5-isopropoxy-2-methyl-4-nitrophenyl)-N,N-dimethylcyclohex-3-enamine

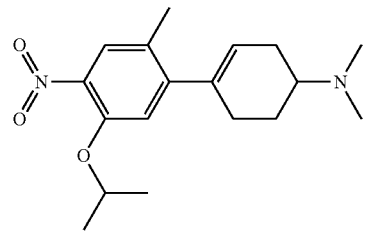 [SMILES: Cc1cc([N+](=O)[O-])c(OC(C)C)cc1C1=CCC(N(C)C)CC1]

To a solution of 4-(5-isopropoxy-2-methyl-4-nitrophenyl)cyclohex-3-enone (0.1 mmol) and dimethylamine (0.11 mmol) in 2 mL of 1,2-dicholoroethane, is added AcOH (0.1 mmol) and NaBH(OAc)₃ (0.11 mmol). The reaction mixture is stirred at room temperature for 10 hours. After workup and silica flash chromatography (CH₂Cl₂/MeOH 9:1), 4-(5-isopropoxy-2-methyl-4-nitrophenyl)-N,N-dimethylcyclohex-3-enamine is obtained. MS (ES+): 319.19 (M+1)⁺.

Step 5: 4-(4-(dimethylamino)cyclohexyl)-2-isopropoxy-5-methylaniline

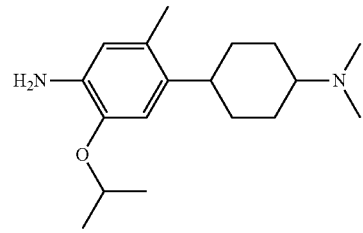 [SMILES: Cc1cc(N)c(OC(C)C)cc1C1CCC(N(C)C)CC1]

To a solution of 4-(5-isopropoxy-2-methyl-4-nitrophenyl)-N,N-dimethylcyclohex-3-enamine (0.1 mmol) in 10 mL of MeOH, is added Pd/C (5 mg) under argon. The suspension is stirred under 1 atm. H₂ for 6 hours. After filtering, solvent is removed and 4-(4-(dimethylamino)cyclohexyl)-2-isopropoxy-5-methylaniline is obtained. MS (ES+): 291.24 (M+1)⁺.

Step 6

Following the procedure previously described (Example 7, Step 4) using the product from Step 5 generates the title compound 5-Chloro-N2-[4-(4-dimethylamino-cyclohexyl)-2-isopropoxy-5-methyl-phenyl]-N4-[2-(propane-2-sulfonyl)-phenyl]-pyrimidine-2,4-diamine (21). ¹H NMR (CD₃OD, 400 MHz) δ 8.36-8.38 (d, 1H), 8.20 (s, 1H), 7.97-7.99 (m, 1H), 7.69-7.73 (m, 1H), 7.46-7.52 (m, 2H), 6.89-7.02 (d, 1H), 4.60-4.66 (m, 1H), 3.37-3.39 (m, 1H), 3.00 (s, 3H), 2.90 (s, 3H), 2.17-2.22 (m, 4H), 1.64-2.01 (m, 8H), 1.25-1.32 (m, 12H); MS (ES+): 600.3 (M+1)⁺.

Exemplary compounds of the invention are set forth below. Table 1 shows exemplary compounds of Formula (IA).

TABLE 1

| Structure | Physical Data<br>$^1$H NMR 400 MHz (DMSO-d6)<br>and/or MS (m/z) |
|---|---|
| 1 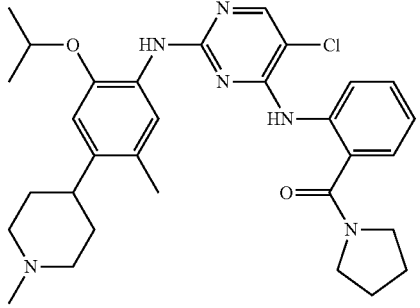 [SMILES: Cc1cc(Nc2ncc(Cl)c(Nc3ccccc3C(=O)N3CCCC3)n2)c(OC(C)C)cc1C1CCN(C)CC1]<br>(2-(5-chloro-2-(2-isopropoxy-5-methyl-4-(1-methylpiperidin-4-yl)phenylamino)pyrimidin-4-ylamino)phenyl)(pyrrolidin-1-yl)methanone | MS (ES$^+$): 563.1 (M + 1)$^+$. |
| 2 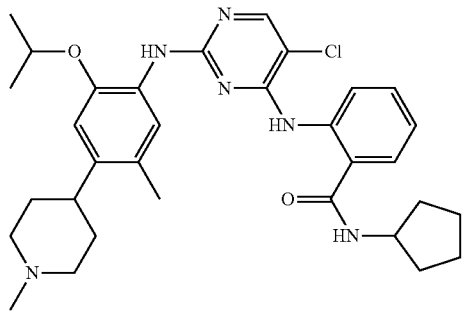 [SMILES: Cc1cc(Nc2ncc(Cl)c(Nc3ccccc3C(=O)NC3CCCC3)n2)c(OC(C)C)cc1C1CCN(C)CC1]<br>2-(5-chloro-2-(2-isopropoxy-5-methyl-4-(1-methylpiperidin-4-yl)phenylamino)pyrimidin-4-ylamino)-N-cyclopentylbenzamide | MS (ES$^+$): 577.2 (M + 1)$^+$. |
| 3 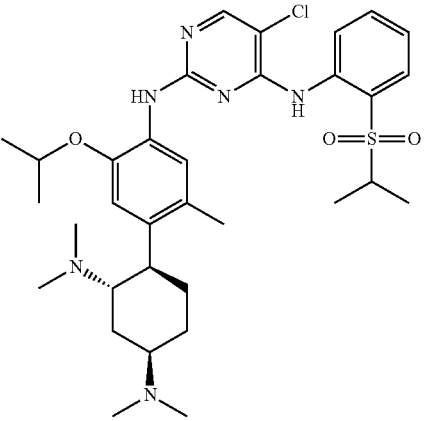 [SMILES: Cc1cc(Nc2ncc(Cl)c(Nc3ccccc3S(=O)(=O)C(C)C)n2)c(OC(C)C)cc1[C@H]1CC[C@H](N(C)C)C[C@@H]1N(C)C]<br>N2-(4-((1R,2S,4R)-2,4-bis(dimethylamino) cyclohexyl)-2-isopropoxy-5-methylphenyl)-5-chloro-N4-(2-(isopropylsulfonyl)phenyl)pyrimidine-2,4-diamine | MS (ES$^+$): 643.3 (M + 1)$^+$. |

TABLE 1-continued

| | Structure | Physical Data<br>¹H NMR 400 MHz (DMSO-d6)<br>and/or MS (m/z) |
|---|---|---|
| 4 | N2-(4-((1R,2S,4S)-2,4-bis(dimethylamino) cyclohexyl)-<br>2-isopropoxy-5-methylphenyl)-5-chloro-N4-(2-<br>(isopropylsulfonyl)phenyl)pyrimidine-2,4-diamine | MS (ES⁺): 643.3 (M + 1)⁺. |
| 5 | 2-(5-chloro-2-(4-((1s,4s)-4-(dimethylamino) cyclohexyl)-<br>2-isopropoxy-5-methylphenylamino) pyrimidin-4-<br>ylamino)-N,N dimethylbenzenesulfonamide | MS (ES⁺): 601.2 (M + 1)⁺. |
| 6 | 2-(5-chloro-2-(4-((1r,4r)-4-(dimethylamino)cyclohexyl)-<br>2-isopropoxy-5-methylphenylamino)pyrimidin-4-<br>ylamino)-N,N-dimethylbenzenesulfonamide | MS (ES⁺): 601.2 (M + 1)⁺. |

TABLE 1-continued

| | Structure | Physical Data<br>¹H NMR 400 MHz (DMSO-d6)<br>and/or MS (m/z) |
|---|---|---|
| 7 | 2-(5-chloro-2-(2-isopropoxy-5-methyl-4-(1-methylpiperidin-4-yl)phenylamino)pyrimidin-4-ylamino)-N-cyclobutylbenzamide | MS (ES⁺): 563.1 (M + 1)⁺. |
| 8 | azetidin-1-yl(2-(5-chloro-2-(2-isopropoxy-5-methyl-4-(1-methylpiperidin-4-yl)phenylamino)pyrimidin-4-ylamino)phenyl)methanone | MS (ES⁺): 549.1 (M + 1)⁺. |
| 9 | 5-chloro-N2-(4-((1r,4r)-4-(dimethylamino) cyclohexyl)-2-isopropoxy-5-methylphenyl)-N4-(2-(pyrrolidin-1-ylsulfonyl)phenyl)pyrimidine-2,4-diamine | MS (ES⁺): 627.2 (M + 1)⁺. |

TABLE 1-continued

| | Structure | Physical Data<br>¹H NMR 400 MHz (DMSO-d6)<br>and/or MS (m/z) |
|---|---|---|
| 10 | 5-chloro-N2-(4-((1s,4s)-4-(dimethylamino) cyclohexyl)-2-isopropoxy-5-methylphenyl)-N4-(2-(pyrrolidin-1-ylsulfonyl)phenyl)pyrimidine-2,4-diamine | MS (ES⁺): 627.2 (M + 1)⁺. |
| 11 | N2-(4-((1r,4r)-4-(dimethylamino)cyclohexyl)-2-isopropoxy-5-methylphenyl)-N4-(2-(isopropylsulfonyl)phenyl)-5-methylpyrimidine-2,4-diamine | MS (ES⁺): 580.8 (M + 1)⁺. |
| 12 | N2-(4-((1s,4s)-4-(dimethylamino)cyclohexyl)-2-isopropoxy-5-methylphenyl)-N4-(2-(isopropylsulfonyl)phenyl)-5-methylpyrimidine-2,4-diamine | MS (ES⁺): 580.8 (M + 1)⁺. |

TABLE 1-continued

| | Structure | Physical Data $^1$H NMR 400 MHz (DMSO-d6) and/or MS (m/z) |
|---|---|---|
| 13 | 2-(5-chloro-2-(2-isopropoxy-5-methyl-4-(1-methylpiperidin-4-yl)phenylamino)pyrimidin-4-ylamino)-N-cyclopropylbenzamide | MS (ES$^+$): 549.1 (M + 1)$^+$. |
| 14 | (2-(5-chloro-2-(2-isopropoxy-5-methyl-4-(1-methylpiperidin-4-yl)phenylamino)pyrimidin-4-ylamino)phenyl)(piperidin-1-yl)methanone | MS (ES$^+$): 577.1 (M + 1)$^+$. |
| 15 | (S)-5-chloro-N2-(2-isopropoxy-5-methyl-4-(piperidin-2-yl)phenyl)-N4-(2-(isopropylsulfonyl)phenyl)pyrimidine-2,4-diamine | MS (ES$^+$): 558.1 (M + 1)$^+$. |

TABLE 1-continued

| | Structure | Physical Data<br>¹H NMR 400 MHz (DMSO-d6)<br>and/or MS (m/z) |
|---|---|---|
| 16 | (R)-5-chloro-N2-(2-isopropoxy-5-methyl-4-(piperidin-2-yl)phenyl)-N4-(2-(isopropylsulfonyl)phenyl) pyrimidine-2,4-diamine | MS (ES⁺): 558.1 (M + 1)⁺. |
| 17 | (cis,trans) 5-Chloro-N2-{2-isopropoxy-5-methyl-4-[4-(4-methyl-piperazin-1-yl)-cyclohexyl]-phenyl}-N4-[2-(propane-2-sulfonyl)-phenyl]-pyrimidine-2,4-diamine | ¹H NMR (CD₃OD, 400 MHz) δ 8.34-8.37 (m, 1H), 8.17 (s, 1H), 7.89-7.96 (m, 1H), 7.64-7.71 (m, 1H), 7.42-7.49 (m, 2H), 6.86-6.96 (d, 1H), 4.55-4.65 (m, 1H), 3.34-3.53 (m, 1H), 2.15-2.91 (m, 12H), 1.94-1.97 (m, 4H), 1.23-1.72 (m, 20H); MS (ES⁺): 654.8 (M + 1)⁺. |
| 18 | (cis,trans) 5-chloro-N2-{4-[4-(2-dimethylamino-ethyl amino)-cyclohexyl]-2-isopropoxy-5-methyl-phenyl}-N4-[2-(propane-2-sulfonyl)-phenyl]-pyrimidine-2,4-diamine | ¹H NMR (CD₃OD, 400 MHz) δ 8.35-8.37 (d, 1H), 8.20 (s, 1H), 7.97-8.00 (m, 1H), 7.7-7.74 (m, 1H), 7.46-7.51 (m, 2H), 6.89-7.03 (d, 1H), 4.60-4.64 (m, 1H), 3.30-3.60 (m, 5H), 3.01 (s, 6H), 2.81-2.84 (m, 1H), 1.25-2.30 (m, 24H); MS (ES⁺): 643.3 (M + 1)⁺. |

TABLE 1-continued

| | Structure | Physical Data<br>¹H NMR 400 MHz (DMSO-d6)<br>and/or MS (m/z) |
|---|---|---|
| 19 | 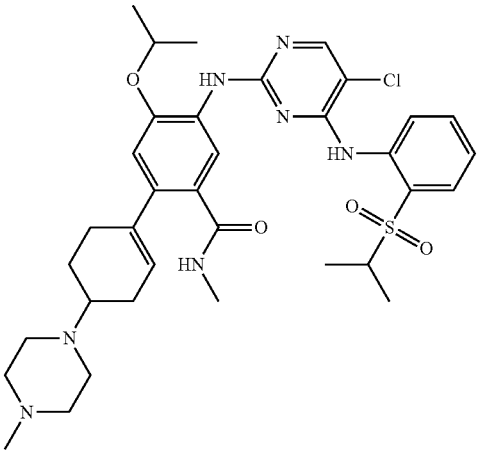 [SMILES: CNC(=O)c1cc(Nc2ncc(Cl)c(Nc3ccccc3S(=O)(=O)C(C)C)n2)c(OC(C)C)cc1C1=CCC(N2CCN(C)CC2)CC1]<br>5-{5-Chloro-4-[2-(propane-2-sulfonyl)-phenylamino]-pyrimidin-2-ylamino}-4-isopropoxy-N-methyl-2-[4-(4-methyl-piperazin-1-yl)-cyclohex-1-enyl]-benzamide | ¹H NMR (CD₃OD, 400 MHz) δ 8.51-8.56 (t, 1H), 8.41 (s, 1H), 8.19 (s, 1H), 7.86-7.89 (m, 1H), 7.54-7.58 (m, 1H), 7.27-7.31 (m, 1H), 6.97-7.00 (m, 1H), 4.77-4.84 (m, 1H), 2.66-3.32 (m, 15H), 1.22-2.21 (m, 18H); MS (ES⁺): 696.2 (M + 1)⁺. |
| 20 | 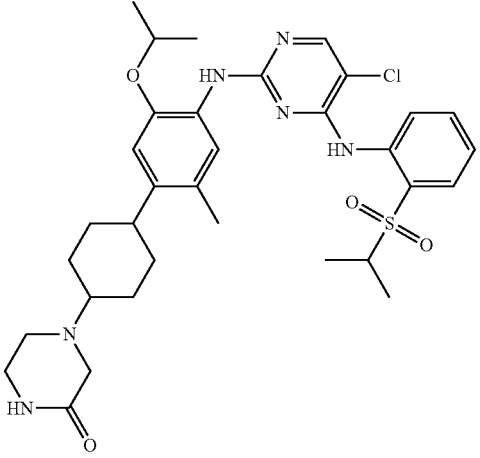 [SMILES: Cc1cc(Nc2ncc(Cl)c(Nc3ccccc3S(=O)(=O)C(C)C)n2)c(OC(C)C)cc1C1CCC(N2CCNC(=O)C2)CC1]<br>4-[4-(4-{5-Chloro-4-[2-(propane-2-sulfonyl)-phenylamino]-pyrimidin-2-ylamino}-5-isopropoxy-2-methyl-phenyl)-cyclohexyl]-piperazin-2-one | ¹H NMR (CD₃OD, 400 MHz) δ 8.34-8.36 (d, 1H), 8.21 (s, 1H), 7.98-8.00 (m, 1H), 7.69-7.73 (m, 1H), 7.45-7.52 (m, 2H), 6.90-7.01 (d, 1H), 4.60-4.66 (m, 1H), 3.99 (s, 2H), 3.36-3.62 (m, 6H), 1.65-2.42 (m, 12H), 1.24-1.31 (m, 12H); MS (ES⁺): 655.3 (M + 1)⁺. |
| 21 | 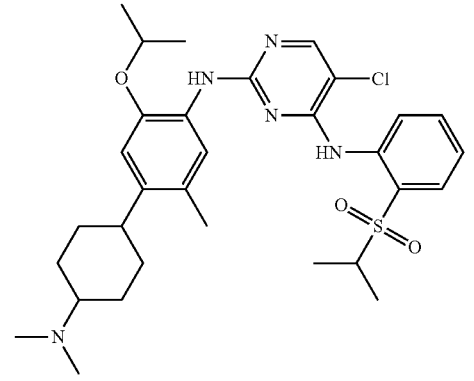 [SMILES: Cc1cc(Nc2ncc(Cl)c(Nc3ccccc3S(=O)(=O)C(C)C)n2)c(OC(C)C)cc1C1CCC(N(C)C)CC1]<br>5-Chloro-N2-[4-(4-dimethylamino-cyclohexyl)-2-isopropoxy-5-methyl-phenyl]-N4-[2-(propane-2-sulfonyl)-phenyl]-pyrimidine-2,4-diamine | ¹H NMR (CD₃OD, 400 MHz) δ 8.36-8.38 (d, 1H), 8.20 (s, 1H), 7.97-7.99 (m, 1H), 7.69-7.73 (m, 1H), 7.46-7.52 (m, 2H), 6.89-7.02 (d, 1H), 4.60-4.66 (m, 1H), 3.37-3.39 (m, 1H), 3.00 (s, 3H), 2.90 (s, 3H), 2.17-2.22 (m, 4H), 1.64-2.01 (m, 8H), 1.25-1.32 (m, 12H); MS (ES⁺): 600.3 (M + 1)⁺. |

TABLE 1-continued

| | Structure | Physical Data<br>¹H NMR 400 MHz (DMSO-d6)<br>and/or MS (m/z) |
|---|---|---|
| 22 | 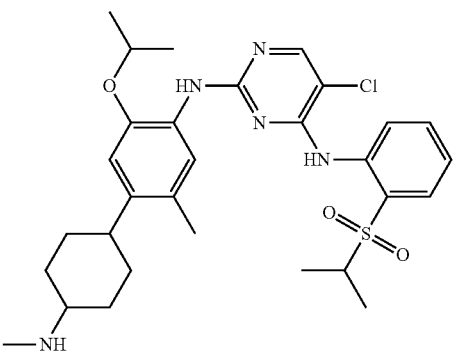 [SMILES: CNC1CCC(c2cc(OC(C)C)c(Nc3ncc(Cl)c(Nc4ccccc4S(=O)(=O)C(C)C)n3)cc2C)CC1]<br>5-Chloro-N2-[2-isopropoxy-5-methyl-4-(4-methylamino-cyclohexyl)-phenyl]-N4-[2-(propane-2-sulfonyl)-phenyl]-pyrimidine-2,4-diamine | ¹H NMR (CD₃OD, 400 MHz) δ 8.32-8.34 (d, 1H), 8.22 (s, 1H), 7.98-8.00 (m, 1H), 7.69-7.73 (m, 1H), 7.49-7.53 (m, 1H), 7.40-7.41 (d, 1H), 6.91-7.02 (d, 1H), 4.61-4.66 (m, 1H), 3.36-3.40 (m, 1H), 2.74-2.78 (d, 3H), 2.17-2.28 (m, 4H), 1.64-2.03 (m, 8H), 1.24-1.31 (m, 12H); MS (ES⁺): 586.2 (M + 1)⁺. |
| 23 | 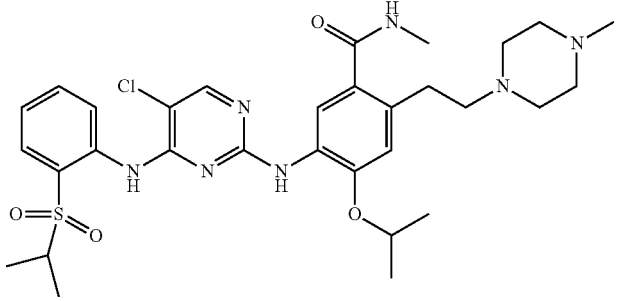 [SMILES: CNC(=O)c1cc(Nc2ncc(Cl)c(Nc3ccccc3S(=O)(=O)C(C)C)n2)c(OC(C)C)cc1CCN1CCN(C)CC1]<br>5-(4-(2-(isopropylsulfonyl)phenylamino)-5-chloropyrimidin-2-ylamino)-4-isopropoxy-N-methyl-2-(2-(4-methylpiperazin-1-yl)ethyl)benzamide | MS (ES⁺): 645.2 (M + 1)⁺ |
| 24 | 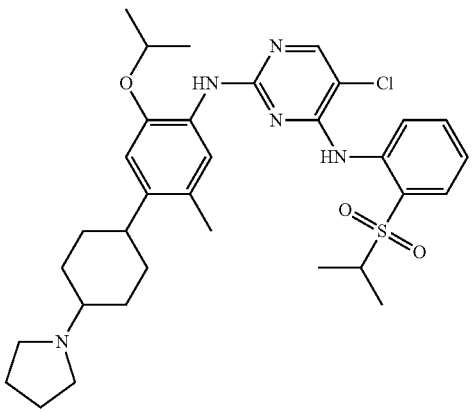 [SMILES: Cc1cc(Nc2ncc(Cl)c(Nc3ccccc3S(=O)(=O)C(C)C)n2)c(OC(C)C)cc1C1CCC(N2CCCC2)CC1]<br>5-Chloro-N2-[2-isopropoxy-5-methyl-4-(4-pyrrolidin-1-yl-cyclohexyl)-phenyl]-N4-[2-(propane-2-sulfonyl)-phenyl]-pyrimidine-2,4-diamine | ¹H NMR (CD₃OD, 400 MHz) δ 8.36-8.38 (d, 1H), 8.20 (s, 1H), 7.97-7.99 (m, 1H), 7.69-7.73 (m, 1H), 7.45-7.52 (m, 2H), 6.88-7.02 (d, 1H), 4.60-4.66 (m, 1H), 3.65-3.85 (m, 2H), 3.32-3.34 (m, 1H), 3.16-3.20 (m, 2H), 2.77-2.96 (m, 1H), 1.22-2.35 (m, 28H); MS (ES⁺): 626.3 (M + 1)⁺. |

TABLE 1-continued

| | Structure | Physical Data<br>¹H NMR 400 MHz (DMSO-d6)<br>and/or MS (m/z) |
|---|---|---|
| 25 | 5-Chloro-N2-(2-isopropoxy-4-{4-[2-methoxy-ethyl)-methyl-amino]-cyclohexyl}-5-methyl-phenyl)-N4-[2-(propane-2-sulfonyl)-phenyl]-pyrimidine-2,4-diamine | ¹H NMR (CD₃OD, 400 MHz) δ 8.36-8.38 (d, 1H), 8.20-8.21 (m, 1H), 7.96-7.99 (m, 1H), 7.69-7.73 (m, 1H), 7.45-7.54 (m, 2H), 6.90-7.02 (d, 1H), 4.60-4.66 (m, 1H), 3.32-3.77 (m, 8H), 2.90-2.99 (m, 3H), 2.77-2.96 (m, 1H), 1.22-2.33 (m, 24H); MS (ES⁺): 644.3 (M + 1)⁺. |
| 26 | 5-{5-Chloro-4-[2-(propane-2-sulfonyl)-phenylamino]-pyrimidin-2-ylamino}-4-isopropoxy-N-methyl-2-[3-(4-methyl-piperazin-1-yl)-propyl]-benzamide | ¹H NMR (CD₃OD, 400 MHz) δ 8.44-8.46 (d, 1H), 8.25 (s, 1H), 8.13 (s, 1H), 7.94-7.96 (m, 1H), 7.64-7.67 (m, 1H), 7.42-7.46 (m, 1H), 7.06 (s, 1H), 4.77-4.83 (m, 1H), 3.48-3.54 (m, 8H), 3.32-3.35 (m, 1H), 3.06-3.10 (m, 2H), 2.96 (s, 3H), 2.81-2.87 (m, 5H), 2.16-2.20 (m, 2H), 1.27-1.39 (m, 12H); MS (ES⁺): 658.3 (M + 1)⁺. |
| 27 | 5-chloro-N2-(4-((1s,4s)-4-(dimethylamino) cyclohexyl)-2-isopropoxy-5-methylphenyl)-N4-(2-(isopropylsulfonyl)phenyl)pyrimidine-2,4-diamine | MS (ES⁺): 600.2 (M + 1)⁺. |

TABLE 1-continued

| Structure | Physical Data<br>¹H NMR 400 MHz (DMSO-d6)<br>and/or MS (m/z) |
|---|---|
| 28<br>5-chloro-N2-(2-isopropoxy-5-methyl-4-(piperidin-2-yl)phenyl)-N4-(2-(isopropylsulfonyl)phenyl)pyrimidine-2,4-diamine | MS (ES$^+$): 558.2 (M + 1)$^+$. |
| 29<br>5-chloro-N2-(2-isopropoxy-4-methyl-5-(piperidin-4-yl)phenyl)-N4-(2-(isopropylsulfonyl)phenyl) pyrimidine-2,4-diamine | MS (ES$^+$): 558.2 (M + 1)$^+$. |
| 30<br>5-chloro-N2-(2-isopropoxy-4-methyl-5-(piperidin-4-yl)phenyl)-N4-(2(morpholinosulfonamido)phenyl)pyrimidine-2,4-diamine | MS (ES$^+$): 601.2 (M + 1)$^+$. |

TABLE 1-continued

| | Physical Data<br>¹H NMR 400 MHz (DMSO-d6)<br>and/or MS (m/z) |
|---|---|
| Structure | |

31

2-(2-(2-isopropoxy-4-methyl-5-(piperidin-4-yl)phenylamino)-5-chloropyrimidin-4-ylamino)-N-isopropylbenzamide

MS (ES⁺): 537.3 (M + 1)⁺.

32

5-chloro-N2-(4-((1r,4r)-4-(dimethylamino) cyclohexyl)-2-isopropoxy-5-methylphenyl)-N4-(2-(isopropylsulfonyl)phenyl)pyrimidine-2,4-diamine

MS (ES⁺): 600.3 (M + 1)⁺.

33

5-chloro-N2-(2-isopropoxy-5-methyl-4-((1s,4s)-4-(4-methylpiperazin-1-yl)cyclohexyl)phenyl)-N4-(2-(isopropylsulfonyl)phenyl)pyrimidine-2,4-diamine

MS (ES⁺): 655.3 (M + 1)⁺.

TABLE 1-continued

| Structure | Physical Data<br>¹H NMR 400 MHz (DMSO-d6)<br>and/or MS (m/z) |
|---|---|
| 34 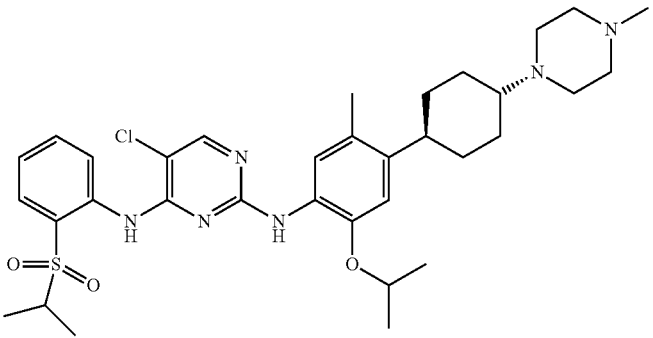<br>5-chloro-N2-(2-isopropoxy-5-methyl-4-((1r,4r)-4-(4-methylpiperazin-1-yl)cyclohexyl)phenyl)-N4-(2-(isopropylsulfonyl)phenyl)pyrimidine-2,4-diamine | MS (ES$^+$): 655.3 (M + 1)$^+$. |
| 35 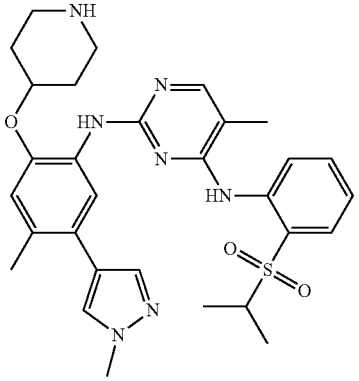 [SMILES: Cc1cc(OC2CCNCC2)c(Nc2ncc(C)c(Nc3ccccc3S(=O)(=O)C(C)C)n2)cc1-c1cnn(C)c1]<br>5-Methyl-N2-[4-methyl-5-(1-methyl-1H-pyrazol-4-yl)-2-(piperidin-4-yloxy)-phenyl]-N4-[2-(propane-2-sulfonyl)-phenyl]-pyrimidine-2,4-diamine | 1.10 (6H, d, J = 5.7), 1.89 (2H, br), 2.03 (2H, br), 2.16 (3H, s), 2.32 (3H, s), 3.05 (2H, br), 3.49 (3H, br), 3.89 (3H, s), 4.72 (1H, br), 7.06 (1H, s), 7.21 (1H, br), 7.30 (1H, br), 7.41 (1H, br.s), 7.46 (1H, br.s), 7.69 (1H, s), 7.79 (1H, d, J = 7.4), 7.95 (1H, br), 8.04 (1H, br.s), 9.79 (2H, br.s). MS (ES$^+$): 576.3 (M + 1)$^+$. |
| 36 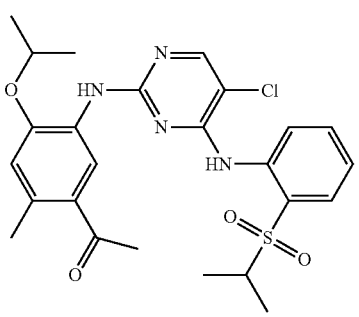 [SMILES: CC(=O)c1cc(Nc2ncc(Cl)c(Nc3ccccc3S(=O)(=O)C(C)C)n2)c(OC(C)C)cc1C]<br>1-(5-{5-Chloro-4-[2-(propane-2-sulfonyl)-phenylamino]-pyrimidin-2-ylamino}-4-isopropoxy-2-methyl-phenyl)-ethanone | 1.10 (6H, d, J = 5.7), 1.89 (2H, br), 2.03 (2H, br), 2.16 (3H, s), 2.32 (3H, s), 3.05 (2H, br), 3.49 (3H, br), 3.89 (3H, s), 4.72 (1H, br), 7.06 (1H, s), 7.21 (1H, br), 7.30 (1H, br), 7.41 (1H, br.s), 7.46 (1H, br.s), 7.69 (1H, s), 7.79 (1H, d, J = 7.4), 7.95 (1H, br), 8.04 (1H, br.s), 9.79 (2H, br.s). MS (ES$^+$): 517.2 (M + 1)$^+$. |

TABLE 1-continued

| | Structure | Physical Data<br>¹H NMR 400 MHz (DMSO-d6)<br>and/or MS (m/z) |
|---|---|---|
| 37 | N2-{2-Isopropoxy-4-methyl-5-[1-(2-morpholin-4-yl-ethyl)-1H-pyrazol-4-yl]-phenyl}-5-methyl-N4-[2-(propane-2-sulfonyl)-phenyl]-pyrimidine-2,4-diamine | 1.14 (6H, d, J = 6.8), 1.25 (6H, d, J = 6.0), 2.12 (3H, s), 2.33 (3H, s), 2.52 (overlapping with DMSO), 3.14 (2H, very br.) 3.45 (1H, sept, J = 6.8), 3.70 (4H, very br), 3.93 (2H, very br), 4.6 (1 or 2H, br.S), 4.63 (1H, sept, J = 6.1), 6.99 (1H, s), 7.23 (2H, m), 7.53 (1H, s), 7.78 (2H, m) 7.91 (1H, s), 8.01 (1H, s), 8.33 (1H, br.s), missing anilino NH. MS (ES⁺): 634.3 (M + 1)⁺. |
| 38 | N2-(5-(6-(3-(dimethylamino)propoxy)pyridin-3-yl)-2-isopropoxy-4-methylphenyl)-N4-(2-(isopropyl sulfonyl)phenyl)-5-methylpyrimidine-2,4-diamine | 1.06 (6H, d, J = 6.7), 1.28 (6H, d, J = 6.0), 2.15 (6H, s), 2.19 (2H, br.m), 2.80 (3H, s), 2.82 (3H, s), 3.25 (2H, m), 3.39 (1H, m), 4.39 (2H, t, J = 6.1), 4.70 (1H, sept, J = 6.1), 6.86 (1H, d, J = 8.5), 7.07 (1H, s), 7.19 (1H, br.s), 7.35 (2H, br.s), 7.48 (1H, br.m) 7.74 (1H, br.d, J = 6.4), 7.84 (2H, br.s), 8.05 (1H, br.s), 9.76 (1H, s), 10.15 (1H, br.s). MS (ES⁺): 633.8 (M + 1)⁺. |
| 39 | N2-(2-isopropoxy-4-methyl-5-(6-(4-methylpiperazin-1-yl)pyridin-3-yl)phenyl)-N4-(2-(isopropylsulfonyl)phenyl)-5-methylpyrimidine-2,4-diamine | 1.06 (6H, d, J = 6.7), 1.28 (6H, d, J = 6.0), 2.15 (6H, s), 2.19 (2H, br.m), 2.80 (3H, s), 2.82 (3H, s), 3.25 (2H, m), 3.39 (1H, m), 4.39 (2H, t, J = 6.1), 4.70 (1H, sept, J = 6.1), 6.86 (1H, d, J = 8.5), 7.07 (1H, s), 7.19 (1H, br.s), 7.35 (2H, br.s), 7.48 (1H, br.m) 7.74 (1H, br.d, J = 6.4), 7.84 (2H, br.s), 8.05 (1H, br.s), 9.76 (1H, s), 10.15 (1H, br.s). MS (ES⁺): 630.8 (M + 1)⁺. |

TABLE 1-continued

| | Structure | Physical Data<br>¹H NMR 400 MHz (DMSO-d6)<br>and/or MS (m/z) |
|---|---|---|
| 40 | N2-(2-isopropoxy-4-methyl-5-(6-morpholinopyridin-3-yl)phenyl)-N4-(2-(isopropylsulfonyl)phenyl)-5-methylpyrimidine-2,4-diamine | 1.08 (6H, d, J = 6.7), 1.28 (6H, d, J = 6.0), 2.15 (3H, s), 2.19 (3H, s), 3.59 (4H, br), 3.78 (4H, br) 4.70 (1H, sept, J = 6.1), 7.02 (1H, br.s), 7.07 (1H, s), 7.24 (1H, br.s), 7.35 (2H, br.s), 7.49 (1H, br.s), 7.75 (1H br.d, J = 6.8), 7.81 (1H, br.s), 7.86 (1H, br), 8.04 (1H, br.s), 9.76 (1H, br.s). MS (ES⁺): 617.8 (M + 1)⁺. |
| 41 | N2-(2-isopropoxy-4-methyl-5-(6-(piperazin-1-yl)pyridin-3-yl)phenyl)-N4-(2-(isopropylsulfonyl) phenyl)-5-methylpyrimidine-2,4-diamine | 1.12 (6H, d, J = 6.7), 1.31 (6H, d, J = 6.0), 2.09 (3H, s), 2.18 (3H, s), 3.25 (4H, br.s), 3.39 (1H, sept, J = 6.8), 3.75 (4H, br.t, J = 5.1), 4.68 (1H, sept, J = 6.1), 6.90 (1H, d, J = 9.0), 6.98 (1H, s), 7.01 (1H, br.s), 7.11 (1H, br.s), 7.44 (1H, s), 7.47 (1H, s) 7.70 (1H, d, J = 7.7), 7.92 (1H, s) 8.04 (1H, s), 8.23 (1H, br.s), 8.90 (1H, br.s), 8.94 (1H, br.s). MS (ES⁺): 616.8 (M + 1)⁺. |
| 42 | N2-(5-(6-(2-morpholinoethylamino)pyridin-3-yl)-2-isopropoxy-4-methylphenyl)-N4-(2-(isopropyl-sulfonyl)phenyl)-5-methylpyrimidine-2,4-diamine | MS (ES⁺): 660.8 (M + 1)⁺. |

| | Structure | Physical Data<br>¹H NMR 400 MHz (DMSO-d6)<br>and/or MS (m/z) |
|---|---|---|
| 43 | N2-(2-isopropoxy-4-methyl-5-(2-(4-methylpiperazin-1-yl)pyridin-4-yl)phenyl)-N4-(2-(isopropylsulfonyl)phenyl)-5-methylpyrimidine-2,4-diamine | 1.13 (6H, d, J = 6.8), 1.32 (6H, d, 6.0), 20.9 (3H, s), 2.20 (3H, s), 2.76 (3H, br.s), 3.1 (4H, very br.), 3.38 (H₂O overlap), 3.40 (1H, sept, J = 6.8), 4.36 (1H, very br), 4.70 (1H, sept, J = 6.0), 6.60 (1H, d, J = 4.7), 6.73 (1H, s), 7.00 (3h, br) 7.68 (1H, s), 7.72 (1H, dd, J = 1.8, 7.5), 7.95 (1H, s), 8.03 (1H, s), 8.12 (1H, d, J = 5.1), 8.31 (1H, br.d, J = 7.6), 8.91 (1H, s). 630.8 (M + 1)⁺. |
| 44 | 5-chloro-N2-(2-isopropoxy-5-methyl-4-((1s,4s)-4-(methylamino)cyclohexyl)phenyl)-N4-(2-(isopropylsulfonyl)phenyl)pyrimidine-2,4-diamine | MS (ES⁺): 586.3 (M + 1)⁺ |
| 45 | 5-chloro-N2-(2-isopropoxy-5-methyl-4-((1r,4r)-4-(methylamino)cyclohexyl)phenyl)-N4-(2-(isopropylsulfonyl)phenyl)pyrimidine-2,4-diamine | MS (ES⁺): 586.3 (M + 1)⁺ |

TABLE 1-continued

| | Structure | Physical Data<br>¹H NMR 400 MHz (DMSO-d6)<br>and/or MS (m/z) |
|---|---|---|
| 46 | 5-chloro-N2-(2-isopropoxy-4-methyl-5-(3-methylisoxazol-5-yl)phenyl)-N4-(2-(isopropylsulfonyl)phenyl)pyrimidine-2,4-diamine | 1H NMR (400 MHz, MeOD-d4) δ 8.15 (1H, s), 8.12 (1H, d, J = 7.6 Hz), 7.93 (1H, s), 7.78 (1H, d, J = 7.6 Hz), 7.20 (2H, m), 6.96 (1H, s), 6.18 (1H, s), 4.68 (1H, m), 3.28 (1H, m), 2.38 (3H, s), 2.23 (3H, s), 1.26 (6H, d, J = 6.0 Hz), 1.16 (6H, d, J = 6.8 Hz). MS (ES⁺): 556.2 (M + 1)⁺. |
| 47 | 2-(5-chloro-2-(2-isopropoxy-4-methyl-5-(3-methylisoxazol-5-yl)phenylamino)pyrimidin-4-ylamino)-N,N-dimethylbenzenesulfonamide | 1H NMR (400 MHz, MeOD-d4) δ 8.20 (1H, s), 8.12 (1H, d, J = 7.6 Hz), 7.97 (1H, s), 7.78 (1H, d, J = 7.6 Hz), 7.20 (2H, m), 7.01 (1H, s), 6.24 (1H, s), 4.74 (1H, m), 2.68 (6H, s), 2.43 (3H, s), 2.29 (3H, s), 1.32 (6H, d, J= 6.0 Hz). MS (ES⁺): 557.2 (M + 1)⁺. |
| 48 | 5-chloro-N2-(2-isopropoxy-4-methyl-5-(5-methyl-1H-pyrazol-3-yl)phenyl)-N4-(2-(isopropylsulfonyl)phenyl)pyrimidine-2,4-diamine | 1H NMR (400 MHz, MeOD-d4) δ 8.29 (1H, s), 8.13 (1H, bs), 7.97 (1H, s), 7.87 (1H, d, J = 7.6 Hz), 7.75 (1H, s), 7.35 (2H, m), 7.09 (1H, s), 6.41 (1H, s), 4.80 (1H, m), 3.40 (1H, m), 2.50 (3H, s), 2.40 (3H, s), 1.36 (6H, d, J = 6.0 Hz), 1.25 (3H, d, J = 6.8 Hz). MS (ES⁺): 555.2 (M + 1)⁺. |

TABLE 1-continued

| | Structure | Physical Data<br>¹H NMR 400 MHz (DMSO-d6)<br>and/or MS (m/z) |
|---|---|---|
| 49 | 5-chloro-N2-(2-isopropoxy-4-methyl-5-(1H-pyrazol-3-yl)phenyl)-N4-(2-(isopropylsulfonyl) phenyl)pyrimidine-2,4-diamine | 1H NMR (400 MHz, MeOD-d4) δ 8.27 (1H, s), 8.20 (1H, bs), 7.90 (1H, d, J = 6.4 Hz), 7.81 (1H, bs), 7.67 (1H, s), 7.37 (2H, bs), 7.08 (1H, s), 6.45 (1H, s), 4.76 (1H, m), 3.38 (1H, m), 2.41 (3H, s), 1.35 (6H, d, J = 6.0 Hz), 1.25 (3H, d, J = 6.8 Hz). MS (ES⁺): 541.2 (M + 1)⁺. |
| 50 | 2-(5-chloro-2-(2-isopropoxy-5-(isoxazol-5-yl)-4-methylphenylamino)pyrimidin-4-ylamino)-N,N-dimethylbenzenesulfonamide | 1H NMR (400 MHz, MeOD-d4) δ 8.31 (1H, s), 8.16 (1H, s), 8.03 (1H, bs), 7.92 (1H, s), 7.74 (1H, d, J = 7.2 Hz), 7.17 (2H, bs), 6.99 (1H, s), 6.34 (1H, s), 4.69 (1H, m), 2.64 (6H, s), 2.39 (3H, s), 1.27 (6H, d, J = 6.0 Hz). MS (ES⁺): 543.2 (M + 1)⁺. |
| 51 | 2-(5-chloro-2-(2-isopropoxy-4-methyl-5-(2-methyl-1H-imidazol-4-yl)phenylamino)pyrimidin-4-ylamino)-N,N-dimethylbenzenesulfonamide | 1H NMR (400 MHz, MeOD-d4) δ 8.18 (1H, s), 7.94 (1H, d, J = 5.2 Hz), 7.72 (1H, s), 7.70 (1H, s), 7.29 (2H, bs), 7.21 (2H, bs), 7.00 (1H, s), 4.68 (1H, m), 2.65 (6H, s), 2.58 (3H, s), 2.28 (3H, s), 1.27 (6H, d, J = 6.0 Hz). MS (ES⁺): 556.2 (M + 1)⁺. |

TABLE 1-continued

| | Structure | Physical Data<br>¹H NMR 400 MHz (DMSO-d6)<br>and/or MS (m/z) |
|---|---|---|
| 52 | 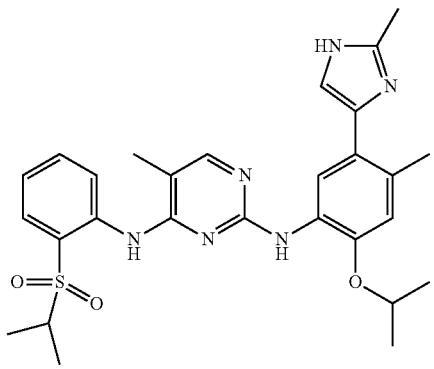 [SMILES: Cc1nc(-c2cc(Nc3ncc(C)c(Nc4ccccc4S(=O)(=O)C(C)C)n3)c(OC(C)C)cc2C)c[nH]1]<br>5-chloro-N2-(2-isopropoxy-4-methyl-5-(2-methyl-1H-imidazol-4-yl)phenyl)-N4-(2-(isopropylsulfonyl)phenyl)pyrimidine-2,4-diamine | 1H NMR (400 MHz, MeOD-d4) δ 8.10 (1H, bs), 7.90 (1H, s), 7.85 (1H, d, J = 7.6 Hz), 7.65 (1H, s), 7.48 (1H, bs), 7.36 (2H, bs), 7.12 (1H, s), 4.70 (1H, m), 3.39 (1H, m), 2.70 (3H, s), 2.40 (3H, s), 2.26 (3H, s), 1.34 (6H, d, J = 6.0 Hz), 1.24 (6H, d, J = 6.8 Hz). MS (ES⁺): 535.2 (M + 1)⁺. |
| 53 | 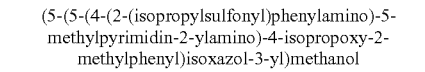<br>(5-(5-(4-(2-(isopropylsulfonyl)phenylamino)-5-methylpyrimidin-2-ylamino)-4-isopropoxy-2-methylphenyl)isoxazol-3-yl)methanol | 1H NMR (400 MHz, MeOD-d4) δ 8.39 (1H, s), 8.31 (1H, d, J = 8.0 Hz), 7.98 (1H, s), 7.81 (1H, d, J = 7.2 Hz), 7.19 (1H, bs), 7.10 (1H, bs), 6.97 (1H, s), 6.29 (1H, s), 4.78 (1H, m), 4.66 (2H, s), 3.39 (1H, m), 2.44 (3H, s), 2.18 (3H, s), 2.26 (3H, s), 1.41 (6H, d, J = 5.6 Hz), 1.27 (6H, d, J = 6.8 Hz). MS (ES⁺): 552.6 (M+1)⁺. |
| 54 | 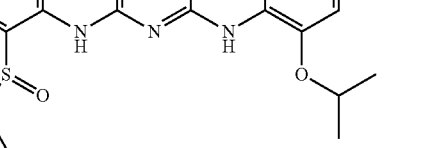<br>N2-(2-isopropoxy-4-methyl-5-(3-((piperazin-1-yl)methyl)isoxazol-5-yl)phenyl)-N4-(2-(isopropyl-sulfonyl)phenyl)-5-methylpyrimidine-2,4-diamine | 1H NMR (400 MHz, MeOD-d4) δ 8.31 (1H, d, J = 8.4 Hz), 8.29 (1H, s), 7.88 (1H, s), 7.71 (1H, d, J = 8.0 Hz), 7.11 (1H, t, J = 8.8 Hz), 6.98 (1H, t, J = 7.2 Hz), 6.88 (1H, s), 6.25 (1H, s), 4.67 (1H, m), 3.59 (2H, s), 3.22 (1H, m), 3.03 (4H, bs), 2.61 (4H, bs), 2.35 (3H, s), 2.07 (3H, s), 1.30 (6H, d, J = 5.6 Hz), 1.17 (6H, d, J = 6.8 Hz). MS (ES⁺): 620.8 (M + 1)⁺. |

TABLE 1-continued

| | Structure | Physical Data<br>$^1$H NMR 400 MHz (DMSO-d6)<br>and/or MS (m/z) |
|---|---|---|
| 55 | 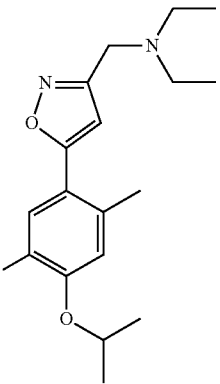<br>N2-(5-(3-((diethylamino)methyl)isoxazol-5-yl)-2-isopropoxy-4-methylphenyl)-N4-(2-(isopropyl-sulfonyl)phenyl)-5-methylpyrimidine-2,4-diamine | 1H NMR (400 MHz, MeOD-d4) δ 8.35 (1H, s), 8.33 (1H, d, J = 8.4 Hz), 7.89 (1H, s), 7.72 (1H, d, J = 8.0 Hz), 7.15 (1H, t, J = 8.8 Hz), 7.01 (1H, t, J = 7.2 Hz), 6.90 (1H, s), 6.47 (1H, s), 4.69 (1H, m), 4.19 (2H, s), 3.24 (1H, m), 3.00 (4H, bs), 2.38 (3H, s), 2.08 (3H, s), 1.22 (6H, t, J = 7.2 Hz), 1.17 (6H, d, J = 6.8 Hz). MS (ES$^+$): 607.8 (M + 1)$^+$. |
| 56 | 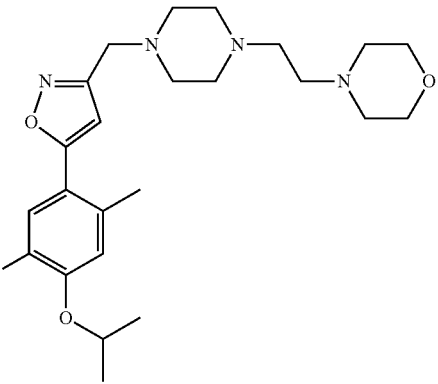<br>N2-(2-isopropoxy-4-methyl-5-(3-((4-(2-morpholinoethyl)piperazin-1-yl)methyl)isoxazol-5-yl)phenyl)-N4-(2-(isopropylsulfonyl)phenyl)-5-methylpyrimidine-2,4-diamine | 1H NMR (400 MHz, MeOD-d4) δ 8.31 (1H, d, J = 8.4 Hz), 8.28 (1H, s), 7.87 (1H, s), 7.70 (1H, d, J = 8.0 Hz), 7.08 (1H, t, J = 8.8 Hz), 6.99 (1H, t, J = 7.2 Hz), 6.87 (1H, s), 6.25 (1H, s), 4.66 (1H, m), 3.61 (4H, m), 3.55 (2H, s), 3.21 (1H, m), 2.34-2.59 (12H, m), 2.35 (3H, s), 2.06 (3H, s), 1.29 (6H, d, J = 6.0 Hz), 1.16 (6H, d, J = 6.8 Hz). MS (ES$^+$): 733.4 (M + 1)$^+$. |
| 57 | 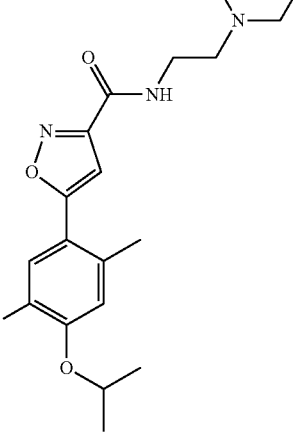<br>5-(5-(4-(2-(isopropylsulfonyl)phenylamino)-5-chloropyrimidin-2-ylamino)-4-isopropoxy-2-methylphenyl)-N-(2-morpholinoethyl)isoxazole-3-carboxamide | 1H NMR (400 MHz, MeOD-d4) δ 8.33 (1H, s), 8.17 (1H, bs), 7.93 (1H, s), 7.92 (1H, d, J = 7.2 Hz), 7.91 (1H, s), 7.37-7.39 (2H, m), 7.17 (1H, s), 6.83 (1H, s), 4.84 (1H, m), 4.11 (2H, dd, J = 2.8 and 12.8 Hz) 3.83-3.88 (4H, m), 3.70 (2H, d, J = 12.4 Hz), 3.42-3.48 (3H, m), 3.21 (2H, m), 2.54 (3H, s), 1.36 (6H, d, J = 6.0 Hz), 1.26 (6H, d, J = 6.8 Hz). MS (ES$^+$): 698.2 (M + 1)$^+$. |

TABLE 1-continued

| | Structure | Physical Data<br>$^1$H NMR 400 MHz (DMSO-d6)<br>and/or MS (m/z) |
|---|---|---|
| 58 | 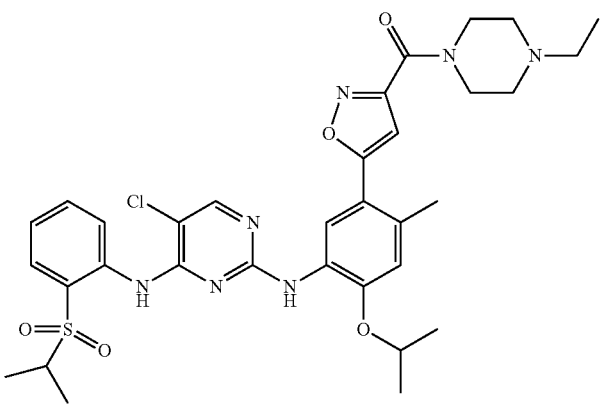 [SMILES: CCN1CCN(C(=O)c2cc(-c3cc(Nc4ncc(Cl)c(Nc5ccccc5S(=O)(=O)C(C)C)n4)c(OC(C)C)cc3C)on2)CC1]<br>(5-(5-(4-(2-(isopropylsulfonyl)phenylamino)-5-chloropyrimidin-2-ylamino)-4-isopropoxy-2-methylphenyl)isoxazol-3-yl)(4-ethylpiperazin-1-yl)methanone | 1H NMR (400 MHz, MeOD-d4) δ 8.33 (1H, s), 8.12 (1H, bs), 7.93 (1H, s), 7.95 (1H, s), 7.91 (1H, d, J = 8.8 Hz), 7.35-7.44 (2H, m), 7.15 (1H, s), 6.76 (1H, s), 4.85 (1H, m), 3.66-3.76 (4H, m) 3.38-3.43 (2H, m), 3.10 (2H, m), 2.54 (3H, s), 1.42 (3H, t, J = 7.2 Hz), 1.37 (6H, d, J = 6.0 Hz), 1.27 (6H, d, J = 6.8 Hz). MS (ES$^+$): 682.3 (M + 1)$^+$. |
| 59 | 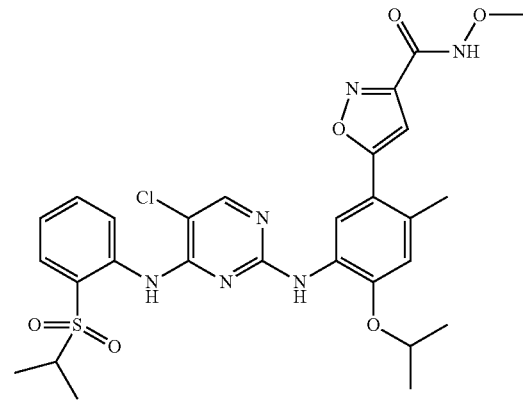 [SMILES: CONC(=O)c1cc(-c2cc(Nc3ncc(Cl)c(Nc4ccccc4S(=O)(=O)C(C)C)n3)c(OC(C)C)cc2C)on1]<br>(5-(5-(4-(2-(isopropylsulfonyl)phenylamino)-5-chloropyrimidin-2-ylamino)-4-isopropoxy-2-methylphenyl)-N-methoxyisoxazole-3-carboxamide | 1H NMR (400 MHz, MeOD-d4) δ 8.17 (1H, s), 8.06 (1H, d, J = 8.0 Hz), 8.02 (1H, s), 7.77 (1H, d, J = 7.6 Hz), 7.21 (1H, bs), 7.12 (1H, t, J = 7.6 Hz), 6.97 (1H, s), 6.51 (1H, s), 4.71 (1H, m), 3.77 (3H, s), 3.29 (1H, m), 2.39 (3H, s), 1.28 (6H, d, J = 6.0 Hz), 1.17 (6H, d, J = 6.8 Hz). MS (ES$^+$): 615.1 (M + 1)$^+$. |
| 60 | 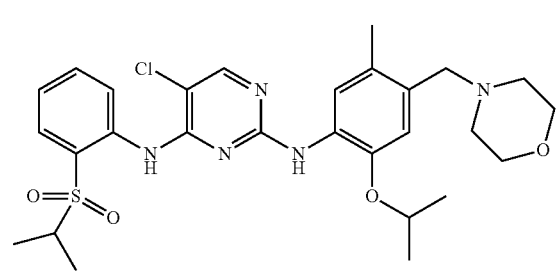 [SMILES: Cc1cc(Nc2ncc(Cl)c(Nc3ccccc3S(=O)(=O)C(C)C)n2)c(OC(C)C)cc1CN1CCOCC1]<br>5-Chloro-N2-(2-isopropoxy-5-methyl-4-morpholin-4-ylmethyl-phenyl)-N4-[2-(propane-2-sulfonyl)-phenyl]-pyrimidine-2,4-diamine | 1H NMR (400 MHz, CDCl3) 10.35 (s, 1H), 8.38 (d, 1H0, 7.93 (d, 1H), 7.59 (m, 2H), 7.41-7.36 (m, 2H), 4.70-4.63 (br, 1H), 4.30-4.18 (br, 2H), 4.15-4.10 (br, 2H), 4.00-3.97 (br, 2H), 3.52-3.46 (br, 2H), 3.20 (m, 1H), 2.95-2.84 (br, 2H), 2.24 (s, 3H), 1.31 (d, 12H). MS (ES$^+$): 574.2 (M + 1)$^+$. |

TABLE 1-continued

| | Structure | Physical Data<br>¹H NMR 400 MHz (DMSO-d6)<br>and/or MS (m/z) |
|---|---|---|
| 61 | N2-(4-(1H-benzo[d]imidazol-2-yl)-2-isopropoxy-5-methylphenyl)-5-chloro-N4-(2-(isopropylsulfonyl)phenyl)pyrimidine-2,4-diamine | 1H NMR (400 MHz, CDCl3) 10.43 (s, 1H), 9.68 (s, 1H), 8.32 (d, 1H), 8.04 (s, 1H), 7.93 (d, 1H), 7.71-7.65 (m, 3H), 7.59 (s, 1H), 7.40-7.37 (, 3H), 4.46-4.43 (m, 1H), 3.31-3.20 (m, 1H), 2.38 (s, 3H), 1.32 (d, 6H), 1.15 (d, 6H). MS (ES⁺): 591.2 (M + 1)⁺. |
| 62 | 5-(4-(2-(isopropylsulfonyl)phenylamino)-5-chloropyrimidin-2-ylamino)-4-isopropoxy-N-methyl-2-((pyrrolidin-1-yl)methyl)benzamide | MS (ES⁺): 601.2 (M+1)⁺. |
| 63 | 5-(4-(2-(isopropylsulfonyl)phenylamino)-5-chloropyrimidin-2-ylamino)-4-isopropoxy-N-methyl-2-(piperidin-4-yl)benzamide | 1H NMR: (DMSO-d6 + trace D2O): δ 8.46 (d, 1H); 8.30 (s, 1H); 7.83 (s, 1H); 7.81 (s, 1H); 7.58 (t, 1); 7.33 (t, 1H); 6.88 (s, 1H); 4.65 (m, 1H); 3.37 (m, 1H); 3.35 (d, 2H); 3.18 (m, 1H); 2.98 (m, 2H); 2.65 (s, 3H); 1.90 (d, 2H); 1.84 (m, 2H); 1.28 (d, 6H); 1.17 (d, 6H). MS (ES⁺): 602.2 (M + 1)⁺. |

TABLE 1-continued

| | Structure | Physical Data<br>¹H NMR 400 MHz (DMSO-d6)<br>and/or MS (m/z) |
|---|---|---|
| 64 | 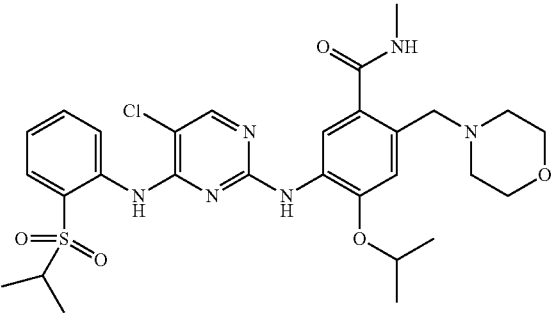 [SMILES: CNC(=O)c1cc(Nc2ncc(Cl)c(Nc3ccccc3S(=O)(=O)C(C)C)n2)c(OC(C)C)cc1CN1CCOCC1]<br>5-(4-(2-(isopropylsulfonyl)phenylamino)-5-chloropyrimidin-2-ylamino)-4-isopropoxy-N-methyl-2-(morpholinomethyl)benzamide | 1H NMR: (DMSO-d6 + trace D2O): δ 8.48 (d, 1H); 8.36 (s, 1H); 8.27 (s, 1H); 7.82 (dd, 1H); 7.52 (m, 1H); 7.36 (d, 1H); 7.33 (s, 1H); 4.76 (m, 1H); 7.36 (d, 1H); 4.01 (d, 2H); 3.70 (t, 2H); 3.44 (m, 1H); 3.36 (d, 2H); 3.19 (t, 2H); 2.66 (s, 3H); 1.30 (d, 6H); 1.18 (d, 6H). MS (ES+): 617.2 (M + 1)+. |
| 65 | 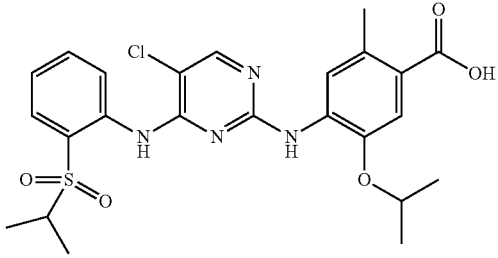 [SMILES: Cc1cc(Nc2ncc(Cl)c(Nc3ccccc3S(=O)(=O)C(C)C)n2)c(OC(C)C)cc1C(=O)O]<br>4-(4-(2-(isopropylsulfonyl)phenylamino)-5-chloropyrimidin-2-ylamino)-5-isopropoxy-2-methylbenzoic acid | (TFA salt, CD3OD) δ 8.44 (d, 1H), 8.31 (s, 1H), 8.09 (s, 1H), 7.98 (d, 1H), 7.80 (dd, 1H), 7.59 (s, 1H), 7.45 (dd, 1H), 4.75-4.65 (m, 1H), 3.40-3.30 (m, 1H, partially obscured by CD3OD peak), 2.36 (s, 3H), 1.41 (d, 6H), 1.31 (d, 6H). MS (ES+): 519.1 (M + 1)+. |
| 66 | 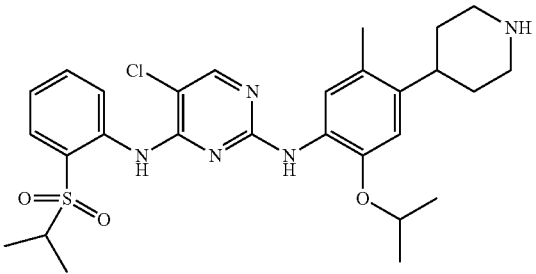 [SMILES: Cc1cc(Nc2ncc(Cl)c(Nc3ccccc3S(=O)(=O)C(C)C)n2)c(OC(C)C)cc1C1CCNCC1]<br>5-chloro-N2-(2-isopropoxy-5-methyl-4-(piperidin-4-yl)phenyl)-N4-[2-(propane-2-sulfonyl)-phenyl]-pyrimidine-2,4-diamine | (HCl salt, DMSO-d6 + trace D2O) δ 8.32 (s, 1H), 8.27 (d, 1H), 7.88 (d, 1H), 7.67 (dd, 1H), 7.45 (dd, 1H), 7.42 (s, 1H), 6.79 (s, 1H), 4.56-4.48 (m, 1H), 3.49-3.32 (m, 3H), 3.10-2.91 (m, 3H), 2.09 (s, 3H), 1.89-1.77 (m, 4H), 1.22 (d, 6H), 1.13 (d, 6H). MS (ES+): 558.1 (M + 1)+. |
| 67 | 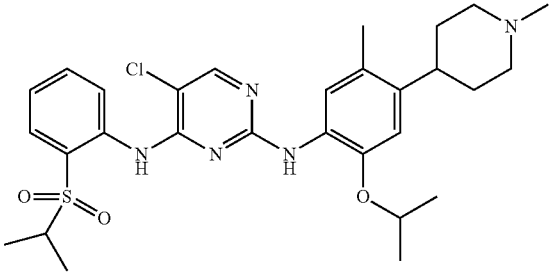 [SMILES: Cc1cc(Nc2ncc(Cl)c(Nc3ccccc3S(=O)(=O)C(C)C)n2)c(OC(C)C)cc1C1CCN(C)CC1]<br>5-chloro-N2-(2-isopropoxy-5-methyl-4-(1-methylpiperidin-4-yl)phenyl)-N4-[2-(propane-2-sulfonyl)phenyl]-pyrimidine-2,4-diamine | (HCl salt, DMSO-d6 + trace D2O) δ 8.28 (s, 1H), 8.19 (d, 1H), 7.86 (d, 1H), 7.66 (dd, 1H), 7.45 (dd, 1H), 7.37 (s, 1H), 6.77 (s, 1H), 4.56-4.49 (m, 1H), 3.51-3.37 (m, 3H), 3.16-3.08 (m, 2H), 2.98-2.88 (m, 1H), 2.77 (s, 3H), 2.05 (s, 3H), 1.90-1.81 (m, 4H), 1.19 (d, 6H), 1.11 (d, 6H). MS (ES+): 572.2 (M + 1)+. |

TABLE 1-continued

| | Structure | Physical Data<br>¹H NMR 400 MHz (DMSO-d6)<br>and/or MS (m/z) |
|---|---|---|
| 68 | (4-(4-(2-(isopropylsulfonyl)phenylamino)-5-chloropyrimidin-2-ylamino)-5-isopropoxy-2-methylphenyl)(4-methylpiperazin-1-yl)methanone | MS (ES⁺): 601.2 (M + 1)⁺. |
| 69 | 5-chloro-N2-(2-isopropoxy-5-methyl-4-(1-(1-methylpiperidin-4-yl)piperidin-4-yl)phenyl)-N4-(2-(isopropylsulfonyl)phenyl)pyrimidine-2,4-diamine | MS (ES⁺): 655.3 (M + 1)⁺. |
| 70 | 5-chloro-N2-(2-isopropoxy-5-methyl-4-(6-(4-methylpiperazin-1-yl)pyridin-3-yl)phenyl)-N4-(2-(isopropylsulfonyl)phenyl)pyrimidine-2,4-diamine | MS (ES⁺): 650.3 (M + 1)⁺. |
| 71 | 5-chloro-N2-(2-cyclobutoxy-5-methyl-4-(piperidin-4-yl)phenyl)-N4-(2-(isopropylsulfonyl) phenyl)pyrimidine-2,4-diamine | MS (ES⁺): 570.2 (M + 1)⁺. |

TABLE 1-continued

| | Structure | Physical Data $^1$H NMR 400 MHz (DMSO-d6) and/or MS (m/z) |
|---|---|---|
| 72 | 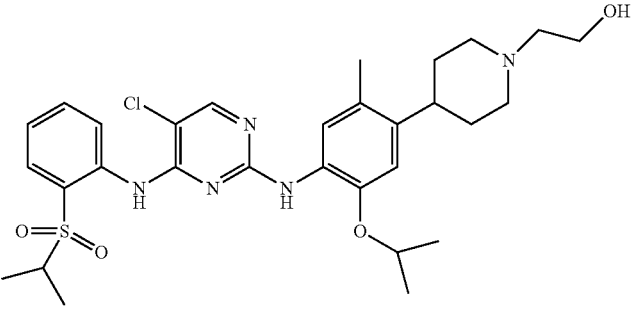 [SMILES: Cc1cc(Nc2ncc(Cl)c(Nc3ccccc3S(=O)(=O)C(C)C)n2)c(OC(C)C)cc1C1CCN(CCO)CC1]<br>2-[4-(4-{5-Chloro-4-[2-(propane-2-sulfonyl)-phenylamino]-pyrimidin-2-ylamino}-5-isopropoxy-2-methyl-phenyl)-piperidin-1-yl]-ethanol | MS (ES$^+$): 602.2 (M + 1)$^+$. |
| 73 | 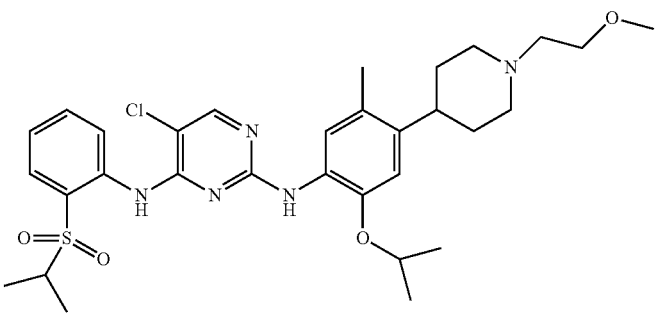 [SMILES: COCCN1CCC(c2cc(OC(C)C)c(Nc3ncc(Cl)c(Nc4ccccc4S(=O)(=O)C(C)C)n3)cc2C)CC1]<br>5-chloro-N2-(2-isopropoxy-4-(1-(2-methoxyethyl)piperidin-4-yl)-5-methylphenyl)-N4-(2-(isopropylsulfonyl)phenyl)pyrimidine-2,4-diamine | MS (ES$^+$): 616.3 (M + 1)$^+$. |
| 74 | 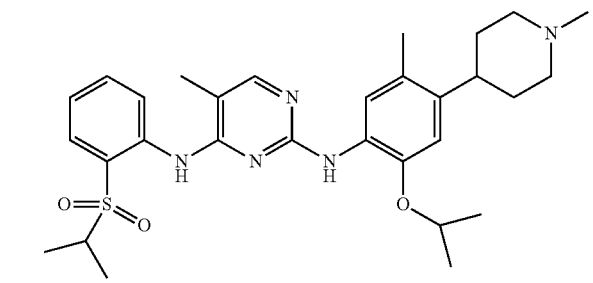 [SMILES: Cc1cc(Nc2ncc(C)c(Nc3ccccc3S(=O)(=O)C(C)C)n2)c(OC(C)C)cc1C1CCN(C)CC1]<br>N2-(2-isopropoxy-5-methyl-4-(1-methylpiperidin-4-yl)phenyl)-N4-(2-(isopropylsulfonyl)phenyl)-5-methylpyrimidine-2,4-diamine | $^1$H NMR (HCl salt, DMSO-d6 + trace D2O, 400 MHz) 8.04 (s, 1H), 7.96 (dd, J = 8.0, 1.6 Hz, 2H), 7.79 (m, 1H), 7.61 (m, 1H), 7.27 (s, 1H), 6.81 (s, 1H), 4.55 (m, 1H), 3.43 (m, 3H), 3.08 (m, 2H), 2.91 (m, 1H), 2.77 (s, 3H), 2.17 (s, 3H), 1.98 (s, 3H), 1.91 (m, 2H), 1.80 (m, 2H), 1.24 (d, J = 6.0 Hz, 6H), 1.10 (d, J = 6.8 Hz, 6H). MS (ES$^+$): 552.7 (M + 1)$^+$. |
| 75 | 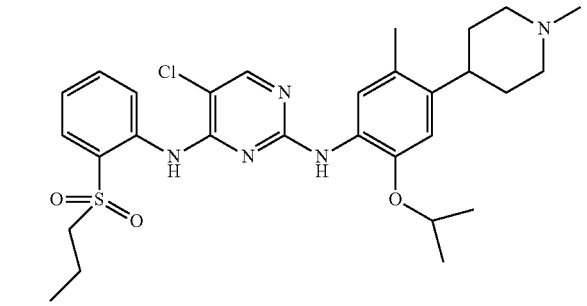 [SMILES: CCCS(=O)(=O)c1ccccc1Nc1nc(Nc2cc(C)c(C3CCN(C)CC3)cc2OC(C)C)ncc1Cl]<br>5-chloro-N2-(2-isopropoxy-5-methyl-4-(1-methylpiperidin-4-yl)phenyl)-N4-(2-(propylsulfonyl)phenyl)pyrimidine-2,4-diamine | $^1$H NMR (HCl salt, CD$_3$OD, 400 MHz) 8.15 (s, 1H), 8.05 (m, 1H), 7.94 (dd, J = 8.0, 1.2 Hz, 1H), 7.66 (m, 1H), 7.50 (m, 1H), 7.19 (s, 1H), 6.83 (s, 1H), 4.60 (m, 1H), 3.54 (m, 2H), 3.13 (m, 4H), 2.99 (m, 1H), 2.82 (s, 3H), 2.06 (s, 3H), 1.91 (m, 4H), 1.54 (m, 2H), 1.19 (d, J = 2.0 Hz, 6H), 0.82 (t, J = 7.6 Hz, 3H). MS (ES$^+$): 572.2 (M + 1)$^+$. MS (ES$^+$): 572.2 (M + 1)$^+$. |

TABLE 1-continued

| | Structure | Physical Data<br>¹H NMR 400 MHz (DMSO-d6)<br>and/or MS (m/z) |
|---|---|---|
| 76 | 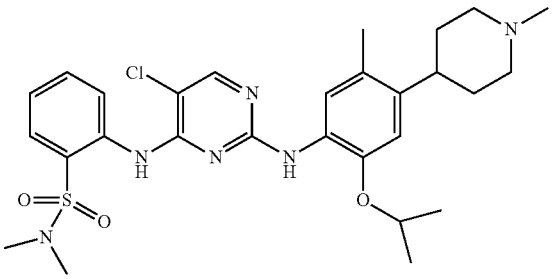<br>2-(5-chloro-2-(2-isopropoxy-5-methyl-4-(1-methylpiperidin-4-yl)phenylamino)pyrimidin-4-ylamino)-N,N-dimethylbenzenesulfonamide | ¹H NMR (HCl salt, CD₃OD, 400 MHz) 8.14 (s, 1H), 8.09 (m, 1H), 7.86 (dd, J = 8.0, 1.6 Hz, 1H), 7.59 (m, 1H), 7.44 (m, 1H), 7.24 (s, 1H), 6.83 (s, 1H), 4.59 (m, 1H), 3.51 (m, 2H), 3.13 (m, 2H), 3.02 (m, 1H), 2.82 (s, 3H), 2.62 (s, 6H), 2.09 (s, 3H), 1.92 (m, 4H), 1.19 (d, J = 6.0 Hz, 6H). MS (ES⁺): 573.1 (M + 1)⁺. |
| 77 | 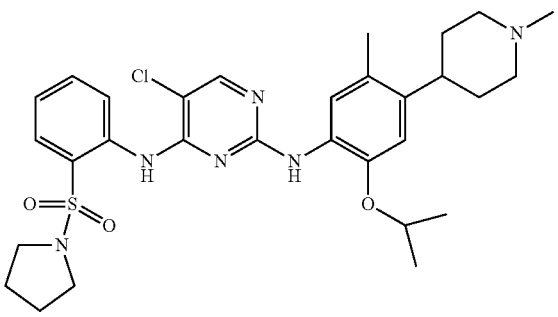 [SMILES: Cc1cc(Nc2ncc(Cl)c(Nc3ccccc3S(=O)(=O)N3CCCC3)n2)c(OC(C)C)cc1C1CCN(C)CC1]<br>5-chloro-N2-(2-isopropoxy-5-methyl-4-(1-methylpiperidin-4-yl)phenyl)-N4-(2-(pyrrolidin-1-ylsulfonyl)phenyl)pyrimidine-2,4-diamine | ¹H NMR (HCl salt, CD₃OD, 400 MHz) 8.14 (s, 1H), 8.09 (m, 1H), 7.89 (dd, J = 8.0, 1.6 Hz, 1H), 7.58 (m, 1H), 7.40 (m, 1H), 7.28 (s, 1H), 6.83 (s, 1H), 4.59 (m, 1H), 3.51 (m, 2H), 3.13 (m, 6H), 3.02 (m, 1H), 2.82 (s, 3H), 2.09 (s, 3H), 1.91 (m, 4H), 1.67 (m, 4H), 1.20 (d, J = 6.0 Hz, 6H). MS (ES⁺): 573.1 (M + 1)⁺. MS (ES⁺): 599.3 (M + 1)⁺. |
| 78 | 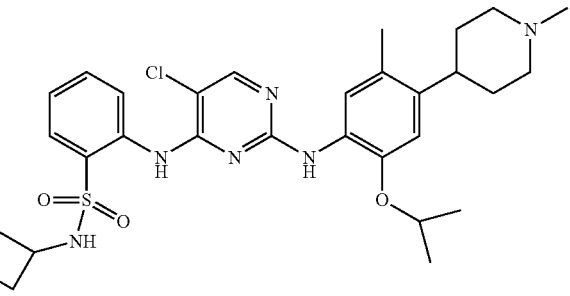<br>5-chloro-N4-(2-(cyclobutylaminosulfonyl)phenyl)-N2-(2-isopropoxy-5-methyl-4-(1-methylpiperidin-4-yl)phenyl)pyrimidine-2,4-diamine | ¹H NMR (HCl salt, CD₃OD, 400 MHz) 8.17 (s, 1H), 8.05 (m, 1H), 7.89 (dd, J = 8.0, 1.6 Hz, 1H), 7.56 (m, 1H), 7.38 (m, 1H), 7.28 (s, 1H), 6.84 (s, 1H), 4.61 (m, 1H), 3.59 (m, 1H), 3.51 (m, 2H), 3.14 (m, 2H), 3.00 (m, 1H), 2.82 (s, 3H), 2.07 (s, 3H), 1.91 (m, 6H), 1.67 (m, 2H), 1.36 (m, 2H), 1.20 (d, J = 6.0 Hz, 6H). MS (ES⁺): 599.3 (M + 1)⁺. |
| 79 | 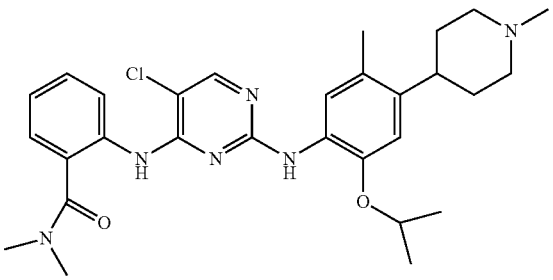<br>2-(2-(2-isopropoxy-5-methyl-4-(1-methylpiperidin-4-yl)phenylamino)-5-chloropyrimidin-4-ylamino)-N,N-dimethylbenzamide | ¹H NMR (HCl salt, CD₃OD, 400 MHz) 8.15 (s, 1H), 7.78 (m, 1H), 7.59 (m, 1H), 7.54 (m, 1H), 7.46 (m, 1H), 7.33 (s, 1H), 6.90 (s, 1H), 4.69 (m, 1H), 3.61 (m, 2H), 3.22 (m, 2H), 3.09 (m, 1H), 3.06 (s, 3H), 2.92 (s, 6H), 2.17 (s, 3H), 2.00 (m, 4H), 1.30 (d, J = 6.0 Hz, 6H). MS (ES⁺): 537.3 (M + 1)⁺. |

TABLE 1-continued

| | Structure | Physical Data<br>¹H NMR 400 MHz (DMSO-d6)<br>and/or MS (m/z) |
|---|---|---|
| 80 | 2-(2-(2-isopropoxy-5-methyl-4-(1-methylpiperidin-4-yl)phenylamino)-5-chloropyrimidin-4-ylamino)benzamide | ¹H NMR (HCl salt, CD₃OD, 400 MHz) 8.60 (s, 1H), 8.15 (s, 1H), 7.88 (m, 1H), 7.48 (m, 1H), 7.44 (m, 1H), 7.33 (m, 1H), 6.99 (s, 1H), 4.69 (m, 1H), 3.64 (m, 2H), 3.28 (m, 3H), 2.95 (s, 3H), 2.32 (s, 3H), 2.08 (m, 4H), 1.30 (d, J = 6.0 Hz, 6H). MS (ES⁺): 509.2 (M + 1)⁺. |
| 81 | 5-chloro-N2-(2-isopropoxy-5-methyl-4-(1-methylpiperidin-4-yl)phenyl)-N4-(2-(aminosulfonyl)phenyl)pyrimidine-2,4-diamine | ¹H NMR (HCl salt, CD₃OD, 400 MHz) 8.12 (s, 1H), 8.09 (s, 1H), 7.94 (dd, J = 8.0, 1.6 Hz, 1H), 7.52 (m, 1H), 7.36 (m, 1H), 7.28 (s, 1H), 6.85 (s, 1H), 4.60 (m, 1H), 3.51 (m, 2H), 3.09 (m, 2H), 3.02 (m, 1H), 2.82 (s, 3H), 2.11 (s, 3H), 1.92 (m, 4H), 1.19 (d, J = 6.0 Hz, 6H). MS (ES⁺): 545.2 (M + 1)⁺. |
| 82 | 5-chloro-N2-(2-isopropoxy-5-methyl-4-(1-methylpiperidin-4-yl)phenyl)-N4-(2-(methylsulfonyl)phenyl)pyrimidine-2,4-diamine | ¹H NMR (HCl salt, CD₃OD, 400 MHz) 8.14 (s, 1H), 8.04 (s, 1H), 8.00 (dd, J = 8.0, 1.6 Hz, 1H), 7.67 (m, 1H), 7.49 (m, 1H), 7.23 (s, 1H), 6.82 (s, 1H), 4.58 (m, 1H), 3.54 (m, 2H), 3.14 (m, 2H), 3.10 (s, 3H), 3.00 (m, 1H), 2.82 (s, 3H), 2.08 (s, 3H), 1.89 (m, 4H), 1.19 (d, J = 6.0 Hz, 6H). MS (ES⁺): 544.2 (M + 1)⁺. |
| 83 | 5-chloro-N2-(2-fluoro-5-methyl-4-(1-methylpiperidin-4-yl)phenyl)-N4-(2-(aminosulfonyl)phenyl)pyrimidine-2,4-diamine | ¹H NMR (HCl salt, DMSO-d6, 400 MHz) 9.61 (s, 1H), 9.39 (s, 1H), 9.11 (s, 1H), 8.38 (d, J = 8.0 Hz, 1H), 8.23 (s, 1H), 7.84 (dd, J = 8.0, 1.6 Hz, 1H), 7.70 (s, 2H), 7.41 (m, 1H), 7.33 (d, J = 8.0 Hz, 1H), 7.20 (m, 1H), 7.00 (d, J = 12.4 Hz, 1H), 3.52 (m, 2H), 3.11 (m, 2H), 2.99 (m, 1H), 2.82 (d, J = 4.8 Hz, 3H), 2.25 (s, 3H), 1.92 (m, 2H), 1.81 (m, 2H). MS (ES⁺): 505.2 (M + 1)⁺. |

TABLE 1-continued

| | Structure | Physical Data<br>¹H NMR 400 MHz (DMSO-d6)<br>and/or MS (m/z) |
|---|---|---|
| 84 | 5-chloro-N4-(2-(cyclobutylsulfonyl)phenyl)-N2-(2-isopropoxy-5-methyl-4-(1-methylpiperidin-4-yl)phenyl)pyrimidine-2,4-diamine | ¹H NMR (HCl salt, CD₃OD, 400 MHz) 8.15 (s, 1H), 8.07 (s, 1H), 7.92 (dd, J = 8.0, 1.6 Hz, 1H), 7.65 (m, 1H), 7.47 (m, 1H), 7.20 (s, 1H), 6.84 (s, 1H), 4.58 (m, 1H), 3.99 (m, 1H), 3.52 (m, 2H), 3.14 (m, 2H), 3.02 (m, 1H), 2.83 (s, 3H), 2.35 (m, 2H), 2.08 (s, 3H), 2.00 (m, 2H), 1.89 (m, 6H), 1.19 (d, J = 6.0 Hz, 6H). MS (ES⁺): 584.2 (M + 1)⁺. |
| 85 | 5-chloro-N4-(2-(isopropylsulfonyl)phenyl)-N2-(2-methoxy-5-methyl-4-phenyl)-phenyl)pyrimidine-2,4-diamine | MS (ES⁺): 523.2 (M + 1)⁺. |
| 86 | 5-chloro-N4-(2-cyanophenyl)-N2-(2-methoxy-5-methyl-4-phenyl)-phenyl)pyrimidine-2,4-diamine | MS (ES⁺): 442.1 (M + 1)⁺. |
| 87 | 2-(5-chloro-2-(5-methoxy-2-methylbiphenyl-4-ylamino)pyrimidin-4-ylamino)-N,N-dimethylbenzenesulfonamide | MS (ES⁺): 524.1 (M + 1)⁺. |

TABLE 1-continued

| | Structure | Physical Data<br>¹H NMR 400 MHz (DMSO-d6)<br>and/or MS (m/z) |
|---|---|---|
| 88 | 5-chloro-N4-(2-(isopropylsulfonyl)phenyl)-N2-(2-methoxy-5-methyl-4-(4-methylphenyl)-phenyl)pyrimidine-2,4-diamine | MS (ES+): 537.0 (M + 1)+. |
| 89 | 5-chloro-N4-(2-(isopropylsulfonyl)phenyl)-N2-(2-methoxy-5-methyl-4-(4-fluorophenyl)-phenyl)pyrimidine-2,4-diamine | MS (ES+): 541.1 (M + 1)+. |
| 90 | 5-chloro-N4-(2-(isopropylsulfonyl)phenyl)-N2-(2-methoxy-5-methyl-4-(2,4-difluorophenyl)-phenyl)pyrimidine-2,4-diamine | MS (ES+): 559.0 (M + 1)+. |
| 91 | 2-(5-chloro-2-(4'-(dimethylamino)-5-methoxy-2,3'-dimethylbiphenyl-4-ylamino)pyrimidin-4-ylamino)-N,N-dimethylbenzenesulfonamide | MS (ES+): 581.2 (M + 1)+. |

TABLE 1-continued

| | Structure | Physical Data<br>¹H NMR 400 MHz (DMSO-d6)<br>and/or MS (m/z) |
|---|---|---|
| 92 | 5-chloro-N2-(2-isopropoxy-5-methyl-4-((1s,4s)-4-(pyrrolidin-1-yl)cyclohexyl)phenyl)-N4-(2-(isopropylsulfonyl)phenyl)pyrimidine-2,4-diamine | MS (ES⁺): 626.3 (M + 1)⁺. |
| 93 | 2-(5-chloro-2-(5-methoxy-2-methyl-4'-morpholinobiphenyl-4-ylamino)pyrimidin-4-ylamino)-N,N-dimethylbenzenesulfonamide | MS (ES⁺): 609.2 (M + 1)⁺. |
| 94 | 2-(5-chloro-2-(5-methoxy-2-methyl-4'-(methylsulfonyl)biphenyl-4-ylamino)pyrimidin-4-ylamino)-N,N-dimethylbenzenesulfonamide | MS (ES⁺): 602.1 (M + 1)⁺. |

TABLE 1-continued

| Structure | Physical Data<br>¹H NMR 400 MHz (DMSO-d6)<br>and/or MS (m/z) |
|---|---|
| 95<br>4'-(5-chloro-4-(2-(N,N-dimethylsulfamoyl)<br>phenylamino)pyrimidin-2-ylamino)-5'-methoxy-2'-<br>methylbiphenyl-4-carboxamide | MS (ES⁺): 567.2 (M + 1)⁺. |
| 96<br>2-(2-(4'-acetyl-5-methoxy-2-methylbiphenyl-4-ylamino)-<br>5-chloropyrimidin-4-ylamino)-N,N-<br>dimethylbenzenesulfonamide | MS (ES⁺): 566.2 (M + 1)⁺. |
| 97<br>4'-(5-chloro-4-(2-(N,N-dimethylsulfamoyl)<br>phenylamino)pyrimidin-2-ylamino)-5'-methoxy-N,2'-<br>dimethylbiphenyl-4-carboxamide | MS (ES⁺): 581.2 (M + 1)⁺. |

TABLE 1-continued

| | Structure | Physical Data<br>¹H NMR 400 MHz (DMSO-d6)<br>and/or MS (m/z) |
|---|---|---|
| 98 | 4'-(5-chloro-4-(2-(N,N-dimethylsulfamoyl)<br>phenylamino)pyrimidin-2-ylamino)-5'-methoxy-2'-<br>methylbiphenyl-4-carboxylic acid | MS (ES⁺): 568.1 (M + 1)⁺. |
| 99 | 2-(5-chloro-2-(2-methoxy-5-methyl-4-(pyridin-4-<br>yl)phenylamino)pyrimidin-4-ylamino)-N,N-<br>dimethylbenzenesulfonamide | MS (ES⁺): 525.1 (M + 1)⁺. |
| 100 | 2-(5-chloro-2-(2-isopropoxy-5-methyl-4-(pyridin-4-<br>yl)phenylamino)pyrimidin-4-ylamino)-N,N-<br>dimethylbenzenesulfonamide | MS (ES⁺): 553.2 (M + 1)⁺. |
| 101 | 2-(5-chloro-2-(5-methyl-2-(1-methylpiperidin-4-yloxy)-4-<br>(pyridin-4-yl)phenylamino)pyrimidin-4-ylamino)-N,N-<br>dimethylbenzenesulfonamide | MS (ES⁺): 608.2 (M + 1)⁺. |

TABLE 1-continued

| | Physical Data |
|---|---|
| Structure | $^1$H NMR 400 MHz (DMSO-d6) and/or MS (m/z) |

102

5-(5-chloro-4-(2-(N,N-dimethylsulfamoyl)phenylamino)pyrimidin-2-ylamino)-4-isopropoxy-N-methyl-2-(pyridin-4-yl)benzamide

MS (ES$^+$): 596.2 (M + 1)$^+$.

103

5-(5-chloro-4-(2-(N,N-dimethylsulfamoyl)phenylamino)pyrimidin-2-ylamino)-2-(2-fluoropyridin-4-yl)-4-isopropoxy-N-methylbenzamide

MS (ES$^+$): 614.2 (M + 1)$^+$.

104

5-(4-(2-(isopropylsulfonyl)phenylamino)-5-chloropyrimidin-2-ylamino)-4-isopropoxy-N,2-dimethylbenzamide

MS (ES$^+$): 532.0 (M + 1)$^+$.

TABLE 1-continued

| | Structure | Physical Data<br>¹H NMR 400 MHz (DMSO-d6)<br>and/or MS (m/z) |
|---|---|---|
| 105 | 5-(4-(2-(isopropylsulfonyl)phenylamino)-5-chloropyrimidin-2-ylamino)-4-isopropoxy-N-methyl-2-(3-methyl-1H-pyrazol-5-yl)benzamide | MS (ES⁺): 598.2 (M + 1)⁺. |
| 106 | 5-(4-(2-(isopropylsulfonyl)phenylamino)-5-chloropyrimidin-2-ylamino)-4-isopropoxy-N-methyl-2-(2-methylthiazol-5-yl)benzamide | MS (ES⁺): 615.2 (M + 1)⁺. |
| 107 | 5-(4-(2-(isopropylsulfonyl)phenylamino)-5-chloropyrimidin-2-ylamino)-4-isopropoxy-2-methyl-N-(1-methylpiperidin-4-yl)benzamide | MS (ES⁺): 615.2 (M + 1)⁺. |

TABLE 1-continued

| Structure | Physical Data<br>¹H NMR 400 MHz (DMSO-d6)<br>and/or MS (m/z) |
|---|---|
| 108 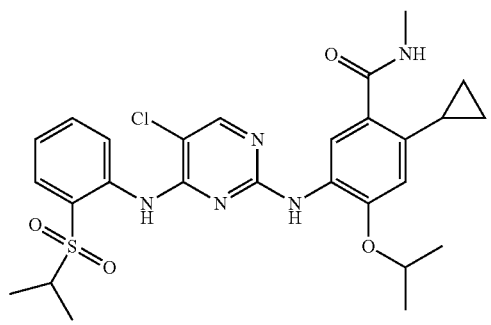 [SMILES: CNC(=O)c1cc(Nc2ncc(Cl)c(Nc3ccccc3S(=O)(=O)C(C)C)n2)c(OC(C)C)cc1C1CC1]<br>5-(4-(2-(isopropylsulfonyl)phenylamino)-5-chloropyrimidin-2-ylamino)-2-cyclopropyl-4-isopropoxy-N-methylbenzamide | MS (ES⁺): 558.2 (M + 1)⁺. |
| 109 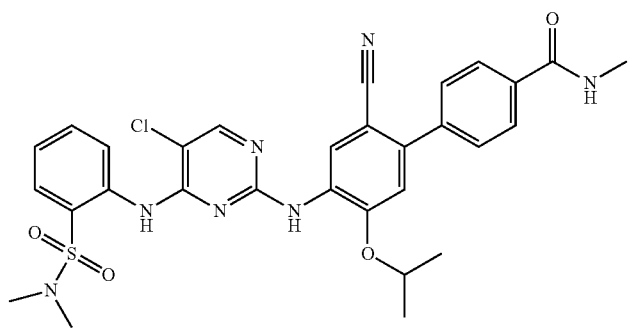<br>4'-(5-chloro-4-(2-(N,N-dimethylsulfamoyl)phenylamino)pyrimidin-2-ylamino)-2'-cyano-5'-isopropoxy-N-methylbiphenyl-4-carboxamide | MS (ES⁺): 620.2 (M + 1)⁺. |
| 110 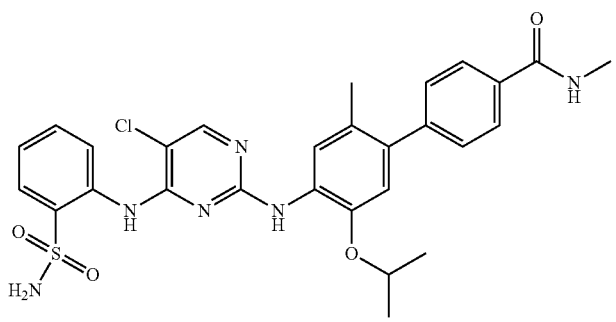 [SMILES: CNC(=O)c1ccc(-c2cc(OC(C)C)c(Nc3ncc(Cl)c(Nc4ccccc4S(N)(=O)=O)n3)cc2C)cc1]<br>5-chloro-N4-(2-(sulfonylamino)phenyl)-N2-(2-methoxy-5-methyl-4-(3-methyl-4-(methylacetamidophenyl)-phenyl)pyrimidine-2,4-diamine | MS (ES⁺): 581.2 (M + 1)⁺. |

TABLE 1-continued

| Structure | Physical Data<br>¹H NMR 400 MHz (DMSO-d6)<br>and/or MS (m/z) |
|---|---|
| 111<br>4'-(5-chloro-4-(2-(N,N-dimethylsulfamoyl)phenylamino)pyrimidin-2-ylamino)-N-cyclopropyl-5'-methoxy-2'-methylbiphenyl-4-carboxamide | MS (ES⁺): 607.2 (M + 1)⁺. |
| 112<br>N-((4'-(5-chloro-4-(2-(N,N-dimethylsulfamoyl)phenylamino)pyrimidin-2-ylamino)-5'-methoxy-2'-methylbiphenyl-4-yl)methyl)acetamide | MS (ES⁺): 595.2 (M + 1)⁺. |
| 113<br>5-chloro-N4-(2-(morpholinosulfonyl)phenyl)-N2-(2-methoxy-5-methyl-4-(4-(methylacetamidophenyl)-phenyl)pyrimidine-2,4-diamine | MS (ES⁺): 623.2 (M + 1)⁺. |

TABLE 1-continued

| Structure | Physical Data<br>¹H NMR 400 MHz (DMSO-d6)<br>and/or MS (m/z) |
|---|---|
| 114 | MS (ES⁺): 607.1 (M + 1)⁺. |

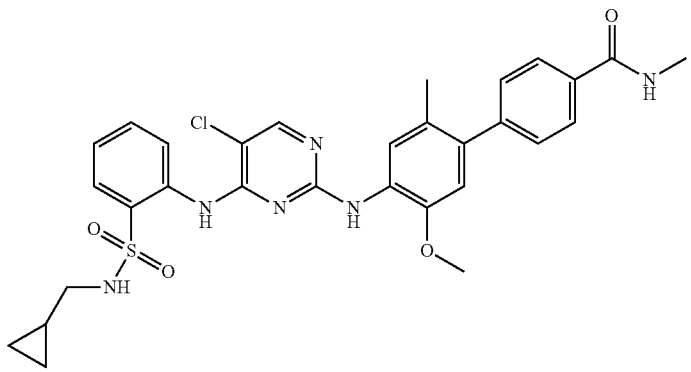 [SMILES: CNC(=O)c1ccc(-c2cc(OC)c(Nc3ncc(Cl)c(Nc4ccccc4S(=O)(=O)NCC4CC4)n3)cc2C)cc1]

4'-(5-chloro-4-(2-(N-(cyclopropylmethyl)
sulfamoyl)phenylamino)pyrimidin-2-ylamino)-5'-
methoxy-N,2'-dimethylbiphenyl-4-carboxamide

| | |
|---|---|
| 115 | MS (ES⁺): 607.1 (M + 1)⁺. |

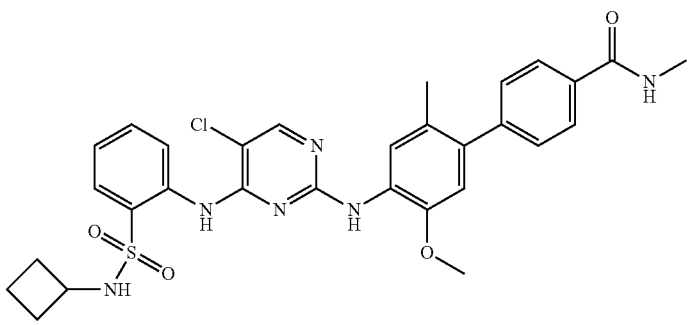 [SMILES: CNC(=O)c1ccc(-c2cc(OC)c(Nc3ncc(Cl)c(Nc4ccccc4S(=O)(=O)NC4CCC4)n3)cc2C)cc1]

4'-(5-chloro-4-(2-(N-cyclobutylsulfamoyl)
phenylamino)pyrimidin-2-ylamino)-5'-methoxy-N,2'-
dimethylbiphenyl-4-carboxamide

| | |
|---|---|
| 116 | MS (ES⁺): 607.2 (M + 1)⁺. |

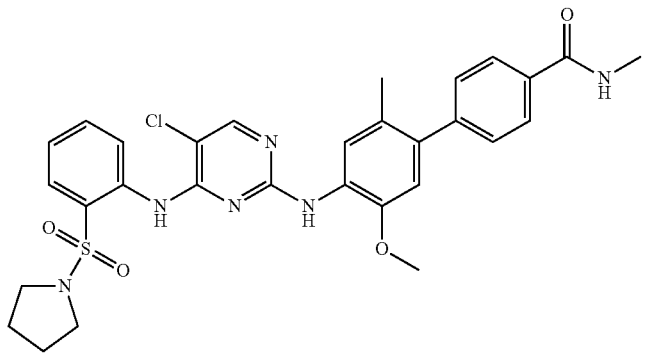 [SMILES: CNC(=O)c1ccc(-c2cc(OC)c(Nc3ncc(Cl)c(Nc4ccccc4S(=O)(=O)N4CCCC4)n3)cc2C)cc1]

5-chloro-N4-(2-(pyrrolidinosulfonyl)phenyl)-N2-(2-
methoxy-5-methyl-4-(4-acetamidomethylphenyl)-
phenyl)pyrimidine-2,4-diamine TABLE 1-continued

| Structure | Physical Data<br>$^1$H NMR 400 MHz (DMSO-d6)<br>and/or MS (m/z) |
|---|---|
| 117    4'-(5-chloro-4-(2-(N,N-dimethylsulfamoyl)phenylamino)pyrimidin-2-ylamino)-5'-methoxy-2'-methylbiphenyl-3-carboxylic acid | MS (ES$^+$): 568.1 (M + 1)$^+$. |
| 118    4'-(4-(2-(N,N-dimethylsulfamoyl)phenylamino)-5-fluoropyrimidin-2-ylamino)-5'-methoxy-N,2'-dimethylbiphenyl-4-carboxamide | MS (ES$^+$): 565.2 (M + 1)$^+$. |
| 119    2-(5-chloro-2-(5-methoxy-2-methyl-4'-(morpholinosulfonyl)biphenyl-4-ylamino)pyrimidin-4-ylamino)-N,N-dimethylbenzenesulfonamide | MS (ES$^+$): 673.2 (M + 1)$^+$. |

TABLE 1-continued

| Structure | Physical Data<br>¹H NMR 400 MHz (DMSO-d6)<br>and/or MS (m/z) |
|---|---|
| 120 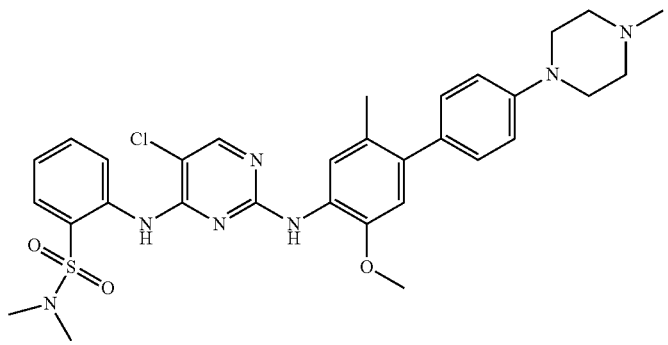<br>2-(5-chloro-2-(5-methoxy-2-methyl-4'-(4-methylpiperazin-1-yl)biphenyl-4-ylamino)pyrimidin-4-ylamino)-N,N-dimethylbenzenesulfonamide | MS (ES⁺): 622.2 (M + 1)⁺. |
| 121 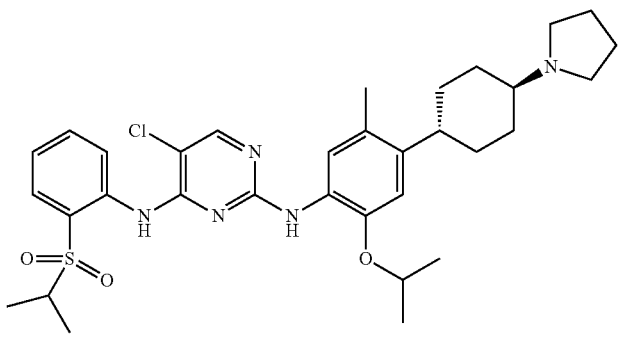 [SMILES: Cc1cc(Nc2ncc(Cl)c(Nc3ccccc3S(=O)(=O)C(C)C)n2)c(OC(C)C)cc1[C@H]1CC[C@H](N2CCCC2)CC1]<br>5-chloro-N2-(2-isopropoxy-5-methyl-4-((1r,4r)-4-(pyrrolidin-1-yl)cyclohexyl)phenyl)-N4-(2-(isopropylsulfonyl)phenyl)pyrimidine-2,4-diamine | MS (ES⁺): 626.3 (M + 1)⁺. |
| 122 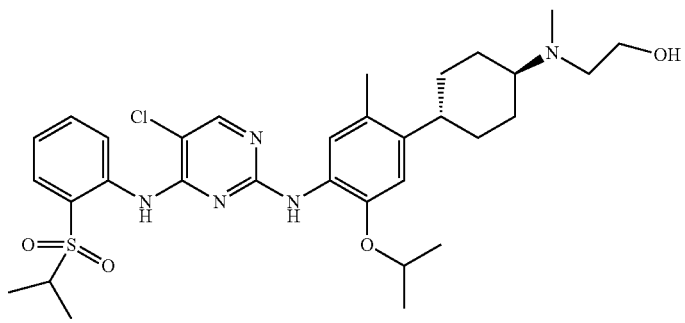 [SMILES: Cc1cc(Nc2ncc(Cl)c(Nc3ccccc3S(=O)(=O)C(C)C)n2)c(OC(C)C)cc1[C@H]1CC[C@H](N(C)CCO)CC1]<br>2-(N-((1r,4r)-4-(4-(4-(2-(isopropylsulfonyl)phenylamino)-5-chloropyrimidin-2-ylamino)-5-isopropoxy-2-methylphenyl)cyclohexyl)-N-methylamino)ethanol | MS (ES⁺): 630.3 (M + 1)⁺. |

TABLE 1-continued

| Structure | Physical Data<br>¹H NMR 400 MHz (DMSO-d6)<br>and/or MS (m/z) |
|---|---|
| 123 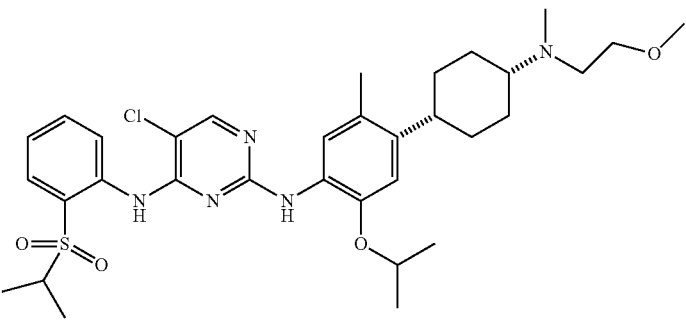<br>N2-(4-((1s,4s)-4-(N-(2-methoxyethyl)-N-methylamino)cyclohexyl)-2-isopropoxy-5-methylphenyl)-5-chloro-N4-(2-(isopropylsulfonyl) phenyl)pyrimidine-2,4-diamine | MS (ES$^+$): 644.3 (M + 1)$^+$. |
| 124 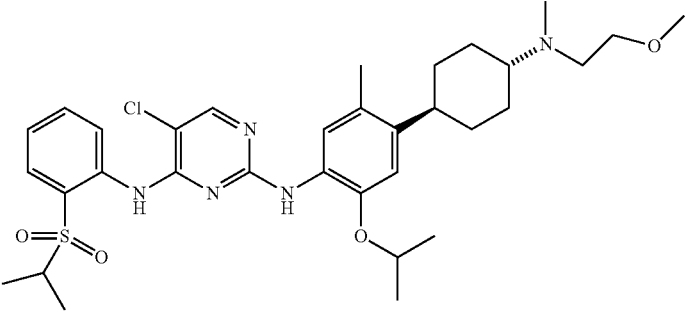 [SMILES: COCCN(C)[C@H]1CC[C@H](c2cc(OC(C)C)c(Nc3ncc(Cl)c(Nc4ccccc4S(=O)(=O)C(C)C)n3)cc2C)CC1]<br>N2-(4-((1r,4r)-4-(N-(2-methoxyethyl)-N-methylamino)cyclohexyl)-2-isopropoxy-5-methylphenyl)-5-chloro-N4-(2-(isopropylsulfonyl)phenyl)pyrimidine-2,4-diamine | MS (ES$^+$): 644.3 (M + 1)$^+$. |
| 125 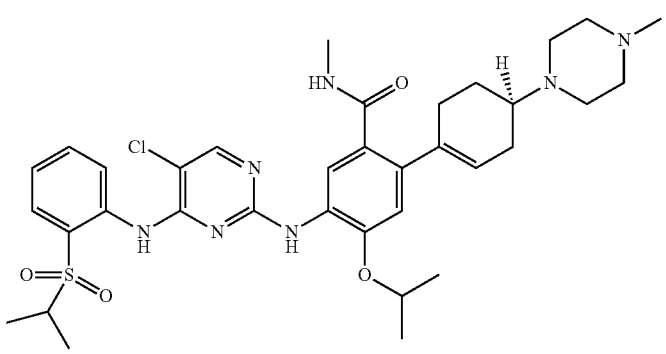 [SMILES: CNC(=O)c1cc(Nc2ncc(Cl)c(Nc3ccccc3S(=O)(=O)C(C)C)n2)c(OC(C)C)cc1C1=CC[C@H](N2CCN(C)CC2)CC1]<br>5-(4-(2-(isopropylsulfonyl)phenylamino)-5-chloropyrimidin-2-ylamino)-4-isopropoxy-N-methyl-2-((R)-4-(4-methylpiperazin-1-yl)cyclohex-1-enyl)benzamide | MS (ES$^+$): 696.3 (M + 1)$^+$. |

TABLE 1-continued

| Structure | Physical Data<br>¹H NMR 400 MHz (DMSO-d6)<br>and/or MS (m/z) |
|---|---|
| 126 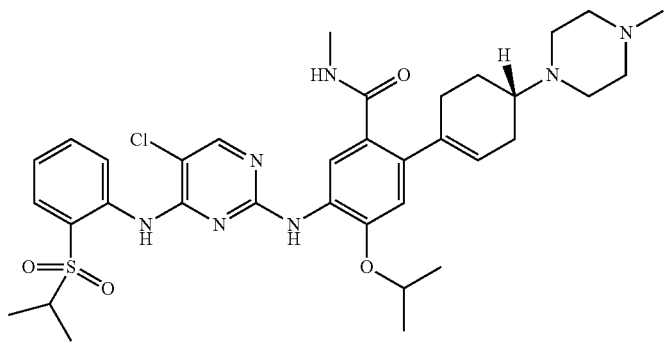 [SMILES: CNC(=O)c1cc(Nc2ncc(Cl)c(Nc3ccccc3S(=O)(=O)C(C)C)n2)c(OC(C)C)cc1C1=CC[C@@H](N2CCN(C)CC2)CC1]<br>5-(4-(2-(isopropylsulfonyl)phenylamino)-5-<br>chloropyrimidin-2-ylamino)-4-isopropoxy-N-methyl-2-<br>((S)-4-(4-methylpiperazin-1-yl)cyclohex-1-<br>enyl)benzamide | MS (ES⁺): 696.3 (M + 1)⁺. |
| 127 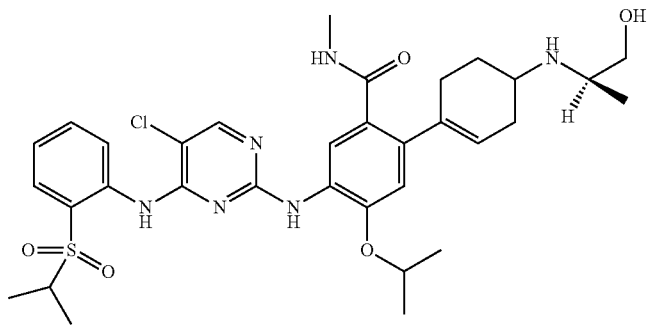 [SMILES: CNC(=O)c1cc(Nc2ncc(Cl)c(Nc3ccccc3S(=O)(=O)C(C)C)n2)c(OC(C)C)cc1C1=CCC(N[C@H](C)CO)CC1]<br>2-(4-((R)-1-hydroxypropan-2-ylamino)cyclohex-1-enyl)-<br>5-(4-(2-(isopropylsulfonyl)phenylamino)-5-<br>chloropyrimidin-2-ylamino)-4-isopropoxy-N-<br>methylbenzamide | MS (ES⁺): 671.3 (M + 1)⁺. |
| 128 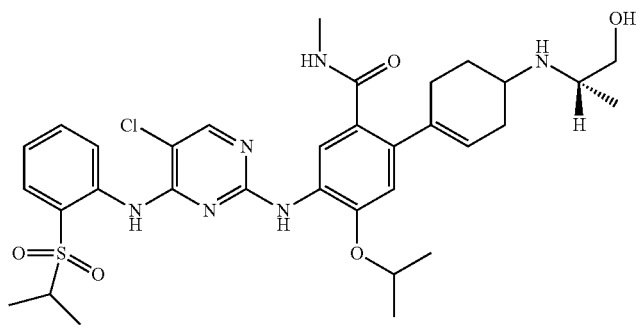 [SMILES: CNC(=O)c1cc(Nc2ncc(Cl)c(Nc3ccccc3S(=O)(=O)C(C)C)n2)c(OC(C)C)cc1C1=CCC(N[C@@H](C)CO)CC1]<br>2-(4-((S)-1-hydroxypropan-2-ylamino)cyclohex-1-enyl)-<br>5-(4-(2-(isopropylsulfonyl)phenylamino)-5-<br>chloropyrimidin-2-ylamino)-4-isopropoxy-N-<br>methylbenzamide | MS (ES⁺): 671.3 (M + 1)⁺. |

TABLE 1-continued

| Structure | Physical Data $^1$H NMR 400 MHz (DMSO-d6) and/or MS (m/z) |
|---|---|
| 129 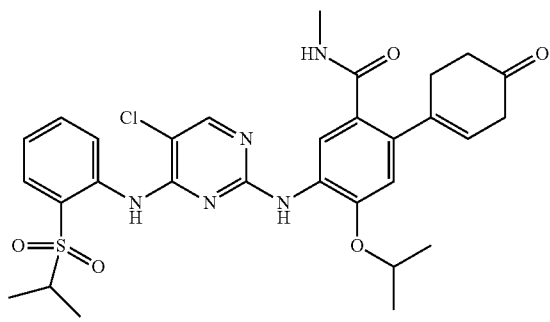 [SMILES: CNC(=O)c1cc(Nc2ncc(Cl)c(Nc3ccccc3S(=O)(=O)C(C)C)n2)c(OC(C)C)cc1C1=CCC(=O)CC1]

5-(4-(2-(isopropylsulfonyl)phenylamino)-5-chloropyrimidin-2-ylamino)-4-isopropoxy-N-methyl-2-(4-oxocyclohex-1-enyl)benzamide | MS (ES$^+$): 612.2 (M + 1)$^+$. |
| 130 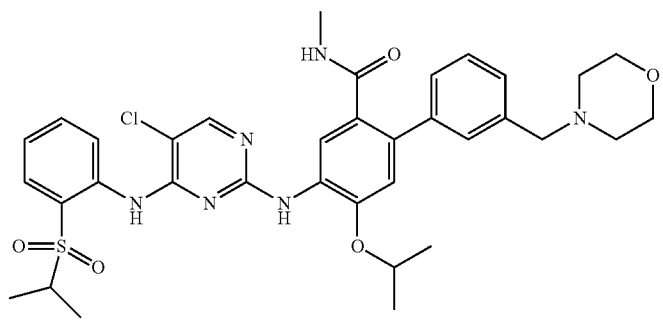 [SMILES: CNC(=O)c1cc(Nc2ncc(Cl)c(Nc3ccccc3S(=O)(=O)C(C)C)n2)c(OC(C)C)cc1-c1cccc(CN2CCOCC2)c1]

5-chloro-N4-(2-(isopropylsulfonyl)phenyl)-N2-(2-isopropoxy-5-(N-methylcarboxamido)-4-(3-methyl-4-(3-morpholinomethyl)-phenyl)pyrimidine-2,4-diamine | MS (ES$^+$): 693.3 (M + 1)$^+$. |
| 131 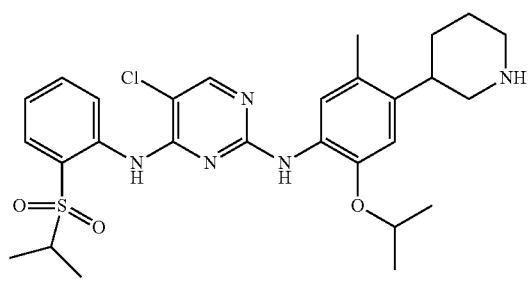 [SMILES: Cc1cc(Nc2ncc(Cl)c(Nc3ccccc3S(=O)(=O)C(C)C)n2)c(OC(C)C)cc1C1CCCNC1]

5-chloro-N2-(2-isopropoxy-5-methyl-4-(piperidin-3-yl)phenyl)-N4-(2-(isopropylsulfonyl) phenyl)pyrimidine-2,4-diamine | MS (ES$^+$): 558.2 (M + 1)$^+$. |

TABLE 1-continued

| | Structure | Physical Data<br>¹H NMR 400 MHz (DMSO-d6)<br>and/or MS (m/z) |
|---|---|---|
| 132 | (2-(5-chloro-2-(2-isopropoxy-5-methyl-4-(1-methylpiperidin-4-yl)phenylamino)pyrimidin-4-ylamino)phenyl)(morpholino)methanone | MS (ES⁺): 579.1 (M + 1)⁺. |
| 133 | 2-((2-(4-(5-chloro-4-(2-(isopropylsulfonyl)phenylamino)pyrimidin-2-ylamino)-5-isopropoxy-2-methylphenyl)propyl)(methyl)amino)ethanol | MS (ES⁺): 590.1 (M + 1)⁺. |
| 134 | 5-chloro-N2-(4-((1r,4r)-4-(dimethylamino) cyclohexyl)-2-methoxy-5-methylphenyl)-N4-(2-(isopropylsulfonyl)phenyl)pyrimidine-2,4-diamine | MS (ES⁺): 572.1 (M + 1)⁺. |

TABLE 1-continued

| Structure | Physical Data <br> ¹H NMR 400 MHz (DMSO-d6) and/or MS (m/z) |
|---|---|
| 135 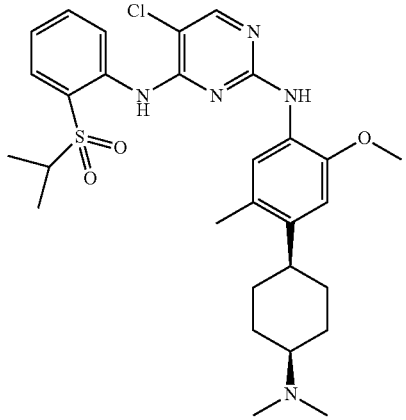 [SMILES: COc1cc([C@H]2CC[C@@H](N(C)C)CC2)c(C)cc1Nc1ncc(Cl)c(Nc2ccccc2S(=O)(=O)C(C)C)n1]<br>5-chloro-N2-(4-((1s,4s)-4-(dimethylamino) cyclohexyl)-2-methoxy-5-methylphenyl)-N4-(2-(isopropylsulfonyl) phenyl)pyrimidine-2,4-diamine | MS (ES⁺): 572.1 (M + 1)⁺. |
| 136 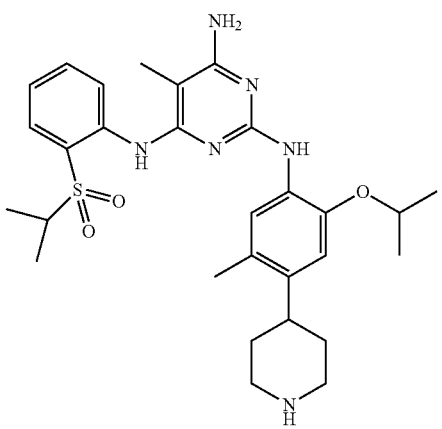 [SMILES: Cc1cc(Nc2nc(N)c(C)c(Nc3ccccc3S(=O)(=O)C(C)C)n2)c(OC(C)C)cc1C1CCNCC1]<br>N2-(2-isopropoxy-5-methyl-4-(piperidin-4-yl)phenyl)-N4-(2-(isopropylsulfonyl)phenyl)-5-methylpyrimidine-2,4,6-triamine | MS (ES⁺): 552.7 (M + 1)⁺. |
| 137 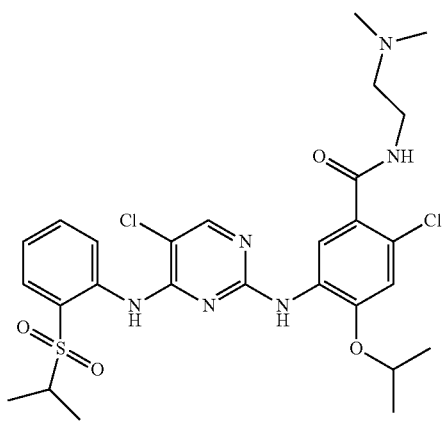 [SMILES: CC(C)Oc1cc(Cl)c(C(=O)NCCN(C)C)cc1Nc1ncc(Cl)c(Nc2ccccc2S(=O)(=O)C(C)C)n1]<br>5-(4-(2-(isopropylsulfonyl)phenylamino)-5-chloropyrimidin-2-ylamino)-2-chloro-N-(2-(dimethylamino)ethyl)-4-isopropoxybenzamide | MS (ES⁺): 610.0 (M + 1)⁺. |

TABLE 1-continued

| Structure | Physical Data<br>¹H NMR 400 MHz (DMSO-d6)<br>and/or MS (m/z) |
|---|---|
| 138 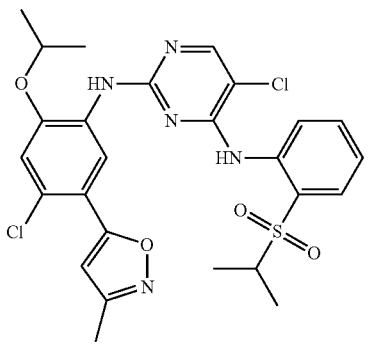 [SMILES: Cc1cc(-c2cc(Nc3ncc(Cl)c(Nc4ccccc4S(=O)(=O)C(C)C)n3)c(OC(C)C)cc2Cl)on1]<br>5-chloro-N2-(4-chloro-2-isopropoxy-5-(3-methylisoxazol-5-yl)phenyl)-N4-(2-(isopropylsulfonyl)phenyl)pyrimidine-2,4-diamine | MS (ES+): 577.5 (M + 1)+. |
| 139 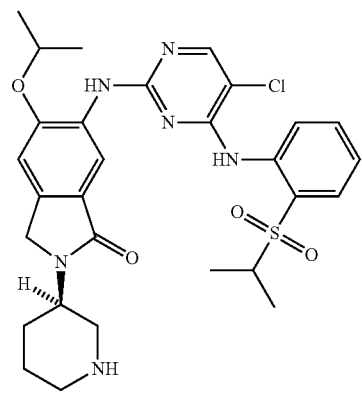 [SMILES: CC(C)Oc1cc2c(cc1Nc1ncc(Cl)c(Nc3ccccc3S(=O)(=O)C(C)C)n1)C(=O)N([C@@H]1CCCNC1)C2]<br>6-(4-(2-(isopropylsulfonyl)phenylamino)-5-chloropyrimidin-2-ylamino)-5-isopropoxy-2-((R)-piperidin-3-yl)isoindolin-1-one | MS (ES+): 599.2 (M + 1)+. |
| 140 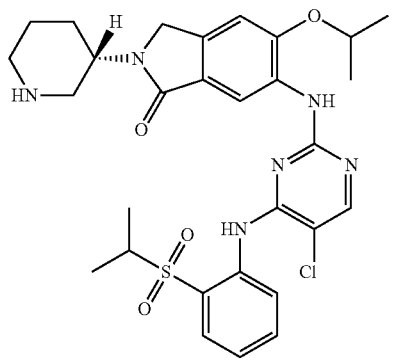 [SMILES: CC(C)Oc1cc2c(cc1Nc1ncc(Cl)c(Nc3ccccc3S(=O)(=O)C(C)C)n1)C(=O)N([C@H]1CCCNC1)C2]<br>6-(4-(2-(isopropylsulfonyl)phenylamino)-5-chloropyrimidin-2-ylamino)-5-isopropoxy-2-((S)-piperidin-3-yl)isoindolin-1-one | MS (ES+): 599.2 (M + 1)+. |

TABLE 1-continued

| Structure | Physical Data<br>¹H NMR 400 MHz (DMSO-d6)<br>and/or MS (m/z) |
|---|---|
| 141 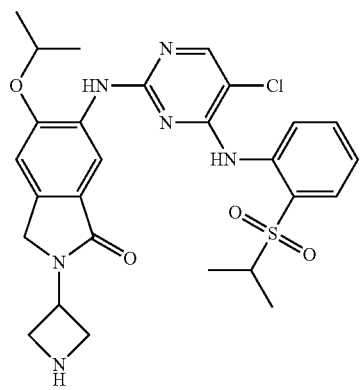 [SMILES: CC(C)Oc1cc2c(cc1Nc1ncc(Cl)c(Nc3ccccc3S(=O)(=O)C(C)C)n1)C(=O)N(C1CNC1)C2]<br>6-(4-(2-(isopropylsulfonyl)phenylamino)-5-chloropyrimidin-2-ylamino)-2-(azetidin-3-yl)-5-isopropoxyisoindolin-1-one | MS (ES⁺): 571.2 (M + 1)⁺. |
| 142 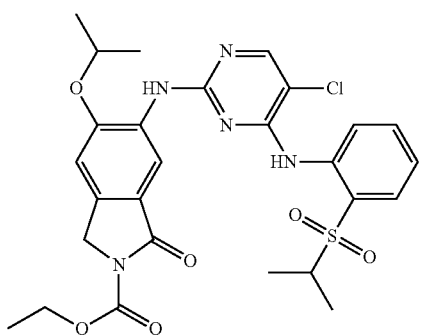 [SMILES: CCOC(=O)N1Cc2cc(OC(C)C)c(Nc3ncc(Cl)c(Nc4ccccc4S(=O)(=O)C(C)C)n3)cc2C1=O]<br>Ethyl 6-(4-(2-(isopropylsulfonyl)phenylamino)-5-chloropyrimidin-2-ylamino)-5-isopropoxy-1-oxoisoindoline-2-carboxylate | MS (ES⁺): 588.2 (M + 1)⁺. |
| 143 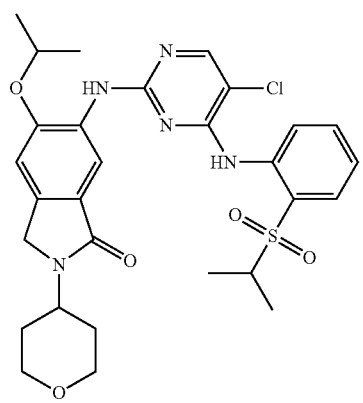 [SMILES: CC(C)Oc1cc2c(cc1Nc1ncc(Cl)c(Nc3ccccc3S(=O)(=O)C(C)C)n1)C(=O)N(C1CCOCC1)C2]<br>6-(4-(2-(isopropylsulfonyl)phenylamino)-5-chloropyrimidin-2-ylamino)-2-(tetrahydro-2H-pyran-4-yl)-5-isopropoxyisoindolin-1-one | MS (ES⁺): 600.2 (M + 1)⁺. |

TABLE 1-continued

| | Structure | Physical Data<br>¹H NMR 400 MHz (DMSO-d6)<br>and/or MS (m/z) |
|---|---|---|
| 144 | 6-(4-(2-(isopropylsulfonyl)phenylamino)-5-chloro pyrimidin-2-ylamino)-2-cyclohexyl-5-isopropoxy-isoindolin-1-one | MS (ES⁺): 598.2 (M + 1)⁺. |
| 145 | 6-(4-(2-(isopropylsulfonyl)phenylamino)-5-chloro pyrimidin-2-ylamino)-5-isopropoxy-2-morpholino-isoindolin-1-one | MS (ES⁺): 601.2 (M + 1)⁺. |
| 146 | 6-(4-(2-(isopropylsulfonyl)phenylamino)-5-chloropyrimidin-2-ylamino)-5-isopropoxy-2-((S)-pyrrolidin-3-yl)isoindolin-1-one | MS (ES⁺): 585.2 (M + 1)⁺. |

TABLE 1-continued

| | Structure | Physical Data<br>¹H NMR 400 MHz (DMSO-d6)<br>and/or MS (m/z) |
|---|---|---|
| 147 | 3-(4-(6-(4-(2-(isopropylsulfonyl)phenylamino)-5-chloropyrimidin-2-ylamino)-5-isopropoxy-1-oxoisoindolin-2-yl)piperidin-1-yl)propanoic acid | MS (ES⁺): 671.2 (M + 1)⁺. |
| 148 | 6-(4-(2-(isopropylsulfonyl)phenylamino)-5-chloropyrimidin-2-ylamino)-5-isopropoxy-2-((R)-pyrrolidin-3-yl)isoindolin-1-one | MS (ES⁺): 585.2 (M + 1)⁺. |
| 149 | 2-[4-(6-{5-Chloro-4-[2-(propane-2-sulfonyl)-phenyl-amino]-pyrimidin-2-ylamino}-5-isopropoxy-1-oxo-1,3-dihydro-isoindol-2-yl)piperidin-1-yl]-acetamide | MS (ES⁺): 656.2 (M + 1)⁺. |

TABLE 1-continued

| | Structure | Physical Data $^1$H NMR 400 MHz (DMSO-d6) and/or MS (m/z) |
|---|---|---|
| 150 | 6-(4-(2-(isopropylsulfonyl)phenylamino)-5-chloropyrimidin-2-ylamino)-2-acetyl-5-isopropoxyisoindolin-1-one | MS (ES$^+$): 558.2 (M + 1)$^+$. |
| 151 | 6-(4-(2-(isopropylsulfonyl)phenylamino)-5-chloropyrimidin-2-ylamino)-2-(2-hydroxyethyl)-5-isopropoxyisoindolin-1-one | MS (ES$^+$): 560.2 (M + 1)$^+$. |
| 152 | (2S, 4S)-methyl 4-(6-(4-(2-(isopropylsulfonyl)phenylamino)-5-chloropyrimidin-2-ylamino)-5-isopropoxy-1-oxoisoindolin-2-yl)pyrrolidine-2-carboxylate | MS (ES$^+$): 643.2 (M + 1)$^+$. |

TABLE 1-continued

| | Structure | Physical Data<br>¹H NMR 400 MHz (DMSO-d6)<br>and/or MS (m/z) |
|---|---|---|
| 153 | 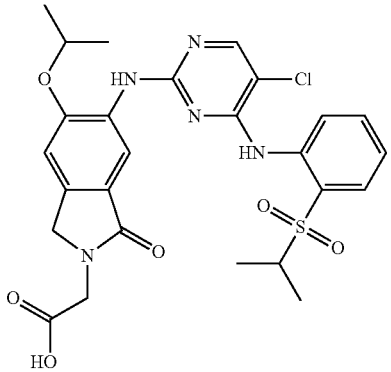<br>2-(6-(4-(2-(isopropylsulfonyl)phenylamino)-5-chloropyrimidin-2-ylamino)-5-isopropoxy-1-oxoisoindolin-2-yl)acetic acid | MS (ES⁺): 574.1 (M + 1)⁺. |
| 154 | 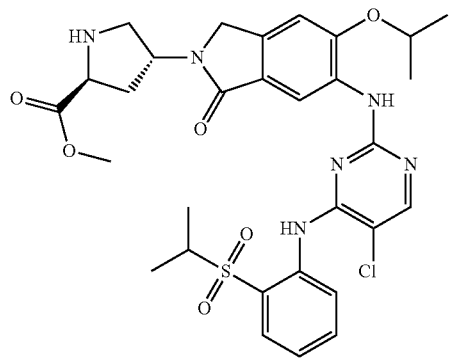<br>(2S,4R)-methyl 4-(6-(4-(2-(isopropylsulfonyl)phenylamino)-5-chloropyrimidin-2-ylamino)-5-isopropoxy-1-oxoisoindolin-2-yl)pyrrolidine-2-carboxylate | MS (ES⁺): 643.2 (M + 1)⁺. |
| 155 | 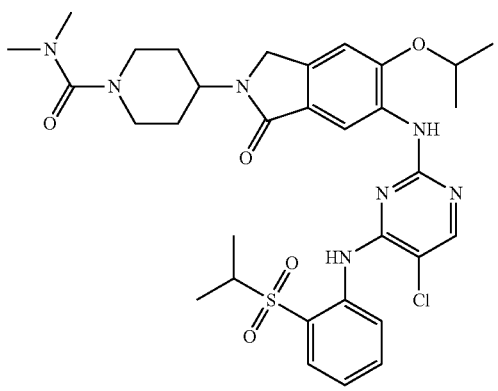<br>4-(6-{5-Chloro-4-[2-(propane-2-sulfonyl)-phenylamino]-pyrimidin-2-ylamino}-5-isopropoxy-1-oxo-1,3-dihydro-isoindol-2-yl)-piperidine-1-carboxylic acid dimethylamide | ¹H NMR (400 MHz, MeOD-d₄) δ 8.29 (s, 1H), 8.26 (br, 1H), 7.96 (dd, 1H), 7.93 (s, 1H), 7.72 (dd, 1H), 7.48 (dd, 1H), 7.35 (s, 1H), 4.50 (s, 2H), 4.35-4.29 (m, 1H), 3.83 (d, 2H), 3.38-3.30 (m, 2H), 3.02-2.95 (m, 3H), 1.36 (d, 6H), 1.25 (d, 6H); ESMS m/z 670.2 (M + H⁺) |

TABLE 1-continued

| | Structure | Physical Data<br>¹H NMR 400 MHz (DMSO-d6)<br>and/or MS (m/z) |
|---|---|---|
| 156 | (2S,4S)-4-(6-(4-(2-(isopropylsulfonyl) phenylamino)-5-chloropyrimidin-2-ylamino)-5-isopropoxy-1-oxoisoindolin-2-yl)pyrrolidine-2-carboxylic acid | MS (ES⁺): 629.2 (M + 1)⁺. |
| 157 | (2S,4R)-4-(6-(4-(2-(isopropylsulfonyl) phenylamino)-5-chloropyrimidin-2-ylamino)-5-isopropoxy-1-oxoisoindolin-2-yl)pyrrolidine-2-carboxylic acid | MS (ES⁺): 629.2 (M + 1)⁺. |
| 158 | 6-(4-(2-(isopropylsulfonyl)phenylamino)-5-chloropyrimidin-2-ylamino)-2-((azetidin-3-yl)methyl)-5-isopropoxyisoindolin-1-one | MS (ES⁺): 585.2 (M + 1)⁺. |

TABLE 1-continued

| Structure | Physical Data<br>¹H NMR 400 MHz (DMSO-d6)<br>and/or MS (m/z) |
|---|---|
| 159 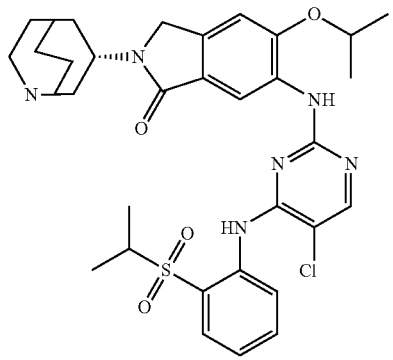<br>6-(4-(2-(isopropylsulfonyl)phenylamino)-5-chloropyrimidin-2-ylamino)-5-isopropoxy-2-((S)-quinuclidin-3-yl)isoindolin-1-one | MS (ES⁺): 625.2 (M + 1)⁺. |
| 160 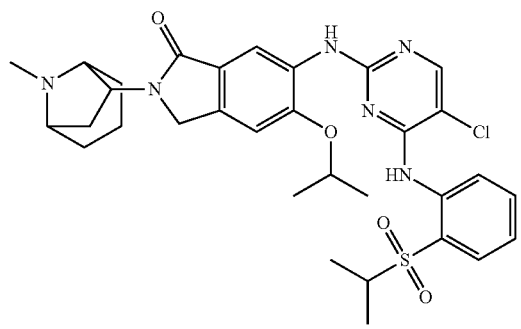<br>6-{5-Chloro-4-[2-(propane-2-sulfonyl)-phenylamino]-pyrimidin-2-ylamino}-5-isopropoxy-2-(8-methyl-8-aza-bicyclo[3.2.1]oct-6-yl)-2,3-dihydro-isoindol-1-one | MS (ES⁺): 639.2 (M + 1)⁺. |
| 161 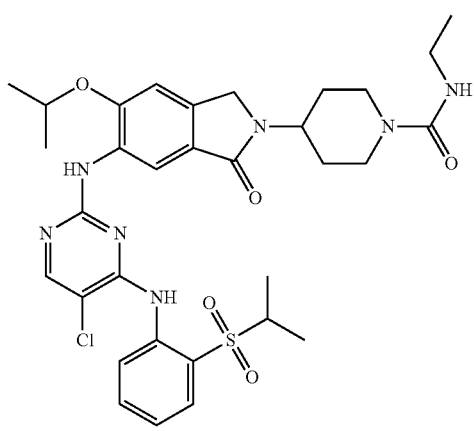<br>4-(6-(4-(2-(isopropylsulfonyl)phenylamino)-5-chloropyrimidin-2-ylamino)-5-isopropoxy-1-oxoisoindolin-2-yl)-N-ethylpiperidine-1-carboxamide | MS (ES⁺): 670.3 (M + 1)⁺. |

TABLE 1-continued

| | Physical Data |
|---|---|
| Structure | $^1$H NMR 400 MHz (DMSO-d6) and/or MS (m/z) |

162  MS (ES$^+$): 642.1 (M + 1)$^+$.

4-(6-(4-(2-(isopropylsulfonyl)phenylamino)-5-chloropyrimidin-2-ylamino)-5-isopropoxy-1-oxoisoindolin-2-yl)piperidine-1-carboxamide

163  MS (ES$^+$): 476.1 (M + 1)$^+$.

6-(4-(2-(isopropylsulfonyl)phenylamino)-5-chloropyrimidin-2-ylamino)-5-fluoroisoindolin-1-one

164  MS (ES$^+$): 456.1 (M + 1)$^+$.

6-(4-(2-(isopropylsulfonyl)phenylamino)-5-methylpyrimidin-2-ylamino)-5-fluoroisoindolin-1-one TABLE 1-continued

| | Structure | Physical Data<br>¹H NMR 400 MHz (DMSO-d6)<br>and/or MS (m/z) |
|---|---|---|
| 165 | Ethyl 7-(4-(2-(isopropylsulfonyl)phenylamino)-5-methylpyrimidin-2-ylamino)-1,4-dihydro-6-isopropoxyindeno[1,2-c]pyrazole-3-carboxylate | MS (ES⁺): 591.2 (M + 1)⁺. |
| 166 | (7-(4-(2-(isopropylsulfonyl)phenylamino)-5-methylpyrimidin-2-ylamino)-1,4-dihydro-6-isopropoxyindeno[1,2-c]pyrazol-3-yl)methanol | MS (ES⁺): 549.2 (M + 1)⁺. |
| 167 | Ethyl 7-(4-(2-(isopropylsulfonyl)phenylamino)-5-chloropyrimidin-2-ylamino)-1,4-dihydro-6-isopropoxyindeno[1,2-c]pyrazole-3-carboxylate | MS (ES⁺): 611.2 (M + 1)⁺. |

TABLE 1-continued

| | Structure | Physical Data<br>¹H NMR 400 MHz (DMSO-d6)<br>and/or MS (m/z) |
|---|---|---|
| 168 | N2-(1,4-dihydro-6-isopropoxy-3-((4-methylpiperazin-1-yl)methyl)indeno[1,2-c]pyrazol-7-yl)-N4-(2-(isopropylsulfonyl)phenyl)-5-methylpyrimidine-2,4-diamine | MS (ES⁺): 631.3 (M + 1)⁺. |
| 169 | N2-(1,4-dihydro-6-isopropoxy-3-(morpholinomethyl)indeno[1,2-c]pyrazol-7-yl)-N4-(2-(isopropylsulfonyl)phenyl)-5-methylpyrimidine-2,4-diamine | MS (ES⁺): 618.3 (M + 1)⁺. |
| 170 | N2-(3-((4-aminopiperidin-1-yl)methyl)-1,4-dihydro-6-isopropoxyindeno[1,2-c]pyrazol-7-yl)-N4-(2-(isopropylsulfonyl)phenyl)-5-methylpyrimidine-2,4-diamine | MS (ES⁺): 631.3 (M + 1)⁺. |

TABLE 1-continued

| Structure | Physical Data<br>¹H NMR 400 MHz (DMSO-d6)<br>and/or MS (m/z) |
|---|---|
| 171 | MS (ES⁺): 631.3 (M + 1)⁺. |

N2-(1,4-dihydro-6-isopropoxy-3-((piperidin-4-ylamino)methyl)indeno[1,2-c]pyrazol-7-yl)-N4-(2-(isopropylsulfonyl)phenyl)-5-methylpyrimidine-2,4-diamine

| | |
|---|---|
| 172 | MS (ES⁺): 515.1 (M + 1)⁺. |

6-(4-(2-(isopropylsulfonyl)phenylamino)-5-chloropyrimidin-2-ylamino)-2,3-dihydro-5-isopropoxyinden-1-one

| | |
|---|---|
| 173 | MS (ES⁺): 495.2 (M + 1)⁺. |

6-(4-(2-(isopropylsulfonyl)phenylamino)-5-methylpyrimidin-2-ylamino)-2,3-dihydro-5-isopropoxyinden-1-one TABLE 1-continued

| Structure | Physical Data<br>¹H NMR 400 MHz (DMSO-d6)<br>and/or MS (m/z) |
|---|---|
| 174 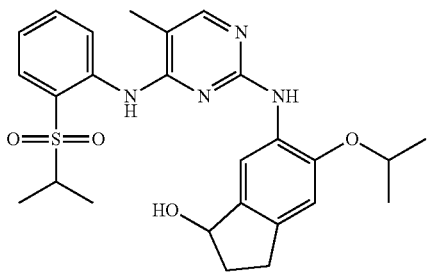<br>6-(4-(2-(isopropylsulfonyl)phenylamino)-5-methyl pyrimidin-2-ylamino)-2,3-dihydro-5-isopropoxy-1H-inden-1-ol | MS (ES⁺): 497.2 (M + 1)⁺. |
| 175 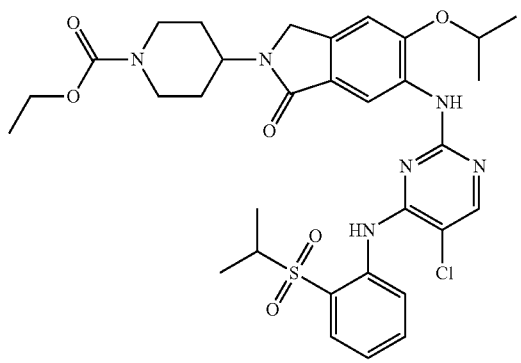<br>4-(6-{5-Chloro-4-[2-(propane-2-sulfonyl)-phenylamino]-pyrimidin-2-ylamino}-5-ispopropoxy-1-oxo-1,3-dihydro-isoindol-2-yl)-piperidine-1-carboxylic acid ethyl ester | ¹H NMR 400 MHz (DMSO-d₆ with trace D₂O) δ 8.55 (d, 1H), 8.32 (s, 1H), 8.14 (s, 1H), 7.82 (dd, 1H), 7.74 (t, 1H), 7.34 (t, 1H), 7.28 (s, 1H), 4.73 (m, 2H), 4.39 (s, 2H), 4.12 (m, 2H), 4.06 (q, 2H), 3.46 (m, 1H), 2.92 (m 2H), 1.76 (m, 2H), 1.68 (m, 2H), 1.29 (d, 6H), 1.20 (t, 3H), 1.17 (d, 6H); MS m/z 671 (M + 1). |
| 176 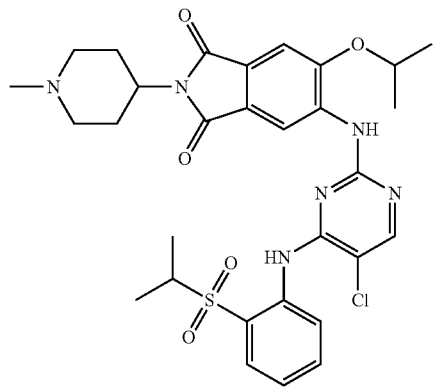<br>5-{5-Chloro-4-[2-(propane-2-sulfonyl)-phenylamino]-pyrimidin-2-ylamino}-6-isopropoxy-2-(1-methyl-piperidin-4-yl)-isoindole-1,3-dione | ¹H NMR 400 MHz (DMSO-d₆ with trace D₂O) δ 8.44 (s, 2H), 8.39 (s, 1H), 7.87 (dd, 1H), 7.78 (dt, 1H), 7.45 (s, 1H), 7.41 (m, 1H), 4.91 (m, 2H), 4.25 (m, 2H), 3.51 (m, 3H), 3.10 (m, 2H), 2.77 (s, 3H), 1.80 (m, 2H), 1.35 (d, 6H), 1.13 (d, 6H); MS m/z 627 (M + 1). |

TABLE 1-continued

| | Structure | Physical Data<br>¹H NMR 400 MHz (DMSO-d6)<br>and/or MS (m/z) |
|---|---|---|
| 177 | 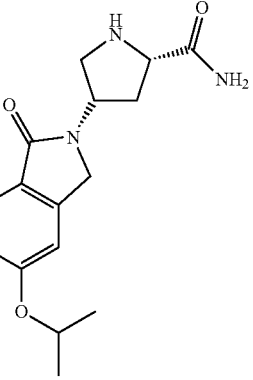<br>(2S,4S)-4-(6-{5-Chloro-4-[2-(propane-2-sulfonyl)-phenylamino]-pyrimidin-2-ylamino}-5-isopropoxy-1-oxo-1,3-dihydro-isoindol-2-yl)-pyrrolidine-2-carboxylic acid amide | ¹H NMR 400 MHz (DMSO-d₆ with trace D₂O) δ 8.47 (d, 1H), 8.25 (s, 1H), 8.07 (s, 1H), 7.78 (dd, 1H), 7.68 (m, 1H), 7.31 (t, 1H), 7,24 (s, 1H), 4.71 (m, 2H), 4.43 (dd, 2H), 3.60 (m, 1H), 3.44 (m, 1H), 3.35 (m, 1H), 2.63 (m, 1H), 2.28 (m, 1H), 1.22 (d, 6H), 1.10 (d, 6H); MS m/z 628 (M + 1). |
| 178 | 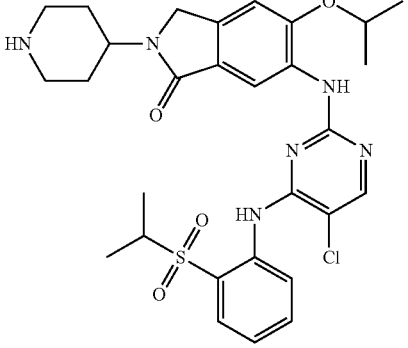<br>6-{5-Chloro-4-[2-(propane-2-sulfonyl)-phenylamino]-pyrimidin-2-ylamino}-5-isopropoxy-2-piperidin-4-yl-2,3-dihydro-isoindol-1-one | ¹H NMR (400 MHz, CDCl₃) δ 10.38 (s, 1H), 10.13 (s, 1H), 9.60-9.50 (br, 1H), 9.34-9.21 (br, 1H), 8.46 (d, 1H), 8.26 (s, 1H), 8.08 (s, 1H), 7.91 (dd, 1H), 7.71 (m, 1H), 7.34 (t, 1H), 7.03 (s, 1H), 4.30 (m, 1H), 4.53 (m, 1H), 4.33 (s, 2H), 3.62 (m, 2H), 3.21-3.09 (m, 3H), 2.31-2.21 (m, 2H), 2.09-2.05 (m, 2H), 1.41 (d, 6H), 2.30 (d, 6H); ESMS m/z 599.2 (M + H⁺). |
| 179 | 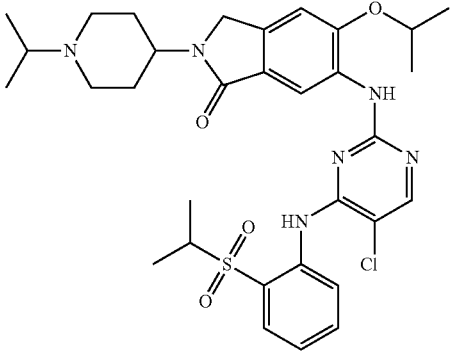<br>6-(4-(2-(isopropylsulfonyl)phenylamino)-5-chloropyrimidin-2-ylamino)-5-isopropoxy-2-(1-isopropylpiperidin-4-yl)isoindolin-1-one | MS (ES⁺): 641.3 (M + 1)⁺. |

TABLE 1-continued

| | Structure | Physical Data<br>¹H NMR 400 MHz (DMSO-d6)<br>and/or MS (m/z) |
|---|---|---|
| 180 | 6-(4-(2-(isopropylsulfonyl)phenylamino)-5-chloropyrimidin-2-ylamino)-5-isopropoxy-2-(2-(4-(piperidin-1-yl)piperidin-1-yl)ethyl)isoindolin-1-one | MS (ES⁺): 710.3 (M + 1)⁺. |
| 181 | 6-{5-Chloro-4-[2-(propane-2-sulfonyl)-phenylamino]-pyrimidin-2-ylamino}-5-isopropoxy-2-(1-methyl-piperidin-4-yl)-2,3-dihydro-isoindol-1-one | ¹H NMR 400 MHz (DMSO-d₆ with trace D₂O) δ 8.46 (d, 1H), 8.35 (s, 1H), 8.09 (s, 1H). 7.82 (d, 1H), 7.74 (t, 1H) 7.36 (t, 1H), 7.33 (s, 1H), 4.75 (m, 1H) 4.41 (s, 2H), 4.29 (m, 1H), 3.65 (m, 2H) 3.44 (m, 1H), 3.17 (t, 2H), 2.79 (s, 3H) 2.07 (m, 2H), 1.98 (d, 2H), 1.28 (d, 6H), 1.14 (d, 6H); MS m/z 613 (M + 1). |
| 182 | 6-(4-(2-(isopropylsulfonyl)phenylamino)-5-chloro pyrimidin-2-ylamino)-2-(1-(2-(dimethylamino)ethyl) piperidin-4-yl)-5-isopropoxyisoindolin-1-one | 8.60 (d, 1H), 8.33 (s, 1H); 8.20 (s, 1H); 7.82 (dd, 1H); 7.77 (dt, 1H); 7.35 (s, 1H); 7.33 (t, 1H); 4.76 (m, 1H); 4.44 (s, 2H); 3.88 (t, 2H); 3.40 (m, 3H); 2.87 (s, 6H); 1.30 (d, 6H); 1.16 (d, 6H). ). MS (ES⁺): 587.2 (M + 1)⁺. |

TABLE 1-continued

| Structure | Physical Data<br>¹H NMR 400 MHz (DMSO-d6)<br>and/or MS (m/z) |
|---|---|
| 183<br><br>6-(4-(2-(isopropylsulfonyl)phenylamino)-5-chloropyrimidin-2-ylamino)-5-isopropoxy-2-(1-(2-(pyrrolidin-1-yl)ethyl)piperidin-4-yl)isoindolin-1-one | 8.60 (d, 1H); 8.32 (s,1H); 8.20 (s, 1H); 7.83 (dd, 1H); 7.78 (dt, 1H); 7.35 (s, 1H); 7.31 (t, 1H); 4.76 (m,1H); 4.46 (s, 2H); 3.87 (t, 2H); 3.63 (m, 2H); 3.48 (m, 1H); 3.09 (m, 2H); 2.05 (m, 2H); 1.85 (m, 2H); 1.30 (d, 6H); 1.17 (d, 6H). MS (ES⁺): 613.2 (M + 1)⁺. |
| 184<br><br>6-(4-(2-(isopropylsulfonyl)phenylamino)-5-chloropyrimidin-2-ylamino)-5-isopropoxy-2-methylisoindolin-1-one | 8.53 (d, 1H); 8.32 (s, 1H), 8.11 (s, 1H); 7.81 (dd, 1H); 7.73 (dt, 1H); 7.33 (t, 1H); 7.28 (s, 1H); 4.72 (m, 1H); 4.39 (s, 2H); 3.30 (m, 1H); 3.06 (s, 3H); 1.28 (d, 6H), 1.15 (d, 6H). MS (ES⁺): 530.2 (M + 1)⁺. |
| 185<br><br>8-(5-chloro-4-(2-(isopropylsulfonyl)phenylamino)pyrimidin-2-ylamino)-9-isopropoxy-3-methyl-1,2,3,4-tetrahydrobenzo[c][1,7]naphthyridin-6(5H)-one | MS (ES⁺): 597.1 (M + 1)⁺. |

TABLE 1-continued

| Structure | Physical Data<br>¹H NMR 400 MHz (DMSO-d6)<br>and/or MS (m/z) |
|---|---|
| 186 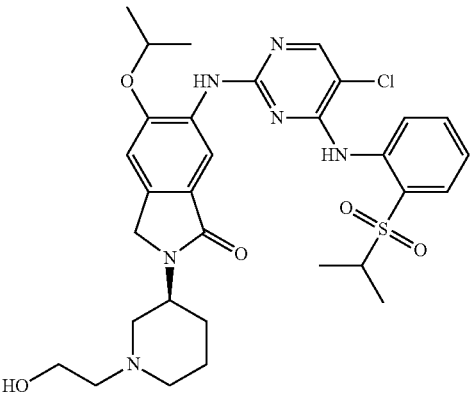<br>(S)-6-(5-chloro-4-(2-(isopropylsulfonyl)phenylamino)<br>pyrimidin-2-ylamino)-2-(1-(2-hydroxyethyl)piperidin-3-<br>yl)-5-isopropoxyisoindolin-1-one | MS (ES⁺): 643.2 (M + 1)⁺. |
| 187 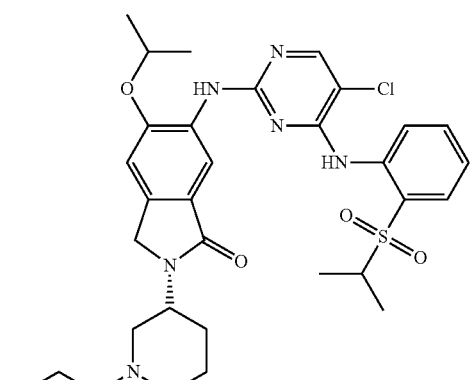<br>(R)-6-(5-chloro-4-(2-(isopropylsulfonyl)phenylamino)<br>pyrimidin-2-ylamino)-2-(1-(2-hydroxyethyl)piperidin-3-<br>yl)-5-isopropoxyisoindolin-1-one | MS (ES⁺): 643.2 (M + 1)⁺. |
| 188 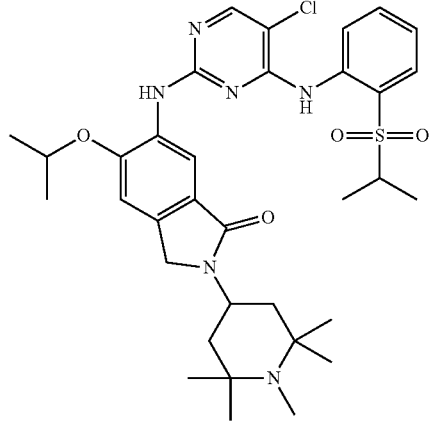<br>6-(5-chloro-4-(2-(isopropylsulfonyl)phenylamino)<br>pyrimidin-2-ylamino)-5-isopropoxy-2-(1,2,2,6,6-<br>pentamethylpiperidin-4-yl)isoindolin-1-one | MS (ES⁺): 669.3 (M + 1)⁺. |

| Structure | Physical Data<br>¹H NMR 400 MHz (DMSO-d6)<br>and/or MS (m/z) |
|---|---|
| 189 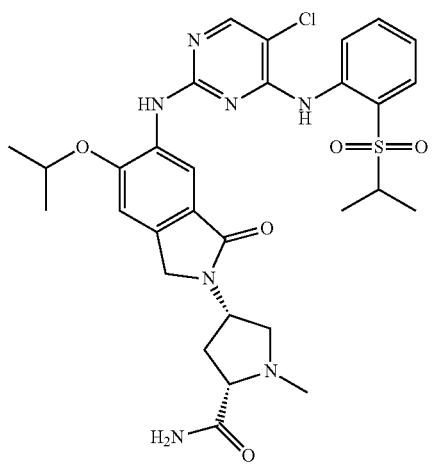<br>(2S,4S)-4-(6-(5-chloro-4-(2-(isopropylsulfonyl)<br>phenylamino)pyrimidin-2-ylamino)-5-isopropoxy-1-<br>oxoisoindolin-2-yl)-1-methylpyrrolidine-2-carboxamide | MS (ES$^+$): 642.2 (M + 1)$^+$. |
| 190 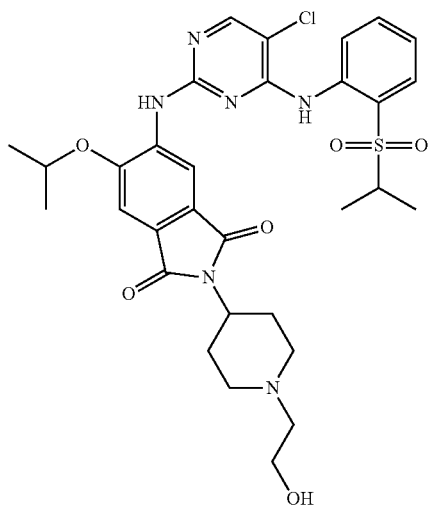<br>5-(5-chloro-4-(2-(isopropylsulfonyl)phenylamino)<br>pyrimidin-2-ylamino)-2-(1-(2-hydroxyethyl)piperidin-4-<br>yl)-6-isopropoxyisoindoline-1,3-dione | MS (ES$^+$): 657.2 (M + 1)$^+$. |

TABLE 1-continued

| Structure | Physical Data<br>¹H NMR 400 MHz (DMSO-d6)<br>and/or MS (m/z) |
|---|---|
| 191 | MS (ES⁺): 670.2 (M + 1)⁺. |

2-(4-(5-(5-chloro-4-(2-(isopropylsulfonyl)phenylamino)
pyrimidin-2-ylamino)-6-isopropoxy-1,3-dioxoisoindolin-
2-yl)piperidin-1-yl)acetamide

| | |
|---|---|
| 192 | MS (ES⁺): 666 (M + 1)⁺. |

3-(4-(5-(5-chloro-4-(2-(isopropylsulfonyl)
phenylamino)pyrimidin-2-ylamino)-6-isopropoxy-1,3-
dioxoisoindolin-2-yl)piperidin-1-yl)propanenitrile TABLE 1-continued

| | Structure | Physical Data<br>¹H NMR 400 MHz (DMSO-d6)<br>and/or MS (m/z) |
|---|---|---|
| 193 | (S)-5-(5-chloro-4-(2-(isopropylsulfonyl)phenylamino)<br>pyrimidin-2-ylamino)-6-isopropoxy-2-(1-<br>methylpyrrolidin-3-yl)isoindoline-1,3-dione | MS (ES⁺): 613.1 (M + 1)⁺. |
| 194 | (S)-5-(5-chloro-4-(2-(isopropylsulfonyl)phenylamino)<br>pyrimidin-2-ylamino)-2-(1-(2-hydroxyethyl)pyrrolidin-3-<br>yl)-6-isopropoxyisoindoline-1,3-dione | MS (ES⁺): 643.1 (M + 1)⁺. |
| 195 | (S)-5-(5-chloro-4-(2-(isopropylsulfonyl)phenylamino)<br>pyrimidin-2-ylamino)-6-isopropoxy-2-(1-<br>methylpyrrolidin-3-yl)isoindoline-1,3-dione | MS (ES⁺): 613.1 (M + 1)⁺. |

TABLE 1-continued

| Structure | Physical Data<br>¹H NMR 400 MHz (DMSO-d6)<br>and/or MS (m/z) |
|---|---|
| 196 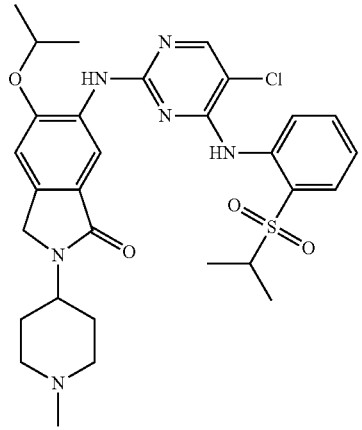<br>6-(4-(2-(isopropylsulfonyl)phenylamino)-5-chloropyrimidin-2-ylamino)-5-isopropoxy-2-(1-methylpiperidin-4-yl)isoindolin-1-one | 8.44 (s, 2H); 8.39 (s, 1H); 7.87 (dd, 1H); 7.78 (dt, 1H); 7.45 (s, 1H); 7.41 (m, 1H); 4.91 (m, 2H); 4.25 (m, 2H); 3.51 (m, 3H); 3.10 (m, 2H); 2.77 (s, 3H); 1.80 (m, 2H), 1.35 (d, 6H); 1.13 (d, 6H). MS (ES⁺): 614.2 (M + 1)⁺. |
| 197 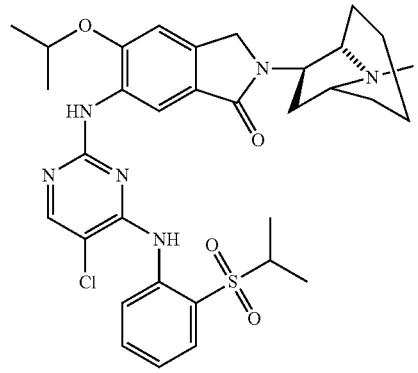<br>6-(4-(2-(isopropylsulfonyl)phenylamino)-5-chloropyrimidin-2-ylamino)-5-isopropoxy-2-((6S,7R)-9-methyl-9-aza-bicyclo[4.2.1]nonan-7-yl)isoindolin-1-one | MS (ES⁺): 654.2 (M + 1)⁺. |
| 198 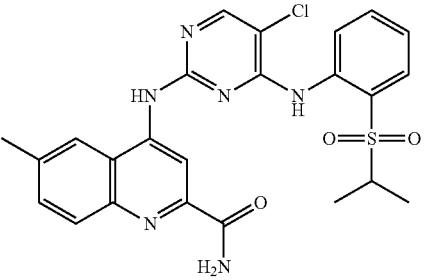<br>4-{5-Chloro-4-[2-(propane-2-sulfonyl)-phenylamino]-pyrimidin-2-ylamino}-6-methyl-quinoline-2-carboxylic acid amide | ¹H NMR (DMSO, 400 MHz) δ 10.04 (s, 1H), 9.66 (s, 1H), 8.47-8.63 (m, 3H), 8.18-8.23 (m, 2H), 7.97-7.99 (d, 1H), 7.54-7.82 (m, 3H), 7.25-7.35 (m, 1H), 3.31-3.33 (m, 1H), 2.54 (s, 3H), 1.15 (d, 6H). MS (ES⁺): 511.1 (M + 1)⁺. |

TABLE 1-continued

| | Structure | Physical Data<br>¹H NMR 400 MHz (DMSO-d6)<br>and/or MS (m/z) |
|---|---|---|
| 199 | 4-{5-Chloro-4-[2-(propane-2-sulfonyl)-phenylamino]-pyrimidin-2-ylamino}-6-methyl-quinoline-2-carboxylic acid methylamide | ¹H NMR (CDCl₃, 400 MHz) δ 9.73 (s, 1H), 8.85 (s, 1H), 8.21-8.55 (m, 1H), 8.21 (s, 1H), 8.08-8.18 (m, 1H) 7.90-7.92 (d, 1H), 7.81-7.83 (dd, 1H), 7.51-7.67 (m, 4H), 7.18-7.21 (m, 1H), 3.13-3.16 (m, 1H), 3.03-3.05 (d, 3H), 1.23-1.25 (d, 3H). MS (ES⁺): 525.7 (M + 1)⁺. |
| 200 | 4-{5-Chloro-4-[2-(propane-2-sulfonyl)-phenylamino]-pyrimidin-2-ylamino}-quinoline-2-carboxylic acid (2-morpholin-4-yl-ethyl)-amide | ¹H NMR (CDCl₃, 400 MHz) δ 9.79 (s, 1H), 9.00 (s, 1H), 8.57-8.59 (m, 2H), 8.30 (s, 1H), 8.11-8.13 (d, 1H), 7.99-8.01 (d, 1H), 7.88-7.91 (dd, 1H), 7.20-7.78 (m, 4H), 7.24-7.26 (m, 1H), 3.78-3.80 (m, 4H), 3.64-3.69 (m, 2H), 3.20-3.23 (m, 1H), 2.67-2.71 (m, 2H), 2.58-2.60 (m, 2H), 1.25-1.31 (d, 3H). MS (ES⁺): 610.7 (M + 1)⁺. |
| 201 | 4-{5-Chloro-4-[2-(propane-2-sulfonyl)-phenylamino]-pyrimidin-2-ylamino}-quinoline-2-carboxylic acid [2-(4-methyl-piperazin-1-yl)-ethyl]-amide | ¹H NMR (CDCl₃, 400 MHz) δ 9.73 (s, 1H), 8.93 (s, 1H), 8.43-8.52 (m, 2H), 8.22 (s, 1H), 8.03-8.05 (d, 1H), 7.93-7.95 (d, 1H), 7.82-7.84 (dd, 1H), 7.54-7.72 (m, 4H), 7.16-7.20 (m, 1H), 4.43-4.48 (m, 8H), 3.58-3.62 (m, 2H), 3.11-3.18 (m, 1H), 2.67-2.71 (m, 2H), 2.46 (s, 3H), 1.23-1.25 (d, 6H). MS (ES⁺): 623.8 (M + 1)⁺. |

TABLE 1-continued

| | Structure | Physical Data<br>$^1$H NMR 400 MHz (DMSO-d6)<br>and/or MS (m/z) |
|---|---|---|
| 202 | 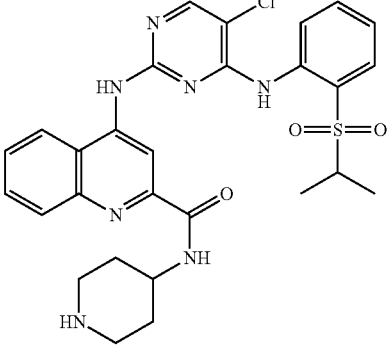<br>4-{5-Chloro-4-[2-(propane-2-sulfonyl)-phenylamino]-pyrimidin-2-ylamino}-quinoline-2-carboxylic acid piperidin-4-ylamide | $^1$H NMR (CD$_3$OD, 400 MHz) δ 8.92 (s, 1H), 8.68-8.70 (d, 1H), 8.46-8.48 (m, 2H), 8.26-8.28 (d, 1H), 7.96-7.99 (m, 2H), 7.79-7.83 (t, 1H), 7.67-7.71 (t, 1H), 7.38-7.42 (t, 1H), 4.31-4.33 (m, 1H), 3.60-3.63 (m, 2H), 3.40-3.46 (m, 1H), 3.27-3.33 (m, 2H), 2.33-2.37 (m, 2H), 2.05-2.08 (m, 2H), 1.35-1.37 (d, 6H). MS (ES$^+$): 580.7 (M + 1)$^+$. |

Table 2 shows exemplary compounds of Formula (1C).

TABLE 2

| | Structure | Physical Data<br>$^1$H NMR 400 MHz (DMSO-d6)<br>and/or MS (m/z) |
|---|---|---|
| 203 | 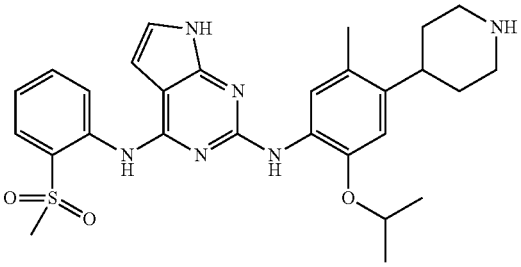<br>N2-(2-isopropoxy-5-methyl-4-(piperidin-4-yl)phenyl)-N4-(2-(methylsulfonyl)phenyl)-7H-pyrrolo[2,3-d]pyrimidine-2,4-diamine | MS (ES$^+$): 534.6 (M + 1)$^+$ |
| 204 | 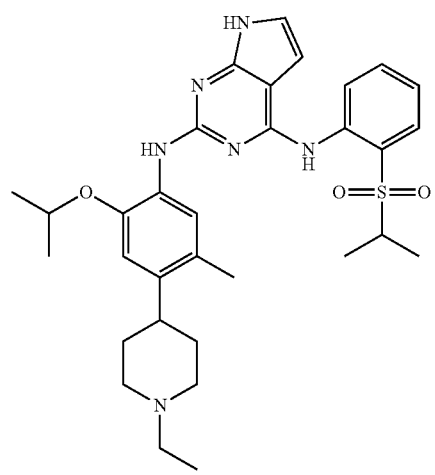<br>N2-(4-(1-ethylpiperidin-4-yl)-2-isopropoxy-5-methylphenyl)-N4-(2-(isopropylsulfonyl)phenyl)-7H-pyrrolo[2,3-d]pyrimidine-2,4-diamine | MS (ES$^+$): 590.8 (M + 1)$^+$. |

TABLE 2-continued
| Structure | Physical Data<br>¹H NMR 400 MHz (DMSO-d6)<br>and/or MS (m/z) |
| --- | --- |
| 205 | MS (ES⁺): 620.3 (M + 1)⁺. |
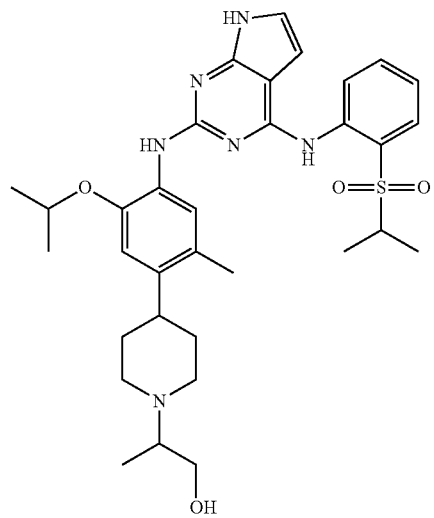
2-(4-(5-isopropoxy-4-(4-(2-(isopropylsulfonyl)
phenylamino)-7H-pyrrolo[2,3-d]pyrimidin-2-ylamino)-2-
methylphenyl)piperidin-1-yl)propan-1-ol
| 206 | MS (ES⁺): 604.8 (M + 1)⁺. |
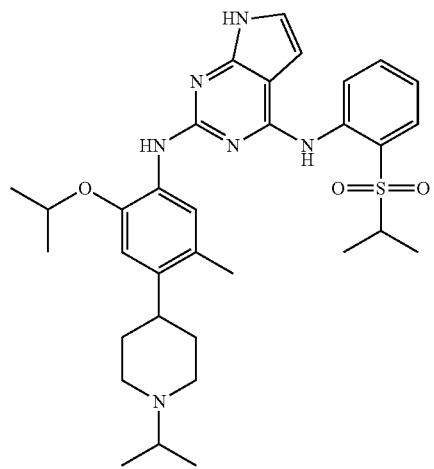
N2-(2-isopropoxy-4-(1-isopropylpiperidin-4-yl)-5-
methylphenyl)-N4-(2-(isopropylsulfonyl)phenyl)-7H-
pyrrolo[2,3-d]pyrimidine-2,4-diamine TABLE 2-continued
| Structure | Physical Data $^1$H NMR 400 MHz (DMSO-d6) and/or MS (m/z) |
|---|---|
| 207 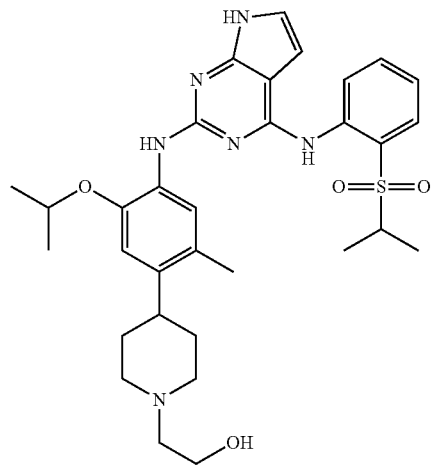
2-(4-(5-isopropoxy-4-(4-(2-(isopropylsulfonyl)phenylamino)-7H-pyrrolo[2,3-d]pyrimidin-2-ylamino)-2-methylphenyl)piperidin-1-yl)ethanol | MS (ES$^+$): 606.8 (M + 1)$^+$. |
| 208 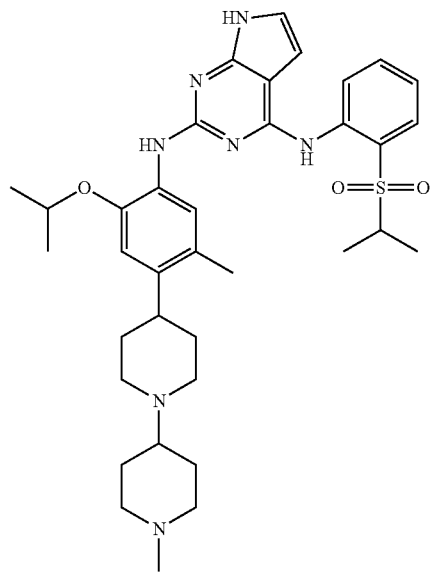
N2-(2-isopropoxy-5-methyl-4-(1'-methyl-1,4'-bipiperidin-4-yl)phenyl)-N4-(2-(isopropylsulfonyl) phenyl)-7H-pyrrolo[2,3-d]pyrimidine-2,4-diamine | MS (ES$^+$): 659.8 (M + 1)$^+$. |

TABLE 2-continued
| | Physical Data $^1$H NMR 400 MHz (DMSO-d6) and/or MS (m/z) |
|---|---|
| Structure | |
| 209 | MS (ES$^+$): 577.7 (M + 1)$^+$. |
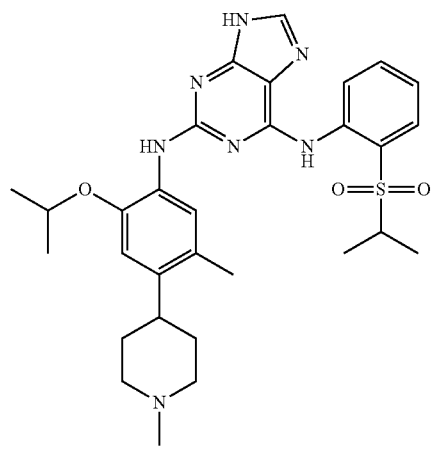
N2-(2-isopropoxy-5-methyl-4-(1-methylpiperidin-4-yl)phenyl)-N6-(2-(isopropylsulfonyl)phenyl)-9H-purine-2,6-diamine
| 210 | MS (ES$^+$): 588.7 (M + 1)$^+$. |
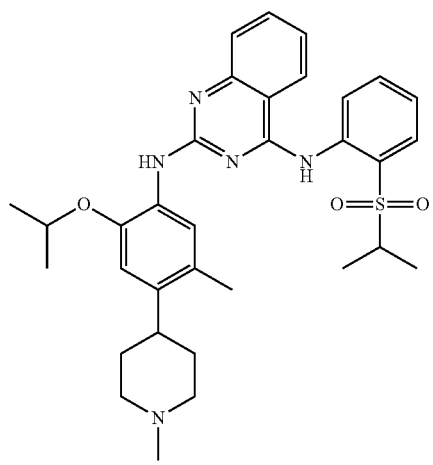
N2-(2-isopropoxy-5-methyl-4-(1-methylpiperidin-4-yl)phenyl)-N4-(2-(isopropylsulfonyl)phenyl)quinazoline-2,4-diamine TABLE 2-continued
| Structure | Physical Data<br>$^1$H NMR 400 MHz (DMSO-d6)<br>and/or MS (m/z) |
|---|---|
| 211 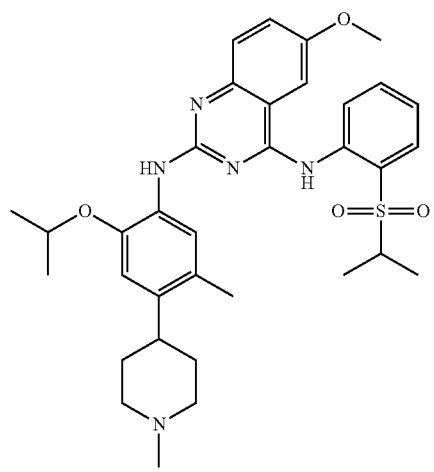<br>N2-(2-isopropoxy-5-methyl-4-(1-methylpiperidin-4-yl)phenyl)-N4-(2-(isopropylsulfonyl)phenyl)-6-methoxyquinazoline-2,4-diamine | MS (ES$^+$): 618.8 (M + 1)$^+$. |
| 212 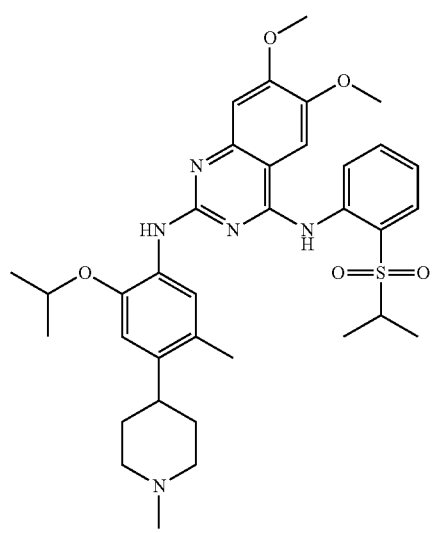<br>N2-(2-isopropoxy-5-methyl-4-(1-methylpiperidin-4-yl)phenyl)-N4-(2-(isopropylsulfonyl)phenyl)-6,7-dimethoxyquinazoline-2,4-diamine | MS (ES$^+$): 648.8 (M + 1)$^+$. |

TABLE 2-continued

| Structure | Physical Data<br>¹H NMR 400 MHz (DMSO-d6)<br>and/or MS (m/z) |
|---|---|
| 213 5-isopropoxy-6-(4-(2-(isopropylsulfonyl)phenylamino)-7H-pyrrolo[2,3-d]pyrimidin-2-ylamino)-2-(piperidin-4-yl)isoindolin-1-one | MS (ES⁺): 604.7 (M + 1)⁺. |
| 214 N2-(4-(4-(dimethylamino)cyclohexyl)-2-isopropoxy-5-methylphenyl)-N6-(2-(isopropylsulfonyl)phenyl)-9H-purine-2,6-diamine | MS (ES⁺): 606.7 (M + 1)⁺. |
| 215 N2-(2-isopropoxy-4-methyl-5-(3-methylisoxazol-5-yl)phenyl)-N4-(2-(isopropylsulfonyl)phenyl)-7H-pyrrolo[2,3-d]pyrimidine-2,4-diamine | MS (ES⁺): 561.6 (M + 1)⁺. |

TABLE 2-continued
| Structure | Physical Data
¹H NMR 400 MHz (DMSO-d6)
and/or MS (m/z) |
| --- | --- |
| 216 | MS (ES⁺): 563.2 (M + 1)⁺. |
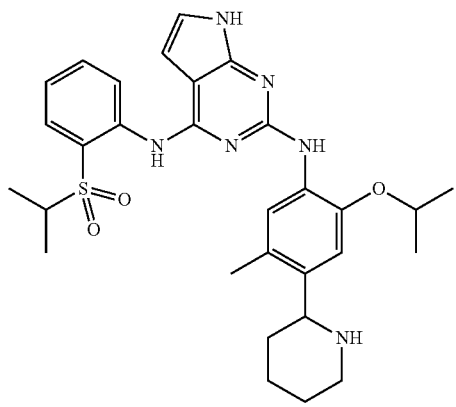
N2-(2-isopropoxy-5-methyl-4-(piperidin-2-yl)phenyl)-N4-
(2-(isopropylsulfonyl)phenyl)-7H-pyrrolo[2,3-
d]pyrimidine-2,4-diamine
| 217 | MS (ES⁺): 621.8 (M + 1)⁺. |
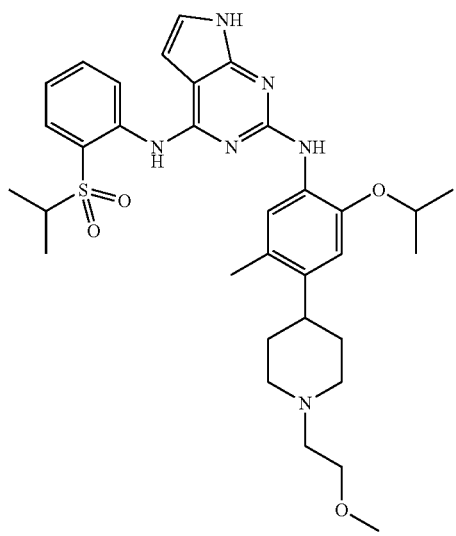
N2-(2-isopropoxy-4-(1-(2-methoxyethyl)piperidin-4-yl)-
5-methylphenyl)-N4-(2-isopropylsulfonyl)phenyl)-7H-
pyrrolo[2,3-d]pyrimidine-2,4-diamine TABLE 2-continued
| | Physical Data $^1$H NMR 400 MHz (DMSO-d6) and/or MS (m/z) |
|---|---|
| Structure | |
| 218 | MS (ES$^+$): 621.8 (M + 1)$^+$. |
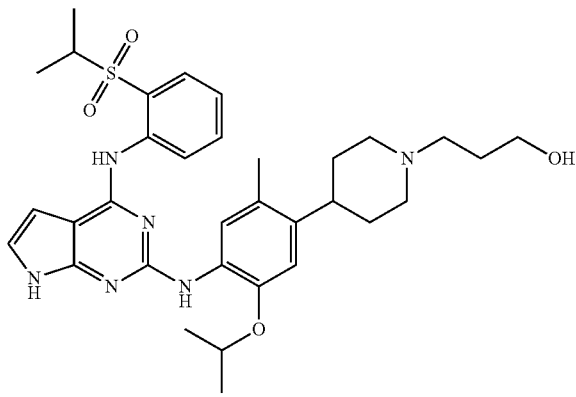
3-(4-(5-isopropoxy-4-(4-(2-(isopropylsulfonyl)
phenylamino)-7H-pyrrolo[2,3-d]pyrimidin-2-ylamino)-2-
methylphenyl)piperidin-1-yl)propan-1-ol
| 219 | MS (ES$^+$): 621.7 (M + 1)$^+$. |
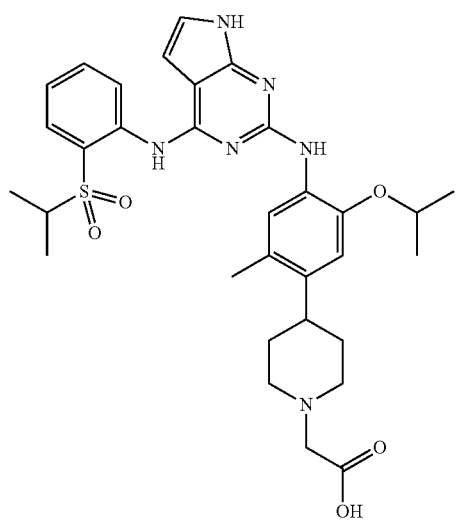
2-(4-(5-isopropoxy-4-(4-(2-(isopropylsulfonyl)
phenylamino)-7H-pyrrolo[2,3-d]pyrimidin-2-ylamino)-2-
methylphenyl)piperidin-1-yl)acetic acid

| Structure | Physical Data<br>¹H NMR 400 MHz (DMSO-d6)<br>and/or MS (m/z) |
|---|---|
| 220 | MS (ES⁺): 635.8 (M + 1)⁺. |
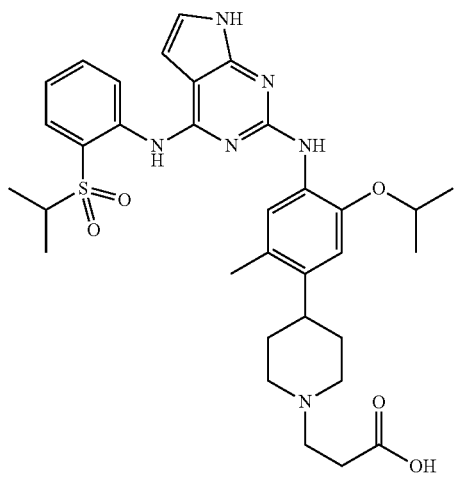
3-(4-(5-isopropoxy-4-(4-(2-(isopropylsulfonyl)
phenylamino)-7H-pyrrolo[2,3-d]pyrimidin-2-ylamino)-2-
methylphenyl)piperidin-1-yl)propanoic acid
| | |
|---|---|
| 221 | MS (ES⁺): 620.2 (M + 1)⁺. |
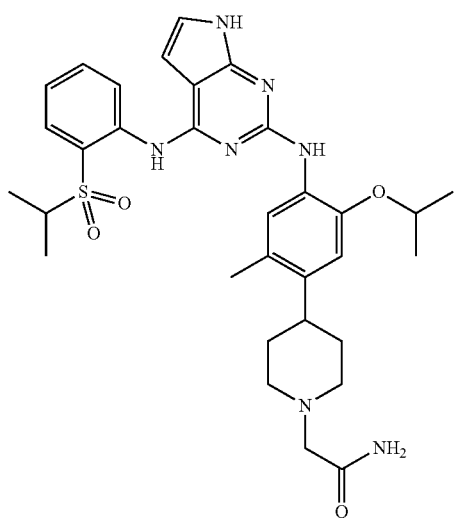
2-(4-(5-isopropoxy-4-(4-(2-(isopropylsulfonyl)
phenylamino)-7H-pyrrolo[2,3-d]pyrimidin-2-ylamino)-2-
methylphenyl)piperidin-1-yl)acetamide TABLE 2-continued
| Structure | Physical Data $^1$H NMR 400 MHz (DMSO-d6) and/or MS (m/z) |
|---|---|
| 222 | MS (ES$^+$): 634.8 (M + 1)$^+$. |
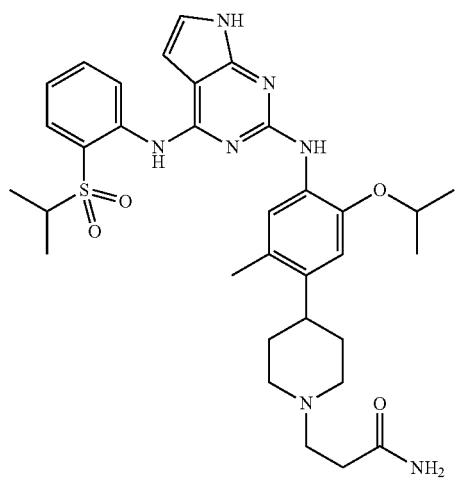
3-(4-(5-isopropoxy-4-(4-(2-(isopropylsulfonyl)
phenylamino)-7H-pyrrolo[2,3-d]pyrimidin-2-ylamino)-2-
methylphenyl)piperidin-1-yl)propanamide
| 223 | MS (ES$^+$): 634.8 (M + 1)$^+$. |
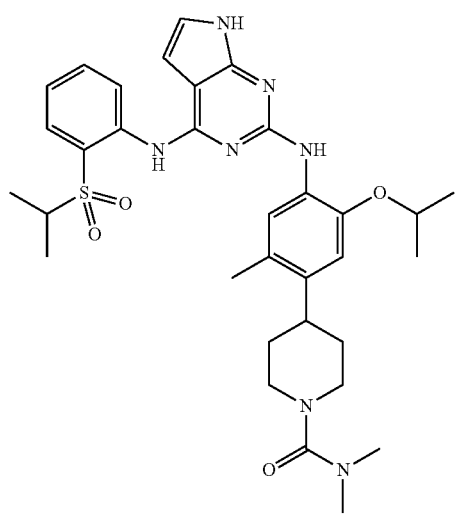
4-(5-isopropoxy-4-(4-(2-(isopropylsulfonyl)
phenylamino)-7H-pyrrolo[2,3-d]pyrimidin-2-ylamino)-2-
methylphenyl)-N,N-dimethylpiperidine-1-carboxamide TABLE 2-continued

| | Structure | Physical Data<br>¹H NMR 400 MHz (DMSO-d6)<br>and/or MS (m/z) |
|---|---|---|
| 224 | N2-(2-isopropoxy-5-methyl-4-(piperidin-3-yl)phenyl)-N4-(2-(isopropylsulfonyl)phenyl)-7H-pyrrolo[2,3-d]pyrimidine-2,4-diamine | MS (ES⁺): 563.7 (M + 1)⁺. |
| 225 | N2-(2-isopropoxy-5-methyl-4-(1-methylpiperidin-3-yl)phenyl)-N4-(2-(isopropylsulfonyl)phenyl)-7H-pyrrolo[2,3-d]pyrimidine-2,4-diamine | MS (ES⁺): 576.7 (M + 1)⁺. |
| 226 | 2-(3-(5-isopropoxy-4-(4-(2-(isopropylsulfonyl)phenylamino)-7H-pyrrolo[2,3-d]pyrimidin-2-ylamino)-2-methylphenyl)piperidin-1-yl)ethanol | MS (ES⁺): 607.8 (M + 1)⁺. |

| Structure | Physical Data<br>¹H NMR 400 MHz (DMSO-d6)<br>and/or MS (m/z) |
|---|---|
| 227 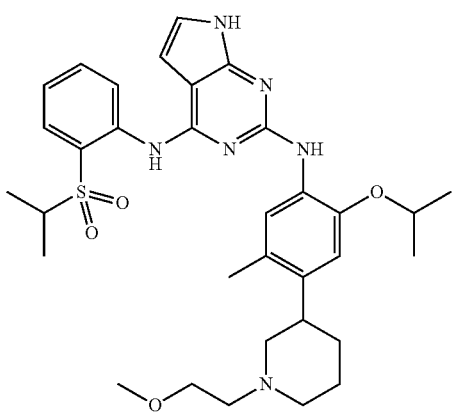<br>N2-(2-isopropoxy-4-(1-(2-methoxyethyl)piperidin-3-yl)-5-methylphenyl)-N4-(2-(isopropylsulfonyl)phenyl)-7H-pyrrolo[2,3-d]pyrimidine-2,4-diamine | MS (ES⁺): 621.8 (M + 1)⁺. |
| 228 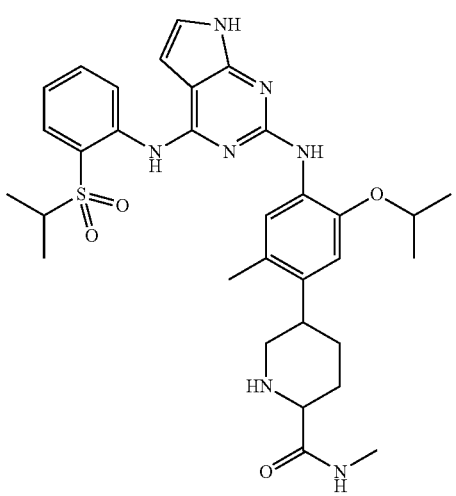<br>5-(5-isopropoxy-4-(4-(2-(isopropylsulfonyl)phenylamino)-7H-pyrrolo[2,3-d]pyrimidin-2-ylamino)-2-methylphenyl)-N-methylpiperidine-2-carboxamide | MS (ES⁺): 620.7 (M + 1)⁺. |

TABLE 2-continued
| Structure | Physical Data<br>$^1$H NMR 400 MHz (DMSO-d6)<br>and/or MS (m/z) |
|---|---|
| 229 | MS (ES$^+$): 564.7 (M + 1)$^+$. |
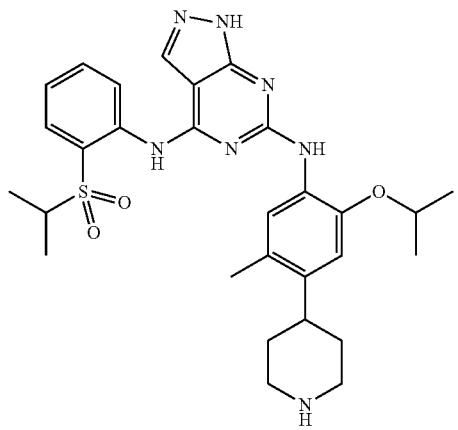
N6-(2-isopropoxy-5-methyl-4-(piperidin-4-yl)phenyl)-N4-
(2-(isopropylsulfonyl)phenyl)-1H-pyrazolo[3,4-
d]pyrimidine-4,6-diamine
| | |
|---|---|
| 230 | MS (ES$^+$): 592.7 (M + 1)$^+$. |
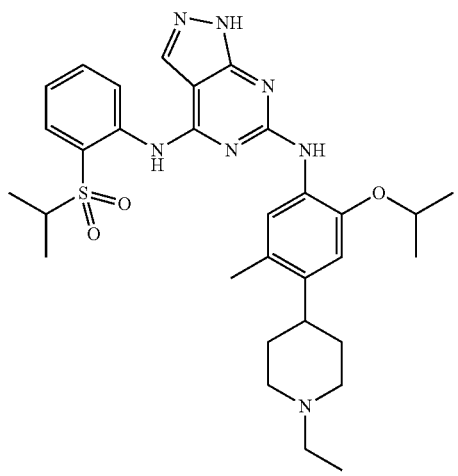
N6-(4-(1-ethylpiperidin-4-yl)-2-isopropoxy-5-
methylphenyl)-N4-(2-(isopropylsulfonyl)phenyl)-1H-
pyrazolo[3,4-d]pyrimidine-4,6-diamine TABLE 2-continued
| | Physical Data<br>$^1$H NMR 400 MHz (DMSO-d6) |
|---|---|
| Structure | and/or MS (m/z) |
231
MS (ES$^+$): 578.7 (M + 1)$^+$.
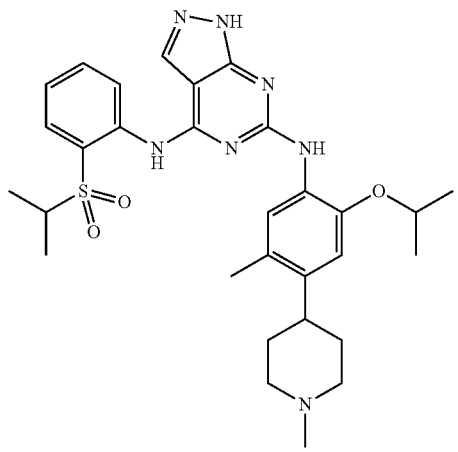
N6-(2-isopropoxy-5-methyl-4-(1-methylpiperidin-4-yl)phenyl)-N4-(2-(isopropylsulfonyl)phenyl)-1H-pyrazolo[3,4-d]pyrimidine-4,6-diamine
232
MS (ES$^+$): 608.7 (M + 1)$^+$.
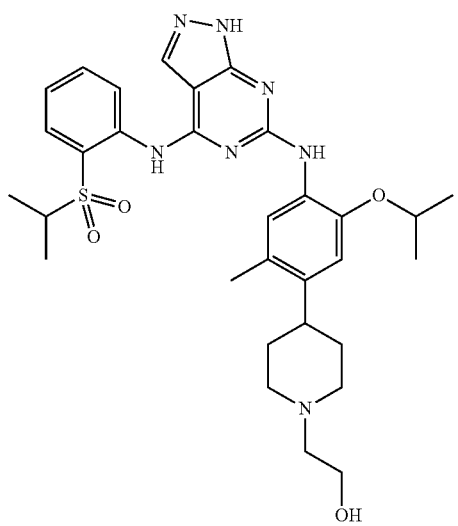
2-(4-(5-isopropoxy-4-(4-(2-(isopropylsulfonyl)phenylamino)-1H-pyrazolo[3,4-d]pyrimidin-6-ylamino)-2-methylphenyl)piperidin-1-yl)ethanol

| Structure | Physical Data <br> ¹H NMR 400 MHz (DMSO-d6) and/or MS (m/z) |
|---|---|
| 233 | MS (ES⁺): 622.7 (M + 1)⁺. |
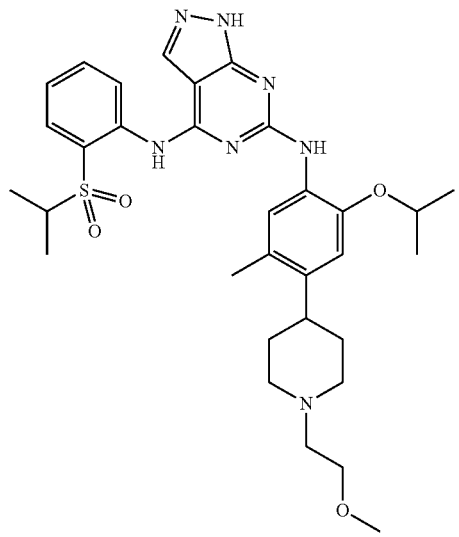
N6-(2-isopropoxy-4-(1-(2-methoxyethyl)piperidin-4-yl)-5-methylphenyl)-N4-(2-(isopropylsulfonyl)phenyl)-1H-pyrazolo[3,4-d]pyrimidine-4,6-diamine
| | |
|---|---|
| 234 | MS (ES⁺): 606.8 (M + 1)⁺. |
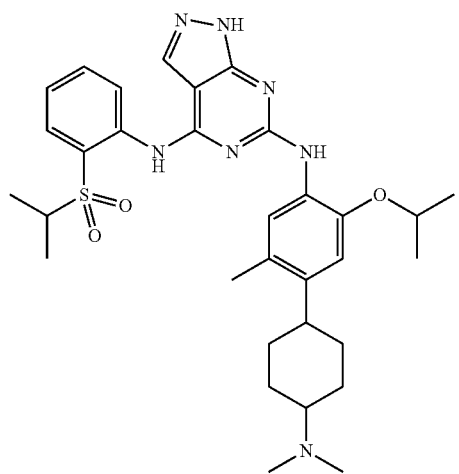
N6-(4-(4-(dimethylamino)cyclohexyl)-2-isopropoxy-5-methylphenyl)-N4-(2-(isopropylsulfonyl)phenyl)-1H-pyrazolo[3,4-d]pyrimidine-4,6-diamine

| | Structure | Physical Data<br>¹H NMR 400 MHz (DMSO-d6)<br>and/or MS (m/z) |
|---|---|---|
| 235 | N6-(2-isopropoxy-5-methyl-4-(piperidin-2-yl)phenyl)-N4-(2-(isopropylsulfonyl)phenyl)-1H-pyrazolo[3,4-d]pyrimidine-4,6-diamine | MS (ES⁺): 564.7 (M + 1)⁺. |
| 236 | 5-isopropoxy-6-(4-(2-(isopropylsulfonyl)phenylamino)-1H-pyrazolo[3,4-d]pyrimidin-6-ylamino)-2-(piperidin-4-yl)isoindolin-1-one | MS (ES⁺): 605.7 (M + 1)⁺. |
| 237 | N2-(2-isopropoxy-5-methyl-4-(piperidin-4-yl)phenyl)-N4-(2-(isopropylsulfonyl)phenyl)-5,6,7,8-tetrahydropyrido[2,3-d]pyrimidine-2,4-diamine | MS (ES⁺): 579.7 (M + 1)⁺. |

TABLE 2-continued
| | Physical Data $^1$H NMR 400 MHz (DMSO-d6) and/or MS (m/z) |
|---|---|
| Structure | |
238
MS (ES$^+$): 575.7 (M + 1)$^+$.
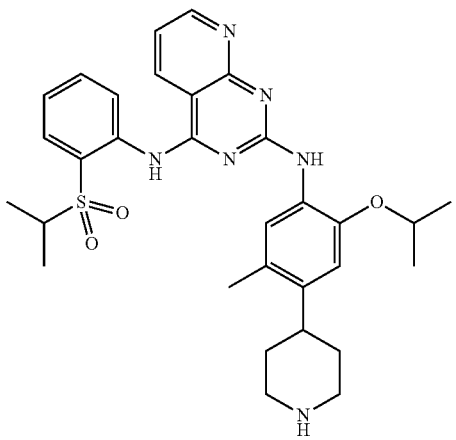
N2-(2-isopropoxy-5-methyl-4-(piperidin-4-yl)phenyl)-N4-
(2-(isopropylsulfonyl)phenyl)pyrido[2,3-d]pyrimidine-
2,4-diamine
239
MS (ES$^+$): 619.7 (M + 1)$^+$.
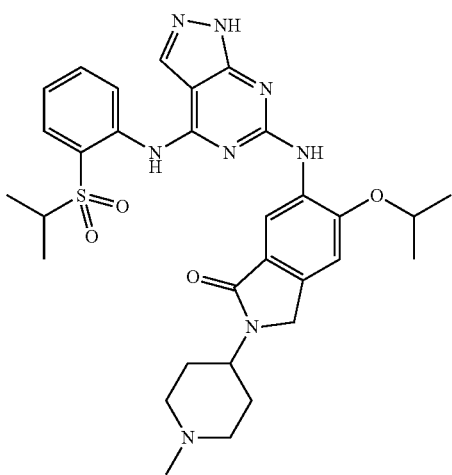
5-isopropoxy-6-(4-(2-(isopropylsulfonyl)phenylamino)-
1H-pyrazolo[3,4-d]pyrimidin-6-ylamino)-2-(1-
methylpiperidin-4-yl)isoindolin-1-one TABLE 2-continued
| Structure | Physical Data
¹H NMR 400 MHz (DMSO-d6)
and/or MS (m/z) |
| --- | --- |
| 240 | MS (ES⁺): 633.7 (M + 1)⁺. |
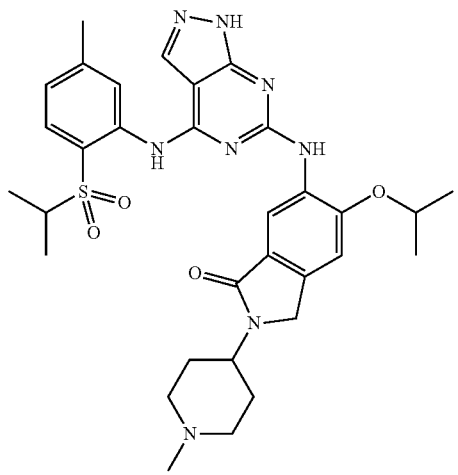
5-isopropoxy-6-(4-(2-(isopropylsulfonyl)-5-
methylphenylamino)-1H-pyrazolo[3,4-d]pyrimidin-6-
ylamino)-2-(1-methylpiperidin-4-yl)isoindolin-1-one
| 241 | MS (ES⁺): 677.8 (M + 1)⁺. |
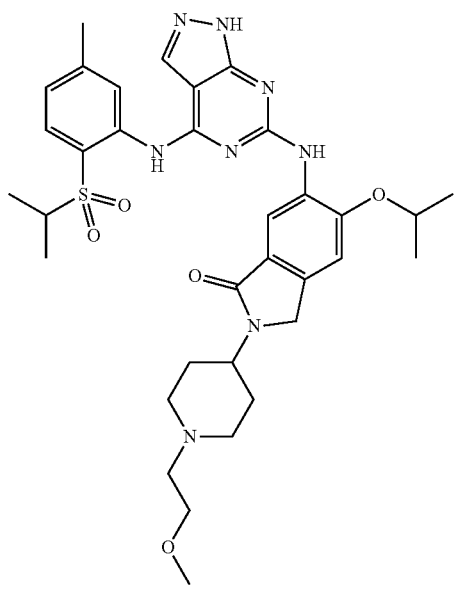
5-isopropoxy-6-(4-(2-(isopropylsulfonyl)-5-
methylphenylamino)-1H-pyrazolo[3,4-d]pyrimidin-6-
ylamino)-2-(1-(2-methoxyethyl)piperidin-4-yl)isoindolin-
1-one TABLE 2-continued

| | Structure | Physical Data<br>¹H NMR 400 MHz (DMSO-d6)<br>and/or MS (m/z) |
|---|---|---|
| 242 | N6-(2-isopropoxy-5-methyl-4-(piperidin-2-yl)phenyl)-N4-(2-(isopropylsulfonyl)-5-methylphenyl)-1H-pyrazolo[3,4-d]pyrimidine-4,6-diamine | MS (ES⁺): 578.7 (M + 1)⁺. |
| 243 | N6-(2-isopropoxy-5-methyl-4-(piperidin-3-yl)phenyl)-N4-(2-(isopropylsulfonyl)-5-methylphenyl)-1H-pyrazolo[3,4-d]pyrimidine-4,6-diamine | MS (ES⁺): 578.7 (M + 1)⁺. |
| 244 | N2-(2-isopropoxy-4-(1-methylpiperidin-4-yl)phenyl)-N4-(2-(isopropylsulfonyl)phenyl)-7H-pyrrolo[2,3-d]pyrimidine-2,4-diamine | MS (ES⁺): 562.3 (M + 1)⁺. |

TABLE 2-continued
| Structure | Physical Data<br>¹H NMR 400 MHz (DMSO-d6)<br>and/or MS (m/z) |
|---|---|
| 245 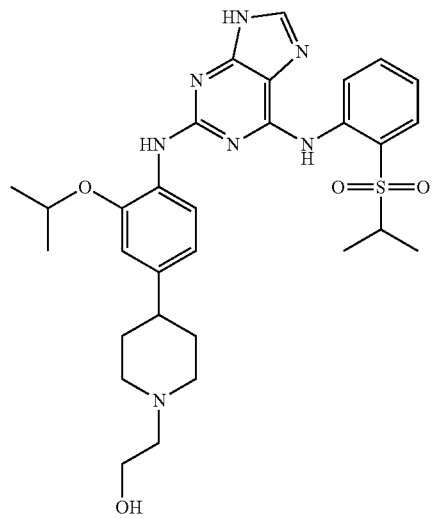<br>2-(4-(3-isopropoxy-4-(6-(2-(isopropylsulfonyl)<br>phenylamino)-9H-purin-2-ylamino)phenyl)piperidin-1-<br>yl)ethanol | MS (ES⁺): 593.7 (M + 1)⁺. |
| 246 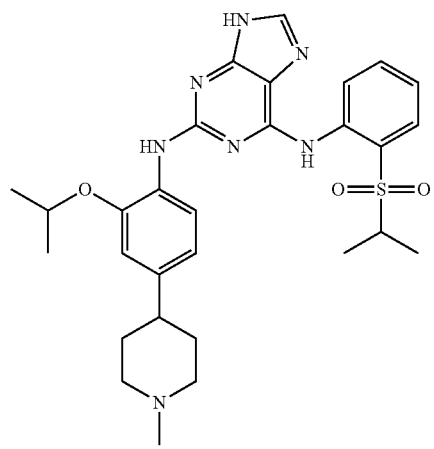<br>N2-(2-isopropoxy-4-(1-methylpiperidin-4-yl)phenyl)-N6-<br>(2-(isopropylsulfonyl)phenyl)-9H-purine-2,6-diamine | MS (ES⁺): 563.7 (M + 1)⁺. |

Example 17

Methyl 4'-(5-chloro-4-(2-(isopropylsulfonyl)phenylamino)pyridin-2-ylamino)-5'-methoxy-2'-methylbiphenyl-4-carboxylate (254)

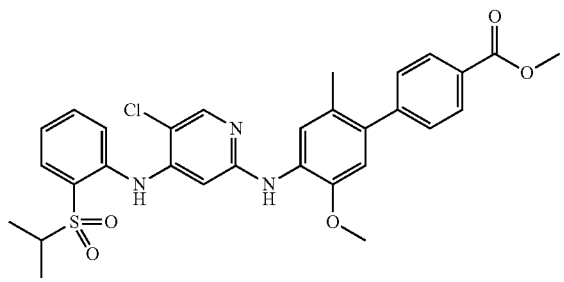

Step 1: Methyl 4'-amino-5'-methoxy-2'-methylbiphenyl-4-carboxylate

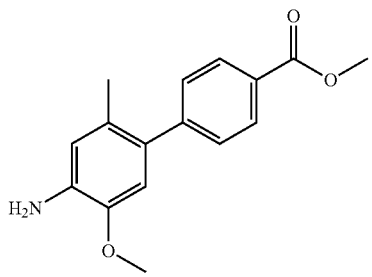

Methyl 4'-amino-5'-methoxy-2'-methylbiphenyl-4-carboxylate; MS m/z 272.1 (M+1), may be synthesized following the procedures previously described (Example 7, Steps 1 and 2) using appropriate reagents.

Step 2: Methyl 4'-(4-bromo-5-chloropyridin-2-ylamino)-5'-methoxy-2'-methylbiphenyl-4-carboxylate

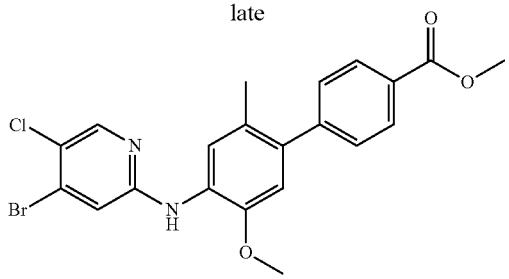

Methyl 4'-amino-5'-methoxy-2'-methylbiphenyl-4-carboxylate generated in Step 1 (200 mg, 0.75 mmol), 2,4-dibromo-5-chloropyridine (222 mg, 0.82 mmol, 1.1 equiv), $Pd_2(dba)_3$ (17 mg, 0.02 mmol, 0.025 equiv.), xantphos (22 mg, 0.04 mmol, 0.05 equiv.), and $Cs_2CO_3$ (365 mg, 1.1 mmol, 1.5 equiv.) are added to THF (5 mL). The resulting mixture is bubbled with $N_2$ gas for 5 minutes and then heated at 150° C. for 4 hours. After cooling to room temperature, the reaction mixture is diluted into EtOAc and washed with $H_2O$. The EtOAc layer is dried over $Mg_2SO_4$ and concentrated in vacuo. Silica gel chromatography (hexanes-EtOAc) affords Methyl 4'-(4-bromo-5-chloropyridin-2-ylamino)-5'-methoxy-2'-methylbiphenyl-4-carboxylate; MS m/z 461.0 (M+1).

Step 3: Methyl 4'-(5-chloro-4-(2-(isopropylsulfonyl)phenylamino)pyridin-2-ylamino)-5'-methoxy-2'-methylbiphenyl-4-carboxylate (254)

Methyl 4'-(4-bromo-5-chloropyridin-2-ylamino)-5'-methoxy-2'-methylbiphenyl-4-carboxylate generated in Step 2 (9 mg, 0.022 mmol), 2-(isopropylsulfonyl)aniline (4 mg, 0.022 mmol, 1 equiv), $Pd_2(dba)_3$ (1.7 mg, 0.002 mmol, 0.1 equiv.), 2-(Dicyclohexylphosphino)-2',4',6'-tri-1-propyl-1,1'-biphenyl (1.8 mg, 0.004 mmol, 0.2 equiv.), and Sodium tert-butoxide (2.7 mg, 0.028 mmol, 1.3 equiv.) are added to THF (1 mL). The resulting mixture is bubbled with $N_2$ gas for 5 minutes and then heated at 150° C. for 4 hours. After cooling to room temperature, the reaction mixture is diluted into EtOAc and washed with $H_2O$. The EtOAc layer is dried over $Mg_2SO_4$ and concentrated in vacuo. Silica gel chromatography (hexanes-EtOAc) affords Methyl 4'-(5-chloro-4-(2-(isopropylsulfonyl)phenylamino)pyridin-2-ylamino)-5'-methoxy-2'-methylbiphenyl-4-carboxylate (254); MS m/z 580.2 (M+1).

Exemplary compounds of the invention are set forth below. Table 3 shows exemplary compounds of Formula (5).

TABLE 3

| | Structure | Physical Data $^1$H NMR 400 MHz (DMSO-d6) and/or MS (m/z) |
|---|---|---|
| 247 | ![structure] 5-chloro-N2-(3-isopropoxy-5-(piperidin-4-yl)pyridin-2-yl)-N4-(2-(isopropylsulfonyl)phenyl)pyridine-2,4-diamine | MS (ES+): 544.2 (M + 1)+. |

TABLE 3-continued

| | Structure | Physical Data<br>¹H NMR 400 MHz (DMSO-d6) and/or MS (m/z) |
|---|---|---|
| 248 | 5-chloro-N2-(3-isopropoxy-5-(1-methylpiperidin-4-yl)pyridin-2-yl)-N4-(2-isopropylsulfonyl)phenyl)pyridine-2,4-diamine | MS (ES⁺): 558.2 (M + 1)⁺. |
| 249 | 5-chloro-N2-(5-(1-ethylpiperidin-4-yl)-3-isopropoxypyridin-2-yl)-N4-(2-(isopropylsulfonyl)phenyl)pyridine-2,4-dione | MS (ES⁺): 572.2 (M + 1)⁺. |
| 250 | 2-(4-(6-(5-chloro-4-(2-(isopropylsulfonyl)phenylamino)pyridin-2-ylamino)-5-isopropoxypyridin-3-yl)piperidin-1-yl)ethanol | MS (ES⁺): 588.2 (M + 1)⁺. |

TABLE 3-continued

| | Structure | Physical Data $^1$H NMR 400 MHz (DMSO-d6) and/or MS (m/z) |
|---|---|---|
| 251 | 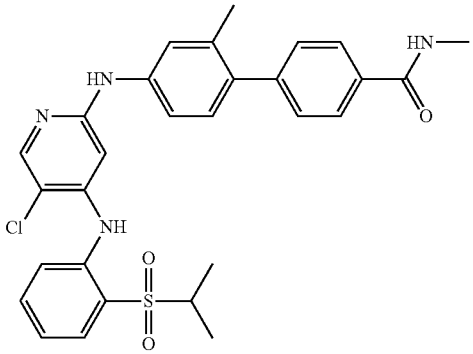<br>4'-(5-chloro-4-(2-(isopropylsulfonyl)phenylamino)pyridin-2-ylamino)-N,2'-dimethylbiphenyl-4-carboxamide | MS (ES$^+$): 549.2 (M + 1)$^+$. |
| 252 | 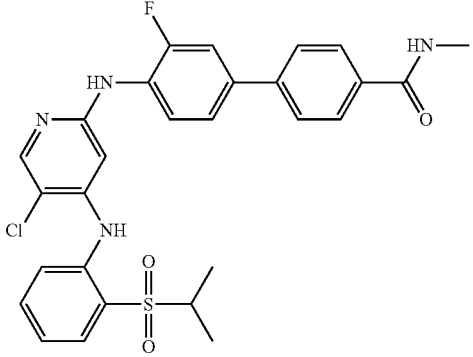<br>4'-(5-chloro-4-(2-(isopropylsulfonyl)phenylamino)pyridin-2-ylamino)-3'-fluoro-N-methylbiphenyl-4-carboxamide | MS (ES$^+$): 553.1 (M + 1)$^+$. |
| 253 | 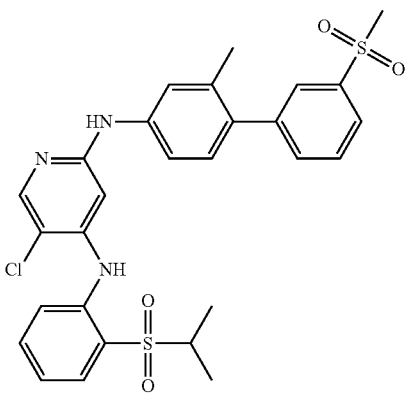<br>5-chloro-N4-(2-(isopropylsulfonyl)phenyl)-N2-(2-methyl-3'-(methylsulfonyl)biphenyl-4-yl)pyridine-2,4-dione | MS (ES$^+$): 570.1 (M + 1)$^+$. |

TABLE 3-continued

| | Structure | Physical Data<br>¹H NMR 400 MHz (DMSO-d6) and/or MS (m/z) |
|---|---|---|
| 254 | 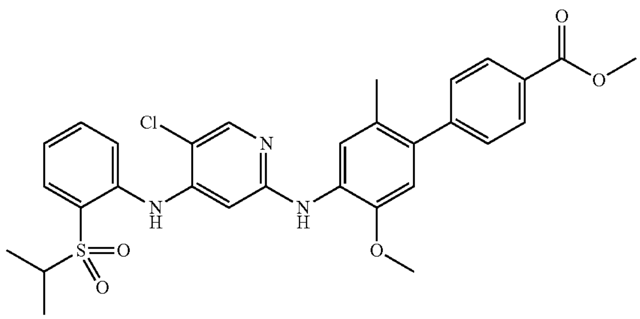 | MS m/z 580.2 (M + 1)⁺. |

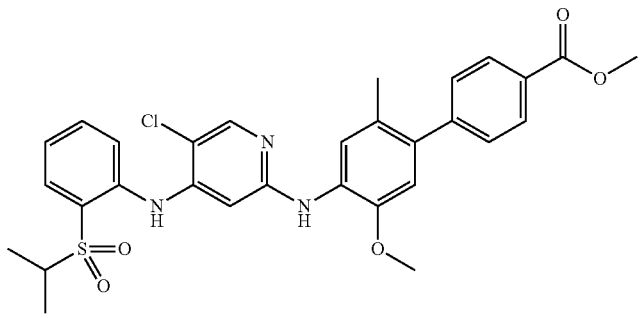

Methyl 4'-(5-chloro-4-(2-(isopropylsulfonyl)
phenylamino)pyridin-2-ylamino)-5'-methoxy-2'-
methylbiphenyl-4-carboxylate

| 255 | | MS (ES⁺): 495.6 (M + 1)⁺. |

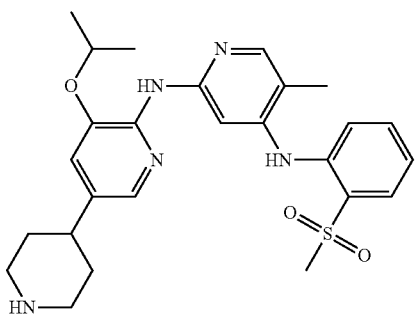

N2-(3-isopropoxy-5-(piperidin-4-yl)pyridin-2-yl)-5-
methyl-N4-(2-(methylsulfonyl)phenyl)pyridine-2,4-
diamine

| 256 | | MS (ES⁺): 534.6 (M + 1)⁺. |

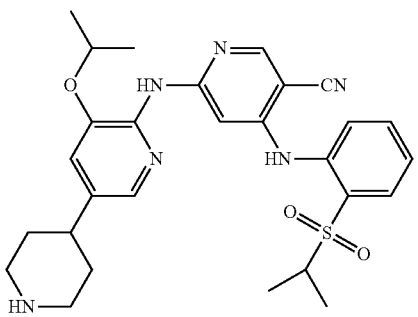

6-(3-isopropoxy-5-(piperidin-4-yl)pyridin-2-ylamino)-4-
(2-(isopropylsulfonyl)phenylamino) nicotinonitrile Table 4 shows other compounds which may be useful treating, ameliorating or preventing a condition which responds to inhibition of anaplastic lymphoma kinase (ALK) activity, focal adhesion kinase (FAK), zeta-chain-associated protein kinase 70 (ZAP-70), insulin-like growth factor (IGF-1R).

TABLE 4

| | Structure | Physical Data $^1$H NMR 400 MHz (DMSO-d6) and/or MS (m/z) |
|---|---|---|
| 257 | N2-(5-Ethynyl-2-isopropoxy-4-methyl-phenyl)-5-methyl-N4-[2-(propane-2-sulfonyl)-phenyl]-pyrimidine-2,4-diamine | MS (ES$^+$): 479.2 (M + 1)$^+$. |
| 258 | 2-(2-(5-ethynyl-2-isopropoxy-4-methylphenylamino)-5-methylpyrimidin-4-ylamino)-N-isopropylbenzamide | MS (ES$^+$): 458.6 (M + 1)$^+$. |
| 259 | 4-(4-(2-(isopropylsulfonyl)phenylamino)-5-chloropyrimidin-2-ylamino)-2,3-dihydro-5-isopropoxyinden-1-one | MS (ES$^+$): 515.1 (M + 1)$^+$. |

TABLE 4-continued

| | Structure | Physical Data<br>¹H NMR 400 MHz (DMSO-d6) and/or MS (m/z) |
|---|---|---|
| 260 | 5-chloro-N4-(2-(isopropylsulfonyl)phenyl)-N2-(5-(piperidin-4-yl)isoquinolin-8-yl)pyrimidine-2,4-diamine | MS (ES⁺): 537.1 (M + 1)⁺. |
| 261 | 2-[5-Chloro-2-(6-chloro-2-methyl-quinolin-4-ylamino)-pyrimidin-4-ylamino]-N,N-dimethyl-benzenesulfonamide | ¹H NMR (CDCl₃, 400 MHz) δ 9.45 (s, 1 H), 8.34-8.37 (d, 1 H), 8.20 (s, 1 H), 8.10 (s, 1 H), 7.82-7.9 (m, 3 H), 7.52-7.60 (m, 3 H), 7.19-7.26 (m, 1 H), 2.69 (s. 6 H), 2.54 (s, 3 H). MS (ES⁺): 503.0 (M + 1)⁺. |
| 262 | N4-(2-(isopropylsulfonyl)phenyl)-N2-(2-methoxy-5-methylphenyl)-7H-pyrrolo[2,3-d]pyrimidine-2,4-diamine | MS (ES⁺): 451.5 (M + 1)⁺. |

TABLE 4-continued

| | Structure | Physical Data<br>¹H NMR 400 MHz (DMSO-d6) and/or MS (m/z) |
|---|---|---|
| 263 | 5-chloro-N2-(2-isopropoxy-4-(1-methylpiperidin-2-yl)phenyl)-N4-(2-(isopropylsulfonyl)phenyl)pyrimidine-2,4-diamine | MS (ES⁺): 558.1 (M + 1)⁺. |
| 264 | 5-chloro-N2-(2-isopropoxy-4-(1-(4-methylpiperazin-1-yl)propan-2-yl)phenyl)-N4-(2-(isopropylsulfonyl)phenyl)pyrimidine-2,4-diamine | MS (ES⁺): 601.2 (M + 1)⁺. |
| 265 | 3-(4-(5-chloro-4-(2-(isopropylsulfonyl)phenylamino)pyrimidin-2-ylamino)-3-isopropoxyphenyl)butan-1-ol | MS (ES⁺): 533.1 (M + 1)⁺. |

TABLE 4-continued

| | Structure | Physical Data<br>¹H NMR 400 MHz (DMSO-d6) and/or MS (m/z) |
|---|---|---|
| 266 | 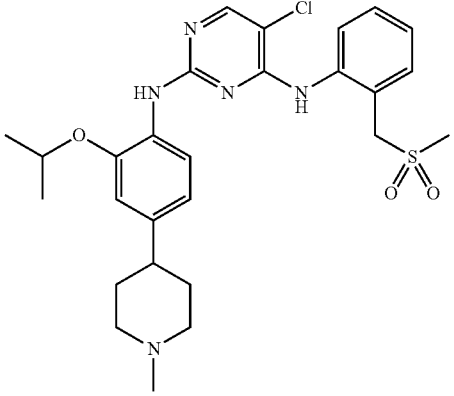<br>5-chloro-N2-(2-isopropoxy-4-(1-methylpiperidin-4-yl)phenyl)-N4-(2-(methylsulfonylmethyl)phenyl)pyrimidine-2,4-diamine | MS (ES⁺): 544.1 (M + 1)⁺. |
| 267 | 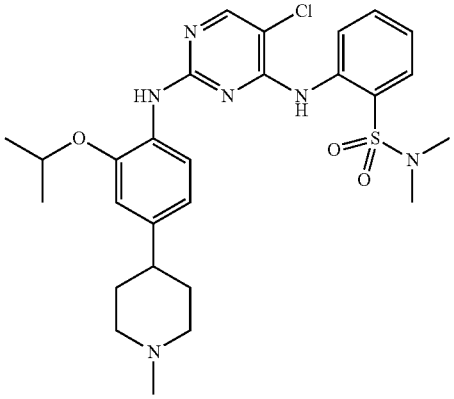<br>2-(5-chloro-2-(2-isopropoxy-4-(1-methylpiperidin-4-yl)phenylamino)pyrimidin-4-ylamino)-N,N-dimethylbenzenesulfonamide | MS (ES⁺): 559.1 (M + 1)⁺. |
| 268 | 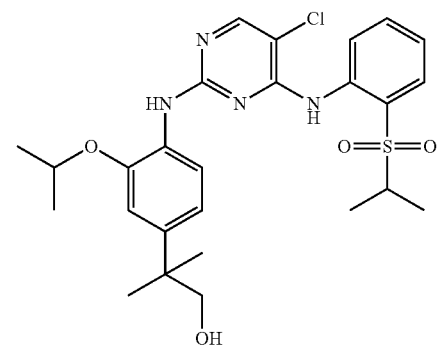<br>2-(4-(5-chloro-4-(2-(isopropylsulfonyl)phenylamino)pyrimidin-2-ylamino)-3-isopropoxyphenyl)-2-methylpropan-1-ol | MS (ES⁺): 533.1 (M + 1)⁺. |

TABLE 4-continued

| | Structure | Physical Data<br>¹H NMR 400 MHz (DMSO-d6) and/or MS (m/z) |
|---|---|---|
| 269 | 5-chloro-N2-(2-isopropoxy-4-(2-methyl-1-(4-methylpiperazin-1-yl)propan-2-yl)phenyl)-N4-(2-(isopropylsulfonyl)phenyl)pyrimidine-2,4-diamine | MS (ES⁺): 615.3 (M + 1)⁺. |
| 270 | 5-chloro-N2-(2-isopropoxy-4-(1-(pyrrolidin-1-yl)propan-2-yl)phenyl)-N4-(2-(isopropylsulfonyl)phenyl)pyrimidine-2,4-diamine | MS (ES⁺): 572.2 (M + 1)⁺. |
| 271 | Methyl 2-(4-(5-chloro-4-(2-(isopropylsulfonyl)phenylamino)pyrimidin-2-ylamino)-3-isopropoxyphenyl)-2-methylpropanoate | MS (ES⁺): 561.1 (M + 1)⁺. |

TABLE 4-continued

| | Structure | Physical Data<br>¹H NMR 400 MHz (DMSO-d6) and/or MS (m/z) |
|---|---|---|
| 272 | 5-chloro-N2-(2-isopropoxy-4-(1-morpholinopropan-2-yl)phenyl)-N4-(2-(isopropylsulfonyl)phenyl)pyrimidine-2,4-diamine | MS (ES⁺): 588.2 (M + 1)⁺. |
| 273 | 5-chloro-N4-(5-fluoro-2-(isopropylsulfonyl)phenyl)-N2-(2-isopropoxy-4-(piperidin-4-yl)phenyl)pyrimidine-2,4-diamine | MS (ES⁺): 562.1 (M + 1)⁺. |
| 274 | 5-chloro-N4-(5-fluoro-2-(isopropylsulfonyl)phenyl)-N2-(2-isopropoxy-4-(1-methylpiperidin-4-yl)phenyl)pyrimidine-2,4-diamine | MS (ES⁺): 576.2 (M + 1)⁺. |

TABLE 4-continued

| Structure | Physical Data<br>¹H NMR 400 MHz (DMSO-d6) and/or MS (m/z) |
|---|---|
| 275<br>5-chloro-N2-(2-isopropoxy-4-(piperidin-4-yl)phenyl)-N4-(2-(pyrrolidin-1-ylsulfonyl)phenyl)pyrimidine-2,4-diamine | MS (ES⁺): 571.1 (M + 1)⁺. |
| 276<br>5-chloro-N2-(2-isopropoxy-4-(piperidin-4-yl)phenyl)-N4-(2-(isopropylsulfonyl)phenyl)pyrimidine-2,4-diamine | MS (ES⁺): 544.1 (M + 1)⁺. |
| 277<br>5-chloro-N2-(2-isopropoxy-4-(1-(1-methylpiperidin-4-yl)piperidin-4-yl)phenyl)-N4-(2-(isopropylsulfonyl)phenyl)pyrimidine-2,4-diamine | MS (ES⁺): 641.3 (M + 1)⁺. |

TABLE 4-continued

| | Structure | Physical Data<br>¹H NMR 400 MHz (DMSO-d6) and/or MS (m/z) |
|---|---|---|
| 278 | 4-(4-(4-(2-isopropylsulfonyl)phenylamino)-5-chloropyrimidin-2-ylamino)-3-isopropoxyphenyl)cyclohexanone | MS (ES⁺): 557.1 (M + 1)⁺. |
| 279 | N2-(2-isopropoxy-4-(piperidin-4-yl)phenyl)-N4-(2-(isopropylsulfonyl)phenyl)-5-methylpyrimidine-2,4-diamine | MS (ES⁺): 524.2 (M + 1)⁺. |
| 280 | 2-(4-(4-(4-(2-(isopropylsulfonyl)phenylamino)-5-methylpyrimidin-2-ylamino)-3-isopropoxy phenyl)piperidin-1-yl)ethanol | MS (ES⁺): 568.7 (M + 1)⁺. |
| 281 | 5-chloro-N2-(2-isopropoxy-4-(1-methylpiperidin-4-yl)phenyl)-N4-(2-(isopropylsulfonyl)phenyl)pyrimidine-2,4-diamine | MS (ES⁺): 558.1 (M + 1)⁺. |

TABLE 4-continued

| Structure | Physical Data<br>$^1$H NMR 400 MHz (DMSO-d6) and/or MS (m/z) |
|---|---|
| 282<br>N2-(2-isopropoxy-4-(1-methylpiperidin-4-yl)phenyl)-N4-(2-(isopropylsulfonyl)phenyl)-5-methylpyrimidine-2,4-diamine | MS (ES$^+$): 538.7 (M + 1)$^+$. |
| 283<br>2-(2-(2-isopropoxy-4-(1-methylpiperidin-4-yl)phenylamino)-5-chloropyrimidin-4-ylamino)-N,N-dimethylbenzamide | MS (ES$^+$): 523.0 (M + 1)$^+$. |
| 284<br>2-(4-(4-(4-(2-(isopropylsulfonyl)phenylamino)-5-chloropyrimidin-2-ylamino)-3-isopropoxyphenyl)piperidin-1-yl)acetamide | MS (ES$^+$): 601.1 (M + 1)$^+$. |

TABLE 4-continued

| | Structure | Physical Data<br>¹H NMR 400 MHz (DMSO-d6) and/or MS (m/z) |
|---|---|---|
| 285 | 5-chloro-N2-(4-isopropoxy-2-(piperidin-4-yl)pyrimidin-5-yl)-N4-(2-(isopropylsulfonyl)phenyl)pyrimidine-2,4-diamine | MS (ES⁺): 546.1 (M + 1)⁺. |
| 286 | 5-chloro-N4-(2-(isopropylsulfonyl)phenyl)-N2-(2-methoxy-6-(piperidin-4-yl)pyridin-3-yl)pyrimidine-2,4-diamine | MS (ES⁺): 517.1 (M + 1)⁺. |
| 287 | 5-chloro-N4-(2-(isopropylsulfonyl)phenyl)-N2-(2-methoxy-6-(4-(piperazin-1-yl)phenyl)pyridin-3-yl)pyrimidine-2,4-diamine | MS (ES⁺): 594.1 (M + 1)⁺. |

| | Structure | Physical Data<br>$^1$H NMR 400 MHz (DMSO-d6) and/or MS (m/z) |
|---|---|---|
| 288 | 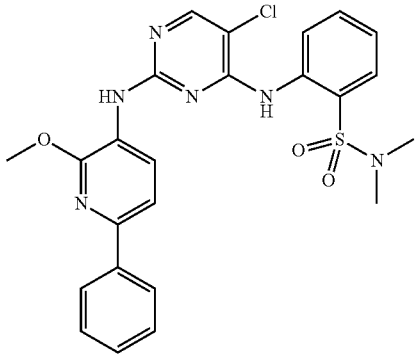<br>2-(5-chloro-2-(2-methoxy-6-phenylpyridin-3-ylamino)pyrimidin-4-ylamino)-N,N-dimethylbenzenesulfonamide | MS (ES$^+$): 511.1 (M + 1)$^+$. |
| 289 | 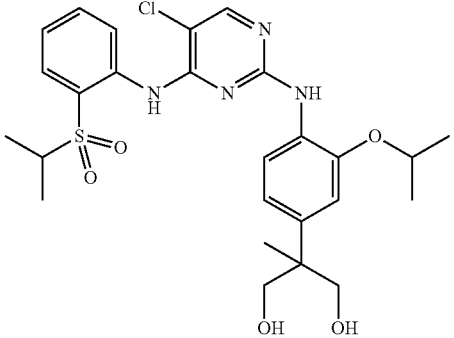<br>2-(4-(5-chloro-4-(2-(isopropylsulfonyl)phenylamino)pyrimidin-2-ylamino)-3-isopropoxyphenyl)-2-methylpropane-1,3-diol | MS (ES$^+$): 548.1 (M + 1)$^+$. |

Compounds of the present invention may be assessed for their ability to inhibit ALK using assays described below, as well as other assays known in the art.

Ba/F3 Cell Line Panel and Reagents

Ba/F3 is a murine IL-3-dependent pro-B lymphoma cell line. Parental Ba/F3 cells are used to generate a panel of sublines whose proliferation and survival is rendered IL-3-independent by stable transduction with individual tyrosine kinases activated by fusion with the amino-terminal portion of TEL (amino acid 1-375) or BCR. In order to generate Ba/F3 cell lines transformed by Tel-Tyrosine Kinase (TK) fusions, parental Ba/F3 cells are infected with a retrovirus harboring each kinase domain and subjected to puromycin selection and IL-3 withdrawal to obtain IL-3-independent, transformed Ba/F3 cells.

Each transformed Ba/F3 cells are cultured in RPMI-1640 media (Gibco Cat #11875093, Carlsbad, Calif.) supplemented with 10% FBS (Hyclone Cat #SV30014.03, Logan, Utah), 4.5 g/L glucose (Sigma #G5400, St. Louis, Mo.), 1.5 g/L sodium bicarbonate (Biowhittaker #17-613E, Walkersville, Md.) and Pen/Strep (Gibco #10378-016, Carlsbad, Calif.). Cells are splitted twice weekly.

Ba/F3 Cell Viability Inhibition Assay

The potency of test compounds against various Tel-TK transformed Ba/F3 lines is determined as follows. Exponentially growing BaF3 Tel-TK cells are diluted in fresh medium to 75,000 cells/mL and seeded into 384-well plates (3750 cells/well) at 50 µL/well using a µFill liquid dispenser (BioTek, Winooski, Vt., USA). Duplicate plates are run for each cell line. Test and control compounds are serially diluted with DMSO and arrayed in a polypropylene 384-well plate. 50 nL of compound is transferred into the assay plates using a pin-transfer device, and the plates are incubated at 37° C. (5% CO2) for 48 hours. 25 µL Bright-Glo (Promega, Madison, Wis., USA) is added and luminescence is quantified using Analyst GT (Perkin Elmer, Wellesley, Mass.). Custom curve-fitting software is used to produce a logistic fit of percent cell viability as a function of the logarithm of inhibitor concentration. The IC$_{50}$ is interpolated as the concentration of compound needed to reduce cell viability to 50% of a DMSO control. Parental Ba/F3 cells that are maintained and cultured in presence of IL-3 (1 ng/ml in final) are diluted in fresh medium containing IL-3 (1 ng/ml in final) to 75,000 cells/mL following the same procedure as described above.

Kapas 299 Cellular Assay

Luciferized Karpas 299 (Karpas299-Luc) is generated by infecting retrovirus encoding luciferase gene, and cultured in RPMI-1649 medium supplemented with 10% FBS, 1% P/S/ L-Glu. At day 1, cells are harvested and resuspended at density of 150,000 cells/ml (cell number is measured using ViCell (BD). Cells are dispensed from a diluted suspension into a 384-well assay plate in 50 μl volume using gill (Bio-TEK). Serially diluted compounds (in DMSO) are transferred into plate using 50 nL pinhead. Assay plates are incubated at 37° C. for 48 hours. At day 4, 25 μl/well of Bright-Glo reagent (Promega) is added using gill (Bio-TEK). Within 30 minutes, a luciferase signal is measured using Analyst GT in default setting for luminescence detection.

Enzymatic HTRF Assay

ALK enzyme and IGF1R and INSR are purchased from Upstate. Following reagents are prepared in-house; 10× kinas buffer (KB) (200 mM Tris (pH 7.0), 100 mM $MgCl_2$, 30 mM $MnCl_2$, 50 nM $NaVO_4$), 10 mM ATP, 100 mg/ml BSA, 0.5 M EDTA, 4 M KF. Proxiplate-384 from Perkin-Elmer is used for set up assay. All the HTRF reagents including substrate (Biotin-poly-GT (61GT0BLB), Mab PT66-K, (61T66KLB), Streptavidin-$XL^{ent}$ (611SAXLB)) are purchased from CIS-US, Inc.

The substrate/ATP mix is prepared by adding ATP (final concentration, 3 μM) and biotinylated poly-GT (final concentration, 10 ng/μl) into 1×KB, and dispensed into Proxiplate-384 at 5 μl/well using gill (Bio-TEK). Serially diluted compounds (in DMSO) are transferred into plate using 50 nL pinhead. 5 μL of prepared Enzyme mix (enzyme (final concentration, 5 ng/μl), mixed with BSA and DTT in 1×KB) is added to initiate kinase reaction using gill (Bio-TEK). Assay plate is incubated at room temperature for 2 hours. Detection mix is prepared by adding both Mab PT66-K and Streptavidin-$XL^{ent}$ into 0.5×KB solution containing KF (final concentration, 125 mM), EDTA (final concentration, 50 mM) and BSA (final concentration, 100 μg/ml) in. At the end of reaction, 10 μL of detection mix is added and incubated for 30 minutes at room temperature before measurement. HTRF signal is detected using Analyst-GT (molecular dynamic).

Reporter Assay in U2OS Cells Using RE1-pGL3 for IGF1-S3-5 or INSR-S3-5

Seed 10M cells/T175 Flask in Mc Coy 10% FBS and 4 days later, suck off media and add fresh media. Next day (5 days after seeding), trypsinize cells, wash once with PBS, then resuspend cells in Mc-Coy media 4% delipidated serum with P/S/G. Count cells and dilute to 400,000 cells/ml.

For 95 ml of cells (400000 cells/ml (40M)), prepare the following DNA/Fugene6 mix: 5 ml Mc-Coy media without serum; 120 μg DNA mix (20 μg IGF1R-S3-5 or INSR-S3-5+ 100 μg RE1-pGL3); and 240 μL Fugene6 reagent. Incubate DNA/Fugene6 mix for 15 min before adding it to cells in 4% delipidated serum. Dispense 50 μL/well in 384 well plate. 22-24 h later, add 50 nL of serially diluted compounds using pinhead. 30 min later, add 2 μL of 26×IGF1 (or 100× Insulin) dose diluted in Mc-Coy 4% delipidated serum using μ-Fill. 30 hours later, add 25 μL 100% bright-glo and read on Analyst-GT for measuring luminescence.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:
1. A compound having Formula (1):

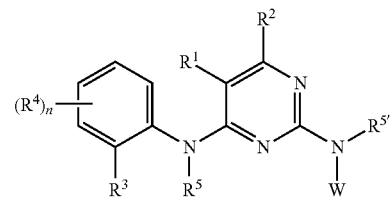

or pharmaceutically acceptable salts thereof; wherein W is

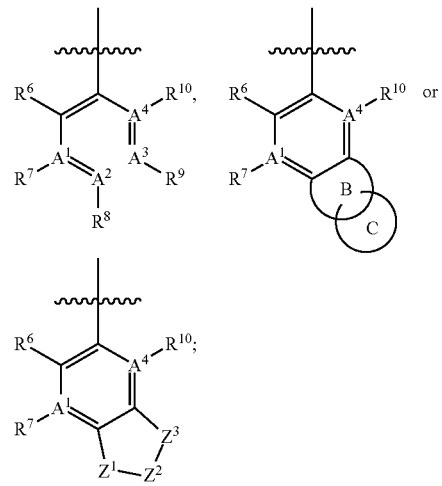

$A^1$ and $A^4$ are independently C;
each $A^2$ and $A^3$ is C;
B and C are independently an optionally substituted 5-7 membered carbocyclic ring, aryl, heteroaryl or heterocyclic ring containing N, O or S;
$Z^1$, $Z^2$ and $Z^3$ are independently $NR^{11}$, C=O, CR—OR, $(CR_2)_{1-2}$ or =C—$R^{12}$;
$R^1$ is halo or $C_{1-6}$ alkyl;
$R^2$ is H;
$R^3$ is $SO_2R^{12}$ or cyano;
$R^4$, $R^7$ and $R^{10}$ are independently H;
R, $R^5$ and $R^{5'}$ are independently H or $C_{1-6}$ alkyl;
$R^6$ is —$OR^{12}$;
one of $R^8$ and $R^9$ is $(CR_2)_qY$ and the other is $C_{1-6}$ alkyl;
$R^{11}$ is H, $C_{1-6}$ alkyl, $C_{2-6}$ alkenyl, $(CR_2)_pCO_{1-2}R$, $(CR_2)_pOR$, $(CR_2)_pR^{13}$, $(CR_2)_pNRR^{12}$, $(CR_2)_pCONRR^{12}$ or $(CR_2)_pSO_{1-2}R^{12}$;
$R^{12}$ and $R^{13}$ are independently an optionally substituted 3-7 membered saturated or partially unsaturated carbocyclic ring, or a 5-7 membered heterocyclic ring comprising N, O and/or S; aryl or heteroaryl; or $R^{12}$ is H or $C_{1-6}$ alkyl;
Y is an optionally substituted 3-12 membered carbocyclic ring, a 5-12 membered aryl, or a 5-12 membered heteroaryl comprising N, O and/or S and attached to $A^2$ or $A^3$ or both via a carbon atom of said heteroaryl
n is 4;
p is 0-4; and
q is 0.

2. The compound of claim 1, wherein $R^{12}$ is $C_{1-6}$ alkyl, $C_{3-7}$ cycloalkyl, $C_{3-7}$ cycloalkenyl, pyrrolidinyl, piperazinyl, piperidinyl or morpholinyl.

3. The compound of claim 1, wherein $R^6$ is —O($C_{1-6}$ alkyl).

4. The compound of claim 1, wherein $R^5$ and $R^{5'}$ are H.

5. The compound of claim 1, wherein said compound is of Formula (2):

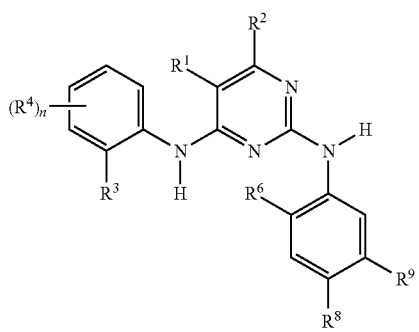

(2)

or pharmaceutically acceptable salts thereof;
wherein $R^1$ is halo or $C_{1-6}$ alkyl;
$R^2$ is H;
$R^6$ is isopropoxy or methoxy;
Y is an optionally substituted $C_{3-7}$ cycloalkyl, $C_{3-7}$ cycloalkenyl, or phenyl; or Y is pyridyl, pyrazolyl, isoxazolyl, imidazolyl, thiazolyl, or benzimidazolyl, each of which is attached to the phenyl ring via a carbon atom; and
$R^3$, $R^4$, $R^8$, $R^9$ and n are as defined in claim 1.

6. The compound of claim 1, wherein said compound is of Formula (3A) or (3B):

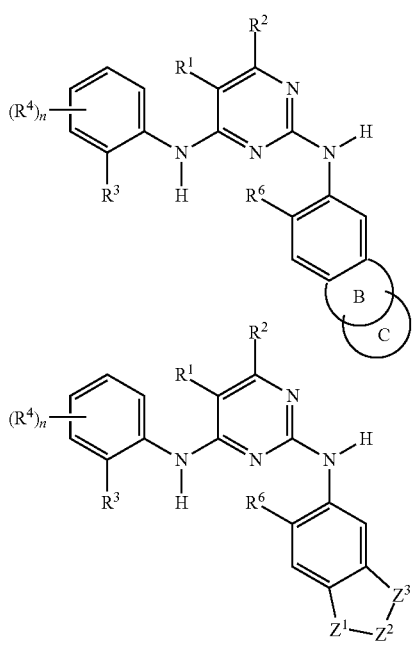

wherein B and C together form

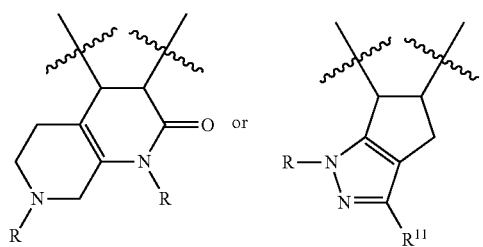

$Z^1$, $Z^2$ and $Z^3$ together form

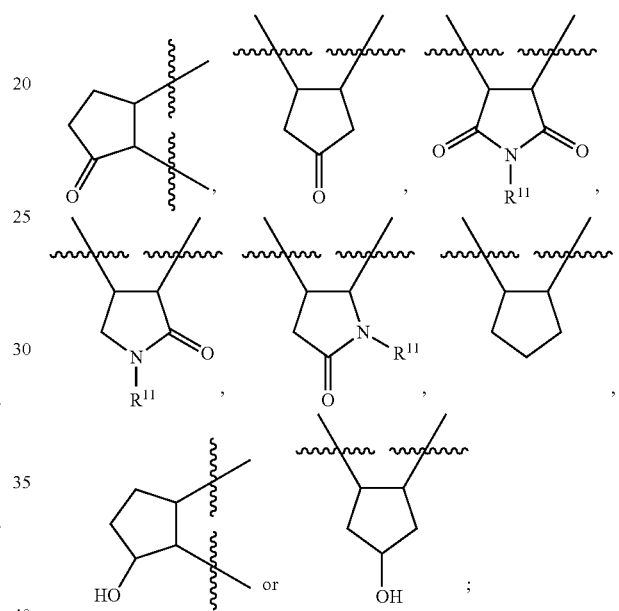

or tautomers thereof;
$R^1$ is halo or $C_{1-6}$ alkyl;
$R^2$ is H; and
$R^6$ is isopropoxy or methoxy.

7. The compound of claim 6, wherein each $R^{11}$ is $(CR_2)_pCO_{1-2}R$, $(CR_2)_pOR$, $(CR_2)_pR^{13}$, $(CR_2)_pNRR^{12}$ or $(CR_2)_pCONRR^{12}$;
R and $R^{12}$ are independently H or $C_{1-6}$ alkyl; and
$R^{13}$ is an optionally substituted piperidinyl, azetidiyl, tetrahydropyranyl, cyclohexyl, morpholinyl, pyrrolidinyl, heptamethyleneimine, octamethyleneimine, a bicyclic amine or diamine derivative, quinuclidin-3-yl, 8-methyl-8-aza-bicyclo[3.2.1]oct-6-yl], or 9-methyl-9-aza-bicyclo[4.2.1]nonan-7-yl.

8. A pharmaceutical composition comprising a therapeutically effective amount of a compound of claim 1 and a pharmaceutically acceptable carrier.

9. A combination comprising a compound of claim 1, or pharmaceutically acceptable salts thereof, and a chemotherapeutic agent.

10. The compound of claim 1, wherein said compound is selected from the group consisting of

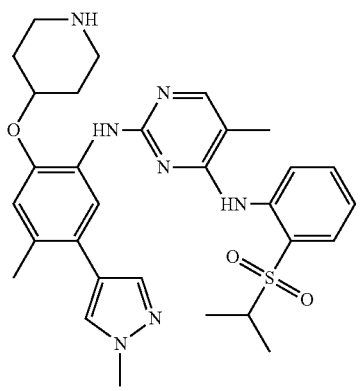

5-Methyl-N2-[4-methyl-5-(1-methyl-1H-pyrazol-4-yl)-2-(piperidin-4-yloxy)-phenyl]-N4-[2-(propane-2-sulfonyl)-phenyl]-pyrimidine-2,4-diamine;

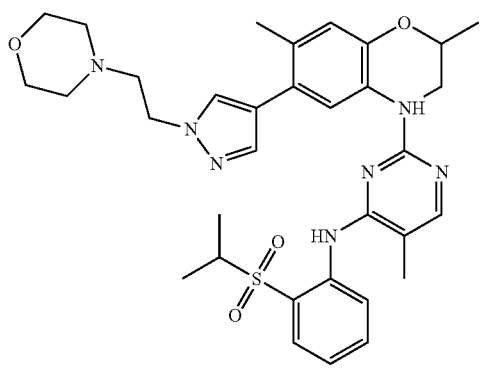

N2-{2-Isopropoxy-4-methlyl-5-[1-(2-morpholin-4-yl-ethyl)-1H-pyrazol-4-yl]-phenyl}-5-methyl-N4-[2-propane-2-sulfonyl)-phenyl]-pyrimidine-2,4-diamine;

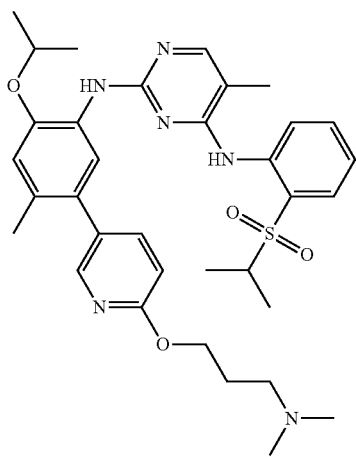

N2-(5-(6-(3-(dimethylamino)propoxy)pyridin-3-yl)-2-isopropoxy-4-methylphenyl)-N4-(2-(isopropylsulfonyl)phenyl)-5-methylpyrimidine-2,4-diamine;

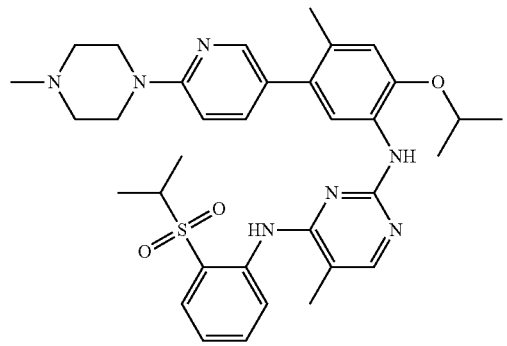

N2-(2-isopropoxy-4-methyl-5-(6-(4-methylpiperazin-1-yl)pyridin-3-yl)phenyl)-N4-(2-(isopropylsulfonyl)phenyl)-5-methylpyrimidine-2,4-diamine;

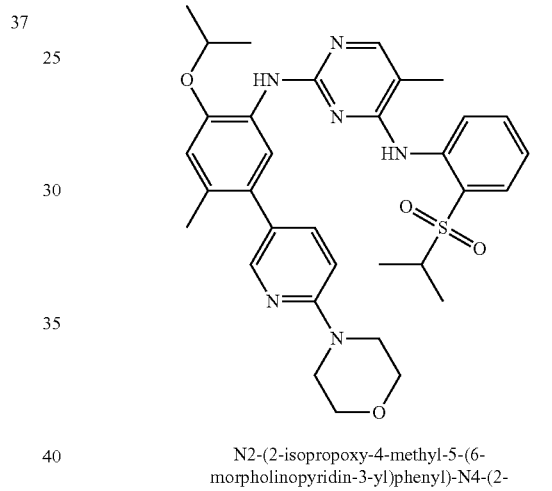

N2-(2-isopropoxy-4-methyl-5-(6-morpholinopyridin-3-yl)phenyl)-N4-(2-(isopropylsulfonyl)phenyl)-5-methylpyrimidine-2,4-diamine;

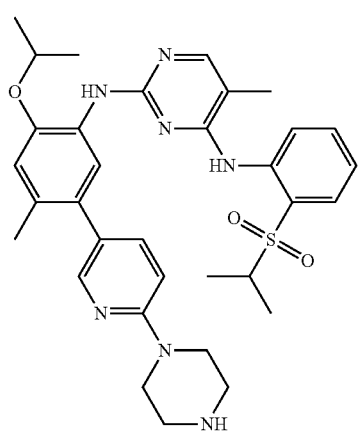

N2-(2-isopropoxy-4-methyl-5-(6-(piperazin-1-yl)pyridin-3-yl)phenyl)-N4-(2-(isopropylsulfonyl) phenyl)-5-methylpyrimidine-2,4-diamine;

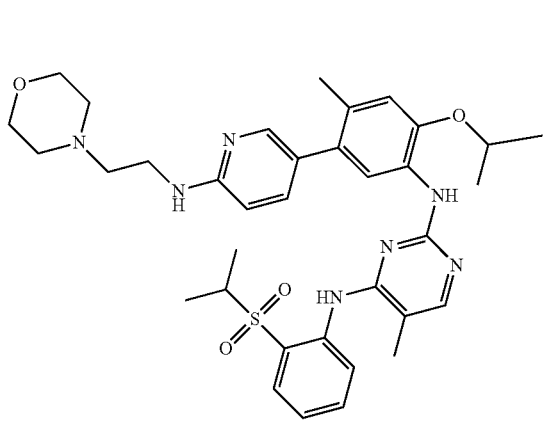

N2-(5-(6-(2-morpholinoethylamino)
pyridin-3-yl)-2-isopropoxy-4-
methylphenyl)-N4-(2-(isopropyl-
sulfonyl)phenyl-5-methylpyrimidine-2,4-
diamine;

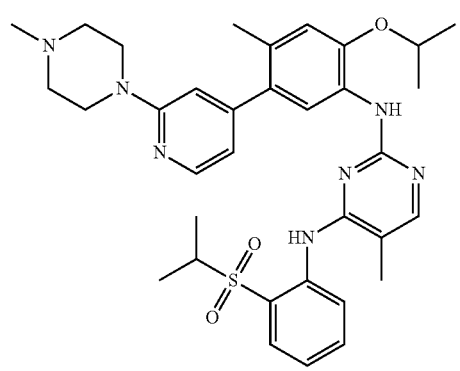

N2-(2-isopropoxy-4-methyl-5-(2-(4-
methylpiperazin-1-yl)pyridin-4-
yl)phenyl)-N4-(2-(isopropylsulfonyl)
phenyl)-5-methylpyrimidine-2,4-diamine;

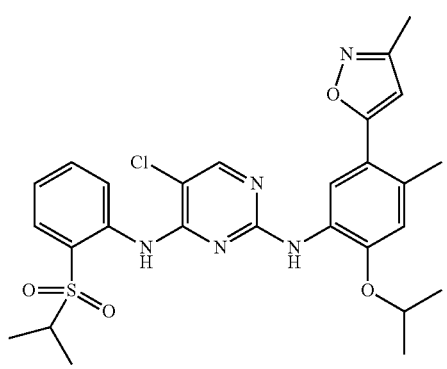

5-chloro-N2-(2-isopropoxy-4-methyl-5-(3-
methylisoxazol-5-yl)phenyl-N4-(2-
(isopropylsulfonyl)phenyl)pyrimidine-2,4-
diamine;

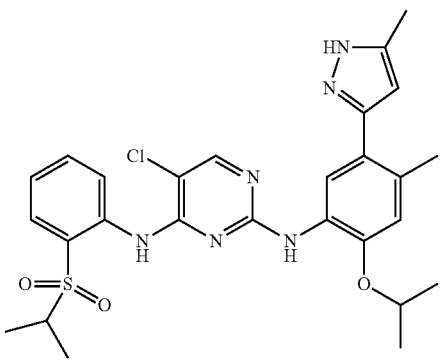

5-chloro-N2-(2-isopropoxy-4-methyl-5-)5-
methyl-1H-pyrazol-3-yl)phenyl)-N4-(2-
(isopropylsulfonyl) phenyl)pyrimidine-
2,4-diamine;

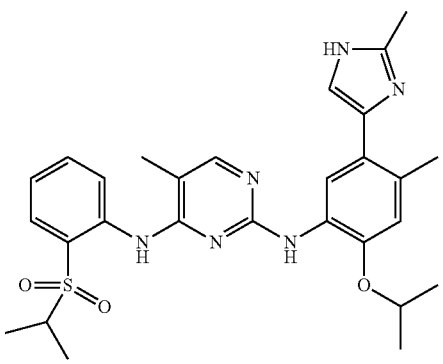

5-chloro-N2-(2-isopropoxy-4-methyl-5-(2-
methyl-1H-imidazol-4-yl)phenyl)-N4-(2-
(isopropylsulfonyl) phenyl)pyrimidine-
2,4-diamine;

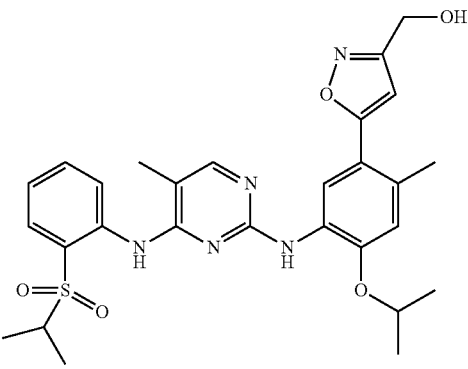

(5-(5-(4-(2-(isopropylsulfonyl)
phenylamino)-5-methylpyrimidin-2-
ylamino)-4-isopropoxy-2-
methylphenyl)isoxazol-3-yl)methanol;

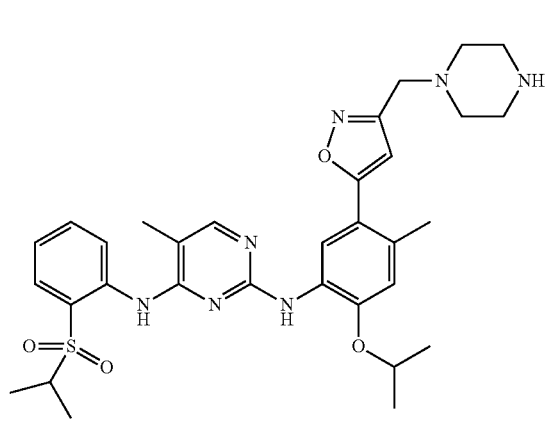

N2-(2-isopropoxy-4-methyl-5-(3-
((piperazin-1-yl)methyl)isoxazol-5-
yl)phenyl)-N4-(2-(isopropyl-
sulfonyl)phenyl)-5-methylpyrimidine-2,4-
diamine;

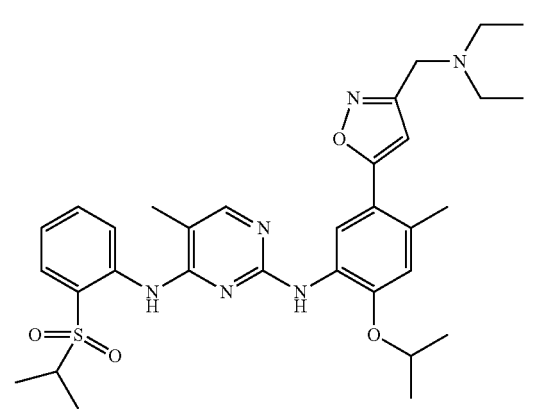

N2-(5-(3-((diethylamino)methyl) isoxazol-
5-yl)-2-isopropoxy-4-methlyphenyl)-N4-
(2-(isopropyl-sulfonyl)phenyl)-5-
methylpyrimidine-2,4-diamine;

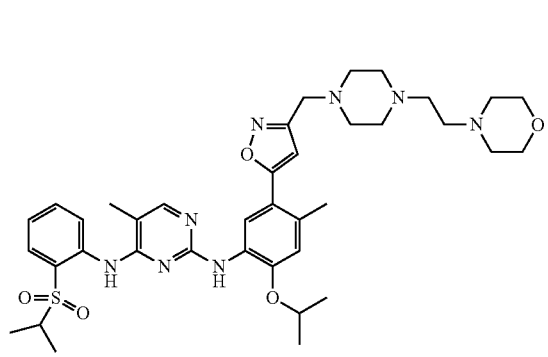

N2-(2-isopropoxy-4-methyl-5-(3-((4-(2-
morpholinoethyl)piperazin-1-
yl)methyl)isoxazol-5-yl)phenyl)-N4-(2-
(isopropylsulfonyl)phenyl)-5-
methylpyrimidine-2,4-diamine;

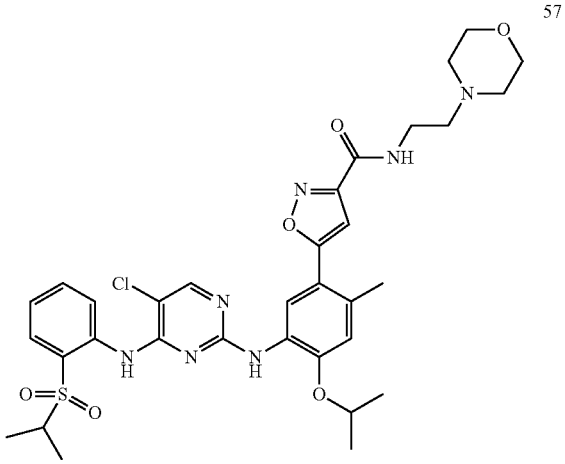

5-(5-(4-(2-(isopropylsulfonyl)
phenylamino)-5-chloropyrimidin-2-
ylamino)-4-isopropoxy-2-methylphenyl)-
N-(2-morpholinoethyl)isoxazole-3-
carboxamide;

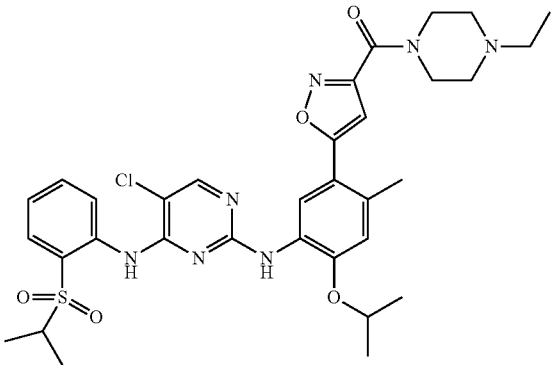

(5-(5-(4-(2-isopropylsulfonyl)
phenylamino)-5-chloropyrimidin-2-
ylamino)-4-isopropoxy-2-
methylphenyl)isoxazol-3-yl)(4-
ethylpiperazin-1-yl)methanone;

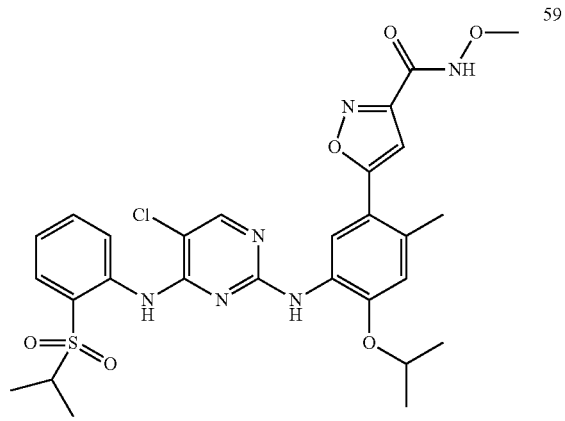

5-(5-(4-(2-
(isopropylsulfonyl)phenylamino)-5-
chloropyrimidin-2-ylamino)-4-
isopropoxy-2-methylphenyl)-N-
methoxyisoxazole-3-carboxamide; and -continued

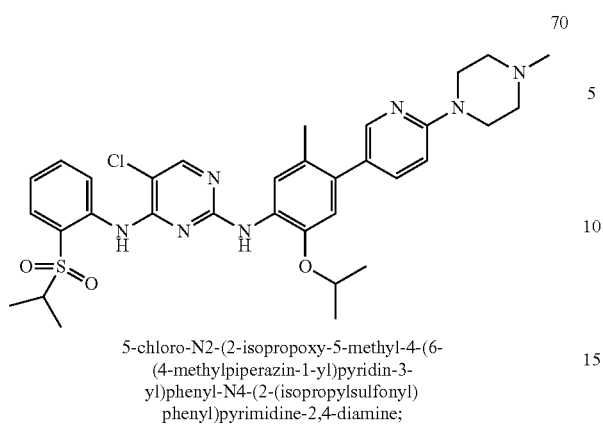

5-chloro-N2-(2-isopropoxy-5-methyl-4-(6-
(4-methylpiperazin-1-yl)pyridin-3-
yl)phenyl-N4-(2-(isopropylsulfonyl)
phenyl)pyrimidine-2,4-diamine;

or a pharmaceutically acceptable salt thereof.

11. The compound of claim 5, wherein said compound is selected from the group consisting of

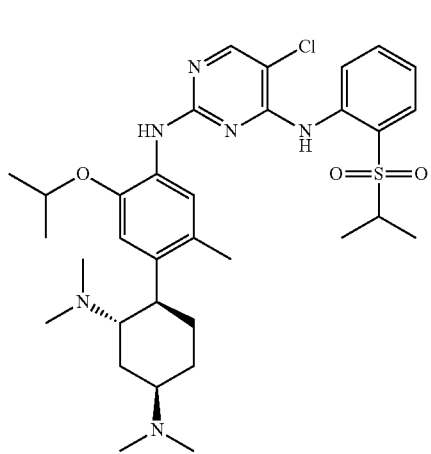

N2-(4-((1R,2S,4R)-2,4-bis(dimethylamino)
cyclohexyl)-2-isopropoxy-5-methylphenyl)-
5-chloro-N4-(2-(isopropylsulfonyl)
phenyl)pyrimidine-2,4-diamine;

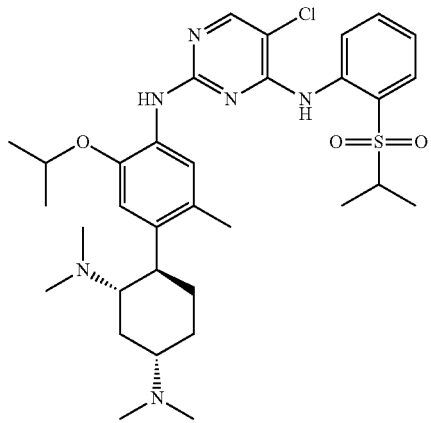

N2-(4-((1R,2S,4S)-2,4-bis(dimethylamino)
cyclohexyl)-2-isopropoxy-5-methylphenyl)-
5-chloro-N4-(2-(isopropylsulfonyl)
phenyl)pyrimidine-2,4-diamine;

-continued

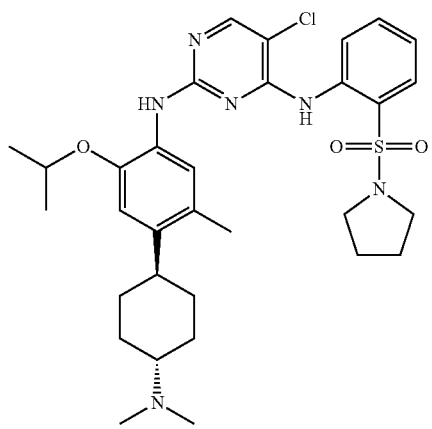

5-chloro-N2-(4-((1r,4r)-4-(dimethylamino)
cyclohexyl)-2-isopropoxy-5-methylphenyl)-
N4-(2-(pyrrolidin-1-ylsulfonyl)phenyl)
pyrimidine-2,4-diamine;

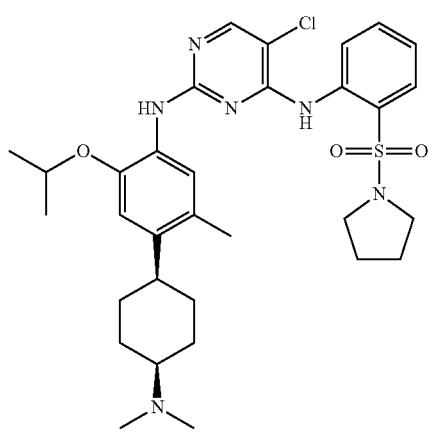

5-chloro-N2-(4-((1s,4s)-4-(dimethylamino)
cyclohexyl)-2-isopropoxy-5-methylphenyl)-
N4-(2-(pyrrolidin-1-ylsulfonyl)phenyl)
pyrimidine-2,4-diamine;

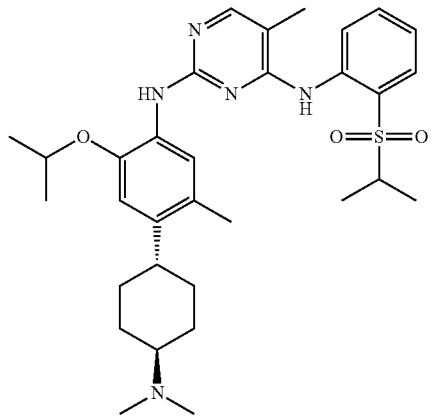

N2-(4-((1r,4r)-4-
(dimethylamino)cyclohexyl)-2-isopropoxy-
5-methylphenyl)-N4-(2-(isopropylsulfonyl)
phenyl)-5-methylpyrimidine-2,4-diamine;

-continued

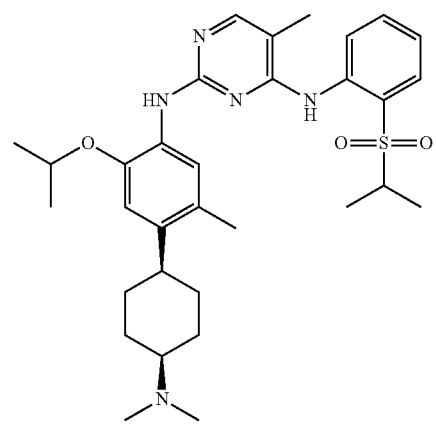

N2-(4-((1s,4s)-4-(dimethylamino)
cyclohexyl)-2-isopropoxy-5-methylphenyl)-
N4-(2-(isopropylsulfonyl) phenyl)-5-
methylpyrimidine-2,4-diamine;

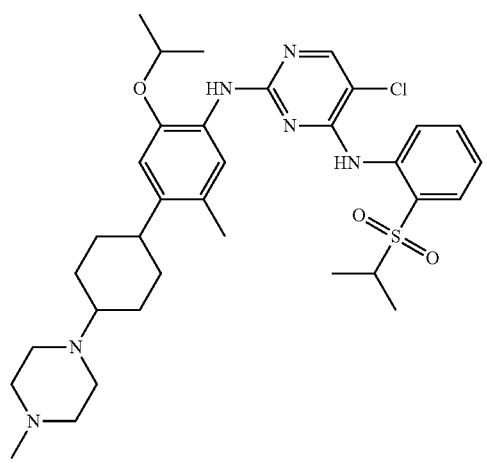

(cis,trans) 5-Chloro-N2-{2-isopropoxy-5-
methyl-4-[4-(4-methyl-piperazin-1-yl)-
cyclohexyl]-phenyl}-N4-[2-(propane-2-
sulfonyl)-phenyl]-pyrimidine-2,4-diamine;

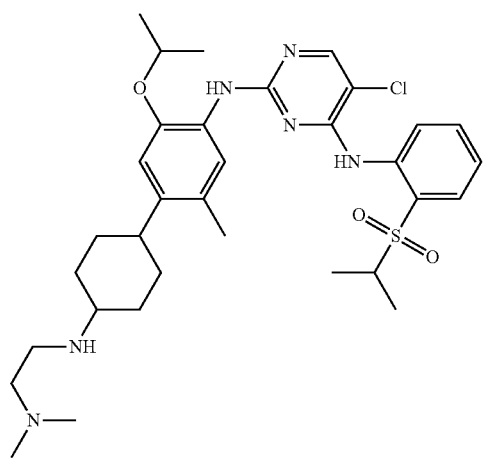

(cis,trans) 5-chloro-N2-{4-[4-(2-
dimethylamino-ethyl amino)-cyclohexyl]-2-
isopropoxy-5-methyl-phenyl}-N4-[2-
(propane-2-sulfonyl)-phenyl]-pyrimidine-
2,4-diamine;

-continued

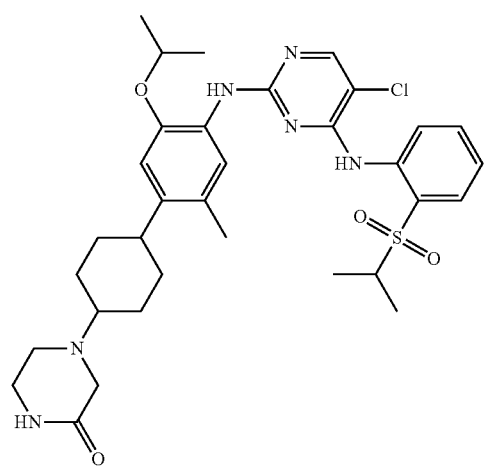

4-[4-(4-{5-Chloro-4-[2-(propane-2-
sulfonyl)-phenylamino]-pyrimidin-2-
ylamino}-5-isopropoxy-2-methyl-phenyl)-
cyclohexyl]-piperazin-2-one;

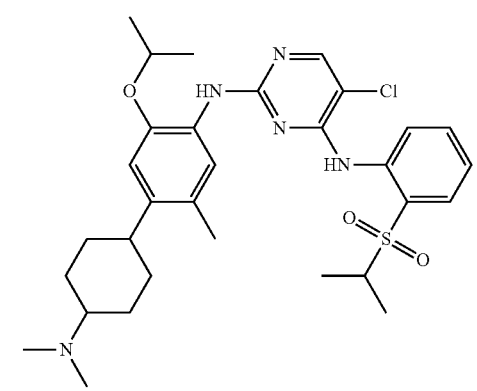

5-Chloro-N2-[4-(4-dimethylamino-
cyclohexyl)-2-isopropoxy-5-methyl-
phenyl]-N4-[2-(propane-2-sulfonyl)-
phenyl]-pyrimidine-2,4-diamine;

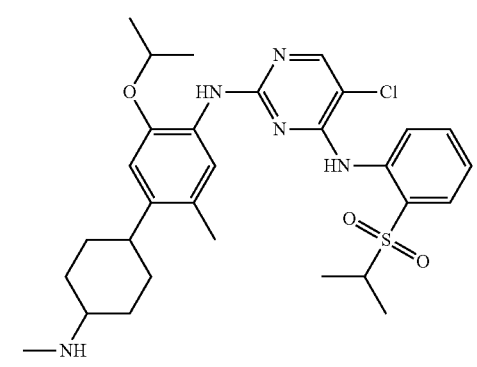

5-Chloro-N2-[2-isopropoxy-5-methyl-4-(4-
methylamino-cyclohexyl)-phenyl]-N4-[2-
(propane-2-sulfonyl)-phenyl]-pyrimidine-
2,4-diamine;

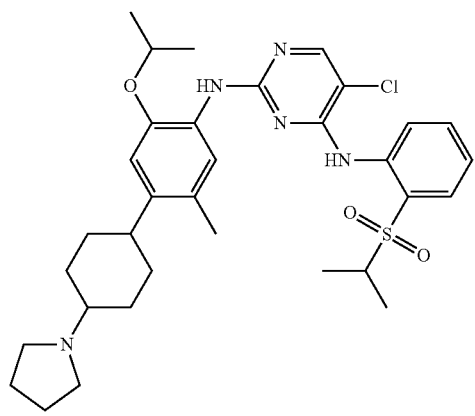

5-Chloro-N2-[2-isopropoxy-5-methyl-4-(4-pyrrolidin-1-yl-cyclohexyl)-phenyl]-N4-[2-(propane-2-sulfonyl)-phenyl]-pyrimidine-2,4-diamine;

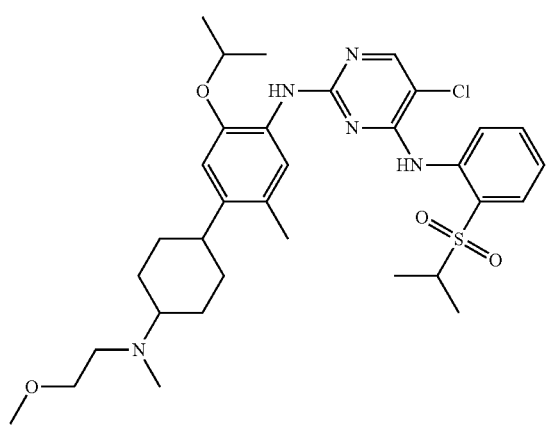

5Chloro-N2-(2-isopropoxy-4-{4-[(2-methoxy-ethyl)-methyl-amino]-cyclohexyl]-5-methyl-phenyl)-N4-[2-(propane-2-sulfonyl)-phenyl]-pyrimidine-2,4-diamine;

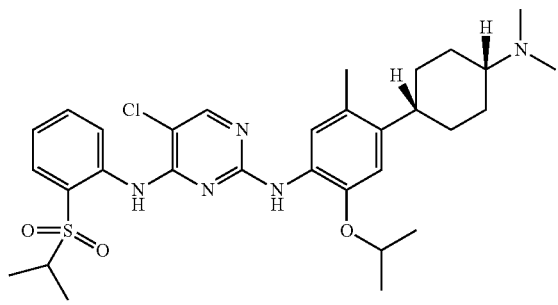

5-chloro-N2-(4-((1s,4s)-4-(dimethylamino)cyclohexyl)-2-isopropoxy-5-methylphenyl)-N4-(2-(isopropylsulfonyl)phenyl)pyrimidine-2,4-diamine;

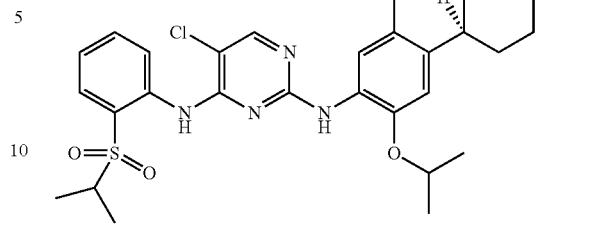

5-chloro-N2-(4-((1r,4r)-4-(dimethylamino)cyclohexyl)-2-isopropoxy-5-methylphenyl)-N4-(2-(isopropylsulfonyl)phenyl)pyrimidine-2,4-diamine;

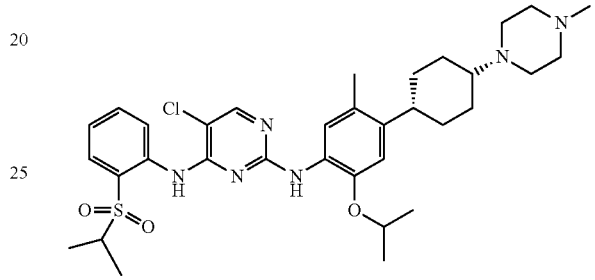

5-chloro-N2-(2-isopropoxy-5-methyl-4-((1s,4s)-4-(4-methylpiperazin-1-yl)cyclohexyl)phenyl-N4-(2-(isopropylsulfonyl)phenyl)pyrimidine-2,4-diamine;

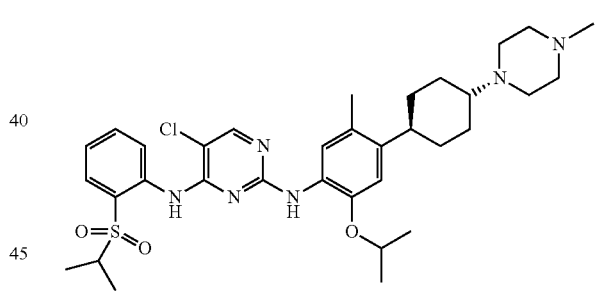

5-chloro-N2-(2-isopropoxy-5-methyl-4-((1r,4r)-4-(4-methylpiperazin-1-yl)cyclohexyl)phenyl)-N4-(2-(isopropylsulfonyl)phenyl)pyrimidine-2,4-diamine;

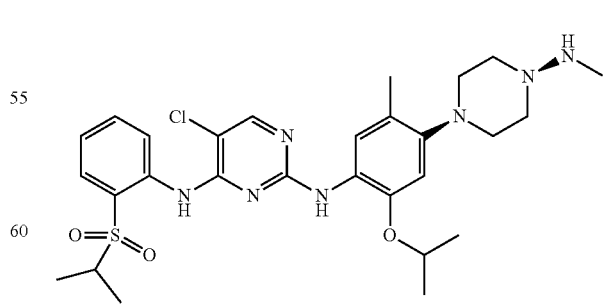

5-chloro-N2-(2-isopropoxy-5-methyl-4-((1s,4s)-4-(methylamino)cyclohexyl)phenyl)-N4-(2-(isopropylsulfonyl)phenyl)pyrimidine-2,4-diamine;

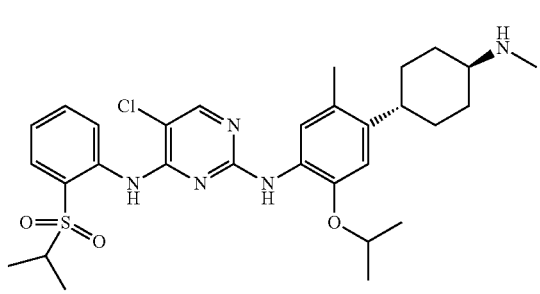

5-chloro-N2-(2-isopropoxy-5-methyl-4-
((1r,4r)-4-(methylamino)cyclohexyl)
phenyl)-N4-(2-(isopropylsulfonyl)phenyl)
pyrimidine-2,4-diamine;

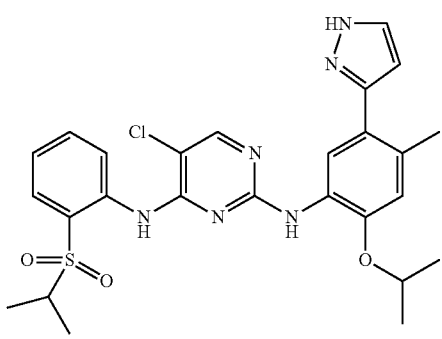

5-chloro-N2-(2-isopropoxy-4-methyl-5-
(1H-pyrazol-3-yl)phenyl-N4-(2-
(isopropylsulfonly) phenyl)pyrimidine-2,4-
diamine;

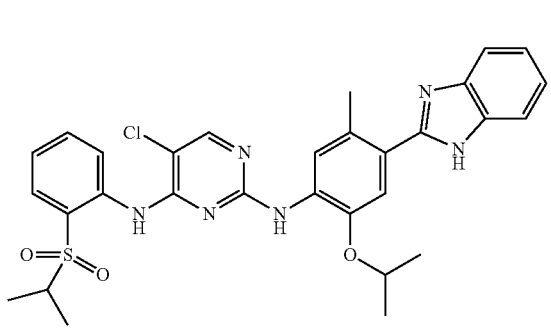

N2-(4-(1H-benzo[d]imidazol-2-yl)-2-
isopropoxy-5-methylphenyl)-5-chloro-N4-
(2-(isopropylsulfonyl) phenylpyrimidine-
2,4-diamine;

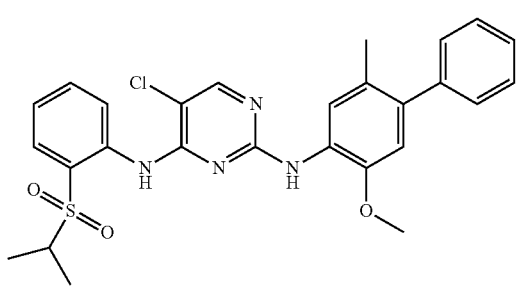

5-chloro-N4-(2-(isopropylsulfonyl) phenyl)-
N2-(2-methoxy-5-methyl-4-phenyl-
phenyl)pyrimidine-2,4-diamine;

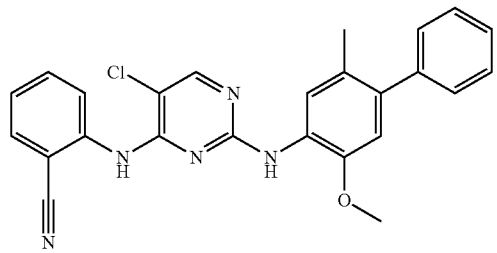

5-chloro-N4-(2-cyanophenyl)-N2-(2-
methoxy-5-methyl-4-phenyl)-
phenyl)pyrimidine-2,4-diamine;

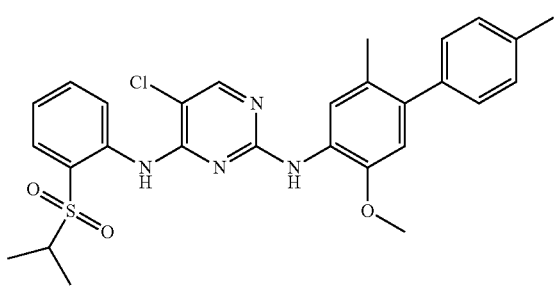

5-chloro-N4-(2-(isopropylsulfonly) phenyl-
N2-(2-methoxy-5-methyl-4-(4-
methylphenly)-phenyl)pyrimidine-2,4-
diamine;

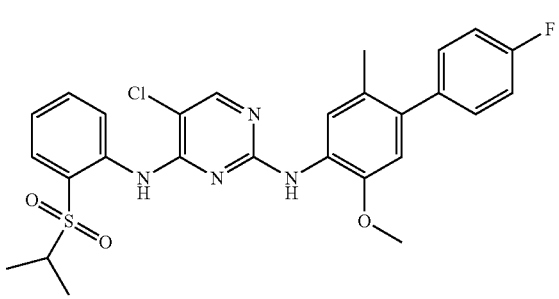

5-chloro-N4-(2-(isopropylsulfonyl) phenyl)-
N2-(2-methoxy-5-methyl-4-(4-
fluorophenyl)-phenyl)pyrimidine-2,4-
diamine;

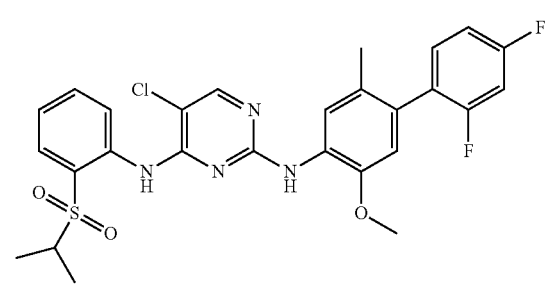

5-chloro-N4-(2-(isopropylsulfonyl) phenyl)-
N2-(2-methoxy-5-methyl-4-(2,4-
difluorophenyl)-phenyl)pyrimidine-2,4-
diamine;

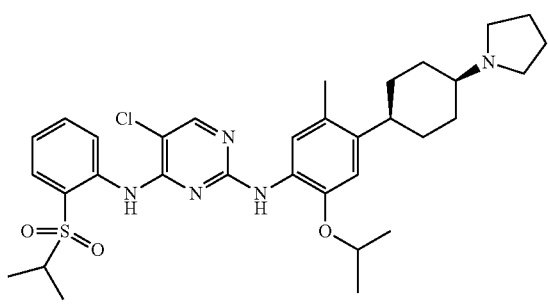

5-chloro-N2-(2-isopropoxy-5-methyl-4-((1s,4s)-4-(pyrrolidin-1-yl)cyclohexyl)phenyl)-N4-(2-(isopropylsulfonyl)phenyl)pyrimidine-2,4-diamine;

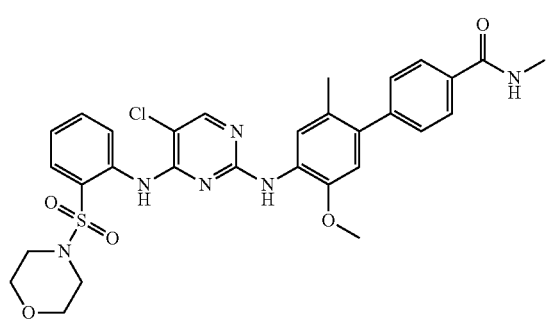

5-chloro-N4-(2-(morpholinosulfonyl)phenyl)-N2-(2-methoxy-5-methyl-4-(4 (methylacetamidophenyl)-phenyl)pyrimidine-2,4-diamine;

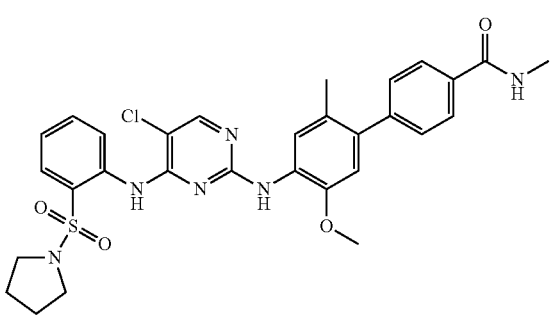

5-chloro-N4-(2-(pyrrolidinosulfonyl)phenyl)-N2-(2-methoxy-5-methyl-4-(4-acetamidomethylphenyl)-phenyl)pyrimidine-2,4-diamine;

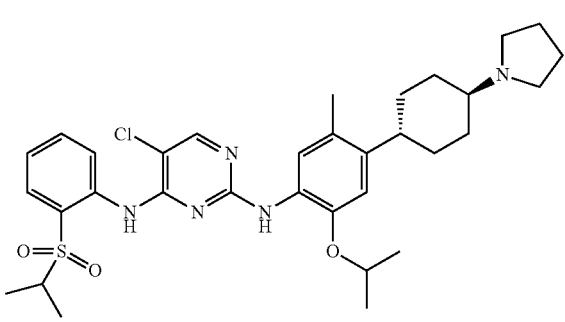

5-chloro-N2-(2-(isopropoxy-5-methyl-4-((1r,4r)-4-(pyrrolidin-1-yl)cyclohexyl)phenyl)-N4-(2-(isopropylsulfonyl)phenyl)pyrimidine-2,4-diamine;

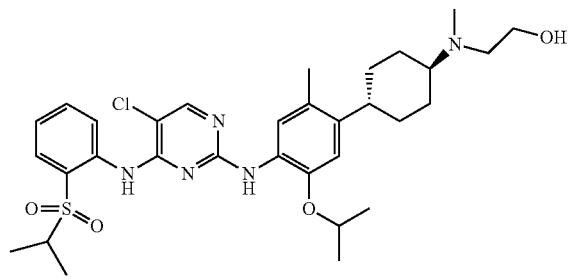

2-(N-((1r,4r)-4-(4-(2-(isopropylsulfonyl)phenylamino)-5-chloropyrimidin-2-ylamino)-5-isopropoxy-2-methylphenyl)cyclohexyl)-N-methylamino)ethanol;

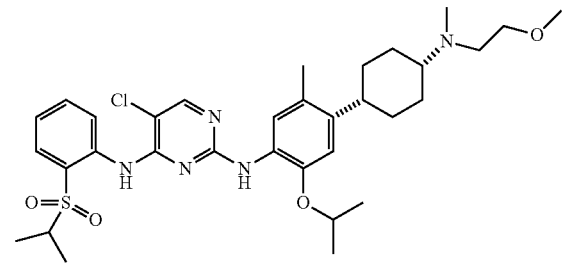

N2-(4-((1s,4s)-4-(N-(2-methoxyethyl)-N-methylamino)cyclohexyl)-2-isopropoxy-5-methylphenyl)-5-chloro-N4-(2-(isopropylsulfonyl) phenyl)pyrimidine-2,4-diamine;

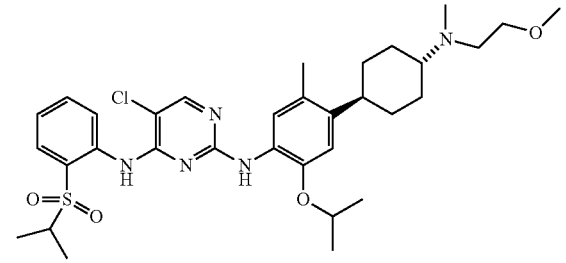

N2-(4-((1r,4r)-4-(N-(2-methoxyethyl)-N-methylamino)cyclohexyl)-2-isopropoxy-5-methylphenyl)-5-chloro-N4-(2-(isopropylsulfonyl)phenyl)pyrimidine-2,4-diamine;

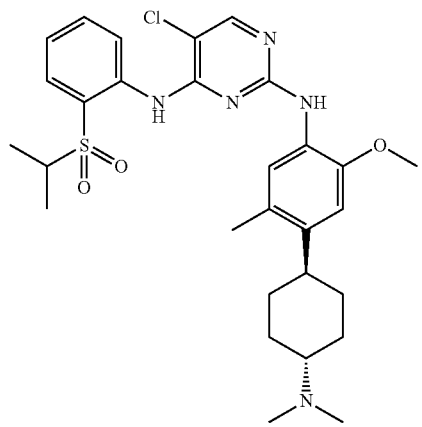

5-chloro-N2-(4-((1r,4r)-4-(dimethylamino)cyclohexyl)-2-methoxy-5-methylphenyl)-N4-(2-(isopropylsulfonyl)phenyl)pyrimidine-2,4-diamine; and

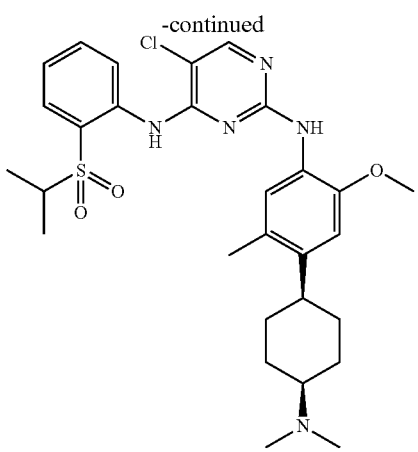

5-chloro-N2-(4-((1s,4s)-4-(dimethylamino)
cyclohexyl)-2-methoxy-5-methylphenyl)-
N4-(2-(isopropylsulfonyl)
phenyl)pyrimidine-2,4-diamine;

or a pharmaceutically acceptable salt thereof.

12. The compound of claim 1, wherein said compound is selected from the group consisting of

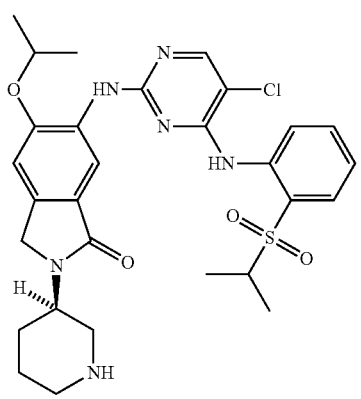

139

6-(4-(2-(isopropylsulfonyl)phenylamino)-5-chloropyrimidin-2-
ylamino)-5-isopropoxy-2-((R)-piperidin-3-yl)isoindolin-1-one;

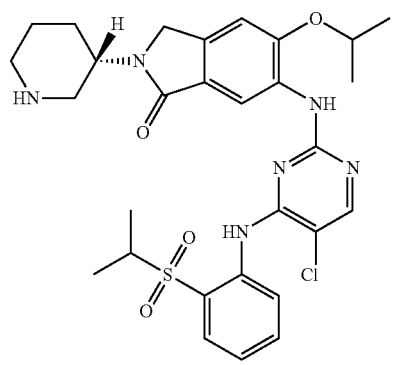

140

6-(4-(2-(isopropylsulfonyl)phenylamino)-5-chloropyrimidin-2-
ylamino)-5-isopropoxy-2-((S)-piperidin-3-yl)isoindolin-1-one;

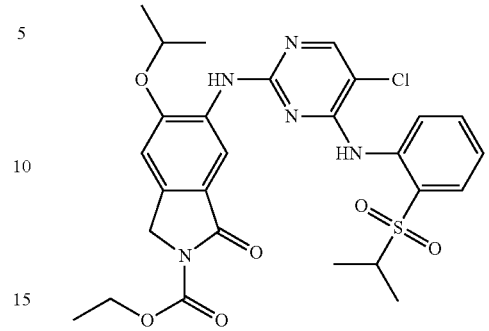

142

Ethyl 6-(4-(2-(isopropylsulfonyl)phenylamino)-5-chloropyrimidin-
2-ylamino)-5-isopropoxy-1-oxoisoindoline-2-carboxylate;

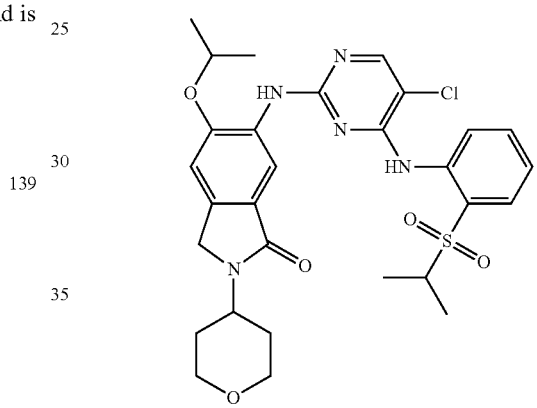

143

6-(4-(2-(isopropylsulfonyl)phenylamino)-5-chloropyrimidin-2-
ylamino)-2-(tetrahydro-2H-pyran-4-yl)-5-isopropoxyisoindolin-1-
one;

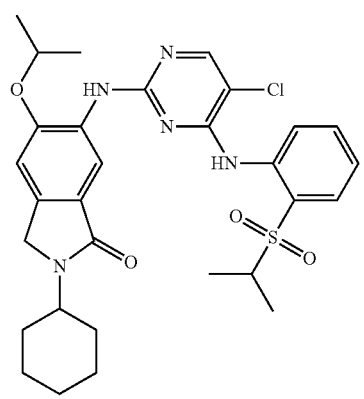 [SMILES: CC(C)Oc1cc2c(cc1Nc1ncc(Cl)c(Nc3ccccc3S(=O)(=O)C(C)C)n1)C(=O)N(C1CCCCC1)C2]

144

6-(4-(2-(isopropylsulfonyl)phenylamino)-5-chloro pyrimidin-2-
ylamino)-2-cyclohexyl-5-isopropoxy-isoindolin-1-one;

145

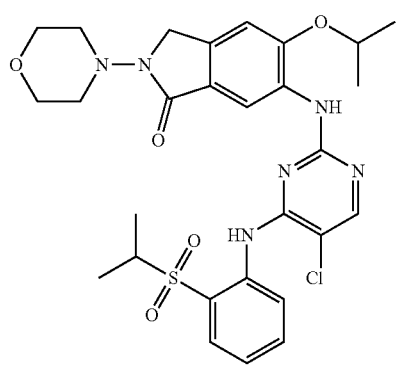 [SMILES: CC(C)Oc1cc2c(cc1Nc1ncc(Cl)c(Nc3ccccc3S(=O)(=O)C(C)C)n1)C(=O)N(N1CCOCC1)C2]

6-(4-(2-(isopropylsulfonyl)phenylamino)-5-chloro pyrimidin-2-ylamino)-5-isopropoxy-2-morpholino-isoindolin-1-one;

146

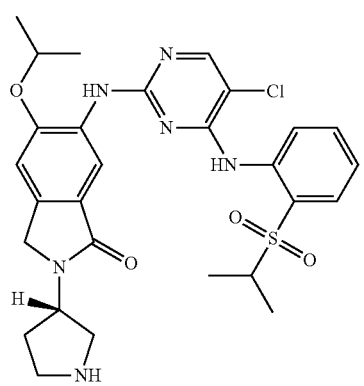 [SMILES: CC(C)Oc1cc2c(cc1Nc1ncc(Cl)c(Nc3ccccc3S(=O)(=O)C(C)C)n1)C(=O)N([C@H]1CCNC1)C2]

6-(4-(2-(isopropylsulfonyl)phenylamino)-5-chloropyrimidin-2-ylamino)-5-isopropoxy-2-((S)-pyrrolidin-3-yl)isoindolin-1-one;

147

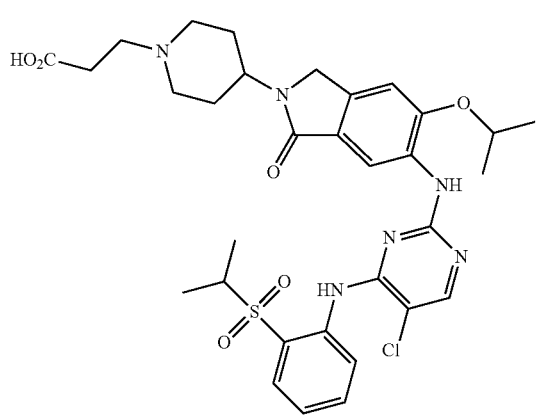

3-(4-(6-(4-(2-(isopropylsulfonyl) phenylamino)-5-chloropyrimidin-2-ylamino)-5-isopropoxy-1-oxoisoindolin-2-yl)piperidin-1-yl)propanoic acid;

148

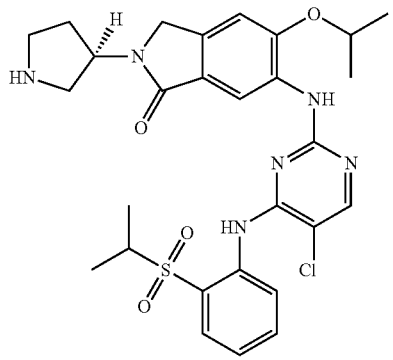 [SMILES: CC(C)Oc1cc2c(cc1Nc1ncc(Cl)c(Nc3ccccc3S(=O)(=O)C(C)C)n1)C(=O)N([C@@H]1CCNC1)C2]

6-(4-(2-(isopropylsulfonyl)phenylamino)-5-chloropyrimidin-2-ylamino)-5-isopropoxy-2-((R)-pyrrolidin-3-yl)isoindolin-1-one;

149

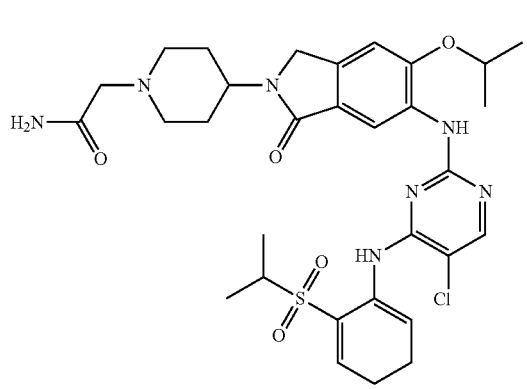

2-[-4-(6-{5-Chloro-4-[2-(propane-2-sulfonyl)-phenyl-amino]pyrimidin-2-ylamino}-5-isopropoxy-1-oxo-1,3-dihydro-isoindol-2-yl)-piperidin-1-yl]-acetamide;

150

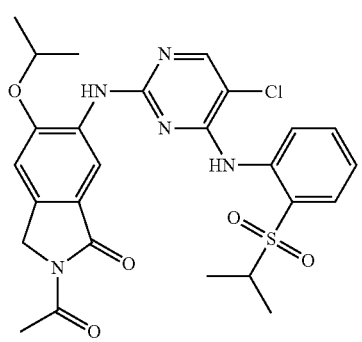 [SMILES: CC(=O)N1Cc2cc(OC(C)C)c(Nc3ncc(Cl)c(Nc4ccccc4S(=O)(=O)C(C)C)n3)cc2C1=O]

6-(4-(2-(isopropylsulfonyl)phenylamino)-5-chloropyrimidin-2-ylamino)-2-acetyl-5-isopropoxyisoindolin-1-one;

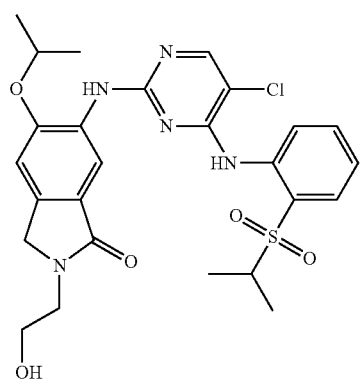 [SMILES: CC(C)Oc1cc2c(cc1Nc1ncc(Cl)c(Nc3ccccc3S(=O)(=O)C(C)C)n1)C(=O)N(CCO)C2]

6-(4-(2-(isopropylsulfonyl)phenylamino)-5-chloropyrimidin-2-ylamino)-2-(2-hydroxyethyl)-5-isopropoxyisoindolin-1-one;

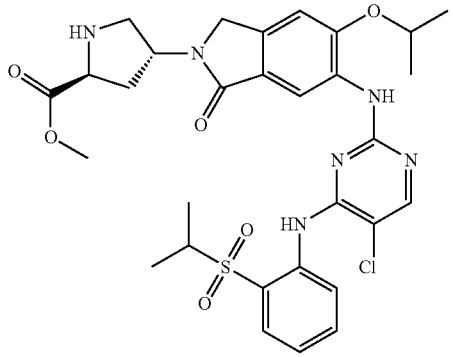

(2S,4R)-methyl 4-(6-(4-(2-isopropylsulfonyl) phenylamino)-5-chloropyrimidin-2-ylamino)-5-isopropoxy-1-oxoisoindolin-2-yl)pyrrolidine-2-carboxylate;

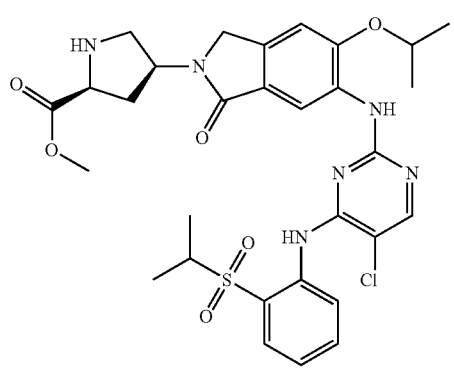

(2S,4S)-methyl 4-(6-(4-(2-(isopropylsulfonyl) phenylamino)-5-chloropyrimidin-2-ylamino)-5-isopropoxy-1-oxoisoindolin-2-yl)pyrrolidine-2-carboxylate;

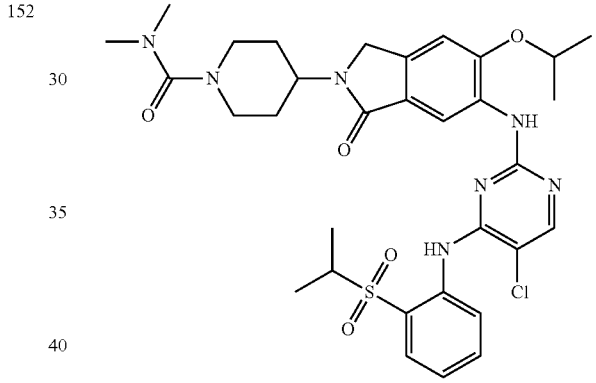

4-(6-{5-Chloro-4-[2-(propane-2-sulfonyl)-phenylamino]pyrimidin-2-ylamino}-5-isopropoxy-1-oxo-1,3-dihydro-isoindol-2-yl)-piperidine-1-carboxylic acid dimethylamide;

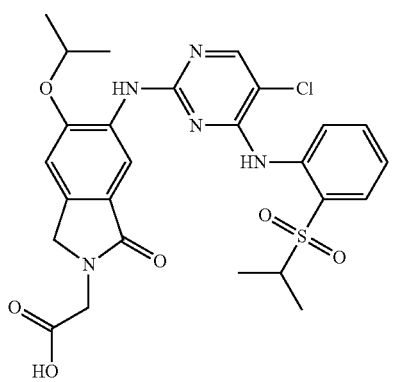 [SMILES: CC(C)Oc1cc2c(cc1Nc1ncc(Cl)c(Nc3ccccc3S(=O)(=O)C(C)C)n1)C(=O)N(CC(=O)O)C2]

2-6-(4-(2-(isopropylsulfonyl) phenylamino)-5-chloropyrimidin-2-ylamino)-5-isopropoxy-1-oxoisoindolin-2-yl)acetic acid;

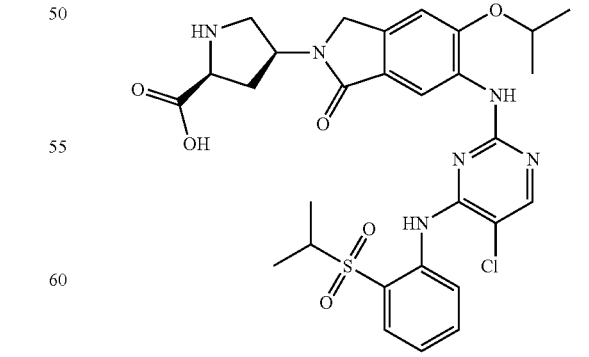

(2S,4S)-4-(6-(4-(2-(isopropylsulfonyl) phenylamino)-5-chloropyrimidin-2-ylamino)-5-isopropoxy-1-oxoisoindolin-2-yl)pyrrolidine-2-carboxylic acid;

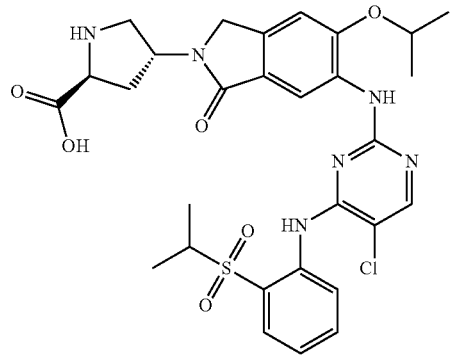 [SMILES: CC(C)Oc1cc2c(cc1Nc1ncc(Cl)c(Nc3ccccc3S(=O)(=O)C(C)C)n1)C(=O)N([C@H]1CN[C@H](C(=O)O)C1)C2]

(2S,4R)-4-(6-(4-(2-(isopropylsulfonyl) phenylamino)-5-chloropyrimidin-2-ylamino)-5-isopropoxy-1-oxoisoindolin-2-yl)pyrrolidine-2-carboxylic acid;

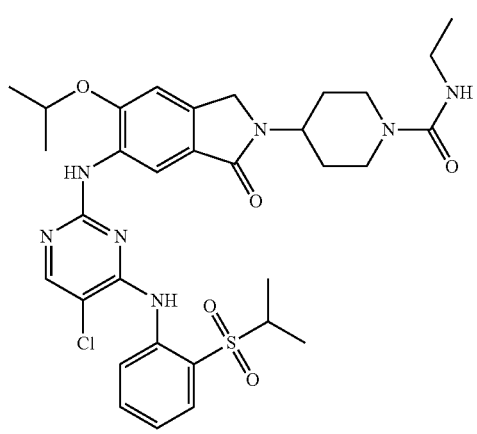 [SMILES: CCNC(=O)N1CCC(N2Cc3cc(OC(C)C)c(Nc4ncc(Cl)c(Nc5ccccc5S(=O)(=O)C(C)C)n4)cc3C2=O)CC1]

4-(6-(4-(2-(isopropylsulfonyl) phenylamino)-5-chloropyrimidin-2-ylamino)-5-isopropoxy-1-oxoisoindolin-2-yl)-N-ethylpiperidine-1-carboxamide;

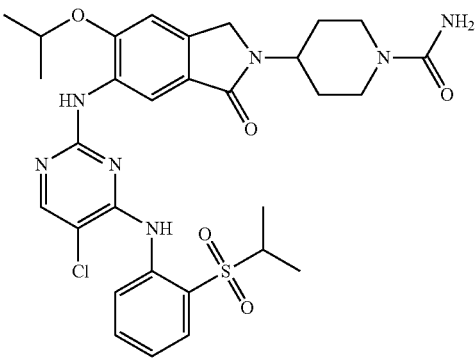 [SMILES: CC(C)Oc1cc2c(cc1Nc1ncc(Cl)c(Nc3ccccc3S(=O)(=O)C(C)C)n1)C(=O)N(C1CCN(C(N)=O)CC1)C2]

4-(6-(4-(2-(isopropylsulfonyl) phenylamino-5-chloropyrimidin-2-ylamino)-5-isopropoxy-1-oxoisoindolin-2-yl)piperidine-1-carboxamide;

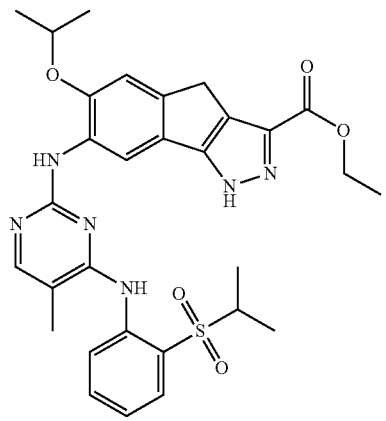 [SMILES: CCOC(=O)c1n[nH]c2c1Cc1cc(OC(C)C)c(Nc3ncc(C)c(Nc4ccccc4S(=O)(=O)C(C)C)n3)cc1-2]

Ethyl 7-(4-(2-(isopropylsulfonyl) phenylamino)-5-methylpyrimidin-2-ylamino)-1,4-dihydo-6-isopropoxyindeno[1,2-c]pyrazole-3-carboxylate;

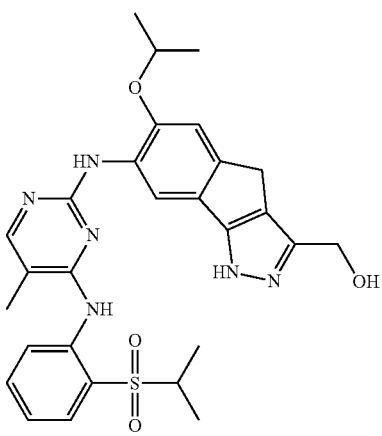 [SMILES: Cc1cnc(Nc2cc3c(cc2OC(C)C)Cc2c(CO)n[nH]c2-3)nc1Nc1ccccc1S(=O)(=O)C(C)C]

(7-(4-(2-(isopropylsulfonyl)phenylamino)-5-methylpyrimidin-2-ylamino)-1,4-dihyrdo-6-isopropoxyindeno[1,2-c]pyrazol-3-yl)methanol;

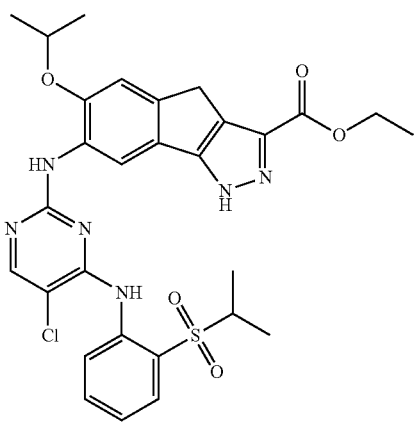 [SMILES: CCOC(=O)c1n[nH]c2c1Cc1cc(OC(C)C)c(Nc3ncc(Cl)c(Nc4ccccc4S(=O)(=O)C(C)C)n3)cc1-2]

Ethyl 7-(4-(2-(isopropylsulfonyl) phenylamino)-5-chloropyrimidin-2-ylamino)-1,4-dihydro-6-isopropoxyindeno[1,2-c]pyrazole-3-carboxylate;

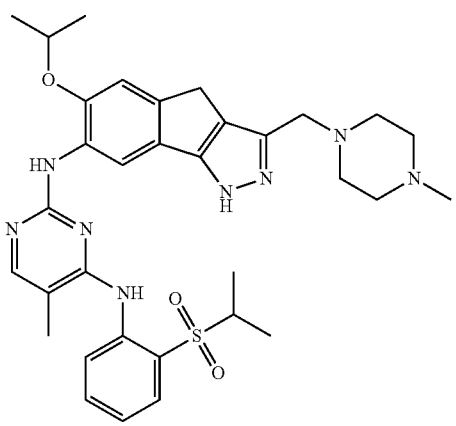

N2-(1,4-dihydro-6-isopropoxy-3-((4-methylpiperazin-1-yl)methyl)indeno[1,2-c]pyrazol-7-yl)-N4-(2-(isopropylsulfonyl)phenyl)-5-methylpyrimidine-2,4-diamine;

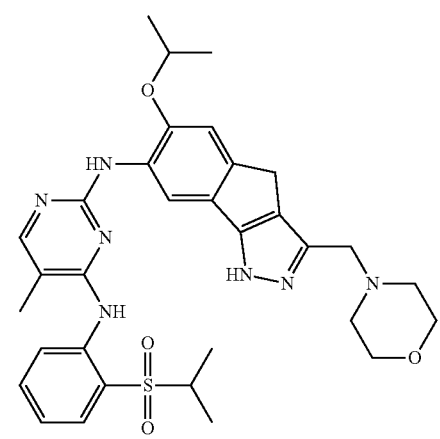 [SMILES: Cc1cnc(Nc2cc3c(cc2OC(C)C)Cc2c(CN4CCOCC4)n[nH]c2-3)nc1Nc1ccccc1S(=O)(=O)C(C)C]

N2-(1,4-dihydro-6-iospropoxy-3-(morpholinomethyl) indeno[1,2-c]pyrazol-7-yl)-N4-(2-(isopropylsulfonyl) phenyl)-5-methylpyrimidine-2,4-diamine;

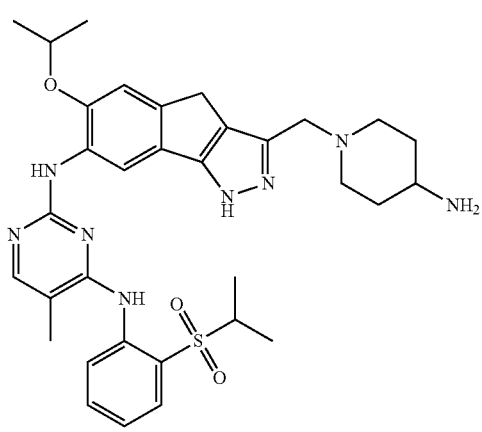 [SMILES: Cc1cnc(Nc2cc3c(cc2OC(C)C)Cc2c(CN4CCC(N)CC4)n[nH]c2-3)nc1Nc1ccccc1S(=O)(=O)C(C)C]

N2-(3-((4-aminopiperidin-1-yl)methyl-1,4-dihydro-6-isopropoxyindeno[1,2-c]pyrazol-7-yl)-N4-(2-(isopropylsulfonyl)phenyl)-5-methylpyrimidine-2,4-diamine;

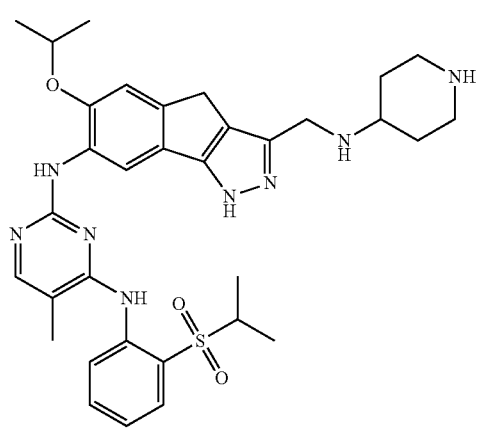 [SMILES: Cc1cnc(Nc2cc3c(cc2OC(C)C)Cc2c(CNC4CCNCC4)n[nH]c2-3)nc1Nc1ccccc1S(=O)(=O)C(C)C]

N2-(1,4-dihydro-6-isopropoxy-3-((piperidin-4-ylamino)methyl)indeno[1,2-c]pyrazol-7-yl)-N4-(2-(isopropylsulfonyl)phenyl)-5-methylpyrimidine-2,4-diamine;

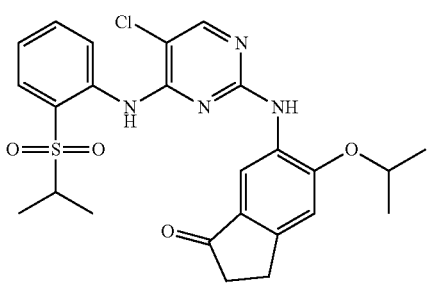 [SMILES: CC(C)Oc1cc2c(cc1Nc1ncc(Cl)c(Nc3ccccc3S(=O)(=O)C(C)C)n1)C(=O)CC2]

6-(4-(2-(isopropylsulfonyl)phenylamino)-5-chloropyrimidin-2-ylamino)-2,3-dihydro-5-isopropoxyinden-1-one;

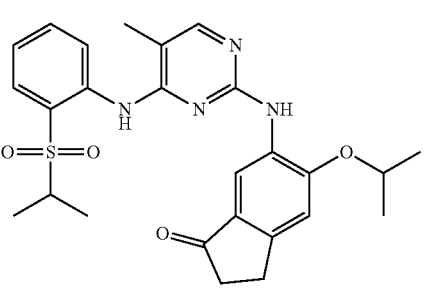 [SMILES: Cc1cnc(Nc2cc3c(cc2OC(C)C)CCC3=O)nc1Nc1ccccc1S(=O)(=O)C(C)C]

6-(4-(2-(isopropylsulfonyl)phenylamino)-5-methylpyrimidin-2-ylamino)-2,3-dihydro-5-isopropoxyinden-1-one;

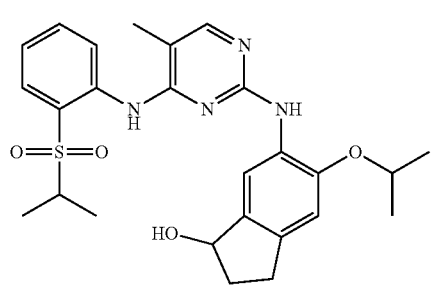

6-(4-(2-(isopropylsulfonyl)phenylamino)-5-methyl pyrimidin-2-ylamino)-2,3-dihydro-5-isopropoxy-1H-inden-1-ol;

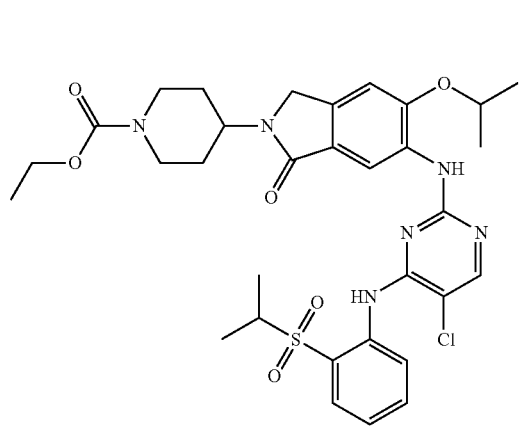 [SMILES: CCOC(=O)N1CCC(N2Cc3cc(OC(C)C)c(Nc4ncc(Cl)c(Nc5ccccc5S(=O)(=O)C(C)C)n4)cc3C2=O)CC1]

4-(6-{5-Chloro-4-[2-(propane-2-sulfonyl)-phenylamino]-pyrimidin-2-ylamino}-5-isopropoxy-1-oxo-1,3-dihydro-isoindol-2-yl)-piperdine-1-carboxylic acid ethyl ester;

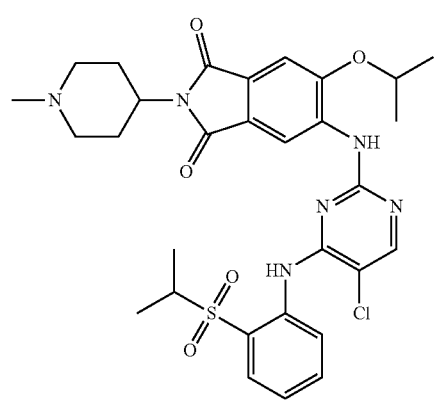

5-{5-Chloro-4-[2-(propane-2-sulfonyl)-phenylamino]-pyrimidin-2-ylamino}-6-isopropoxy-2-(1-methyl-piperidin-4-yl)-isoindole-1,3-dione;

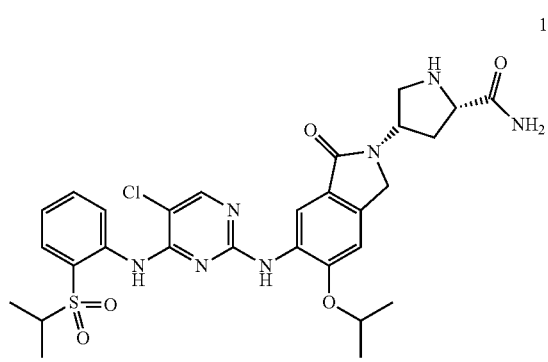

(2S, 4S)-4-(6-{5-Chloro-4-[2-(propane-2-sulfonyl)-phenylamino]-pyrimidin-2-ylamino}-5-isopropoxy-1-oxo-1,3-dihydro-isoindol-2-yl)-pyrrolidine-2-carboxylic acid amide;

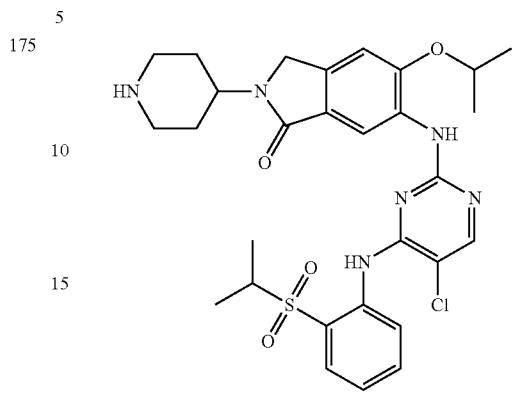

6-{5-Chloro-4-[2-(propane-2-sulfonyl)-phenylamino]-pyrimidin-2-ylamino}-5-isopropoxy-2-piperidin-4-yl-2,3-dihydro-isoindol-1-one;

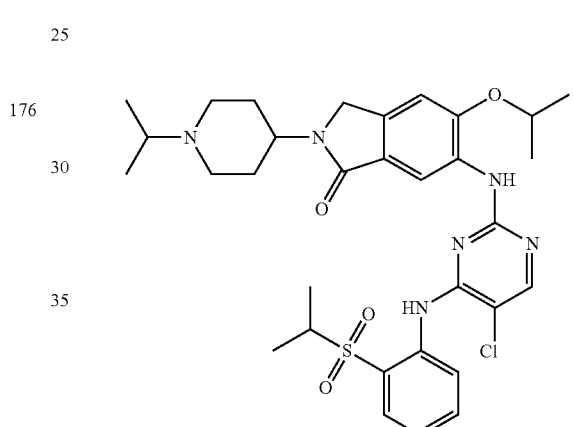

6-(4-(2-(isopropylsulfonyl)phenylamino)-5-chloropyrimidin-2-ylamino)-5-isopropoxy-2-(1-isopropylpiperidin-4-yl)isoindolin-1-one;

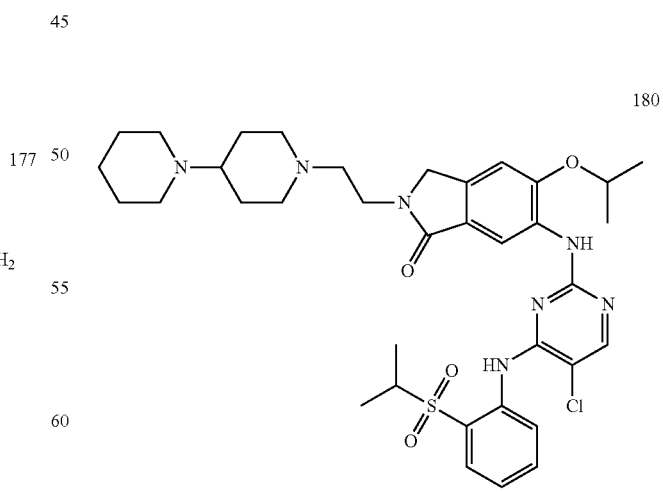

6-(4-(2-(isopropylsulfonyl)phenylamino)-5-chloropyrimidin-2-ylamino)-5-isopropoxy-2-(2-(4-(piperidin-1-yl)piperidin-1-yl)ehtyl)isoindolin-1-one;

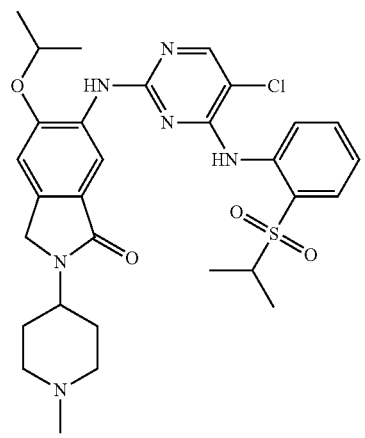 [SMILES: CC(C)Oc1cc2c(cc1Nc1ncc(Cl)c(Nc3ccccc3S(=O)(=O)C(C)C)n1)C(=O)N(C1CCN(C)CC1)C2]

6-{5-Chloro-4-[2-(propane-2-sulfonyl)-phenylamino]-pyrimidin-2-ylamino}-5-isopropoxy-2-(1-methyl-piperidin-4-yl)-2,3-dihydro-isoindol-1-one;

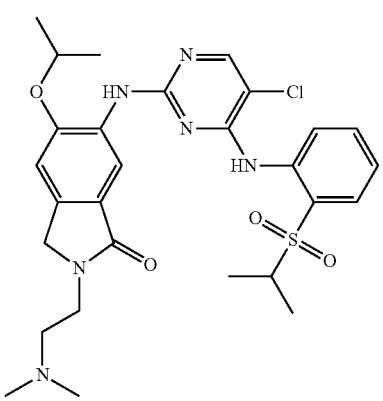 [SMILES: CC(C)Oc1cc2c(cc1Nc1ncc(Cl)c(Nc3ccccc3S(=O)(=O)C(C)C)n1)C(=O)N(CCN(C)C)C2]

6-(4-(2-(isopropylsulfonyl)phenylamino)-5-chloro pyrimidin-2-ylamino)-2-(1-(2-(dimethylamino)ethyl) piperidin-4-yl)-5-isopropoxyisoindolin-1-one;

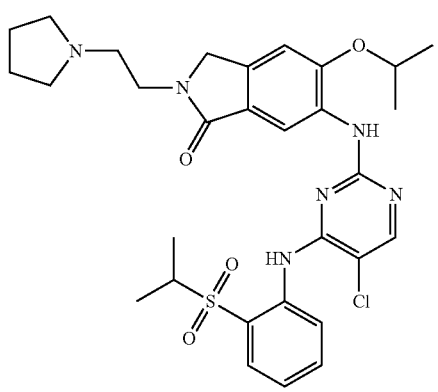 [SMILES: CC(C)Oc1cc2c(cc1Nc1ncc(Cl)c(Nc3ccccc3S(=O)(=O)C(C)C)n1)C(=O)N(CCN1CCCC1)C2]

6-(4-(2-(isopropylsulfonyl)phenylamino)-5-chloropyrimidin-2-ylamino)-5-isopropoxy-2-(1-(2-(pyrrolidin-1-yl)-ethyl)piperidin-4-yl)isoindolin-1-one;

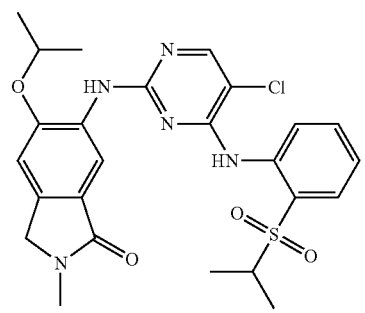 [SMILES: CC(C)Oc1cc2c(cc1Nc1ncc(Cl)c(Nc3ccccc3S(=O)(=O)C(C)C)n1)C(=O)N(C)C2]

6-(4-(2-(isopropylsulfonyl)phenylamino)-5-chloropyrimidin-2-ylamino)-5-isopropoxy-2-methylisoindolin-one;

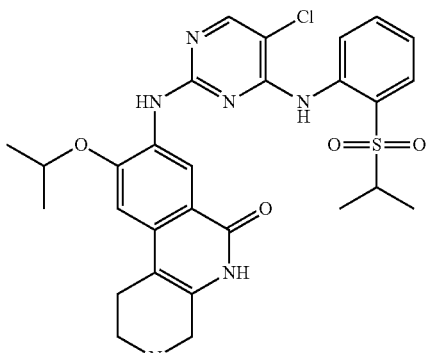

8-(5-chloro-4-(2-(isopropylsulfonyl) phenylamino) pyrimidin-2-ylamino)-9-isopropoxy-3-methyl-1,2,3,4-tetrahydrobenzo[c][1,7]napthyridin-6(5H)-one;

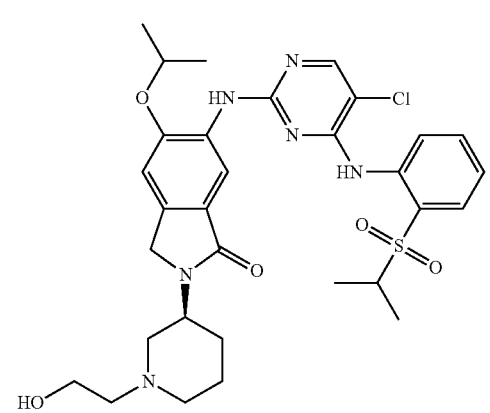 [SMILES: CC(C)Oc1cc2c(cc1Nc1ncc(Cl)c(Nc3ccccc3S(=O)(=O)C(C)C)n1)C(=O)N([C@H]1CCCN(CCO)C1)C2]

(S)-6-(5-chloro-4-(2-(isopropylsulfonyl) phenylamino) pyrimidin-2-ylamino)-2-(1-(2-hydroxyethly)piperidin-3-yl)-5-isopropoxyisoindolin-1-one;

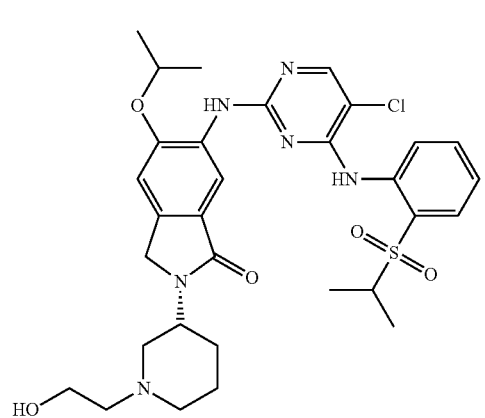

(R)-6-(5-chloro-4-(2-(isopropylsulfonyl)phenylamino) pyrimidin-2-ylamino)-2-(1-(2-hydroxyethly)piperidin-3-yl)-5-isopropoxyisoindolin-1-one;

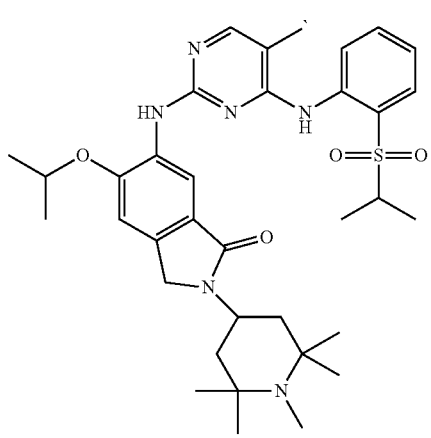

6-(5-chloro-4-(2-(isopropylsulfonyl) phenylamino) pyrimidin-2-ylamino)-5-isopropoxy-2-(1,2,2,6,6-pentamethyl piperidin-4-yl)isoindolin-1-one;

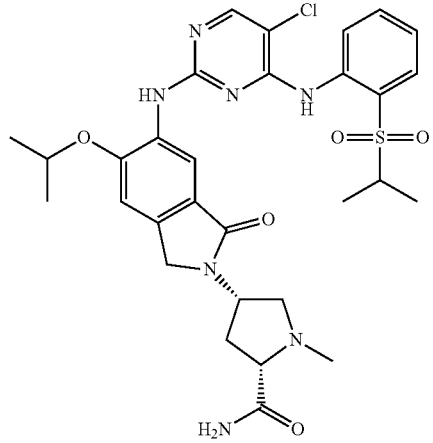

(2S,4S)-4-(6-(5-chloro-4-(2-(isopropylsulfonyl) phenylamino) pyrimidin-2-ylamino)-5-isopropoxyl-1-oxoisoindolin-2-yl)-1-methylpyrrolidine-2-carboxamide;

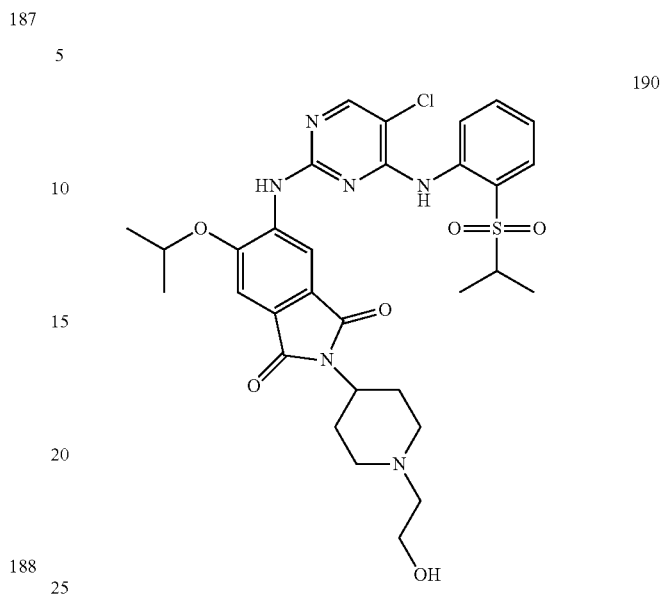

5-(5-chloro-4-(2-(isopropylsulfonyl) phenylamino) pyrimidin-2-ylamino)-2-(1-(2-hydroxyethyl)piperidin-4-yl)-6-isopropoxyisoindoline-1,3-dione;

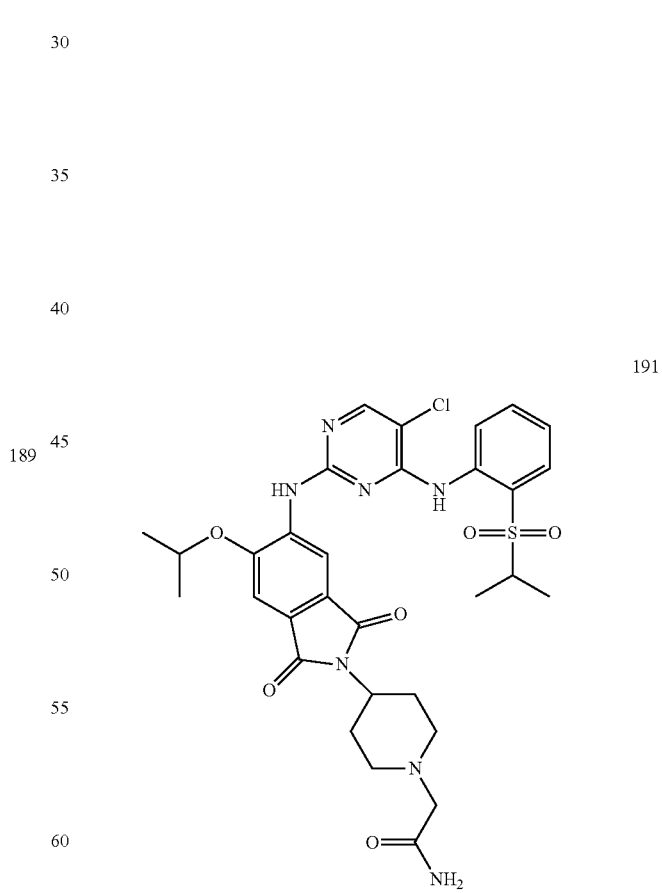

2-(4-(5-(5-chloro-4-(2-(isopropylsulfonyl) phenylamino) pyrimidin-2-ylamino)-6-isoporpoxy-1,3-dioxoisoindolin-2-yl)piperidin-1-yl)acetamide;

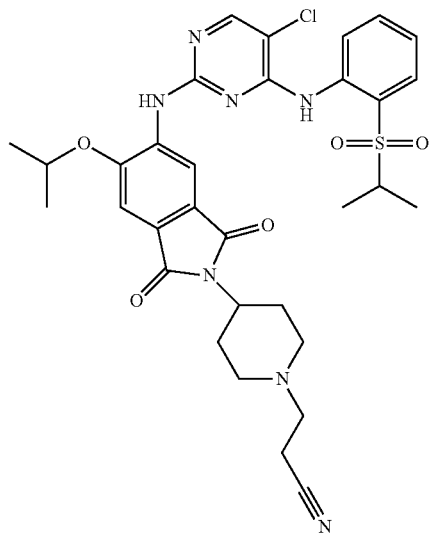

3-(4-(5-(5-chloro-4-(2-(isopropylsulfonyl) phenylamino)pyrimidin-2-ylamino)-6-isopropoxy-1,3-dioxoisoindolin-2-yl)piperidin-1-yl)propanenitrile;

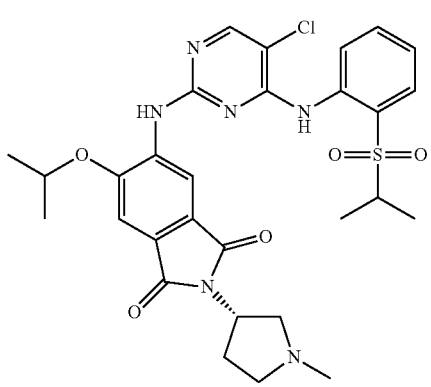

(S)-5-(5-chloro-4-(2-(isopropylsulfonyl) phenlyamino) pyrimidin-2-ylamino)-6-isopropoxy-2-(1-methylpyrrolidin-3-yl)isoindoline-1,3-dione;

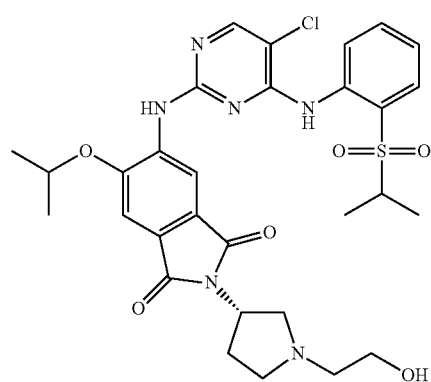

(S)-5-(5-chloro-4-(2-(isopropylsulfonyl) phenlyamino) pyrimidin-2-ylamino)-2-(1-(2-hydroxyethyl)pyrrolidin-3-yl)-6-isopropoxyisoindoline-1,3-dione;

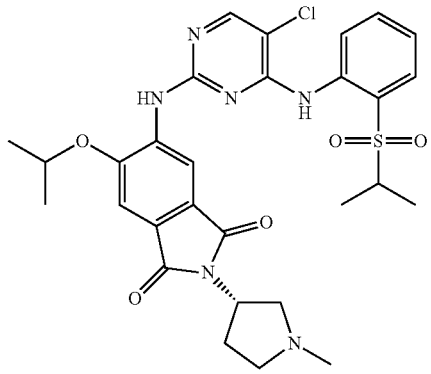

(S)-5-(5-chloro-4-(2-(isopropylsulfonyl) phenlyamino) pyrimidin-2-ylamino)-6-isopropoxy-2-(1-methylpyrrolidin-3-yl)isoindoline-1,3-dione; and

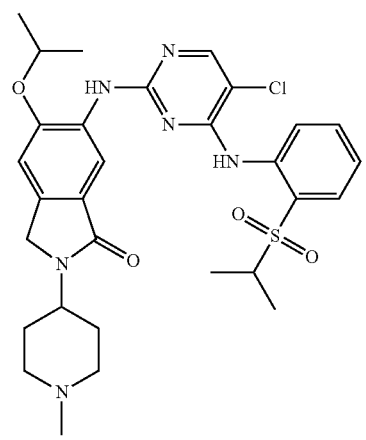 [SMILES: CC(C)Oc1cc2c(cc1Nc1ncc(Cl)c(Nc3ccccc3S(=O)(=O)C(C)C)n1)C(=O)N(C1CCN(C)CC1)C2]

6-(4-(2-(isopropylsulfonyl)phenylamino)-5-chloropyrimidin-2-ylamino)-5-isopropoxy-2-(1-methylpiperidin-4-yl)isoindolin-1-one;

or pharmaceutically acceptable salts thereof.

13. A pharmaceutical composition comprising a therapeutically effective amount of a compound of claim 10 and a pharmaceutically acceptable carrier.

14. A pharmaceutical composition comprising a therapeutically effective amount of a compound of claim 11 and a pharmaceutically acceptable carrier.

15. A pharmaceutical composition comprising a therapeutically effective amount of a compound of claim 12 and a pharmaceutically acceptable carrier.

* * * * *

UNITED STATES PATENT AND TRADEMARK OFFICE
CERTIFICATE OF CORRECTION

PATENT NO. : 8,399,450 B2  Page 1 of 1
APPLICATION NO. : 13/172357
DATED : March 19, 2013
INVENTOR(S) : Michellys et al.

It is certified that error appears in the above-identified patent and that said Letters Patent is hereby corrected as shown below:

In the Claims:

In claim 1, column 252, line 15, please delete "W is 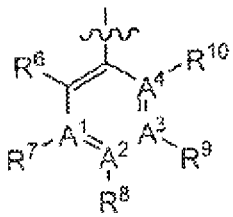", and insert

-- 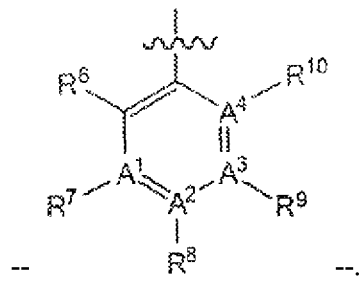 --.

In column 266, lines 55-65, please delete " 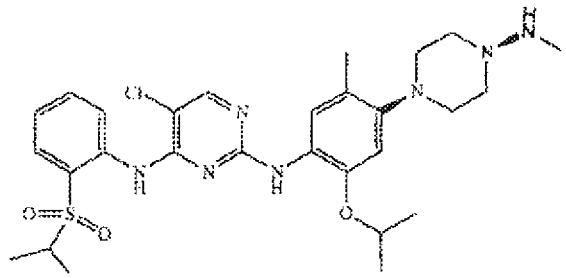 ", and insert -- 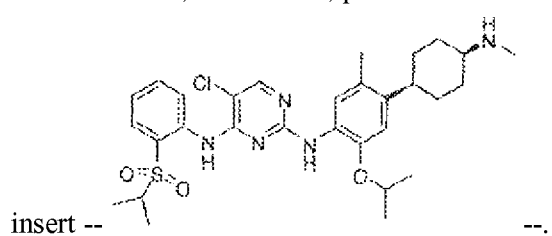 --.

Signed and Sealed this
Second Day of July, 2013

Teresa Stanek Rea
*Acting Director of the United States Patent and Trademark Office*